(12) United States Patent
Boyd et al.

(10) Patent No.: US 8,399,403 B2
(45) Date of Patent: *Mar. 19, 2013

(54) CHEMICAL LINKERS AND CONJUGATES THEREOF

(75) Inventors: Sharon E. Boyd, Albuquerque, NM (US); Liang Chen, Discovery Bay, CA (US); Sanjeev Gangwar, Foster City, CA (US); Vincent Guerlavais, Arlington, MA (US); Kilian Horgan, San Jose, CA (US); Zhi-Hong Li, Burlingame, CA (US); Bilal Sufi, Santa Clara, CA (US)

(73) Assignee: Medarex, Inc., Princeton, NJ (US)

( * ) Notice: Subject to any disclaimer, the term of this patent is extended or adjusted under 35 U.S.C. 154(b) by 554 days.

This patent is subject to a terminal disclaimer.

(21) Appl. No.: 12/610,952

(22) Filed: Nov. 2, 2009

(65) Prior Publication Data

US 2010/0092496 A1 Apr. 15, 2010

Related U.S. Application Data

(62) Division of application No. 11/134,826, filed on May 19, 2005, now Pat. No. 7,691,962.

(60) Provisional application No. 60/572,667, filed on May 19, 2004, provisional application No. 60/661,174, filed on Mar. 9, 2005.

(51) Int. Cl.
*A61K 38/00* (2006.01)

(52) U.S. Cl. ...... 514/1.1; 514/19.2; 514/19.3; 514/21.9; 514/21.91; 530/300; 530/330; 530/331

(58) Field of Classification Search .................. None
See application file for complete search history.

(56) References Cited

U.S. PATENT DOCUMENTS

| | | |
|---|---|---|
| 4,169,888 A | 10/1979 | Hanka et al. |
| 4,391,904 A | 7/1983 | Litman et al. |
| 4,671,958 A | 6/1987 | Rodwell et al. |
| 4,816,567 A | 3/1989 | Cabilly et al. |
| 4,912,227 A | 3/1990 | Kelly et al. |
| 4,923,990 A | 5/1990 | Nakano et al. |
| 4,952,394 A | 8/1990 | Senter |
| 4,975,278 A | 12/1990 | Senter et al. |
| 4,978,757 A | 12/1990 | Kelly et al. |
| 4,994,578 A | 2/1991 | Ohba et al. |
| 5,037,993 A | 8/1991 | Ohba et al. |
| 5,070,092 A | 12/1991 | Kanda et al. |
| 5,084,468 A | 1/1992 | Saito et al. |
| 5,101,038 A | 3/1992 | Nakano et al. |
| 5,117,006 A | 5/1992 | Saito et al. |
| 5,137,877 A | 8/1992 | Kaneko et al. |
| 5,138,059 A | 8/1992 | Takahashi et al. |
| 5,147,786 A | 9/1992 | Feng et al. |
| 5,176,996 A | 1/1993 | Hogan et al. |
| 5,187,186 A | 2/1993 | Kanda et al. |
| 5,223,409 A | 6/1993 | Ladner et al. |
| 5,225,539 A | 7/1993 | Winter |
| 5,288,514 A | 2/1994 | Ellman |
| 5,324,483 A | 6/1994 | Cody et al. |
| 5,332,740 A | 7/1994 | Saito et al. |
| 5,332,837 A | 7/1994 | Kelly et al. |
| 5,334,528 A | 8/1994 | Stanker et al. |
| 5,403,484 A | 4/1995 | Ladner et al. |
| 5,427,908 A | 6/1995 | Dower et al. |
| 5,475,092 A | 12/1995 | Chari et al. |
| 5,495,009 A | 2/1996 | Matteucci et al. |
| 5,530,101 A | 6/1996 | Queen et al. |
| 5,545,806 A | 8/1996 | Lonberg et al. |
| 5,547,667 A | 8/1996 | Angelucci et al. |
| 5,569,825 A | 10/1996 | Lonberg et al. |
| 5,571,698 A | 11/1996 | Ladner et al. |
| 5,573,922 A | 11/1996 | Hoess et al. |
| 5,580,717 A | 12/1996 | Dower et al. |
| 5,582,981 A | 12/1996 | Toole et al. |
| 5,585,089 A | 12/1996 | Queen et al. |
| 5,585,499 A | 12/1996 | Chari et al. |
| 5,587,161 A | 12/1996 | Burke et al. |
| 5,606,017 A | 2/1997 | Willner et al. |
| 5,622,929 A | 4/1997 | Willner et al. |
| 5,625,126 A | 4/1997 | Lonberg et al. |
| 5,629,430 A | 5/1997 | Terashima et al. |
| 5,633,425 A | 5/1997 | Lonberg et al. |
| 5,641,780 A | 6/1997 | Amishiro et al. |
| 5,660,829 A | 8/1997 | Burke et al. |
| 5,661,016 A | 8/1997 | Lonberg et al. |
| 5,686,237 A | 11/1997 | Al-Bayati |
| 5,693,762 A | 12/1997 | Queen et al. |

(Continued)

FOREIGN PATENT DOCUMENTS

| | | |
|---|---|---|
| DE | 10008089 | 10/2001 |
| EP | 0154445 | 9/1985 |

(Continued)

OTHER PUBLICATIONS

Canadian Office Action for Application No. 2,564,076, dated Dec. 15, 2010.
Japanese Office Action for Application No. 2007-527486, dated Nov. 16, 2010.
International Preliminary Report on Patentability for Application No. PCT/US2005/017804, dated Nov. 21, 2006.
International Search Report for Application No. PCT/US2005/017804, dated Oct. 20, 2006.

(Continued)

*Primary Examiner* — Anish Gupta
*Assistant Examiner* — Li Lee
(74) *Attorney, Agent, or Firm* — Nelson Mullins Riley & Scarborough LLP; Jane E. Remillard, Esq.; Pankaj N. Desai

(57) ABSTRACT

The present disclosure provides drug-ligand conjugates that are potent cytotoxins, wherein the drug is linked to the ligand through either a peptidyl, hydrazine, or disulfide linker. The disclosure is also directed to compositions containing the drug-ligand conjugates, and to methods of treatment using them.

13 Claims, No Drawings

U.S. PATENT DOCUMENTS

| | | | |
|---|---|---|---|
| 5,703,080 A | 12/1997 | Nakakura et al. | |
| 5,712,374 A | 1/1998 | Kuntsmann et al. | |
| 5,714,586 A | 2/1998 | Kunstmann et al. | |
| 5,739,116 A | 4/1998 | Hamann et al. | |
| 5,739,350 A | 4/1998 | Kelly et al. | |
| 5,770,429 A | 6/1998 | Lonberg et al. | |
| 5,773,011 A | 6/1998 | Grubhofer et al. | |
| 5,773,435 A | 6/1998 | Kadow et al. | |
| 5,786,377 A | 7/1998 | Garcia et al. | |
| 5,786,486 A | 7/1998 | Fukuda et al. | |
| 5,789,650 A | 8/1998 | Lonberg et al. | |
| 5,814,318 A | 9/1998 | Lonberg et al. | |
| 5,840,867 A | 11/1998 | Toole et al. | |
| 5,846,545 A | 12/1998 | Chari et al. | |
| 5,874,299 A | 2/1999 | Lonberg et al. | |
| 5,877,296 A | 3/1999 | Hamann et al. | |
| 5,877,397 A | 3/1999 | Lonberg et al. | |
| 5,885,793 A | 3/1999 | Griffiths et al. | |
| 5,939,598 A | 8/1999 | Kucherlapati et al. | |
| 5,962,216 A | 10/1999 | Trouet et al. | |
| 5,969,108 A | 10/1999 | McCafferty et al. | |
| 5,985,908 A | 11/1999 | Boger | |
| 6,060,608 A | 5/2000 | Boger | |
| 6,066,742 A | 5/2000 | Fukuda et al. | |
| 6,075,181 A | 6/2000 | Kucherlapati et al. | |
| 6,103,236 A | 8/2000 | Suzawa et al. | |
| 6,114,598 A | 9/2000 | Kucherlapati et al. | |
| 6,130,237 A | 10/2000 | Denny et al. | |
| 6,132,722 A | 10/2000 | Siemers et al. | |
| 6,143,901 A | 11/2000 | Dervan | |
| 6,150,584 A | 11/2000 | Kucherlapati et al. | |
| 6,162,963 A | 12/2000 | Kucherlapati et al. | |
| 6,172,197 B1 | 1/2001 | McCafferty et al. | |
| 6,180,370 B1 | 1/2001 | Queen et al. | |
| 6,194,612 B1 | 2/2001 | Boger et al. | |
| 6,214,345 B1 | 4/2001 | Firestone et al. | |
| 6,262,271 B1 | 7/2001 | Boger | |
| 6,281,354 B1 | 8/2001 | Boger | |
| 6,310,209 B1 | 10/2001 | Boger | |
| 6,329,497 B1 | 12/2001 | Boger | |
| 6,342,480 B1 | 1/2002 | Trouet et al. | |
| 6,486,326 B2 | 11/2002 | Boger | |
| 6,512,101 B1 | 1/2003 | King et al. | |
| 6,521,404 B1 | 2/2003 | Griffiths et al. | |
| 6,534,660 B1 | 3/2003 | Yongxin et al. | |
| 6,544,731 B1 | 4/2003 | Griffiths et al. | |
| 6,548,530 B1 | 4/2003 | Boger | |
| 6,555,313 B1 | 4/2003 | Griffiths et al. | |
| 6,555,693 B2 | 4/2003 | Ge et al. | |
| 6,566,336 B1 | 5/2003 | Sugiyama et al. | |
| 6,593,081 B1 | 7/2003 | Griffiths et al. | |
| 6,630,579 B2 | 10/2003 | Chari et al. | |
| 6,759,509 B1 | 7/2004 | King et al. | |
| 6,762,179 B2 | 7/2004 | Cochran et al. | |
| 6,884,869 B2 | 4/2005 | Senter et al. | |
| 6,897,034 B2 | 5/2005 | Bebbington et al. | |
| 6,946,455 B2 | 9/2005 | Sugiyama et al. | |
| 7,087,600 B2 | 8/2006 | Ng et al. | |
| 7,091,186 B2 | 8/2006 | Senter et al. | |
| 7,115,573 B2 | 10/2006 | Pickford et al. | |
| 7,129,261 B2 | 10/2006 | Ng et al. | |
| 7,180,819 B1 | 2/2007 | Agrawal | |
| 7,214,663 B2 | 5/2007 | Bebbington et al. | |
| 7,223,837 B2 | 5/2007 | De Groot et al. | |
| 7,304,032 B2 | 12/2007 | Bebbington et al. | |
| 7,329,507 B2 | 2/2008 | Pickford et al. | |
| 7,517,903 B2 * | 4/2009 | Chen et al. | 514/411 |
| 7,691,962 B2 * | 4/2010 | Boyd et al. | 530/300 |
| 7,714,016 B2 * | 5/2010 | Gangwar et al. | 514/411 |
| 2002/0082424 A1 | 6/2002 | Boger | |
| 2002/0142955 A1 | 10/2002 | Dubois et al. | |
| 2003/0050331 A1 | 3/2003 | Ng et al. | |
| 2003/0064984 A1 | 4/2003 | Ng et al. | |
| 2003/0073852 A1 | 4/2003 | Ng et al. | |
| 2003/0083263 A1 | 5/2003 | Doronina et al. | |
| 2003/0096743 A1 | 5/2003 | Senter et al. | |
| 2003/0130189 A1 | 7/2003 | Senter et al. | |
| 2004/0121940 A1 | 6/2004 | De Groot et al. | |
| 2005/0014700 A1 | 1/2005 | Boger | |
| 2005/0026987 A1 | 2/2005 | Boger | |
| 2005/0239713 A1 | 10/2005 | Domling et al. | |
| 2005/0249740 A1 | 11/2005 | Domling et al. | |
| 2005/0272798 A1 | 12/2005 | Ng et al. | |
| 2006/0229253 A1 | 10/2006 | Doronina et al. | |

FOREIGN PATENT DOCUMENTS

| | | |
|---|---|---|
| EP | 0360609 | 3/1990 |
| EP | 0386563 | 9/1990 |
| EP | 0537575 | 4/1993 |
| EP | 0563475 | 10/1993 |
| EP | 0624377 | 11/1994 |
| EP | 0867190 | 9/1998 |
| EP | 0689845 | 4/2002 |
| EP | 1243276 | 9/2002 |
| EP | 1370298 A1 | 12/2003 |
| WO | WO-8804659 | 6/1988 |
| WO | WO-9013641 | 11/1990 |
| WO | WO-9015065 | 12/1990 |
| WO | WO-9104753 A1 | 4/1991 |
| WO | WO-9106556 | 5/1991 |
| WO | WO-9106626 | 5/1991 |
| WO | WO-9106629 | 5/1991 |
| WO | WO-9109865 | 7/1991 |
| WO | WO-9111535 | 8/1991 |
| WO | WO-9113080 | 9/1991 |
| WO | WO-9119813 | 12/1991 |
| WO | WO-9205186 | 4/1992 |
| WO | WO-9205285 | 4/1992 |
| WO | WO-9209705 | 6/1992 |
| WO | WO-9210590 | 6/1992 |
| WO | WO-9214843 | 9/1992 |
| WO | WO-9610405 A1 | 4/1996 |
| WO | WO-97/12862 A1 | 4/1997 |
| WO | WO-9732850 | 9/1997 |
| WO | WO-97/45411 | 12/1997 |
| WO | WO-9745411 A1 | 12/1997 |
| WO | WO-98/11101 A2 | 3/1998 |
| WO | WO-9811101 A2 | 3/1998 |
| WO | WO-9825900 A1 | 6/1998 |
| WO | WO-9852925 | 11/1998 |
| WO | WO-9919298 | 4/1999 |
| WO | WO-9929642 | 6/1999 |
| WO | WO-0033888 | 6/2000 |
| WO | WO-01/16104 A1 | 3/2001 |
| WO | WO-0116324 | 3/2001 |
| WO | WO-0149698 | 7/2001 |
| WO | WO-0174898 | 10/2001 |
| WO | WO-0183482 | 11/2001 |
| WO | WO-0185733 | 11/2001 |
| WO | WO-0195943 | 12/2001 |
| WO | WO-0195945 | 12/2001 |
| WO | WO-0200263 | 1/2002 |
| WO | WO-0215700 | 2/2002 |
| WO | WO-0243478 | 6/2002 |
| WO | WO-02083180 | 10/2002 |
| WO | WO-02088172 | 11/2002 |
| WO | WO-02/096910 A1 | 12/2002 |
| WO | WO-0296910 | 12/2002 |
| WO | WO-02096910 | 12/2002 |
| WO | WO-02100353 | 12/2002 |
| WO | WO-03022806 | 3/2003 |
| WO | WO-03026577 | 4/2003 |
| WO | WO-03043583 | 5/2003 |
| WO | WO-03/086318 A2 | 10/2003 |
| WO | WO-03/087055 A1 | 10/2003 |
| WO | WO-2004005326 | 1/2004 |
| WO | WO-2004005327 | 1/2004 |
| WO | WO-2004/032828 A2 | 4/2004 |
| WO | WO-2004043493 | 5/2004 |
| WO | WO-2004/073656 | 9/2004 |
| WO | WO-2004073656 | 9/2004 |
| WO | WO-2004101767 | 11/2004 |
| WO | WO-2005112919 | 12/2005 |
| WO | WO-2006110476 A2 | 10/2006 |
| WO | WO-2007089149 A2 | 8/2007 |

OTHER PUBLICATIONS

Hanka, L. J. et al., "CC-1065 (NSC-298223), A New Antitumor Antibiotic: Production, In Vitro Biological Assays and Taxonomy of the Producing Microorganism," The Journal of Antibiotics, Dec. 1978, XXXI(12):1211-1217.
Martin, D. G. et al., "Structure of CC-1065 (NSC-298223), A New Antitumor Antibiotic," The Journal of Antibiotics, 1980, 33:902-903.
Martin, David G. et al., "CC-1065 (NSC 298223), A Potent New Antitumor Agent Improved Production and Isolation, Characterization and Antitumor Activity," The Journal of Antibiotics, 1981, 34(9):1119-1125.
Li, L. H. et al., "CC-1065 (NSC 298223), a Novel Antitumor Agent That Internects Strongly with Double-stranded DNA," Cancer Research, 1982, 42:999-1004.
Swenson, David H. et al., "Mechanism of Interaction of CC-1065 (NSC 298223) with DNA," Cancer Research, Jul. 1982, 42:2821-2828.
Hurley, Laurence H. et al., "Reaction of the Antitumor Antibiotic CC-1065 with DNA: Structure of a DNA Adduct with DNA Sequence Specificity," Science, Jul. 1984, 226:843-844.
Boger et al., Angewandte Chemie, Intl. Ed. in English. 35:1438-1474 (1996).
Boger, Dale L. et al., "CC-1065 and the Duocarmycins: Synthetic Studies," Chemical Reviews, 1997, 97(3):title page, 787-828.
de Groot, Franciscus M. H. et al., "Synthesis and Biological Evaluation of Novel Produgs of Anthracyclins for Selective Activation by the Tumor-Associated Protease Plasmin," 1999, 42(25):5277-5283.
de Groot, Franciscus M. H. et al., "Synthesis and Biological Evaluation of 2'-Carbamate-Linked and 2'-Carbonate-Linked Prodrugs of Paclitaxel: Selective Activation by the Tumor-Associated Protease Plasmin," Journal of Medicinal Chemistry, 2000, 43(16):3093-3102.
de Groot, Franciscus M. H. et al., "Elongated Multiple Electronic Cascade and Cyclization Spacer Systems in Activatible Anticancer Prodrugs for Enhanced Drug Release," J. Org. Chem., 2001, 66(26):8815-8830.
Carl, Philip L. et al., "A Novel Connector Linkage Applicable in Prodrug Design," Journal of Medicinal Chemistry, May 1981 (24)5:479-480.
Dubowchik, Gene M. et al., "Cathepsin B-Sensitive Dipeptide Prodrugs. 2. Models of Anticancer Drugs Paclitaxel (Taxol®), Mitomycin C and Doxorubicin," Bioorganic & Medicinal Chemistry Letters, 1998, 8:3347-3352.
Sambrook et al. Molecular Cloning: A Laboratory Manual, 2d ed. (1989) Cold Spring Harbor Laboratory Press, Cold Spring Harbor, N.Y.
Batzer et al., Nucleic Acid Res. 19:5081 (1991).
Ohtsuka et al., J. Biol Chem. 260: 2605-2608 (1985).
Rossolini et al., Mol. Cell. Probes 8: 91-98 (1994).
Berge et al., "Pharmaceutical Salts", Journal of Pharmaceutical Science, 66:1-19 (1977).
Ward et al., Nature 341:544-546 (1989).
Bird et al., Science 242:423-426 (1989).
Huston et al., Proc. Natl. Acad. Sci. 85:5879-5883 (1988).
Kohler et al., Nature 256:495-497 (1975).
Kozbor et al., Immunology Today 4(3):72-79 (1983).
Cole et al., pp. 77-96 in Monoclonal Antibodies and Cancer Therapy, Alan R. Liss, Inc. (1985).
Kohler & Milstein, Eur. J. Immunol. 6: 511-519 (1976).
Organic Functional Group Preparations, Sandler and Karo, eds., Academic Press, San Diego, (1989).
Furniss et al. (eds.),Vogel's Encyclopedia of Practical Organic Chemistry 5$^{th}$ Ed., Longman Scientific and Technical Ltd., Essex, 1991, pp. 809-816.
Heller, Acc. Chem. Res. 23: 128 (1990).
Matayoshi et al. Science 247: 954 (1990).
Dunn et al., Meth. Enzymol. 241:254-278 (1994).
Seidah et al. Meth. Enzymol. 244: 175 (1994).
Thornberry, Meth. Enzymol. 244: 615 (1994).
Weber et al. Meth. Enzymol. 244: 595 (1994).
Smith et al. Meth. Enzymol. 244: 412 (1994).
Bouvier et al., Meth. Enzymol. 248:614-633 (1995).
Hardy et al., in Amyloid Protein Precursor in Development, Aging, and Alzheimer's Disease, ed. Masters et al. pp. 190-198 (1994).

Dano, et al. Adv. Cancer. Res., 44: 139 (1985).
Stack, et al., Journal of Biological Chemistry 269 (13): 9416-9419 (1994).
Tam, et al., Am. J. Respir. Cell Mol. Biol. 3: 27-32 (1990).
Molino et al., Journal of Biological Chemistry 272(7): 4043-4049 (1997).
Coussens et al., Genes and Development 13(11):1382-1397 (1999).
Takanami et al., Cancer 88(12): 2686-92 (2000).
Tothet al., Human Pathology 31(8): 955-960 (2000).
Ribatti et al., International Journal of Cancer 85(2): 171-5 (2000).
Zimmerman, M., et al., Analytical Biochemistry 78:47-51 (1977).
Lee, D., et al., Bioorganic and Medicinal Chemistry Letters 9:1667-72 (1999).
Rano, T.A., et al., (1997) Chemistry and Biology 4:149-55.
Dunn, R.L., et al., Eds. Polymeric Drugs and Drug Delivery Systems, ACS Symposium Series vol. 469, American Chemical Society, Washington, D.C. 1991.
Boger, Dale L. et al., "Synthesis and Prelimary Evaluation of Agents Incorporating the Pharamacophore of the Duocarmycin/Pyrindamycin Alkylation Subunit: Identification of the CC-1065/Duocarmycin Common Pharmacophore," 1990, 55:4499-4502.
Boger, Dale L. et al., "Duocarymycin-Pyrindamycin DNA Alkylation Properties and Indentification, Synthesis, and Evaluation of Agents Incorporating the Pharmacophore of the Duocarymycin-Pyrindamycin Alkylation Subunit. Identification of the CC-1065-Duocarymycin Common Pharmacophore," J. Am. Chem. Soc., 1990, 112:8961-8971.
Boger, Dale L. et al., "Isolation and Characterization of the Duocarmycin-Adenine DNA Adduct," J. Am. Chem. Soc., 1991, 113:6645-6649.
Boger, Dale L. et al., "Reversibility of the Duocarmycin A and SA DNA Alkylation Reaction," J. Am. Chem. Soc., 1993, 115:9872-9873.
Boger, Dale L. et al., "DNA Alkylation Properties of the Duocarymycisn: (+)-Duocarymycin A, Epi-(+)-Duocarymycin A, Ent-(−)-Duocarymycin A and Epi,Ent-(−)-Duocarymycin A," Bioorganic & Medicinal Chemistry Letters, 1992, 2(7):759-765.
March, Advanced Organic Chemistry, 4th Edition, John Wiley and Sons (1992).
Organic Functional Group Preparations, Sandler and Karo, eds., 2nd Edition, Academic Press, Inc., (1983).
Wade LG, Compendium of Organic Synthetic Methods, John Wiley and Sons, 1980.
Ford et al., Langmuir 12(8):1944-1946 (1996).
Chrisey et al. Nucleic Acids Res. 24:3031-3039 (1996).
The Peptides: Analysis, Synthesis, Biology, vol. 2: "Special Methods in Peptide Synthesis," Gross, E. and Melenhofer, J., Eds., Academic Press, New York (1980).
Macaya et al. Proc. Natl. Acad. Sci. USA 90:3745-9 (1993).
Bock et al., Nature (London) 355:564-566 (1992).
Wang et al. Biochem. 32:1899-904 (1993).
Ellington and Szostak, Nature 346:818 (1990).
Ching et al. Proc. Natl. Acad. Sci. U.S.A. 86:10006-10010 (1989).
Broder et al., Ann. Int. Med. 113(8):604-618 (1990).
Loreau et al. FEBS Letters 274:53-56 (1990).
van der Krol et al., Biotechniques 6:958-976 (1988).
Stein et al. Cancer Res. 48:2659-2668 (1988).
Campbell et al., J. Biochem. Biophys. Methods 20:259-267(1990).
Froehler et al., Nucleic Acids Res. 16(11):4831 (1988).
Dagle et al., Nucleic Acids Res. 18: 4751 (1990).
Letsinger et al., J. Am. Chem. Soc. 110: 4470-4471 (1988).
Matteucci et al., J. Am. Chem. Soc. 113: 7767-7768 (1991).
Nielsen et al., Science 254: 1497-1500 (1991).
Oligodeoxynucleotides: Antisense Inhibitors of Gene Expression, (1989) Cohen, Ed., CRC Press.
Prospects for Antisense Nucleic Acid Therapeutics for Cancer and AIDS, (1991), Wickstrom, Ed., Wiley-Liss.
Gene Regulation: Biology of Antisense RNA and DNA, (1992) Erickson and Izant, Eds., Raven Press.
Antisense RNA and DNA, (1992), Murray, Ed., Wiley-Liss.
Antisense RNA and DNA, (1988), D. A. Melton, Ed., Cold Spring Harbor Laboratory, Cold Spring Harbor, N.Y.
Ward et al., Photochem. Photobiol. 35:803-808 (1982).

Levine et al., *Comp. Biochem. Physiol.*, 72B:77-85 (1982).
Baldwin et al., *Biochemistry* 29:5509-15 (1990).
Morris et al., Plant Molecular Biology 24:673:77 (1994).
Wilbanks et al., *J. Biol. Chem.* 268:1226-35 (1993).
March, Advanced Organic Chemistry, 3rd Ed., John Wiley & Sons, New York, 1985.
Hermanson, Bioconjugate Techniques, Academic Press, San Diego, 1996.
Feeney et al., Modification of Proteins; Advances in Chemistry Series, vol. 198, American Chemical Society, Washington, D.C., 1982.
*Prodrugs: Topical and Ocular Drug Delivery*, Sloan, ed., Marcel Dekker, Inc., New York (1992).
Bundgaard et al., J. Med. Chem. 31:2066-2069 (1988).
Petracek et al. *Annals NY Acad. Sci.*, 507:353-54 (1987).
Greene et al., Protective Groups in Organic Synthesis, John Wiley & Sons, New York, 1991.
Camps. et al., *Annaks de Quimica*, 70: 848 (1990).
Chen et al., *J. Am. Chem. Soc.*, 116: 2661-2662 (1994).
Ostrove, *Methods Enzymol.* 182: 357-71 (1990).
Ferment, *Bioeng.* 70: 199-209 (1990).
Huang et al., J. Chromatogr. 492:431-469 (1989).
Farooqui, Akhlaq A et al., "Purification of enzymes by heparin-Sepharose affinity chromatography," J. Chromatogr., 184: 335-45 (1980).
Farooqi, *Enzyme Eng.*, 4: 441-2 (1978).
Nishikawa, *Chem. Technol.*, 5(9): 564-71 (1975).
Guilford et al., in, Pract. High Perform. Liq. Chromatogr., Simpson (ed.), 193-206 (1976).
Nishikawa, Proc. Int. Workshop Technol. Protein Sep. Improv. Blood Plasma Fractionation, Sandberg (ed.), 422-35; (1977).
"Affinity chromatography of enzymes," *Affinity Chromatogr., Proc. Int. Symp.* 25-38, (1977).
Affinity Chromatography: A Practical Approach, Dean et al. (ed.), IRL Press Limited, Oxford, England (1985).
Nielsen et al., *Science* 254: 1497 (1991).
Boger, Dale L. et al., "Synthesis, Chemical Properties, and Preliminary Evaluation of Substituted CBI Analogs of CC-1065 and the Duocarmycins Incorporating the 7-Cyano-1,2,9,9a-tetrahydrocyclopropa[c]benz[e]indol-4-one Alkylation Subunit: Hammett Quantification of the Magnitude of Electronic Effects on Functional Reactivity," J. Org. Chem., 1996, 61:4894-4912.
Boger, Dale L. et al., "Duocarmycin SA Shortened, Simplified, and Extended Agents: A Systematic Examination of the Role of the DNA Binding Subunit," J. Am. Chem. Soc., 1997, 119(21):4979-4983.
Boger, Dale L. et al., "Synthesis and Preliminary Evaluation of (+)-CBI-Indole$_2$: An Enhanced Functional Analog of (+)-CC-1065," Bioorganic & Medicinal Chemistry Letters, 1991, 1(2):115-120.
Boger, Dale L. et al., "1,2,9,9a-Tetrahydrocyclopropa[c]benz[e]indol-4-one (CBI) Analogs of CC-1065 and the Duocarmycins: Synthesis and Evaluation," 1995, 3(11): 1429-1453.
Aristoff, Paul A. et al., "Synthesis and Biochemical Evaluation of the CBI-PDE-I-dimer, a Benzannelated Analog of (+)-CC-1065 That Also Produces Delayed Toxicity in Mice," J. Med. Chem., 1996, 36:1956-1963.
Chari, Ravi V. J. et al., "Enhancement of the Selectivity and Antitumor Efficacy of a CC-1065 Analogue Through Immunoconjugate Formation," Cancer Res., Sep. 1995, 55:4079-4084.
Fukuda, Yasumichi et al., "Novel Synthesis of Optically Active CC-1065, U-73,975(Adozelesin), U-80,244(Carzelesin), U-77,779(Bizelesin), KW-2189, and DU-86," Heterocycles, 1997, 45(12):2303-2308.
Li L. H. et al., "Cytotoxicity and Antitumor Activity of Carzelesin, a Prodrug Cyclopropylpyrroloindole Analogue," Cancer Research, Sep. 1992, 52: 4904-4913.
Nagamura, Satoru et al., "Antitumor Antibiotics: Duocarmycins," Chemistry of Heterocyclic Compounds, 1998, 34(12):1386-1405.
Nagamura, Pharm. Soc. Japan 1996.
Nagamura, Satoru et al., "Synthesis and Antitumor Activity of Duocarmycin Derivatives," Chem. Pharm. Bull., 1995, 43(9):1530-1535.

Sun, Daekyu et al., "Structure-Activity Relationships of (+)-C-C-1065 Analogues in the Inhibition of Helicase-Catalyzed Unwinding of Duplex DNA," Journal of Medicinal Chemistry, 1992, 35(10):1773-1782.
Umemoto, Naoji et al., "Preparation and In Vitro Cytotoxity of a Methotrexate-Anti-MM46 Monoclonal Antibody Conjugate Via an Oligopeptide Spacer," Int. J. Cancer, 1989, 43:677-684.
Warpehoski, Drugs of the Future 16(2): 131-141 (1991).
Warpehoski, M. A. et al., "Stereoelectronic Factors Influencing the Biological Activity and DNA Interaction of Synthetic Antitumor Agents Modeled on CC-1065," Journal of Medicinal Chemistry, 1988, 31: 590-603.
Boger, Dale L. et al., "Synthesis of N-(tert-Butyloxycarbonyl)-CBI, CBI, CBI-CDPI$_1$, and CBI-CDPI$_2$:Enhanced Functional Analogues of CC-1065 Incorporating the 1,2,9,9a-Tetrahydrocyclopropa[c]benz[e]indol-4-one (CBI) Left-Hand Subunit," 1990, 55:5823-5832.
Jonkman-De Vries, J. D. et al., "Systematic Study on the Chemical Stability of the Prodrug Antitumor Agent Carzelesin (U-80,244)," Journal of Pharmaceutical Sciences, Nov. 1996, 85(11):1227-1233.
Chau, Ying et al., "Synthesis and Characterization of Dextran-Peptide-Methorexate Conjugates for Tumor Targeting via Mediation by Matrix Metalloproteinase II and Matrix Metalloproteinase IX," Bioconjugate Chem., 2004, 15:931-941.
Bae et al., Drugs Exptl. Clin. Res. 29:15-23 (2003).
Kratz, Felix et al., "Development and In Vitro Efficacy of Novel MMP2 and MMP9 Specific Doxorubicin Albumin Conjugates," Bioorganic & Medicinal Chemistry Letters, 2001, 11:2001-2006.
Kline et al., Mol. Pharmaceut. 1:9-22, 2004.
Liu et al., Cancer Res. 60:6061-6067, 2000.
Lee et.al., J. Biol. Chem. 275:36720-36725, XXXX.
Kurachi and Yamamoto, Handbook of Proeolytic Enzymes, vol. 2, 2nd edition, Barrett, Rawlings & Woessner, eds., pp. 1699-1702, 2004.
Cole et al., Monoclonal Antibodies and Cancer Therapy, Reisfeld et al. (ed), Alan R. Liss, Inc. New York, pp. 77-96 (1985).
Kohler et al., Eur. J. Immunol. 6: 511-519 (1976).
Heller, *Acc. Chem. Res.* 23(5):128-134 (1990).
Matayoshi et al.., *Science* 247:954-958 (1990).
Dunn et at *Meth. Enzymol.* 241:254-278 (1994).
Seidah et al. *Meth. Enzymol.* 244:175-188 (1994).
Thornberry, *Meth. Enzymol.* 244:615-631 (1994).
Weber et al. *Meth. Enzymol.* 244:595-604 (1994).
Smith et al. *Meth. Enzymol.* 244:412-423 (1994).
Dano, et al. *Adv. Cancer. Res.*, 44:139-266 (1985).
Rano, T.A., et al., *Chemistry and Biology* 4:149-55 (1997).
Dunn et al., *Polymeric Drugs and Drug Delivery Systems*, ACS Symposium Series, Dunn et al. (ed), American Chemical Society, Washington, D.C. 469:11-23 (1991).
Boger et al. *J. Org. Chem.* 55(15):4499-4502 (1990).
Boger et al. *J. Am. Chem. Soc.* 112:8961-8971 (1990).
Boger et al., *J. Am. Chem. Soc.* 113:6645-6649 (1991).
Boger et al. *J. Am. Chem. Soc.* 115:9872-9873 (1993).
Boger et al., Bioorg. Med. Chem. Lett. 2(7):759-765 (1992).
Chrisey et al. *Nucleic Acids Res.* 24(15):3031-3039 (1996).
Wang et al. *Biochem.* 32(8):1899-904 (1993).
Ch'ng et al. Proc. Natl. Acad. Sci. U.S.A. 86:10006-10010 (1989).
Broder et al. *Ann. Int. Med.* 113(8):604-618 (1990).
Loreau et al. *FEBS Letters* 274(1,2):53-56 (1990).
van der Krol et al., *Biotechniques* 6(10):958-976 (1988).
Campbell et al., J. Biochem. Biophys. Methods 20(3):259-267(1990).
Froehler et al., *Nucleic Acids Res.* 16(11):4831-4839 (1988).
Dagle et al., *Nucleic Acids Res.* 18(16):4751-4757 (1990).
Norris et al., Plant Molecular Biology 24:673-677 (1994).
Wilbanks et al., *J. Biol. Chem.* 268(2):1226-35 (1993).
Bundgaard et al., *J. Med. Chem.*, 31:2066-2069 (1988).
Farooqui, Akhlaq A., *J. Chromatography* 184: 335-45 (1980).
Lee et al., *Enzyme Eng.*, 4:441-2 (1978).
Nishikawa, *Chemtech* 5(9): 564-571 (1975).
Guilford et al., *Pract. High Perform. Liq. Chromatogr.*, Simpson (ed.), 193-206 (1976).

Dean et at, "Affinity chromatography of enzymes," *Affinity Chromatogr., Proc. Int. Symp.* 25-38, (1977) (Pub. 1978).
Nielsen et al. *Science* 254:1497-1500 (1991).
Chari, *Cancer Res.* 55:4079-4084 (1995).
Li et al., *Cancer Res.* 52: 4904-4913 (1992).
Jonkman-De Vries et al., "Systematic Study on the Chemical Stability of the Prodrug Antitumor Agent Carzelesin (U-80,244)," *J. Pharm. Sci.* 85(11):1227-1233 (1996).
Chau et al., Bioconjugate Chem. 15:931-941 (2004).
Lee et.al., *J. Biol. Chem.* 275:36720-36725 (2000).
Nagamura, Satoru et al., "Synthesis and Antitumor Activity of Duocarmycin Derivatives: Modification of Segment A of Duocarmycin B2," Chem. Pharm. Bull., 1996, 44(9):1723-1730.
Bird et al., *Science* 242:423-426 (1988).
Boger, Dale L. et al., "CC-1065 and the Duocarymycins: Understanding Their Biological Function Through Mechanistic Studies," Angew. Chem. Int. Ed. Engl. 1996, 35:title page, 1438-1474.
Suzawa et al. (2000) "Synthesis of a Novel Duocarmycin Derivative DU-257 and its Application to Immunoconjugate Using Poly(ethylene glycol)-dipeptidyl Linker Capable of Tumor Specific Activation," *Bioorganic & Medicinal Chemistry* 8:2175-2184.
Suzawa et al. (2000). "Synthesis and HPLC analysis of enzymatically cleavable linker consisting of poly(ethylene glycol) and dipeptide for the development of immunoconjugate," *Journal of Controlled Release* 69:27-41.
Dubowchik et al. "Receptor-mediated and enzyme-dependent targeting of cytotoxic anticancer drugs," Pharmacology and Therapeutics, Elsevier, GB, vol. 83, 1999, pp. 67-123.
Hay et al. "A 2-nitroimidazole carbamate prodrug of 5-amino-1-(chloromethyl)-3[5,6,7- trimethoxyindol-2-y1)carbony1]-1, 2-dihydro -3h-benz[e]indole (amino-seco-CBI-TMI) for use with ADEPT and GDEPT," Bioorganic & Medicinal Chemistry Letters, Oxford, GB, vol. 9, No. 15, Aug. 2, 1999, pp. 2237-2242.
Hay, et al., "Structure-Activity Relationshipf for 4-Nitrobenzyl Carbamates of 5-Aminobenz(e)indoline Minor Groove Alkylating Agents as Prodrugs for GDEPT in Conjunction with *E.coli* Nitroreductase," J. Med. Chem., vol. 46, 2003, pp. 2456-2466.
Kline, Toni et al., "Novel Antitumor Prodrugs Designed for Activation by Matrix Metalloproteinases-2 and -9," Molecular Pharmaceutics, 2004, 1(1):9-22.
Wang, et al., "Synthesis and preliminary cytotoxicity study of a cephalosporin-CC-1065 analogue prodrug," Chemical Biology, vol. 1, No. 4, 2001, pp. 1472-1476.
Townes, et al., "Investigation of a Novel Reductively-Activatable Anticancer Prodrug of *SECO*-CBI-TMI, An Analog of Duocarmycin SA," Med Chem Res, vol. 11, No. 4, 2002, pp. 248-253.
Wang, et al., "Synthesis and Preliminary Cytotoxicity Study of Glucuronide Derivatives of CC-1065 Analogues," Bioorganic & Medicinal Chemistry, vol. 11, 2003, pp. 1569-1575.
Tietze, et al., "Highly Selective Glycosylated Prodrugs of Cytostatic CC-1065 Analogues for Antibody-Directed Enzyme Tumor Therapy," Chembiochem, vol. 2, 2001, pp. 758-765.
Jonkman-De Vries et al., "Systematic Study on the Chemical Stability of the Prodrug Antitumor Agent Carzelesin (U-80,244)," J. Pharm. Sci.85(11):1227-1233 (1996).
Hay et al. "A 2-nitroimidazole carbamate prodrug of 5-amino-1-(chloromethyl)-3-[5,6,7-trimethoxyindol-2-yl)carbonyl]-1, 2-dihydro-3h-benz[e]indole (amino-seco-CBI-TMI) for use with ADEPT and GDEPT," Bioorganic & Medicinal Chemistry Letters, Oxford,GB, vol. 9, No. 15, Aug. 2, 1999, pp. 2237-2242.
Hay, et al., "Structure-Activity Relationships for 4-Nitrobenzyl Carbamates of 5-Aminobenz(e)indoline Minor Groove Alkylating Agents as Prodrugs for GDEPT in Conjunction with *E.coli* Nitroreductase," J. Med. Chem., vol. 46, 2003. pp. 2456-2466.
Kline, et al., "Novel Antitumor Prodrugs Designed for Activation by Matrix Metalloproteinases-2 and -9," Molecular Pharmaceutics, vol. 1 , No. 1, 2004, pp. 9-22.
Wang, et al., "Synthesis and preliminary cytotoxicity study of a cephalosporin-CC-1065 analogue prodrug," Chemical Biology, vol. 1, No. 4, Nov. 2, 2001, pp. 1472-1476.
Hanka et al., J. Antibiot. 31:1211-1217 (1978).
Dean et al. "Affinity Chromatography of Enzymes," Affinity Chromatogr. Proc. Int. Symp. 25-38, (1977) (Pub. 1978).

Farooqui, Akhlaq A., J. Chromatography 184: 335-345 (1980).
Aristoff, J. Med. Chem. 36:1956-1963 (1993).
Baldwin et al., Biochemistry 29:5509-5515 (1990).
Berge et al., "Pharmaceutical Salts", Journal of Pharmaceutical Science, 66: 1-19 (1977).
Bird et al. Science 242:423-426 (1988).
Bock et al. Nature (London) 355:564-566 (1992).
Boger et al. J Am. Chem. Soc. 112: 8961-8971 (1990).
Boger et al. J. Am. Chem. Soc. 115: 9872-9873 (1993).
Boger et al. J. Org. Chem. 55(15): 4499-4502 (1990).
Boger et al. J. Org. Chem. 55: 5823-5832 (1990).
Boger et al., Bioorg. & Med. Chem. Letters 1(2):115-120 (1991).
Boger et al., Bioorg. Med. Chem. Lett. 2(7): 759-765 (1992).
Boger et al., Bioorganic & Med. Chem. 3(11): 1429-1453 (1995).
Boger et al., Chem. Rev. 97(3): 787-828 (1997).
Boger et al., J. Am. Chem. Soc. 113: 6645-6649 (1991).
Boger et al., J. Am. Chem. Soc. 119(21):4977-4986 (1997).
Boger et al., J. Org. Chem. 61:4894-4912 (1996).
Bouvier et al. Meth. Enzymol. 248: 614-633 (1995).
Carl et al., J. Med. Chem. 24(5):479-480 (1981).
Chari, Cancer Res. 55: 4079-4084 (1995).
Cole et al., "Monoclonal Antibodies and Cancer Therapy," Reisfeld et al. (ed.), Alan R. Liss, Inc., New York, pp. 77-96 (1985).
Dagle et al., Nucleic Acids Res. 18(16): 4751-4757 (1990).
Dano, et al. Advances in Cancer Research, Academic Press, Inc., 44:139-266 (1985).
de Groot et al., J. Med. Chem. 43(16):3093-3102 (2000).
de Groot et al., J. Med. Chem. 42(25):5277-5283 (1999).
de Groot et al., J. Org. Chem. 66(26): 8815-8830 (2001).
Dubowchik et al., Bioorg & Med. Chem. Lett. 8:3347-3352 (1998).
Dunn et al. Meth. Enzymol. 241:254-278 (1994).
Dunn et al., Polymeric Drugs and Drug Delivery Systems, ACS Symposium Series, Dunn et al. (ed),American Chemical Society, Washington, D.C. 469:11-23 (1991).
Ellington and Szostak, Nature 346:818-822 (1990).
Lee et al., Enzyme Eng., 4:441-442 (1978).
Fukuda et al., Heterocycles 45(12):2303-2308 (1997).
Guilford, H., Pract. High Perform. Liq. Chromatogr., Simpson (ed.), 193-206 (1976).
Hardy et al., Amyloid Protein Precursor in Development, Aging, and Alzheimer's Disease, Masters et al.(ed.), Springer-Verlag, New York, pp. 190-198 (1994).
Heller, A., Acc. Chem. Res. 23(5):128-134 (1990).
Hurley et al., Science 226:843-844(1984).
Huston et al. Proc. Natl. Acad. Sci. 85:5879-5883 (1988).
Kline et al., Mol. Pharmaceut. 1(1):9-22 (2004).
Kratz et al., Bioorg. Med. Chem. Lett 11:2001-2006 (2001).
Lee, D. et al., Bioorganic and Medicinal Chemistry Letters 9:1667-1672 (1999).
Li et al., Cancer Res. 42:999-1004 (1982).
Li et al., Cancer Res. 52:4904-4913 (1992).
Liu et al., Cancer Res. 60:6061-6067 (2000).
Macaya et al. Proc. Natl. Acad. Sci. 90:3745-3749 (1993).
Martin et al., J. Antibiot. 33:902-903 (1980).
Martin et al., J. Antibiot. 34(9):1119-1125 (1981).
Matayoshi et al. Science 247:954-958 (1990).
Matteucci et al., J. Am. Chem. Soc. 113:7767-7768 (1991).
Nagamura et al., Chem. Pharm. Bull. 43(9):1530-1535 (1995).
Nagamura et al., Chem. Pharm. Bull. 44(9):1723-1730 (1996).
Nagamura et al., Chemistry of Heterocyclic Compounds 34(12):1386-1405 (1998).
Nielsen et al., Science 254:1497-1500 (1991).
Nishikawa, Chemtech 5(9): 564-71 (1975).
Nishikawa, Proc. Int. Workshop Technol. Protein Sep. Improv. Blood Plasma Fractionation, Sandberg (ed.), 422-435 (1977).
Ohtsuka et al., J. Biol. Chem. 260: 2605-2608 (1985).
Rano, T.A., et al., Chemistry and Biology 4:149-155 (1997).
Ribatti et al., International Journal of Cancer 85(2):171-175 (2000).
Smith et al. Meth. Enzymol. 244: 412-423 (1994).
Sun et al., J. Med. Chem. 35(10): 1773-1782 (1992).
Swenson et al., Cancer Res. 42: 2821-2828 (1982).
Takanami et al., Cancer 88(12): 2686-2692 (2000).
Thornberry, Meth. Enzymol. 244: 615-631 (1994).

Toth et al., Human Pathology 31(8): 955-960 (2000).
Umemoto et al., Int. J. Cancer 43:677-684 (1989).
Wang et al. Biochem. 32(8):1899-1904 (1993).
Warpehoski, J. Med. Chem. 31(3): 590-603 (1988).
Weber et al. Meth. Enzymol. 244: 595-604 (1994).
Wilbanks et al., J. Biol. Chem. 268(2):1226-1235 (1993).
Atwell et al., "5-Amino-I-(chloromethyl)-1,2-dihydro-3H-b enz[eindoles:" Journal of Medical chemistry, American chemical society Washington, US. vol. 42, No. 17, 1999, pp. 3400-3411. XP002294767; ISSN:0022-2623.

Office Action mailed Jun. 18, 2008 for U.S. Appl. No. 11/134,826, filed May 19, 2006.

Office Action mailed Oct. 19, 2007 for U.S. Appl. No. 11/134,826, filed May 19, 2006.

\* cited by examiner

SEQUENCE LISTING

```
<160> NUMBER OF SEQ ID NOS: 7

<210> SEQ ID NO 1
<211> LENGTH: 4
<212> TYPE: PRT
<213> ORGANISM: artificial
<220> FEATURE:
<223> OTHER INFORMATION: synthetic

<400> SEQUENCE: 1

Ala Leu Ala Leu
1

<210> SEQ ID NO 2
<211> LENGTH: 4
<212> TYPE: PRT
<213> ORGANISM: artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is beta-Ala

<400> SEQUENCE: 2

Xaa Leu Ala Leu
1

<210> SEQ ID NO 3
<211> LENGTH: 4
<212> TYPE: PRT
<213> ORGANISM: artificial
<220> FEATURE:
<223> OTHER INFORMATION: synthetic

<400> SEQUENCE: 3

Gly Phe Leu Gly
1

<210> SEQ ID NO 4
<211> LENGTH: 4
<212> TYPE: PRT
<213> ORGANISM: artificial
<220> FEATURE:
```

```
<223> OTHER INFORMATION: synthetic

<400> SEQUENCE: 4

Pro Arg Phe Lys
1

<210> SEQ ID NO 5
<211> LENGTH: 4
<212> TYPE: PRT
<213> ORGANISM: artificial
<220> FEATURE:
<223> OTHER INFORMATION: synthetic

<400> SEQUENCE: 5

Thr Arg Leu Arg
1

<210> SEQ ID NO 6
<211> LENGTH: 4
<212> TYPE: PRT
<213> ORGANISM: artificial
<220> FEATURE:
<223> OTHER INFORMATION: synthetic

<400> SEQUENCE: 6

Ser Lys Gly Arg
1

<210> SEQ ID NO 7
<211> LENGTH: 4
<212> TYPE: PRT
<213> ORGANISM: artificial
<220> FEATURE:
<223> OTHER INFORMATION: synthetic

<400> SEQUENCE: 7

Pro Asn Asp Lys
1
```

CHEMICAL LINKERS AND CONJUGATES THEREOF

CROSS-REFERENCE TO RELATED APPLICATIONS

This application is a Divisional of U.S. patent application Ser. No. 11/134,826, filed May 19, 2005, which claims the benefit under 35 USC 119(e) of U.S. Provisional Patent Application Ser. Nos. 60/572,667, filed on May 19, 2004, and 60/661,174, filed on Mar. 9, 2005, which are herein incorporated by reference.

FIELD OF THE INVENTION

The present invention provides linkers that attach to a drug and a ligand and are cleaved in vivo. The linkers are of use in forming prodrugs and conjugates of the cytotoxins of the invention as well as other diagnostic and therapeutic moieties.

BACKGROUND OF THE INVENTION

Many therapeutic agents, particularly those that are especially effective in cancer chemotherapy, often exhibit acute toxicity in vivo, especially bone marrow and mucosal toxicity, as well as chronic cardiac and neurological toxicity. Such high toxicity can limit their applications. Development of more and safer specific therapeutic agents, particularly anti-tumor agents, is desirable for greater effectiveness against tumor cells and a decrease in the number and severity of the side effects of these products (toxicity, destruction of non-tumor cells, etc.). Another difficulty with some existing therapeutic agents is their less than optimal stability in plasma. Addition of functional groups to stabilize these compounds resulted in a significant lowering of the activity. Accordingly, it is desirable to identify ways to stabilize compounds while maintaining acceptable therapeutic activity levels.

The search for more selective cytotoxic agents has been extremely active for many decades, the dose limiting toxicity (i.e. the undesirable activity of the cytotoxins on normal tissues) being one of the major causes of failures in cancer therapy. For example, CC-1065 and the duocarmycins are known to be extremely potent cytotoxins.

CC-1065 was first isolated from *Streptomyces zelensis* in 1981 by the Upjohn Company (Hanka et al., *J. Antibiot.* 31: 1211 (1978); Martin et al., *J. Antibiot.* 33: 902 (1980); Martin et al., *J. Antibiot.* 34: 1119 (1981)) and was found to have potent antitumor and antimicrobial activity both in vitro and in experimental animals (Li et al., *Cancer Res.* 42: 999 (1982)). CC-1065 binds to double-stranded B-DNA within the minor groove (Swenson et al., *Cancer Res.* 42: 2821 (1982)) with the sequence preference of 5'-d(A/GNTTA)-3' and 5'-d(AAAAA)-3' and alkylates the N3 position of the 3'-adenine by its CPI left-hand unit present in the molecule (Hurley et al., *Science* 226: 843 (1984)). Despite its potent and broad antitumor activity, CC-1065 cannot be used in humans because it causes delayed death in experimental animals.

Many analogues and derivatives of CC-1065 and the duocarmycins are known in the art. The research into the structure, synthesis and properties of many of the compounds has been reviewed. See, for example, Boger et al., *Angew. Chem. Int. Ed. Engl.* 35: 1438 (1996); and Boger et al., *Chem. Rev.* 97: 787 (1997).

A group at Kyowa Hakko Kogya Co., Ltd. has prepared a number of CC-1065 derivatives. See, for example, U.S. Pat. Nos. 5,101,038; 5,641,780; 5,187,186; 5,070,092; 5,703,080; 5,070,092; 5,641,780; 5,101,038; and 5,084,468; and published PCT application, WO 96/10405 and published European application 0 537 575 A1.

The Upjohn Company (Pharmacia Upjohn) has also been active in preparing derivatives of CC-1065. See, for example, U.S. Pat. Nos. 5,739,350; 4,978,757, 5,332,837 and 4,912,227.

Research has also focused on the development of new therapeutic agents which are in the form of prodrugs, compounds that are capable of being converted to drugs (active therapeutic compounds) in vivo by certain chemical or enzymatic modifications of their structure. For purposes of reducing toxicity, this conversion is preferably confined to the site of action or target tissue rather than the circulatory system or non-target tissue. However, even prodrugs are problematic as many are characterized by a low stability in blood and serum, due to the presence of enzymes that degrade or activate the prodrugs before the prodrugs reach the desired sites within the patient's body.

Bristol-Myers Squibb has described particular lysosomal enzyme-cleavable antitumor drug conjugates. See, for example, U.S. Pat. No. 6,214,345. This patent provides an aminobenzyl oxycarbonyl.

Seattle Genetics has published applications U.S. Pat. Appl. 2003/0096743 and U.S. Pat. Appl. 2003/0130189, which describe p-aminobenzylethers in drug delivery agents. The linkers described in these applications are limited to aminobenzyl ether compositions.

Other groups have also described linkers. See for example de Groot et al., *J. Med. Chem.* 42, 5277 (1999); de Groot et al. *J. Org. Chem.* 43, 3093 (2000); de Groot et al., *J. Med. Chem.* 66, 8815, (2001); WO 02/083180; Carl et al., *J. Med. Chem. Lett.* 24, 479, (1981); Dubowchik et al., *Bioorg & Med. Chem. Lett.* 8, 3347 (1998). These linkers include aminobenzyl ether spacer, elongated electronic cascade and cyclization spacer systems, cyclisation eliminations spacers, such as w-amino aminocarbonyls, and a p aminobenzyl oxycarbonyl linker.

Stability of cytotoxin drugs, including in vivo stability, is still an important issue that needs to be addressed. In addition, the toxicity of many compounds makes them less useful, so compositions that will reduce drug toxicity, such as the formation of a cleaveable prodrug, are needed. Therefore, in spite of the advances in the art, there continues to be a need for the development of improved therapeutic agents for the treatment of mammals, and humans in particular, more specifically cytotoxins that exhibit high specificity of action, reduced toxicity, and improved stability in blood relative to known compounds of similar structure. The instant invention addresses those needs.

SUMMARY OF THE INVENTION

The present invention relates to drug-ligand conjugates where the drug and ligand are linked through a peptidyl, hydrazine, or disulfide linker. These conjugates are potent cytotoxins that can be selectively delivered to a site of action of interest in an active form and then cleaved to release the active drug. The new linker arms of the invention can be cleaved from the cytotoxic drugs by, for example, enzymatic or reductive means in vivo, releasing an active drug moiety from the prodrug derivative. Furthermore, the invention includes conjugates between the linker arms and the cytotoxins of the invention, and conjugates between the linker arms, the cytotoxin and a targeting agent, such as an antibody or a peptide.

The invention also relates to groups useful for stabilizing therapeutic agents and markers. The stabilizing groups are selected, for example, to limit clearance and metabolism of the therapeutic agent or marker by enzymes that may be present in blood or non-target tissue. The stabilizing groups can serve to block degradation of the agent or marker and may also act in providing other physical characteristics of the agent or marker, for example to increase the solubility of the compound or to decrease the aggregation properties of the compound. The stabilizing group may also improve the agent or marker's stability during storage in either a formulated or non-formulated form.

In a first aspect, the invention provides a cytotoxic drug-ligand compound having a structure according to any of Formulas 1-3:

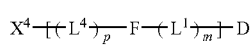 (1)

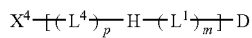 (2)

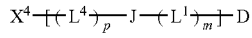 (3)

wherein the symbol D is a drug moiety having pendant to the backbone thereof a chemically reactive functional group, said functional group selected from the group consisting of a primary or secondary amine, hydroxyl, sulfhydryl, carboxyl, aldehyde, and a ketone.

The symbol $L^1$ represents a self-immolative spacer where m is an integer of 0, 1, 2, 3, 4, 5, or 6.

The symbol $X^4$ represents a member selected from the group consisting of protected reactive functional groups, unprotected reactive functional groups, detectable labels, and targeting agents.

The symbol $L^4$ represents a linker member, and p is 0 or 1. $L^4$ is a moiety that imparts increased solubility or decreased aggregation properties to the conjugates. Examples of $L^4$ moieties include substituted alkyl, unsubstituted alkyl, substituted aryl, unsubstituted aryl, substituted heteroalkyl, or unsubstituted heteroalkyl, any of which may be straight, branched, or cyclic, a positively or negatively charged amino acid polymer, such as polylysine or polyargenine, or other polymers such as polyethylene glycol.

The symbols F, H, and J represent linkers, as described further herein.

In one embodiment, the invention pertains to peptide linker conjugate of the structure:

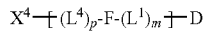

wherein

D is a drug moiety having pendant to the backbone thereof a chemically reactive functional group, said functional group selected from the group consisting of a primary or secondary amine, hydroxyl, thiol, carboxyl, aldehyde, and a ketone;

$L^1$ is a self-immolative linker;

m is an integer 0, 1, 2, 3, 4, 5, or 6;

F is a linker comprising the structure:

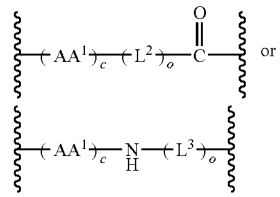

wherein $AA^1$ is one or more members independently selected from the group consisting of natural amino acids and unnatural α-amino acids;

c is an integer from 1 to 20;

$L^2$ is a self-immolative linker;

$L^3$ is a spacer group comprising a primary or secondary amine or a carboxyl functional group; wherein if $L^3$ is present, m is 0 and either the amine of $L^3$ forms an amide bond with a pendant carboxyl functional group of D or the carboxyl of $L^3$ forms an amide bond with a pendant amine functional group of D;

o is 0 or 1;

$L^4$ is a linker member, wherein $L^4$ does not comprise a carboxylic acyl group directly attached to the N-terminus of $(AA^1)_c$;

p is 0 or 1; and $X^4$ is a member selected from the group consisting of protected reactive functional groups, unprotected reactive functional groups, detectable labels, and targeting agents.

In one embodiment, the peptide linker conjugate comprises the following structure:

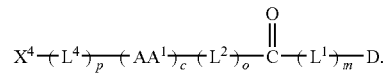

In another embodiment, the peptide linker conjugate comprises the following structure:

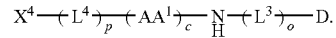

In a preferred embodiment, $L^3$ comprises an aromatic group. For example, $L^3$ can comprise a benzoic acid group, an aniline group, or an indole group. Non-limiting examples of -$L^3$-NH— include structures selected from the following group:

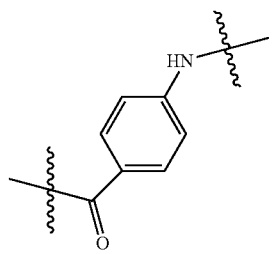

-continued

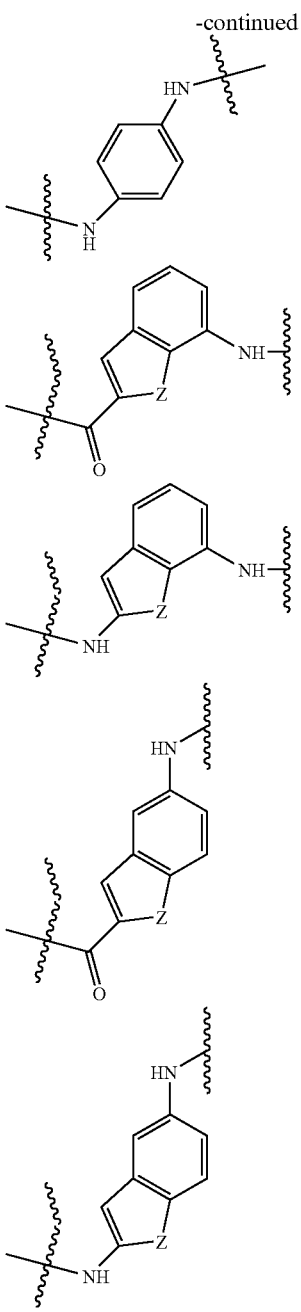

wherein Z is a member selected from O, S and NR$^{23}$, and wherein R$^{23}$ is a member selected from H, substituted or unsubstituted alkyl, substituted or unsubstituted heteroalkyl, and acyl.

In preferred embodiments of the peptide linker, (AA$^1$)$_c$ is a peptide sequence cleavable by a protease expressed in tumor tissue. A preferred protease is a lysosomal protease. In preferred embodiments, c is an integer from 2 to 6, or c is 2, 3 or 4. In certain embodiments, the amino acid in (AA$^1$)$_c$ located closest to the drug moiety is selected from the group consisting of: Ala, Asn, Asp, Cit, Cys, Gln, Glu, Gly, Ile, Leu, Lys, Met, Phe, Pro, Ser, Thr, Trp, Tyr, and Val. In preferred embodiments, (AA$^1$)$_c$ is a peptide sequence selected from the group consisting of Val-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), β-Ala-Leu-Ala-Leu (SEQ ID NO: 2) and Gly-Phe-Leu-Gly (SEQ ID NO: 3). In particularly preferred embodiments, (AA$^1$)$_c$ is Val-Cit or Val-Lys.

In some preferred embodiments, the peptide linker, F, comprises the structure:

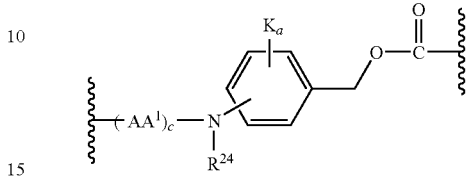

wherein
R$^{24}$ is selected from the group consisting of H, substituted alkyl, unsubstituted alkyl, substituted heteroalkyl, and unsubstituted heteroalkyl;
Each K is a member independently selected from the group consisting of substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, halogen, NO$_2$, NR$^{21}$R$^{22}$, NR$^{21}$COR$^{22}$, OCONR$^{21}$R$^{22}$, and OROR$^{21}$, and OR$^{21}$
wherein
R$^{21}$ and R$^{22}$ are independently selected from the group consisting of H, substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl; and
a is an integer of 0, 1, 2, 3, or 4.

In other preferred embodiments, —F-(L$^1$)$_m$- comprises the structure:

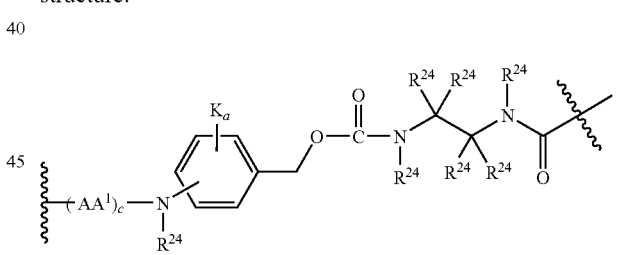

wherein
each R$^{24}$ is a member independently selected from the group consisting of H, substituted alkyl, unsubstituted alkyl, substituted heteroalkyl, and unsubstituted heteroalkyl.

In another aspect, the invention pertains to hydrazine linker conjugates of the structure:

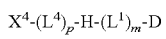

wherein
D is a drug moiety having pendant to the backbone thereof a chemically reactive functional group, said function group selected from the group consisting of a primary or secondary amine, hydroxyl, thiol, carboxyl, aldehyde, and a ketone;
L$^1$ is a self-immolative linker;
m is an integer selected from 0, 1, 2, 3, 4, 5, or 6;

$X^4$ is a member selected from the group consisting of protected reactive functional groups, unprotected reactive functional groups, detectable labels, and targeting agents;
$L^4$ is a linker member;
p is 0 or 1;
H is a linker comprising the structure:

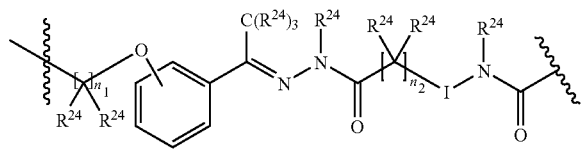

wherein
$n_1$ is an integer from 1-10;
$n_2$ is 0, 1, or 2;
each $R^{24}$ is a member independently selected from the group consisting of H, substituted alkyl, unsubstituted alkyl, substituted heteroalkyl, and unsubstituted heteroalkyl; and
I is either a bond or:

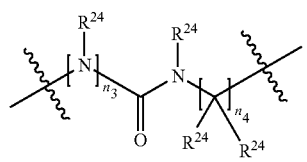

wherein $n_3$ is 0 or 1 with the proviso that when $n_3$ is 0, $n_2$ is not 0; and
$n_4$ is 1, 2, or 3,
wherein when I is a bond, $n_1$ is 3 and $n_2$ is 1, D can not be

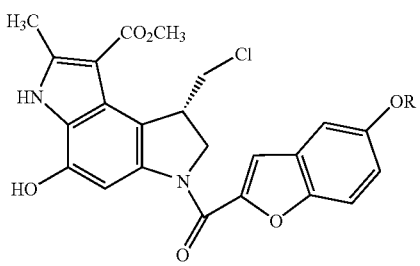

where R is Me or $CH_2$—$CH_2$—$NMe_2$.

In some preferred embodiments, the substitution on the phenyl ring is a para substitution. In some preferred embodiments, $n_1$ is 2, 3, or 4 or $n_1$ is 3 or $n_2$ is 1.

In certain embodiments, I is a bond. In other embodiments, $n_3$ is 0 and $n_4$ is 2.

In various aspects, the invention provides hydrazine linkers, H, that can form a 6-membered self immolative linker upon cleavage, or two 5-membered self immolative linkers upon cleavage, or a single 5-membered self immolative linker upon cleavage, or a single 7-membered self immolative linker upon cleavage, or a 5-membered self immolative linker and a 6-membered self immolative linker upon cleavage.

In a preferred embodiment, H comprises a geminal dimethyl substitution.

In a preferred embodiment, H comprises the structure:

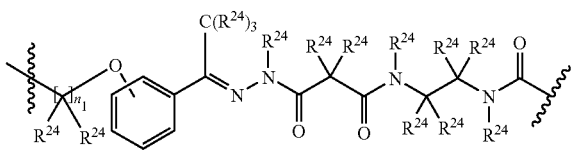

Preferably, $n_1$ is 2, 3, or 4, more preferably $n_1$ is 3. Preferably, each $R_{24}$ is independently selected from $CH_3$ and H. In certain preferred embodiments, each $R_{24}$ is H.

In another preferred embodiment, H comprises the structure:

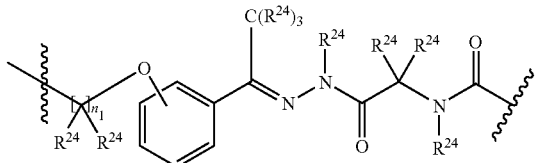

Preferably, $n_1$ is 3. Preferably, each $R_{24}$ is independently selected from $CH_3$ and H.

In yet other preferred embodiments, H comprises the structure:

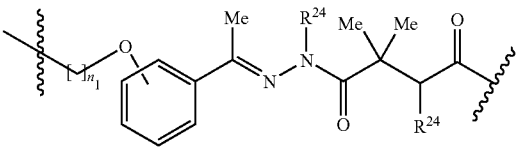

Preferably, each $R^{24}$ independently an H or a substituted or unsubstituted alkyl.

In another aspect, the invention pertains to hydrazine linker conjugates of the structure:

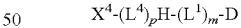

$$X^4\text{-}(L^4)_p\text{-}H\text{-}(L^1)_m\text{-}D$$

wherein
D is a drug moiety having pendant to the backbone thereof a chemically reactive functional group, said function group selected from the group consisting of a primary or secondary amine, hydroxyl, thiol, carboxyl, aldehyde, and a ketone;
$L^1$ is a self-immolative linker;
m is an integer selected from 0, 1, 2, 3, 4, 5, or 6;
$X^4$ is a member selected from the group consisting of protected reactive functional groups, unprotected reactive functional groups, detectable labels, and targeting agents;
$L^4$ is a linker member;
p is 0 or 1; and H comprises the structure:

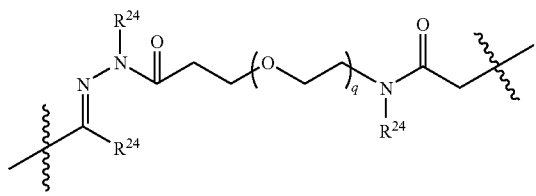

where q is 0, 1, 2, 3, 4, 5, or 6; and
each $R^{24}$ is a member independently selected from the group consisting of H, substituted alkyl, unsubstituted alkyl, substituted heteroalkyl, and unsubstituted heteroalkyl.

In yet another aspect, the invention pertains to disulfide linker conjugates of the structure:

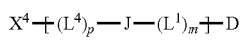

wherein
D is a drug moiety having pendant to the backbone thereof a chemically reactive functional group, said function group selected from the group consisting of a primary or secondary amine, hydroxyl, thiol, carboxyl, aldehyde, and a ketone;
$L^1$ is a self-immolative linker;
m is an integer selected from 0, 1, 2, 3, 4, 5, or 6;
$X^4$ is a member selected from the group consisting of protected reactive functional groups, unprotected reactive functional groups, detectable labels, and targeting agents;
$L^4$ is a linker member;
P is 0 or 1;
J is a linker comprising the structure:

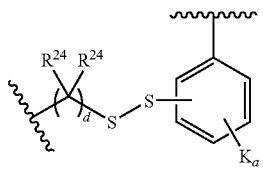

wherein
each $R^{24}$ is a member independently selected from the group consisting of H, substituted alkyl, unsubstituted alkyl, substituted heteroalkyl, and unsubstituted heteroalkyl;
each K is a member independently selected from the group consisting of H, substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, halogen, $NO_2$, $NR^{21}R^{22}$, $NR^{21}COR^{22}$, $OCONR^{21}R^{22}$, $OCOR^{21}$, and $OR^{21}$
wherein
$R^{21}$ and $R^{22}$ are independently selected from the group consisting of H, substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl and unsubstituted heterocycloalkyl;
a is an integer of 0, 1, 2, 3, or 4; and
d is an integer of 0, 1, 2, 3, 4, 5, or 6.

In various embodiments, J can comprise one of the following structures:

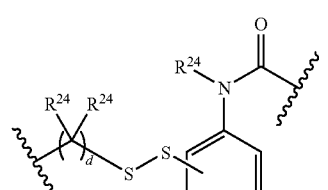

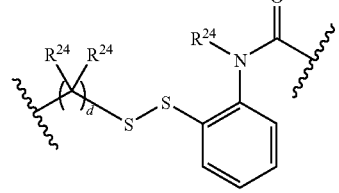

wherein d is 1 or 2;

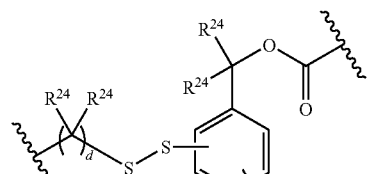

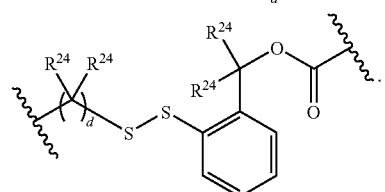

In all of the foregoing linker conjugates, D preferably is a cytotoxic drug. In preferred embodiments, D has a chemically reactive function group selected from the group consisting of a primary or secondary amine, hydroxyl, sulfhydryl and carboxyl. Non-limiting examples of preferred drugs, D, include duocarmycins and duocarmycin analogs and derivatives, CC-1065, CBI-based duocarmycin analogues, MCBI-based duocarmycin analogues, CCBI-based duocarmycin analogues, doxorubicin, doxorubicin conjugates, morpholino-doxorubicin, cyanomorpholino-doxorubicin, dolastatins, dolestatin-10, combretastatin, calicheamicin, maytansine, maytansine analogues, DM-1, auristatin E, auristatin EB (AEB), auristatin EFP (AEFP), monomethyl auristatin E (MMAE), 5-benzoylvaleric acid-AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloromethotrexate, 5-fluorouracil, 6-mercaptopurine, cytosine arabinoside, melphalan, leurosine, leurosideine, actinomycin, daunorubicin, daunorubicin conjugates, mitomycin C, mitomycin A, caminomycin, aminopterin, tallysomycin, podophyllotoxin, podophyllotoxin derivatives, etoposide, etoposide phosphate, vincristine, taxol, taxotere retinoic acid, butyric acid, $N^8$-acetyl spermidine and camptothecin.

In a preferred embodiment, D is a duocarmycin analog or derivative that comprises a structure:

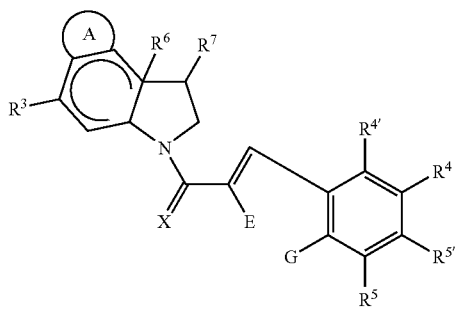

wherein the ring system A is a member selected from substituted or unsubstituted aryl, substituted or unsubstituted heteroaryl and substituted or unsubstituted heterocycloalkyl groups;

E and G are members independently selected from H, substituted or unsubstituted alkyl, substituted or unsubstituted heteroalkyl, a heteroatom, a single bond, or E and G are joined to form a ring system selected from substituted or unsubstituted aryl, substituted or unsubstituted heteroaryl and substituted or unsubstituted heterocycloalkyl;

X is a member selected from O, S and $NR^{23}$;

$R^{23}$ is a member selected from H, substituted or unsubstituted alkyl, substituted or unsubstituted heteroalkyl, and acyl;

$R^3$ is a member selected from the group consisting of (=O), $SR^{11}$, $NHR^{11}$ and $OR^{11}$, wherein $R^{11}$ is a member selected from the group consisting of H, substituted alkyl, unsubstituted alkyl, substituted heteroalkyl, unsubstituted heteroalkyl, diphosphates, triphosphates, acyl, $C(O)R^{12}R^{13}$, $C(O)OR^{12}$, $C(O)NR^{12}R^{13}$, $P(O)(OR^{12})_2$, $C(O)CHR^{12}R^{13}$, $SR^{12}$ and $SiR^{12}R^{13}R^{14}$, in which $R^{12}$, $R^{13}$ and $R^{14}$ are members independently selected from H, substituted or unsubstituted alkyl, substituted or unsubstituted heteroalkyl and substituted or unsubstituted aryl, wherein $R^{12}$ and $R^{13}$ together with the nitrogen or carbon atom to which they are attached are optionally joined to form a substituted or unsubstituted heterocycloalkyl ring system having from 4 to 6 members, optionally containing two or more heteroatoms;

$R^4$, $R^{4'}$, $R^5$ and $R^{5'}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$, $OR^{15}$, $CR^{15}$=$NR^{16}$, and $O(CH_2)_nN(CH_3)_2$ wherein n is an integer from 1 to 20;

$R^{15}$ and $R^{16}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms;

$R^6$ is a single bond which is either present or absent and when present $R^6$ and $R^7$ are joined to form a cyclopropyl ring; and $R^7$ is $CH_2$—$X^1$ or $CH_2$— joined in said cyclopropyl ring with $R^6$, wherein $X^1$ is a leaving group, wherein at least one of $R^{11}$, $R^{12}$, $R^{13}$, $R^{15}$ or $R^{16}$ links said drug to $L^1$, if present, or to F, H, or J.

In a preferred embodiment, D has the structure:

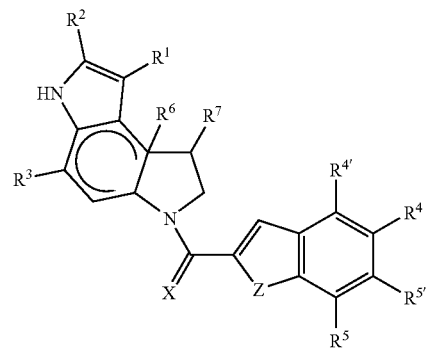

wherein

Z is a member selected from O, S and $NR^{23}$ wherein $R^{23}$ is a member selected from H, substituted or unsubstituted alkyl, substituted or unsubstituted heteroalkyl, and acyl;

$R^1$ is H, substituted or unsubstituted lower alkyl, $C(O)R^8$, or $CO_2R^8$, wherein $R^8$ is a member selected from group consisting of substituted alkyl, unsubstituted alkyl, $NR^9R^{10}$, $NR^9NHR^{10}$, and $OR^9$ in which $R^9$ and $R^{10}$ are members independently selected from H, substituted or unsubstituted alkyl and substituted or unsubstituted heteroalkyl; and $R^2$ is H, substituted alkyl or unsubstituted lower alkyl;

wherein at least one of $R^{11}$, $R^{12}$, $R^{13}$, $R^{15}$ or $R^{16}$ links said drug to $L^1$, if present, or to F, H, or J.

In a preferred embodiment of the above, $R^2$ is an unsubstituted lower alkyl.

In another preferred embodiment, D has the structure:

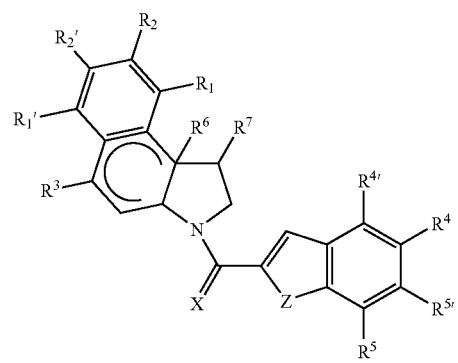

wherein

Z is a member selected from O, S and $NR^{23}$ wherein $R^{23}$ is a member selected from H, substituted or unsubstituted alkyl, substituted or unsubstituted heteroalkyl, and acyl;

R¹ is H, substituted or unsubstituted lower alkyl, C(O)R⁸, or CO₂R⁸, wherein R⁸ is a member selected from NR⁹R¹⁰ and OR⁹, in which R⁹ and R¹⁰ are members independently selected from H, substituted or unsubstituted alkyl and substituted or unsubstituted heteroalkyl;

R¹' is H, substituted or unsubstituted lower alkyl, or C(O)R⁸, wherein R⁸ is a member selected from NR⁹R¹⁰ and OR⁹, in which R⁹ and R¹⁰ are members independently selected from H, substituted or unsubstituted alkyl and substituted or unsubstituted heteroalkyl;

R² is H, or substituted or unsubstituted lower alkyl or unsubstituted heteroalkyl or cyano or alkoxy; and R²' is H, or substituted or unsubstituted lower alkyl or unsubstituted heteroalkyl, wherein at least one of R¹¹, R¹², R¹³, R¹⁵ or R¹⁶ links said drug to L¹, if present, or to F, H, or J.

In all of the foregoing linker conjugate structures, L⁴ preferably comprises a non-cyclic moiety. L⁴ preferably increases solubility of the compound as compared to the compound lacking L⁴ and/or L⁴ decreases aggregation of the compound as compared to the compound lacking L⁴. In a preferred embodiment, L⁴ comprises a polyethylene glycol moiety. The polyethylene glycol moiety can contain, for example, 3-12 repeat units, or 2-6 repeat units or, more preferably, 4 repeat units.

In yet another aspect, the invention provides a cytotoxic drug-ligand compound having a structure according to the following formula:

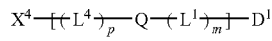

wherein the symbol L¹ represents a self-immolative spacer where m is an integer of 0, 1, 2, 3, 4, 5, or 6.

The symbol X⁴ represents a member selected from the group consisting of protected reactive functional groups, unprotected reactive functional groups, detectable labels, and targeting agents.

The symbol L⁴ represents a linker member, and p is 0 or 1. L⁴ is a moiety that imparts increased solubility or decreased aggregation properties to the conjugates. Examples of L⁴ moieties include substituted alkyl, unsubstituted alkyl, substituted aryl, unsubstituted aryl, substituted heteroalkyl, or unsubstituted heteroalkyl, any of which may be straight, branched, or cyclic, a positively or negatively charged amino acid polymer, such as polylysine or polyargenine, or other polymers such as polyethylene glycol.

The symbol Q represent any cleavable linker including, but not limited to, any of the peptidyl, hydrozone, and disulfide linkers described herein. Cleavable linkers include those that can be selectively cleaved by a chemical or biological process and upon cleavage separate the drug, D¹, from X⁴.

The symbol D¹ represents a drug having the following formula:

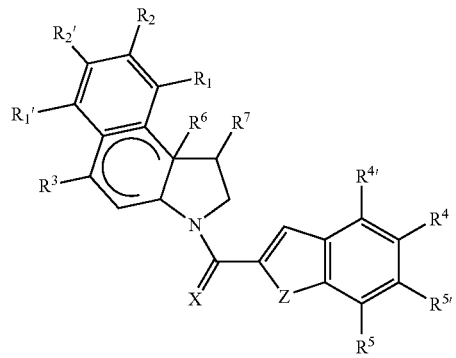

wherein X and Z are members independently selected from O, S and NR²³;

R²³ is a member selected from H, substituted or unsubstituted alkyl, substituted or unsubstituted heteroalkyl, and acyl;

R¹ is H, substituted or unsubstituted lower alkyl, C(O)R⁸, or CO₂R⁸,

R¹' is H, substituted or unsubstituted lower alkyl, or C(O)R⁸, wherein R⁸ is a member selected from NR⁹R¹⁰ and OR⁹ and R⁹ and R¹⁰ are members independently selected from H, substituted or unsubstituted alkyl and substituted or unsubstituted heteroalkyl;

R² is H, or substituted or unsubstituted lower alkyl or unsubstituted heteroalkyl or cyano or alkoxy;

R²' is H, or substituted or unsubstituted lower alkyl or unsubstituted heteroalkyl, R³ is a member selected from the group consisting of SR¹¹, NHR¹¹ and OR¹¹, wherein R¹¹ is a member selected from the group consisting of H, substituted alkyl, unsubstituted alkyl, substituted heteroalkyl, unsubstituted heteroalkyl, diphosphates, triphosphates, acyl, C(O)R¹²R¹³, C(O)OR¹², C(O)NR¹²R¹³, P(O)(OR¹²)₂, C(O)CHR¹²R¹³, SR¹² and SiR¹²R¹³R¹⁴, in which R¹², R¹³, and R¹⁴ are members independently selected from H, substituted or unsubstituted alkyl, substituted or unsubstituted heteroalkyl and substituted or unsubstituted aryl, wherein R¹² and R¹³ together with the nitrogen or carbon atom to which they are attached are optionally joined to form a substituted or unsubstituted heterocycloalkyl ring system having from 4 to 6 members, optionally containing two or more heteroatoms;

wherein at least one of R¹¹, R¹², and R¹³ links said drug to L¹, if present, or to Q, R⁶ is a single bond which is either present or absent and when present R⁶ and R⁷ are joined to form a cyclopropyl ring; and R⁷ is CH₂—X¹ or CH₂— joined in said cyclopropyl ring with R⁶, wherein X¹ is a leaving group, R⁴, R⁴', R⁵ and R⁵' are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, NO₂, NR¹⁵R¹⁶, NC(O)R¹⁵, OC(O)NR¹⁵R¹⁶, OC(O)OR¹⁵, C(O)R¹⁵, SR¹⁵, OR¹⁵, CR¹⁵=NR¹⁶, and O(CH₂)ₙNR²⁴R²⁵ wherein n is an integer from 1 to 20;

$R^{15}$ and $R^{16}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms;

and $R^{24}$ and $R^{25}$ are independently selected from unsubstituted alkyl, and wherein at least one of $R^4$, $R^{4'}$, $R^5$ and $R^{5'}$ is $O(CH_2)_n NR^{24}R^{25}$.

In yet another aspect, the invention pertains to pharmaceutical formulations. Such formulations typically comprise a conjugate compound of the invention and a pharmaceutically acceptable carrier.

In still a further aspect, the invention pertains to methods of using the conjugate compounds of the invention. For example, the invention provides a method of killing a cell, wherein a conjugate compound of the invention is administered to the cell an amount sufficient to kill the cell. In a preferred embodiment, the cell is a tumor cell. In another embodiment, the invention provides a method of retarding or stopping the growth of a tumor in a mammalian subject, wherein a conjugate compound of the invention is administered to the subject an amount sufficient to retard or stop growth of the tumor.

Other aspects, advantages and objects of the invention will be apparent from review of the detailed description below.

DETAILED DESCRIPTION OF THE INVENTION

Abbreviations

As used herein, "Ala," refers to alanine.
"Boc," refers to t-butyloxycarbonyl.
"CPI," refers to cyclopropapyrroloindole.
"Cbz," is carbobenzoxy.
As used herein, "DCM," refers to dichloromethane.
"DDQ," refers to 2,3-dichloro-5,6-dicyano-1,4-benzoquinone.
DIPEA is diisopropylethalamine
"DMDA" is N,N'-dimethylethylene diamine
"RBF" is a round bottom flask
"DMF" is N,B-dimethylformamide
"HATU" is N-[[(dimethylamino)-1H-1,2,3-triazolo[4,5-b]pyridin-1-yl]methylene]-N-methylmethanaminium hexafluorophosphate N-oxide
As used herein, the symbol "E," represents an enzymatically cleaveable group.
"EDCI" is 1-(3-dimethylaminopropyl)-3-ethylcarbodiimide.
As used herein, "FMOC," refers to 9-fluorenylmethyloxycarbonyl.
"FMOC" refers to 9-fluorenylmethoxycarbonyl.
"HOAt" is 7-Aza-1-hydroxybenzotriazole.
"Leu" is leucine.
"PABA" refers to para-aminobenzoic acid.
PEG refers to polyethylene glycol
"PMB," refers to para-methoxybenzyl.
"TBAF," refers to tetrabutylammonium fluoride.
The abbreviation "TBSO," refers to t-butyldimethylsilyl ether.
As used herein, "TEA," refers to triethylamine.
"TFA," refers to trifluororoacetic acid.

The symbol "Q" refers to a therapeutic agent, diagnostic agent or detectable label.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The term "therapeutic agent" is intended to mean a compound that, when present in a therapeutically effective amount, produces a desired therapeutic effect on a mammal. For treating carcinomas, it is desirable that the therapeutic agent also be capable of entering the target cell.

The term "cytotoxin" is intended to mean a therapeutic agent having the desired effect of being cytotoxic to cancer cells. Cytotoxic means that the agent arrests the growth of, or kills the cells. Exemplary cytotoxins include, by way of example and not limitation, combretastatins, duocarmycins, the CC-1065 anti-tumor antibiotics, anthracyclines, and related compounds. Other cytotoxins include mycotoxins, ricin and its analogues, calicheamycins, doxirubicin and maytansinoids.

The term "prodrug" and the term "drug conjugate" are used herein interchangeably. Both refer to a compound that is relatively innocuous to cells while still in the conjugated form but which is selectively degraded to a pharmacologically active form by conditions, e.g., enzymes, located within or in the proximity of target cells.

The term "marker" is intended to mean a compound useful in the characterization of tumors or other medical condition, for example, diagnosis, progression of a tumor, and assay of the factors secreted by tumor cells. Markers are considered a subset of "diagnostic agents."

The term "selective" as used in connection with enzymatic cleavage means that the rate of rate of cleavage of the linker moiety is greater than the rate of cleavage of a peptide having a random sequence of amino acids.

The terms "targeting group" and "targeting agent" are intended to mean a moiety that is (1) able to direct the entity to which it is attached (e.g., therapeutic agent or marker) to a target cell, for example to a specific type of tumor cell or (2) is preferentially activated at a target tissue, for example a tumor. The targeting group or targeting agent can be a small molecule, which is intended to include both non-peptides and peptides. The targeting group can also be a macromolecule, which includes saccharides, lectins, receptors, ligand for receptors, proteins such as BSA, antibodies, and so forth. In a preferred embodiment of the current invention, the targeting group is an antibody or an antibody fragment, more preferably a monoclonal antibody or monoclonal antibody fragment The term "self-immolative spacer" refers to a bifunctional chemical moiety that is capable of covalently linking two chemical moieties into a normally stable tripartate molecule. The self-immolative spacer is capable of spontaneously separating from the second moiety if the bond to the first moiety is cleaved.

The term "detectable label" is intended to mean a moiety having a detectable physical or chemical property.

The term "cleaveable group" is intended to mean a moiety that is unstable in vivo. Preferably the "cleaveable group" allows for activation of the marker or therapeutic agent by cleaving the marker or agent from the rest of the conjugate. Operatively defined, the linker is preferably cleaved in vivo by the biological environment. The cleavage may come from any process without limitation, e.g., enzymatic, reductive, pH, etc. Preferably, the cleaveable group is selected so that activation occurs at the desired site of action, which can be a site in or near the target cells (e.g., carcinoma cells) or tissues such as at the site of therapeutic action or marker activity. Such cleavage may be enzymatic and exemplary enzymatically cleaveable groups include natural amino acids or peptide sequences that end with a natural amino acid, and are attached at their carboxyl terminus to the linker. While the degree of cleavage rate enhancement is not critical to the invention, preferred examples of cleaveable linkers are those in which at least about 10% of the cleaveable groups are cleaved in the blood stream within 24 hours of administration, most preferably at least about 35%.

The term "ligand" means any molecule that specifically binds or reactively associates or complexes with a receptor, substrate, antigenic determinant, or other binding site on a target cell or tissue. Examples of ligands include antibodies and fragments thereof (e.g., a monoclonal antibody or fragment thereof), enzymes (e.g., fibrinolytic enzymes), biologic response modifiers (e.g., interleukins, interferons, erythropeoitin, or colony stimulating factors), peptide hormones, and antigen-binding fragments thereof.

The terms "hydrazine linker" and "self-cyclizing hydrazine linker" are used interchangeably herein. These terms refer to a linker moiety that, upon a change in condition, such as a shift in pH, will undergo a cyclization reaction and form one or more rings. The hydrazine moiety is converted to a hydrazone when attached. This attachment can occur, for example, through a reaction with a ketone group on the $L^4$ moiety. Therefore, the term hydrazone linker can also be used to describe the linker of the current invention because of this conversion to a hydrazone upon attachment.

The term "five-membered hydrazine linker" or "5-membered hydrazine linker" refers to hydrazine-containing molecular moieties that, upon a change in condition, such as a shift in pH, will undergo a cyclization reaction and form one or more 5-membered rings. Alternatively, this five membered linker may similarly be described as a five-membered hydrazone linker or a 5-membered hydrazone linker.

The term "six-membered hydrazine linker" or "6-membered hydrazine linker" refers to hydrazine-containing molecular moieties that, upon a change in condition such as a shift in pH, will undergo a cyclization reaction and form one or more 6-membered rings. This six membered linker may similarly be described as a six-membered hydrazone linker or a 6-membered hydrazone linker.

The term "cyclization reaction," when referring to the cyclization of a peptide, hydrazine, or disulfide linker, indicates the cyclization of that linker into a ring and initiates the separation of the drug-ligand complex. This rate can be measured ex situ, and is completed when at least 90%, 95%, or 100% of the product is formed.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. These terms also encompass the term "antibody."

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. One amino acid that may be used in particular is citrulline, which is a precursor to arginine and is involved in the formation of urea in the liver. Amino acid mimetics refers to chemical compounds that have a structure that is different from the general chemical structure of an amino acid, but functions in a manner similar to a naturally occurring amino acid. The term "unnatural amino acid" is intended to represent the "D" stereochemical form of the twenty naturally occurring amino acids described above. It is further understood that the term unnatural amino acid includes homologues of the natural amino acids, and synthetically modified forms of the natural amino acids. The synthetically modified forms include, but are not limited to, amino acids having alkylene chains shortened or lengthened by up to two carbon atoms, amino acids comprising optionally substituted aryl groups, and amino acids comprised halogenated groups, preferably halogenated alkyl and aryl groups. When attached to a linker or conjugate of the invention, the amino acid is in the form of an "amino acid side chain", where the carboxylic acid group of the amino acid has been replaced with a keto (C(O)) group. Thus, for example, an alanine side chain is —C(O)—CH(NH$_2$)—CH$_3$, and so forth.

Amino acids and peptides may be protected by blocking groups. A blocking group is an atom or a chemical moiety that protects the N-terminus of an amino acid or a peptide from undesired reactions and can be used during the synthesis of a drug-ligand conjugate. It should remain attached to the N-terminus throughout the synthesis, and may be removed after completion of synthesis of the drug conjugate by chemical or other conditions that selectively achieve its removal. The blocking groups suitable for N-terminus protection are well known in the art of peptide chemistry. Exemplary blocking groups include, but are not limited to, hydrogen, D-amino acid, and carbobenzoxy (Cbz) chloride.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); Rossolini et al., *Mol. Cell. Probes* 8: 91-98 (1994)). The term nucleic acid is used interchangeably with gene, cDNA, mRNA, oligonucleotide, and polynucleotide.

The symbol ∿∿∿, whether utilized as a bond or displayed perpendicular to a bond indicates the point at which the displayed moiety is attached to the remainder of the molecule, solid support, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homo alkyl".

The term "alkylene" by itself or as part of another substituent means a divalent radical derived from an alkane, as exemplified, but not limited, by $CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen, carbon and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH— O—$CH_3$, —Si($CH_3$)$_3$, —$CH_2$—CH=N—O$CH_3$, and CH=CH—N($CH_3$)—$CH_3$. Up to two heteroatoms may be consecutive, such as, for example, —$CH_2$—NH—O$CH_3$ and $CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$— $CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). The terms "heteroalkyl" and "heteroalkylene" encompass poly(ethylene glycol) and its derivatives (see, for example, Shearwater Polymers Catalog, 2001). Still further, for alkylene and heteroalkylene linking groups, no orientation of the linking group is implied by the direction in which the formula of the linking group is written. For example, the formula C(O)$_2$R'— represents both C(O)$_2$R'— and —R'C(O)$_2$—.

The term "lower" in combination with the terms "alkyl" or "heteroalkyl" refers to a moiety having from 1 to 6 carbon atoms.

The terms "alkoxy," "alkylamino," "alkylsulfonyl," and "alkylthio" (or thioalkoxy) are used in their conventional sense, and refer to those alkyl groups attached to the remainder of the molecule via an oxygen atom, an amino group, an $SO_2$ group or a sulfur atom, respectively. The term "arylsulfonyl" refers to an aryl group attached to the remainder of the molecule via an $SO_2$ group, and the term "sulfhydryl" refers to an SH group.

In general, an "acyl substituent" is also selected from the group set forth above. As used herein, the term "acyl substituent" refers to groups attached to, and fulfilling the valence of a carbonyl carbon that is either directly or indirectly attached to the polycyclic nucleus of the compounds of the present invention.

The terms "cycloalkyl" and "heterocycloalkyl", by themselves or in combination with other terms, represent, unless otherwise stated, cyclic versions of substituted or unsubstituted "alkyl" and substituted or unsubstituted "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The heteroatoms and carbon atoms of the cyclic structures are optionally oxidized.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a substituted or unsubstituted polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen, carbon and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Aryl" and "heteroaryl" also encompass ring systems in which one or more non-aromatic ring systems are fused, or otherwise bound, to an aryl or heteroaryl system.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroalkyl substituents," respectively, and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively and are varied and selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN and NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R'" and R"" groups when more than one of these groups is present.

Two of the aryl substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$) alkyl.

As used herein, the term "diphosphate" includes but is not limited to an ester of phosphoric acid containing two phosphate groups. The term "triphosphate" includes but is not limited to an ester of phosphoric acid containing three phosphate groups. For example, particular drugs having a diphosphate or a triphosphate include:

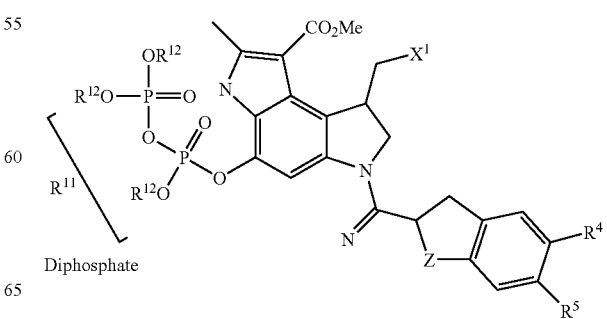

Diphosphate

-continued

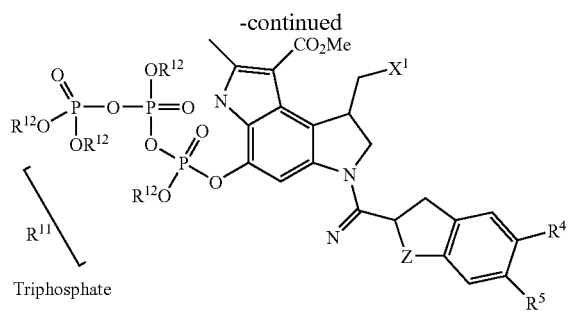

Triphosphate

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent. Pharmaceutically acceptable carriers include pharmaceutically acceptable salts, where the term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "attaching moiety" or "moiety for attaching a targeting group" refers to a moiety which allows for attachment of a targeting group to the linker. Typical attaching groups include, by way of illustration and not limitation, alkyl, aminoalkyl, aminocarbonylalkyl, carboxyalkyl, hydroxyalkyl, alkyl-maleimide, alkyl-N-hydroxylsuccinimide, poly(ethylene glycol)-maleimide and poly(ethylene glycol)-N-hydroxylsuccinimide, all of which may be further substituted. The linker can also have the attaching moiety be actually appended to the targeting group.

As used herein, the term "leaving group" refers to a portion of a substrate that is cleaved from the substrate in a reaction.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region ($V_H$) and a heavy chain constant region. The heavy chain constant region is comprised of three domains, $C_{H1}$, $C_{H2}$ and $C_{H3}$, and may be of the mu, delta, gamma, alpha or epsilon isotype. Each light chain is comprised of a light chain variable region ($V_L$) and a light chain constant region. The light chain constant region is comprised of one domain, $C_L$, which may be of the kappa or lambda isotype. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The terms "antibody fragment" or "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antibody fragment" or "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The terms "monoclonal antibody" as used herein refers to a preparation of antibody molecules of single molecular composition. A monoclonal antibody composition displays a single binding specificity and affinity for a particular epitope.

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in MONOCLONAL ANTIBODIES AND CANCER THERAPY, Alan R. Liss, Inc. (1985)).

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired.

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6: 511-519 (1976)). Alternative methods of immortalization include transformation with Epstein Barr Virus, oncogenes, or retroviruses, or other methods well known in the art.

In a preferred embodiment, the antibody is a chimeric or humanized antibody. Chimeric or humanized antibodies of the present invention can be prepared based on the sequence of a murine monoclonal antibody. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In another preferred embodiment, the antibody is a human antibody. Such human antibodies can be generated by immunizing transgenic or transchromosomic mice in which the endogenous mouse immunoglobulin genes have been inactivated and exogenous human immunoglobulin genes have been introduced. Such mice are known in the art (see e.g., U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. Nos. 5,939,598; 6,075,181; 6,114,598; 6,150,584 and 6,162,963 to Kucherlapati et al.; and PCT Publication WO 02/43478 to Ishida et al.) Human antibodies can also be prepared using phage display methods for screening libraries of human immunoglobulin genes. Such phage display methods for isolating human antibodies also are know in the art (see e.g., U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582, 915 and 6,593,081 to Griffiths et al.).

"Solid support," as used herein refers to a material that is substantially insoluble in a selected solvent system, or which can be readily separated (e.g., by precipitation) from a selected solvent system in which it is soluble. Solid supports useful in practicing the present invention can include groups that are activated or capable of activation to allow selected species to be bound to the solid support. A solid support can also be a substrate, for example, a chip, wafer or well, onto which an individual, or more than one compound, of the invention is bound.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like (see, for example, Hermanson, BIOCONJUGATE TECHNIQUES, Academic press, San Diego, 1996). Methods to prepare each of these functional groups are well known in the art and their application to or modification for a particular purpose is within the ability of one of skill in the art (see, for example, Sandler and Karo, eds.

ORGANIC FUNCTIONAL GROUP PREPARATIONS, Academic Press, San Diego, 1989). The reactive functional groups may be protected or unprotected.

The compounds of the invention are prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

Linkers

The present invention provides for drug-ligand conjugates where the drug is linked to the ligand through a chemical linker. This linker is either a peptidyl, hydrazine, or disulfide linker, and is depicted herein as $(L^4)_p$-F-$(L^1)_m$, $(L^4)_p$-H-$(L^1)_m$, or $(L^4)_p$-J-$(L^1)_m$, respectively. In addition to the linkers as being attached to the drug, the present invention also provides cleaveable linker arms that are appropriate for attachment to essentially any molecular species. The linker arm aspect of the invention is exemplified herein by reference to their attachment to a therapeutic moiety. It will, however, be readily apparent to those of skill in the art that the linkers can be attached to diverse species including, but not limited to, diagnostic agents, analytical agents, biomolecules, targeting agents, detectable labels and the like.

In one aspect, the present invention relates to linkers that are useful to attach targeting groups to therapeutic agents and markers. In another aspect, the invention provides linkers that impart stability to compounds, reduce their in vivo toxicity, or otherwise favorably affect their pharmacokinetics, bioavailability and/or pharmacodynamics. It is generally preferred that in such embodiments, the linker is cleaved, releasing the active drug, once the drug is delivered to its site of action. Thus, in one embodiment of the invention, the linkers of the invention are traceless, such that once removed from the therapeutic agent or marker (such as during activation), no trace of the linker's presence remains.

In another embodiment of the invention, the linkers are characterized by their ability to be cleaved at a site in or near the target cell such as at the site of therapeutic action or marker activity. Such cleavage can be enzymatic in nature. This feature aids in reducing systemic activation of the therapeutic agent or marker, reducing toxicity and systemic side effects. Preferred cleaveable groups for enzymatic cleavage include peptide bonds, ester linkages, and disulfide linkages. In other embodiments, the linkers are sensitive to pH and are cleaved through changes in pH.

An important aspect of the current invention is the ability to control the speed with which the linkers cleave. For example, the hydrazine linkers described herein are particularly useful because, depending on which particular structure is used, one can vary the speed at which the linker cyclizes and thereby cleaves the drug from the ligand. WO 02/096910 provides several specific ligand-drug complexes having a hydrazine linker. However, there is no way to "tune" the linker composition dependent upon the rate of cyclization required, and the particular compounds described cleave the ligand from the drug at a slower rate than is preferred for many drug-linker conjugates. In contrast, the hydrazine linkers of the current invention provide for a range of cyclization rates, from very fast to very slow, thereby allowing for the selection of a particular hydrazine linker based on the desired rate of cyclization. For example, very fast cyclization can be achieved with hydrazine linkers that produce a single 5-membered ring upon cleavage. Preferred cyclization rates for targeted delivery of a cytotoxic agent to cells are achieved using hydrazine linkers that produce, upon cleavage, either two 5-membered rings or a single 6-membered ring resulting from a linker having two methyls at the geminal position. The gem-dimethyl effect has been shown to accelerate the rate of the cyclization reaction as compared to a single 6-membered ring without the two methyls at the geminal position. This results from the strain being relieved in the ring. Sometimes, however, substitutents may slow down the reaction instead of making it faster. Often the reasons for the retardation can be traced to steric hindrance. As shown in Example 2.4, the gem dimethyl substitution allows for a much faster cyclization reaction to occur compared to when the geminal carbon is a $CH_2$.

It is important to note, however, that in some embodiments, a linker that cleaves more slowly may be preferred. For example, in a sustained release formulation or in a formulation with both a quick release and a slow release component, it may be useful to provide a linker which cleaves more slowly. In certain embodiments, a slow rate of cyclization is achieved using a hydrazine linker that produces, upon cleavage, either a single 6-membered ring, without the gem-dimethyl substitution, or a single 7-membered ring.

The linkers also serve to stabilize the therapeutic agent or marker against degradation while in circulation. This feature provides a significant benefit since such stabilization results in prolonging the circulation half-life of the attached agent or marker. The linker also serves to attenuate the activity of the attached agent or marker so that the conjugate is relatively benign while in circulation and has the desired effect, for example is toxic, after activation at the desired site of action. For therapeutic agent conjugates, this feature of the linker serves to improve the therapeutic index of the agent.

The stabilizing groups are preferably selected to limit clearance and metabolism of the therapeutic agent or marker by enzymes that may be present in blood or non-target tissue and are further selected to limit transport of the agent or marker into the cells. The stabilizing groups serve to block degradation of the agent or marker and may also act in providing other physical characteristics of the agent or marker. The stabilizing group may also improve the agent or marker's stability during storage in either a formulated or non-formulated form.

Ideally, the stabilizing group is useful to stabilize a therapeutic agent or marker if it serves to protect the agent or marker from degradation when tested by storage of the agent or marker in human blood at 37° C. for 2 hours and results in less than 20%, preferably less than 10%, more preferably less than 5% and even more preferably less than 2%, cleavage of the agent or marker by the enzymes present in the human blood under the given assay conditions.

The present invention also relates to conjugates containing these linkers. More particularly, the invention relates to prodrugs that may be used for the treatment of disease, especially for cancer chemotherapy. Specifically, use of the linkers described herein provide for prodrugs that display a high specificity of action, a reduced toxicity, and an improved stability in blood relative to prodrugs of similar structure.

The linkers of the present invention as described herein may be present at any position within the cytotoxic conjugate.

Thus, there is provided a linker that may contain any of a variety of groups as part of its chain that will cleave in vivo, e.g., in the blood stream at a rate which is enhanced relative to that of constructs that lack such groups. Also provided are conjugates of the linker arms with therapeutic and diagnostic agents. The linkers are useful to form prodrug analogs of therapeutic agents and to reversibly link a therapeutic or diagnostic agent to a targeting agent, a detectable label, or a solid support. The linkers may be incorporated into complexes that include the cytotoxins of the invention.

In addition to the cleaveable peptide, hydrazine, or disulfide group, one or more self-immolative linker groups $L^1$ are optionally introduced between the cytotoxin and the targeting agent. These linker groups may also be described as spacer groups and contain at least two reactive functional groups. Typically, one chemical functionality of the spacer group bonds to a chemical functionality of the therapeutic agent, e.g., cytotoxin, while the other chemical functionality of the spacer group is used to bond to a chemical functionality of the targeting agent or the cleaveable linker. Examples of chemical functionalities of spacer groups include hydroxy, mercapto, carbonyl, carboxy, amino, ketone, and mercapto groups.

The self-immolative linkers, represented by $L^1$, are generally substituted or unsubstituted alkyl, substituted or unsubstituted aryl, substituted or unsubstituted heteroaryl or a substituted or unsubstituted heteroalkyl group. In one embodiment, the alkyl or aryl groups may comprise between 1 and 20 carbon atoms. They may also comprise a polyethylene glycol moiety.

Exemplary spacer groups include, for example, 6-aminohexanol, 6-mercaptohexanol, 10-hydroxydecanoic acid, glycine and other amino acids, 1,6-hexanediol, β-alanine, 2-aminoethanol, cysteamine(2-aminoethanethiol), 5-aminopentanoic acid, 6-aminohexanoic acid, 3-maleimidobenzoic acid, phthalide, α-substituted phthalides, the carbonyl group, aminal esters, nucleic acids, peptides and the like.

The spacer can serve to introduce additional molecular mass and chemical functionality into the cytotoxin-targeting agent complex. Generally, the additional mass and functionality will affect the serum half-life and other properties of the complex. Thus, through careful selection of spacer groups, cytotoxin complexes with a range of serum half-lives can be produced.

The spacer(s) located directly adjacent to the drug moiety is also denoted as $(L^1)_m$, wherein m is an integer selected from 0, 1, 2, 3, 4, 5, or 6. When multiple $L^1$ spacers are present, either identical or different spacers may be used. $L^1$ may be any self-immolative group. In one embodiment, $L^1$ is preferably is a substituted alkyl, unsubstituted alkyl, substituted heteroalkyl, and unsubstituted heteroalkyl, unsubstituted heterocycloalkyl, and substituted heterocycloalkyl. When the drug-ligand conjugate comprises a hydrazine linker, $L^1$ does not comprise a disulfide bond.

$L^4$ is a linker moiety that imparts increased solubility or decreased aggregation properties to conjugates utilizing a linker that contains the moiety. The $L^4$ linker does not have to be self immolative. In one embodiment, the $L^4$ moiety is substituted alkyl, unsubstituted alkyl, substituted aryl, unsubstituted aryl, substituted heteroalkyl, or unsubstituted heteroalkyl, any of which may be straight, branched, or cyclic. The substitutions may be, for example, a lower ($C^1$-$C^6$) alkyl, alkoxy, aldylthio, alkylamino, or dialkylamino. In certain embodiments, $L^4$ comprises a non-cyclic moiety. In another embodiment, $L^4$ comprises any positively or negatively charged amino acid polymer, such as polylysine or polyarginine. $L^4$ can comprise a polymer such as a polyethylene glycol moiety. Additionally the $L^4$ linker comprises, for example, both a polymer component and a small chemical moiety.

In a preferred embodiment, $L^4$ comprises a polyethylene glycol (PEG) moiety. The PEG portion of $L^4$ may be between 1 and 50 units long. Preferably, the PEG will have 1-12 repeat units, more preferably 3-12 repeat units, more preferably 2-6 repeat units, or even more preferably 3-5 repeat units and most preferably 4 repeat units. $L^4$ may consist solely of the PEG moiety, or it may also contain an additional substituted or unsubstituted alkyl or heteroalkyl. It is useful to combine PEG as part of the $L^4$ moiety to enhance the water solubility of the complex. Additionally, the PEG moiety reduces the degree of aggregation that may occur during the conjugation of the drug to the antibody.

(1) Peptide Linkers (F)

As discussed above, the peptidyl linkers of the invention can be represented by the general formula: $(L^4)_p$-F-$(L^1)_m$, wherein F represents the linker portion comprising the peptidyl moiety. In one embodiment, the F portion comprises an optional additional self-immolative linker(s), $L^2$, and a carbonyl group. In another embodiment, the F portion comprises an amino group and an optional spacer group(s), $L^3$.

Accordingly, in one embodiment, the conjugate comprising the peptidyl linker comprises a structure of the Formula 4:

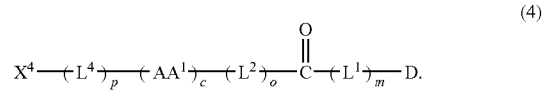

(4)

In this embodiment, $L^1$ is a self-immolative linker, as described above, and $L^4$ is a moiety that imparts increased solubility, or decreased aggregation properties, as described above. $L^2$ represents a self-immolative linker(s). m is 0, 1, 2, 3, 4, 5, or 6; o and p are independently 0 or 1. In one embodiment, m is 3, 4, 5 or 6. $AA^1$ represents one or more natural amino acids, and/or unnatural α-amino acids; c is an integer between 1 and 20.

In the peptide linkers of the invention of the above Formula 4, $AA^1$ is linked, at its amino terminus, either directly to $L^4$ or, when $L^4$ is absent, directly to the $X^4$ group (i.e., the targeting agent, detectable label, protected reactive functional group or unprotected reactive functional group). In some embodiments, when $L^4$ is present, $L^4$ does not comprise a carboxylic acyl group directly attached to the N-terminus of $(AA^1)_c$. Thus, it is not necessary in these embodiments for there to be a carboxylic acyl unit directly between either $L^4$ or $X^4$ and $AA^1$, as is necessary in the peptidic linkers of U.S. Pat. No. 6,214,345.

In another embodiment, the conjugate comprising the peptidyl linker comprises a structure of the Formula 5:

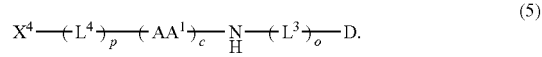

(5)

In this embodiment, $L^4$ is a moiety that imparts increased solubility, or decreased aggregation properties, as described above; $L^3$ is a spacer group comprising a primary or secondary amine or a carboxyl functional group, and either the amine of $L^3$ forms an amide bond with a pendant carboxyl functional group of D or the carboxyl of $L^3$ forms an amide bond with a pendant amine functional group of D; and o and p are independently 0 or 1. $AA^1$ represents one or more natural amino acids, and/or unnatural α-amino acids; c is an integer between 1 and 20. In this embodiment, $L^1$ is absent (i.e., m is 0 is the general formula).

In the peptide linkers of the invention of the above Formula 5, $AA^1$ is linked, at its amino terminus, either directly to $L^4$ or, when $L^4$ is absent, directly to the $X^4$ group (i.e., the targeting agent, detectable label, protected reactive functional group or unprotected reactive functional group). In some embodiments, when $L^4$ is present, $L^4$ does not comprise a carboxylic acyl group directly attached to the N-terminus of $(AA^1)_c$. Thus, it is not necessary in these embodiments for there to be a carboxylic acyl unit directly between either $L^4$ or $X^4$ and $AA^1$, as is necessary in the peptidic linkers of U.S. Pat. No. 6,214,345.

The Self-Immolative Linker $L^2$

The self-immolative linker $L^2$ is a bifunctional chemical moiety which is capable of covalently linking together two spaced chemical moieties into a normally stable tripartate molecule, releasing one of said spaced chemical moieties from the tripartate molecule by means of enzymatic cleavage; and following said enzymatic cleavage, spontaneously cleaving from the remainder of the molecule to release the other of said spaced chemical moieties. In accordance with the present invention, the self-immolative spacer is covalently linked at one of its ends to the peptide moiety and covalently linked at its other end to the chemical reactive site of the drug moiety whose derivatization inhibits pharmacological activity, so as to space and covalently link together the peptide moiety and the drug moiety into a tripartate molecule which is stable and pharmacologically inactive in the absence of the target enzyme, but which is enzymatically cleavable by such target enzyme at the bond covalently linking the spacer moiety and the peptide moiety to thereby effect release of the peptide moiety from the tripartate molecule. Such enzymatic cleavage, in turn, will activate the self-immolating character of the spacer moiety and initiate spontaneous cleavage of the bond covalently linking the spacer moiety to the drug moiety, to thereby effect release of the drug in pharmacologically active form.

The self-immolative linker $L^2$ may be any self-immolative group. Preferably $L^2$ is a substituted alkyl, unsubstituted alkyl, substituted heteroalkyl, unsubstituted heteroalkyl, unsubstituted heterocycloalkyl, substituted heterocycloalkyl, substituted and unsubstituted aryl, and substituted and unsubstituted heteroaryl.

One particularly preferred self-immolative spacer $L^2$ may be represented by the formula 6:

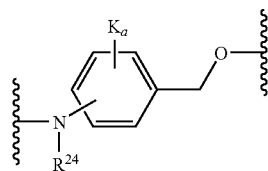

(6)

The aromatic ring of the aminobenzyl group may be substituted with one or more "K" groups. A "K" group is a substituent on the aromatic ring that replaces a hydrogen otherwise attached to one of the four non-substituted carbons that are part of the ring structure. The "K" group may be a single atom, such as a halogen, or may be a multi-atom group, such as alkyl, heteroalkyl, amino, nitro, hydroxy, alkoxy, haloalkyl, and cyano. Each K is independently selected from the group consisting of substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, halogen, $NO_2$, $NR^{21}R^{22}$, $NR^{21}COR^{22}$, $OCONR^{21}R^{22}$, $OCOR^{21}$, and $OR^{21}$, wherein $R^{21}$ and $R^{22}$ are independently selected from the group consisting of H, substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl and unsubstituted heterocycloalkyl. Exemplary K substituents include, but are not limited to, F, Cl, Br, I, $NO_2$, OH, $OCH_3$, $NHCOCH_3$, $N(CH_3)_2$, $NHCOCF_3$ and methyl. For "Ka", a is an integer of 0, 1, 2, 3, or 4. In one preferred embodiment, a is 0.

The ether oxygen atom of the structure shown above is connected to a carbonyl group. The line from the $NR^{24}$ functionality into the aromatic ring indicates that the amine functionality may be bonded to any of the five carbons that both form the ring and are not substituted by the $CH_2$—O— group. Preferably, the $NR^{24}$ functionality of X is covalently bound to the aromatic ring at the para position relative to the —$CH_2$—O— group. $R^{24}$ is a member selected from the group consisting of H, substituted alkyl, unsubstituted alkyl, substituted heteroalkyl, and unsubstituted heteroalkyl. In a specific embodiment, $R^{24}$ is hydrogen.

In a preferred embodiment, the invention provides a peptide linker of formula (4) above, wherein F comprises the structure:

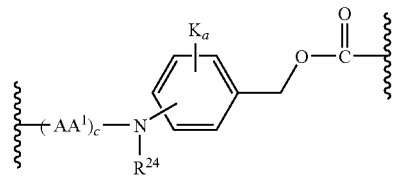

wherein $R^{24}$ is selected from the group consisting of H, substituted alkyl, unsubstituted alkyl, substituted heteroalkyl, and unsubstituted heteroalkyl;

Each K is a member independently selected from the group consisting of substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, halogen, $NO_2$, $NR^{21}R^{22}$, $NR^{21}COR^{22}$, $OCONR^{21}R^{22}$, $OCOR^{21}$, and $OR^{21}$ wherein $R^{21}$ and $R^{22}$ are independently selected from the group consisting of H, substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl; and a is an integer of 0, 1, 2, 3, or 4.

In another embodiment, the peptide linker of formula (4) above comprises a —F-(L¹)$_m$- that comprises the structure:

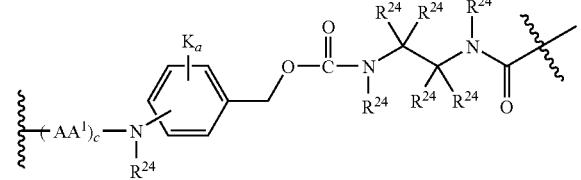

wherein each $R^{24}$ is a member independently selected from the group consisting of H, substituted alkyl, unsubstituted alkyl, substituted heteroalkyl, and unsubstituted heteroalkyl.

The Spacer Group $L^3$

The spacer group $L^3$ is characterized in that it comprises a primary or secondary amine or a carboxyl functional group, and either the amine of the $L^3$ group forms an amide bond with a pendant carboxyl functional group of D or the carboxyl of $L^3$ forms an amide bond with a pendant amine functional group of D. $L^3$ can be selected from the group consisting of substituted or unsubstituted alkyl, substituted or unsubstituted heteroalkyl, substituted or unsubstituted aryl, substituted or unsubstituted heteroaryl, or substituted or unsubstituted heterocycloalkyl. In a preferred embodiment, $L^3$ comprises an aromatic group. More preferably, $L^3$ comprises a benzoic acid group, an aniline group or indole group. Non-limiting examples of structures that can serve as an -$L^3$-NH— spacer include the following structures:

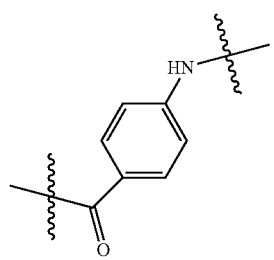

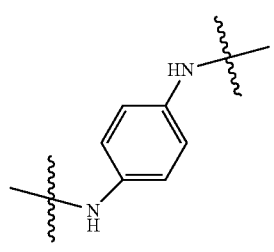

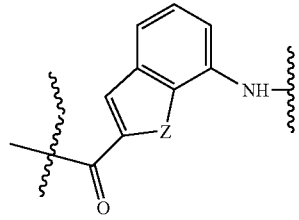

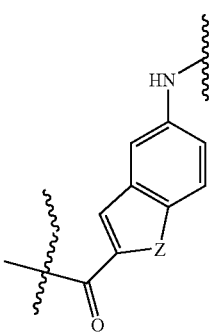

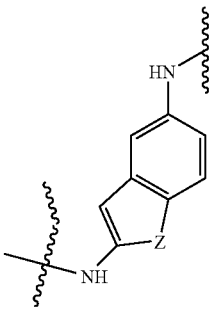

wherein Z is a member selected from O, S and $NR^{23}$, and wherein $R^{23}$ is a member selected from H, substituted or unsubstituted alkyl, substituted or unsubstituted heteroalkyl, and acyl.

Upon cleavage of the linker of the invention containing $L^3$, the $L^3$ moiety remains attached to the drug, D. Accordingly, the $L^3$ moiety is chosen such that its presence attached to D does not significantly alter the activity of D. In another embodiment, a portion of the drug D itself functions as the $L^3$ spacer. For example, in one embodiment, the drug, D, is a duocarmycin derivative in which a portion of the drug functions as the $L^3$ spacer. Non-limiting examples of such embodiments include those in which $NH_2$-($L^3$)-D has a structure selected from the group consisting of:

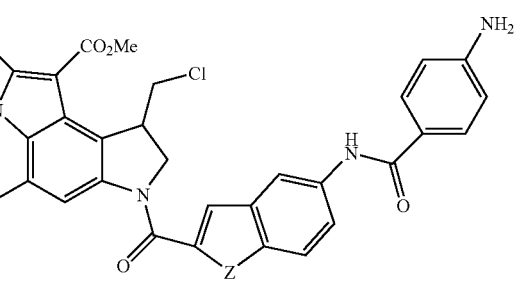

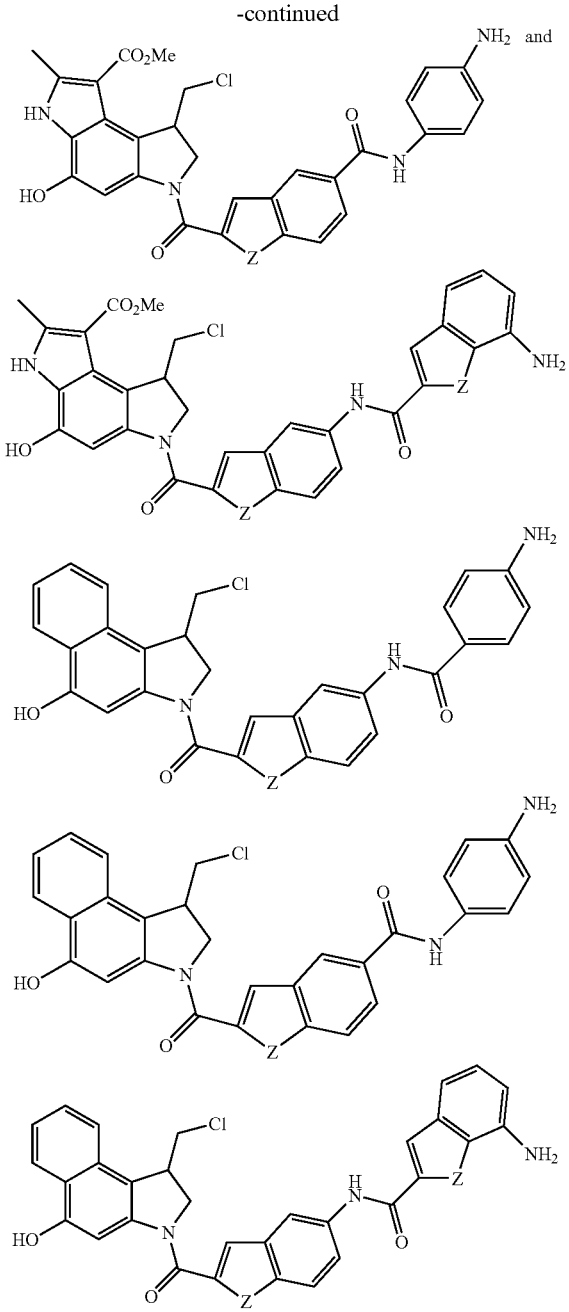

wherein Z is a member selected from O, S and NR$^{23}$, wherein R$^{23}$ is a member selected from H, substituted or unsubstituted alkyl, substituted or unsubstituted heteroalkyl, and acyl; and wherein the NH$_2$ group on each structure reacts with $(AA^1)_c$ to form $(AA^1)_c$-NH—.

The Peptide Sequence AA$^1$

The group AA$^1$ represents a single amino acid or a plurality of amino acids that are joined together by amide bonds. The amino acids may be natural amino acids and/or unnatural α-amino acids.

The peptide sequence $(AA^1)_c$ is functionally the amidification residue of a single amino acid (when c=1) or a plurality of amino acids joined together by amide bonds. The peptide of the current invention is selected for directing enzyme-catalyzed cleavage of the peptide by an enzyme in a location of interest in a biological system. For example, for conjugates that are targeted to a cell using a targeting agent, and then taken up by the cell, a peptide is chosen that is cleaved by one or more lysosomal proteases such that the peptide is cleaved intracellularly within the lysosome. The number of amino acids within the peptide can range from 1 to 20; but more preferably there will be 2-8 amino acids, 2-6 amino acids or 2, 3 or 4 amino acids comprising $(AA^1)_c$. Peptide sequences that are susceptible to cleavage by specific enzymes or classes of enzymes are well known in the art.

Many peptide sequences that are cleaved by enzymes in the serum, liver, gut, etc. are known in the art. An exemplary peptide sequence of the invention includes a peptide sequence that is cleaved by a protease. The focus of the discussion that follows on the use of a protease-sensitive sequence is for clarity of illustration and does not serve to limit the scope of the present invention.

When the enzyme that cleaves the peptide is a protease, the linker generally includes a peptide containing a cleavage recognition sequence for the protease. A cleavage recognition sequence for a protease is a specific amino acid sequence recognized by the protease during proteolytic cleavage. Many protease cleavage sites are known in the art, and these and other cleavage sites can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al., in AMYLOID PROTEIN PRECURSOR IN DEVELOPMENT, AGING, AND ALZHEIMER'S DISEASE, ed. Masters et al. pp. 190-198 (1994).

The amino acids of the peptide sequence $(AA^1)_c$ are chosen based on their suitability for selective enzymatic cleavage by particular molecules such as tumor-associated protease. The amino acids used may be natural or unnatural amino acids. They may be in the L or the D configuration. In one embodiment, at least three different amino acids are used. In another embodiment, only two amino acids are used.

In a preferred embodiment, the peptide sequence $(AA^1)_c$ is chosen based on its ability to be cleaved by a lysosomal proteases, non-limiting examples of which include cathepsins B, C, D, H, L and S. Preferably, the peptide sequence $(AA^1)_c$ is capable of being cleaved by cathepsin B in vitro, which can be tested using in vitro protease cleavage assays known in the art.

In another embodiment, the peptide sequence $(AA^1)_c$ is chosen based on its ability to be cleaved by a tumor-associated protease, such as a protease that is found extracellularly in the vicinity of tumor cells, non-limiting examples of which include thimet oligopeptidase (TOP) and CD10. The ability of a peptide to be cleaved by TOP or CD10 can be tested using in vitro protease cleavage assays known in the art.

Suitable, but non-limiting, examples of peptide sequences suitable for use in the conjugates of the invention include Val-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), 13-Ala-Leu-Ala-Leu (SEQ ID NO: 2) and Gly-Phe-Leu-Gly (SEQ ID NO: 3). Preferred peptides sequences are Val-Cit and Val-Lys.

In another embodiment, the amino acid located the closest to the drug moiety is selected from the group consisting of Ala, Asn, Asp, Cit, Cys, Gln, Glu, Gly, Ile, Leu, Lys, Met, Phe, Pro, Ser, Thr, Trp, Tyr, and Val. In yet another embodiment, the amino acid located the closest to the drug moiety is selected from the group consisting of: Ala, Asn, Asp, Cys, Gln, Glu, Gly, Ile, Leu, Met, Phe, Pro, Ser, Thr, Trp, Tyr, and Val.

Proteases have been implicated in cancer metastasis. Increased synthesis of the protease urokinase was correlated with an increased ability to metastasize in many cancers. Urokinase activates plasmin from plasminogen, which is ubiquitously located in the extracellular space and its activation can cause the degradation of the proteins in the extracellular matrix through which the metastasizing tumor cells invade. Plasmin can also activate the collagenases thus promoting the degradation of the collagen in the basement membrane surrounding the capillaries and lymph system thereby allowing tumor cells to invade into the target tissues (Dano, et al. *Adv. Cancer. Res.*, 44: 139 (1985)). Thus, it is within the scope of the present invention to utilize as a linker a peptide sequence that is cleaved by urokinase.

The invention also provides the use of peptide sequences that are sensitive to cleavage by tryptases. Human mast cells express at least four distinct tryptases, designated $\alpha\beta I$, $\beta II$, and $\beta III$. These enzymes are not controlled by blood plasma proteinase inhibitors and only cleave a few physiological substrates in vitro. The tryptase family of serine proteases has been implicated in a variety of allergic and inflammatory diseases involving mast cells because of elevated tryptase levels found in biological fluids from patients with these disorders. However, the exact role of tryptase in the pathophysiology of disease remains to be delineated. The scope of biological functions and corresponding physiological consequences of tryptase are substantially defined by their substrate specificity.

Tryptase is a potent activator of pro-urokinase plasminogen activator (uPA), the zymogen form of a protease associated with tumor metastasis and invasion. Activation of the plasminogen cascade, resulting in the destruction of extracellular matrix for cellular extravasation and migration, may be a function of tryptase activation of pro-urokinase plasminogen activator at the P4-P1 sequence of Pro-Arg-Phe-Lys (SEQ ID NO: 4) (Stack, et al., *Journal of Biological Chemistry* 269 (13): 9416-9419 (1994)). Vasoactive intestinal peptide, a neuropeptide that is implicated in the regulation of vascular permeability, is also cleaved by tryptase, primarily at the Thr-Arg-Leu-Arg (SEQ ID NO: 5) sequence (Tam, et al., *Am. J. Respir. Cell Mol. Biol.* 3: 27-32 (1990)). The G-protein coupled receptor PAR-2 can be cleaved and activated by tryptase at the Ser-Lys-Gly-Arg (SEQ ID NO: 6) sequence to drive fibroblast proliferation, whereas the thrombin activated receptor PAR-1 is inactivated by tryptase at the Pro-Asn-Asp-Lys (SEQ ID NO: 7) sequence (Molino et al., *Journal of Biological Chemistry* 272(7): 4043-4049 (1997)). Taken together, this evidence suggests a central role for tryptase in tissue remodeling as a consequence of disease. This is consistent with the profound changes observed in several mast cell-mediated disorders. One hallmark of chronic asthma and other long-term respiratory diseases is fibrosis and thickening of the underlying tissues that could be the result of tryptase activation of its physiological targets. Similarly, a series of reports have shown angiogenesis to be associated with mast cell density, tryptase activity and poor prognosis in a variety of cancers (Coussens et al., *Genes and Development* 13(11): 1382-97 (1999)); Takanami et al., *Cancer* 88(12): 2686-92 (2000); Toth-Jakatics et al., *Human Pathology* 31(8): 955-960 (2000); Ribatti et al., *International Journal of Cancer* 85(2): 171-5 (2000)).

Methods are known in the art for evaluating whether a particular protease cleaves a selected peptide sequence. For example, the use of 7-amino-4-methyl coumarin (AMC) fluorogenic peptide substrates is a well-established method for the determination of protease specificity (Zimmerman, M., et al., (1977) *Analytical Biochemistry* 78:47-51). Specific cleavage of the anilide bond liberates the fluorogenic AMC leaving group allowing for the simple determination of cleavage rates for individual substrates. More recently, arrays (Lee, D., et al., (1999) *Bioorganic and Medicinal Chemistry Letters* 9:1667-72) and positional-scanning libraries (Rano, T. A., et al., (1997) *Chemistry and Biology* 4:149-55) of AMC peptide substrate libraries have been employed to rapidly profile the N-terminal specificity of proteases by sampling a wide range of substrates in a single experiment. Thus, one of skill in the art may readily evaluate an array of peptide sequences to determine their utility in the present invention without resort to undue experimentation.

(2) Hydrazine Linkers (H)

In a second embodiment, the conjugate of the invention comprises a hydrazine self-immolative linker, wherein the conjugate has the structure:

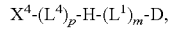

wherein D, $L^1$, $L^4$, and $X^4$ are as defined above and described further herein, and H is a linker comprising the structure:

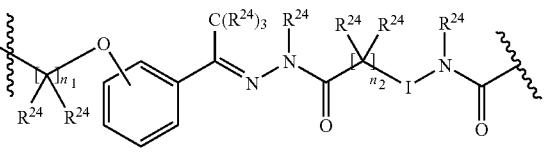

wherein
$n_1$ is an integer from 1-10;
$n_2$ is 0, 1, or 2;
each $R^{24}$ is a member independently selected from the group consisting of H, substituted alkyl, unsubstituted alkyl, substituted heteroalkyl, and unsubstituted heteroalkyl; and
I is either a bond (i.e., the bond between the carbon of the backbone and the adjacent nitrogen) or:

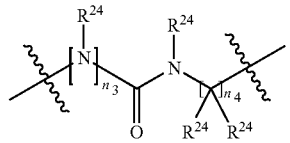

wherein $n_3$ is 0 or 1, with the proviso that when $n_3$ is 0, $n_2$ is not 0; and
$n_4$ is 1, 2, or 3,
wherein when I is a bond, $n_1$ is 3 and $n_2$ is 1, D can not be

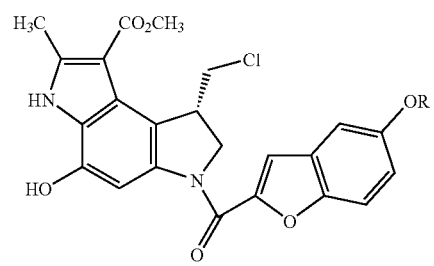

where R is Me or $CH_2$—$CH_2$—$NMe_2$.

In one embodiment, the substitution on the phenyl ring is a para substitution. In preferred embodiments, $n_1$ is 2, 3, or 4 or $n_1$ is 3. In preferred embodiments, $n_2$ is 1. In preferred embodiments, I is a bond (i.e., the bond between the carbon of the backbone and the adjacent nitrogen). In one aspect, the hydrazine linker, H, can form a 6-membered self immolative linker upon cleavage, for example, when $n_3$ is 0 and $n_4$ is 2. In another aspect, the hydrazine linker, H, can form two 5-membered self immolative linkers upon cleavage. In yet other aspects, H forms a 5-membered self immolative linker, H forms a 7-membered self immolative linker, or H forms a 5-membered self immolative linker and a 6-membered self immolative linker, upon cleavage. The rate of cleavage is affected by the size of the ring formed upon cleavage. Thus, depending upon the rate of cleavage desired, an appropriate size ring to be formed upon cleavage can be selected.

Five Membered Hydrazine Linkers

In one embodiment, the hydrazine linker comprises a 5-membered hydrazine linker, wherein H comprises the structure:

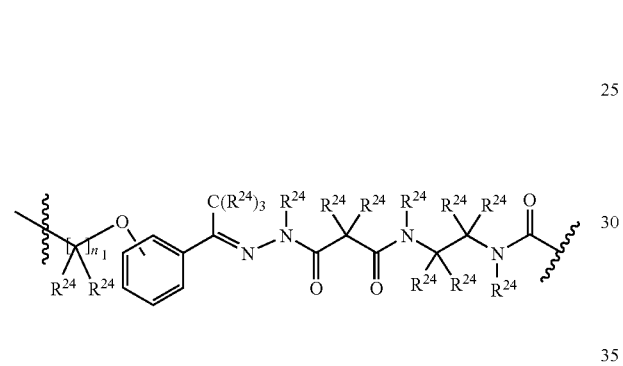

In a preferred embodiment, $n_1$ is 2, 3, or 4. In another preferred embodiment, $n_1$ is 3. In the above structure, each $R^{24}$ is a member independently selected from the group consisting of H, substituted alkyl, unsubstituted alkyl, substituted heteroalkyl, and unsubstituted heteroalkyl. In one embodiment, each $R^{24}$ is independently H or a $C_1$-$C_6$ alkyl. In another embodiment, each $R^{24}$ is independently H or a $C_1$-$C_3$ alkyl, more preferably H or $CH_3$. In another embodiment, at least one $R^{24}$ is a methyl group. In another embodiment, each $R_{24}$ is H. Each $R^{24}$ is selected to tailor the compounds steric effects and for altering solubility.

The 5-membered hydrazine linkers can undergo one or more cyclization reactions that separate the drug from the linker, and can be described, for example, by:

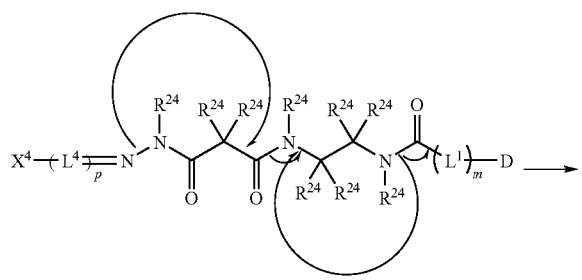

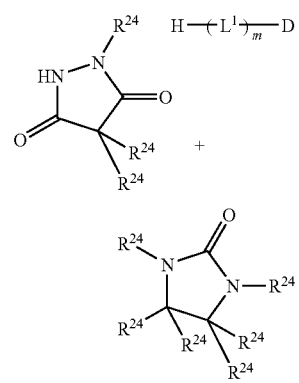

An exemplary synthetic route for preparing a five membered linker of the invention is:

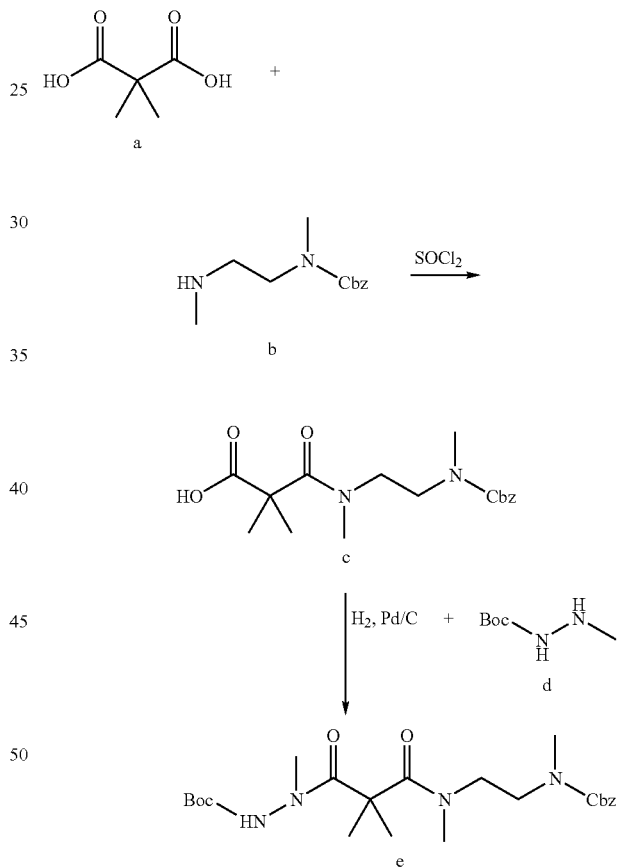

The Cbz-protected DMDA b is reacted with 2,2-Dimethylmalonic acid a in solution with thionyl chloride to form a Cbz-DMDA-2,2-dimethylmalonic acid c. Compound c is reacted with Boc-N-methyl hydrazine d in the presence of hydrogen to form DMDA-2,2-dimethylmalonic-Boc-N-methylhydrazine e.

Six Membered Hydrazine Linkers

In another embodiment, the hydrazine linker comprises a 6-membered hydrazine linker, wherein H comprises the structure:

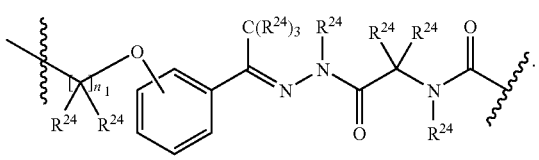

In a preferred embodiment, $n_1$ is 3. In the above structure, each $R^{24}$ is a member independently selected from the group consisting of H, substituted alkyl, unsubstituted alkyl, substituted heteroalkyl, and unsubstituted heteroalkyl. In one embodiment, each $R^{24}$ is independently H or a $C_1$-$C_6$ alkyl. In another embodiment, each $R^{24}$ is independently H or a $C_1$-$C_3$ alkyl, more preferably H or $CH_3$. In another embodiment, at least one $R^{24}$ is a methyl group. In another embodiment, each $R_{24}$ is H. Each $R^{24}$ is selected to tailor the compounds steric effects and for altering solubility. In a preferred embodiment, H comprises the structure:

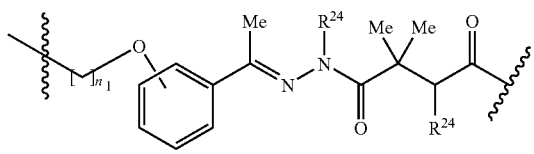

In one embodiment, H comprises a geminal dimethyl substitution. In one embodiment of the above structure, each $R^{24}$ independently an H or a substituted or unsubstituted alkyl.

The 6-membered hydrazine linkers will undergo a cyclization reaction that separates the drug from the linker, and can be described as:

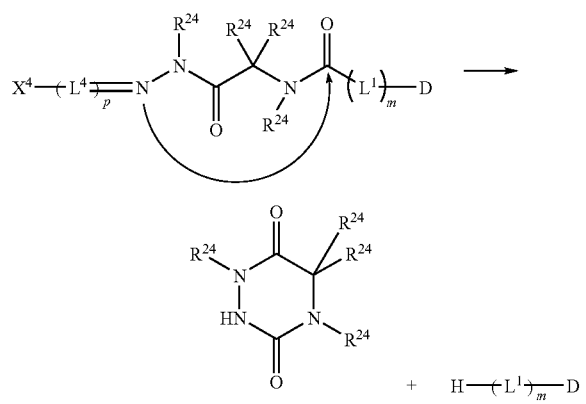

An exemplary synthetic route for preparing a six membered linker of the

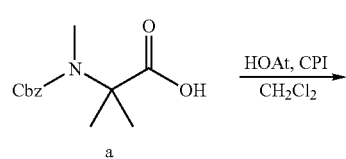

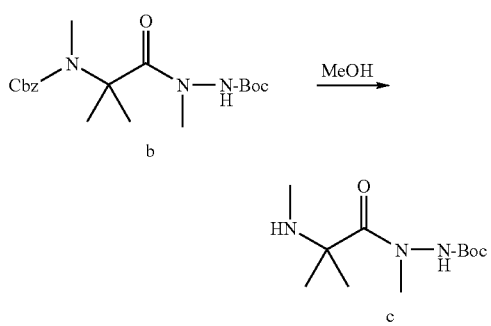

The Cbz-protected dimethyl alanine a in solution with dichlormethane, was reacted with HOAt, and CPI to form a Cbz-protected dimethylalanine hydrazine b. The hydrazine b is deprotected by the action of methanol, forming compound c.

Other Hydrazine Linkers

It is contemplated that the invention comprises a linker having seven members. This linker would likely not cyclize as quickly as the five or six membered linkers, but this may be preferred for some drug-ligand conjugates. Similarly, the hydrazine linker may comprise two six membered rings or a hydrazine linker having one six and one five membered cyclization products. A five and seven membered linker as well as a six and seven membered linker are also contemplated.

Another hydrazine structure, H, has the formula:

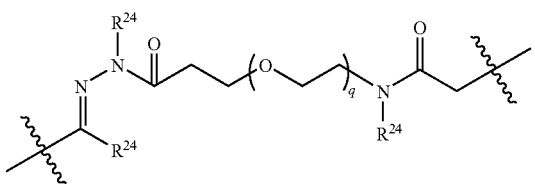

where q is 0, 1, 2, 3, 4, 5, or 6; and each $R^{24}$ is a member independently selected from the group consisting of H, substituted alkyl, unsubstituted alkyl, substituted heteroalkyl, and unsubstituted heteroalkyl. This hydrazine structure can also form five-, six-, or seven-membered rings and additional components can be added to form multiple rings.

(3) Disulfide Linkers (J)

In yet another embodiment, the linker comprises an enzymatically cleavable disulfide group. In one embodiment, the invention provides a cytotoxic drug-ligand compound having a structure according to Formula 3:

wherein D, $L^1$, $L^4$, and $X^4$ are as defined above and described further herein, and J is a disulfide linker comprising a group having the structure:

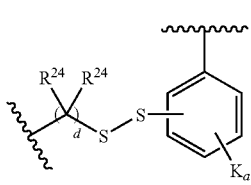

wherein each $R^{24}$ is a member independently selected from the group consisting of H, substituted alkyl, unsubstituted alkyl, substituted heteroalkyl, and unsubstituted heteroalkyl;

each K is a member independently selected from the group consisting of substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, halogen, $NO_2$, $NR^{21}R^{22}$, $NR^{21}COR^{22}$, $OCONR^{21}R^{22}$, $OCOR^{21}$, and $OR^{21}$ wherein $R^{21}$ and $R^{22}$ are independently selected from the group consisting of H, substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl and unsubstituted heterocycloalkyl;

a is an integer of 0, 1, 2, 3, or 4; and d is an integer of 0, 1, 2, 3, 4, 5, or 6.

The aromatic ring of the disulfides linker may be substituted with one or more "K" groups. A "K" group is a substituent on the aromatic ring that replaces a hydrogen otherwise attached to one of the four non-substituted carbons that are part of the ring structure. The "K" group may be a single atom, such as a halogen, or may be a multi-atom group, such as alkyl, heteroalkyl, amino, nitro, hydroxy, alkoxy, haloalkyl, and cyano. Exemplary K substituents independently include, but are not limited to, F, Cl, Br, I, $NO_2$, OH, $OCH_3$, $NHCOCH_3$, $N(CH_3)_2$, $NHCOCF_3$ and methyl. For "Ka", a is an integer of 0, 1, 2, 3, or 4. In a specific embodiment, a is 0.

In a preferred embodiment, the linker comprises an enzymatically cleavable disulfide group of the following formula:

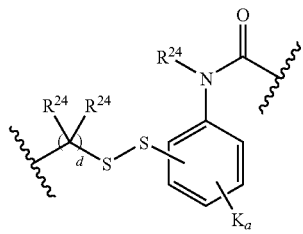

In this embodiment, the identities of $L^4$, $X^4$, p, and $R^{24}$ are as described above, and d is 0, 1, 2, 3, 4, 5, or 6. In a particular embodiment, d is 1 or 2.

A more specific disulfide linker is shown in the formula below:

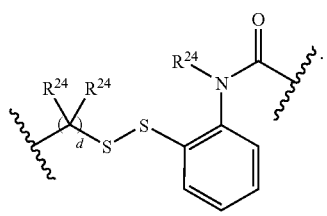

A specific example of this embodiment is as follows:

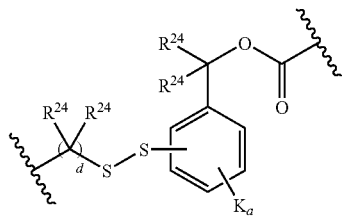

Preferably, d is 1 or 2.

Another disulfide linker is shown in the formula below:

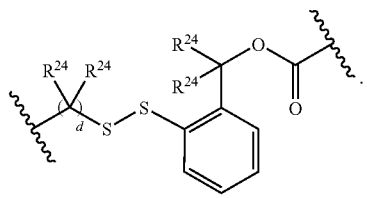

A specific example of this embodiment is as follows:

Preferably, d is 1 or 2.

In various embodiments, the disulfides are ortho to the amine. In another specific embodiment, a is 0. In preferred embodiments, $R^{24}$ is independently selected from H and $CH_3$.

An exemplary synthetic route for preparing a disulfide linker of the invention is as follows:

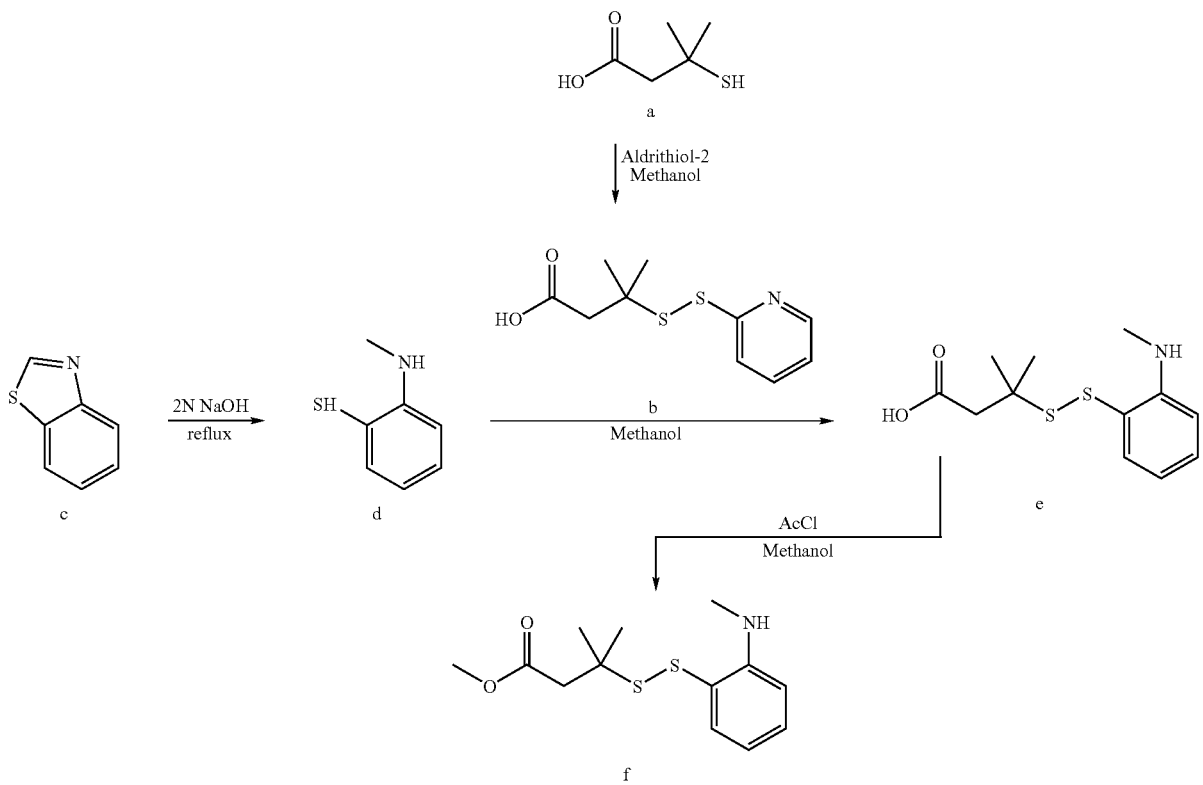

A solution of 3-mercaptopropionic acid a is reacted with aldrithiol-2 to form 3-methyl benzothiazolium iodide b. 3-methylbenzothiazolium iodide c is reacted with sodium hydroxide to form compound d. A solution of compound d with methanol is further reacted with compound b to form compound e. Compound e deprotected by the action of acetyl chloride and methanol forming compound f.

The drug-ligand conjugate of the current invention may optionally contain two or more linkers. These linkers may be the same or different. For example, a peptidyl linker may be used to connect the drug to the ligand and a second peptidyl linker may attach a diagnostic agent the complex. Alternatively, any of a peptidyl, hydrazine, or disulfide linker may connect the drug and ligand complex and any of a peptidyl, hydrazine, or disulfide linker may attach a diagnostic agent to the complex. Other uses for additional linkers include linking analytical agents, biomolecules, targeting agents, and detectable labels to the drug-ligand complex.

Also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, is attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the present invention includes compounds that are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to, for example, replace a hydroxyl group with a diol, or an amine with a quaternary amine, hydroxy amine or similar more water-soluble moiety. In a preferred embodiment, additional water solubility is imparted by substitution at a site not essential for the activity towards the ion channel of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

Drugs

Drugs, depicted as "D" herein, are provided in the current invention as part of a drug-ligand conjugate where the drug is linked to a ligand through either a peptidyl, hydrazine, or disulfide linker. The drug must possess a desired biological activity and contain a reactive functional group in order to link to the ligand. The desired biological activity includes the diagnosis, cure, mitigation, treatment, or prevention of disease in an animal such as a human. Thus, so long as it has the needed reactive functional group, the term "drug" refers to chemicals recognized as drugs in the official United States Pharmacopeia, official Homeopathic Pharmacopeia of the United States, or official National Formulary, or any supplement thereof. Exemplary drugs are set forth in the Physician's Desk Reference (PDR) and in the Orange Book maintained by the U.S. Food and Drug Administration (FDA). New drugs are being continually being discovered and developed, and the present invention provides that these new drugs may also be incorporated into the drug-ligand complex of the current invention.

Preferred functional groups include primary or secondary amines, hydroxyls, sulfhydryls, carboxyls, aldehydes, and ketones. More preferred functional groups include hydroxyls, primary or secondary amines, sulfhydryls and carboxylic acid functional groups. Even more preferred functional groups include hydroxyls, primary and secondary amines and carboxylic acid functional groups. The drug must have at least one, but may have 2, 3, 4, 5, 6 or more reactive functional groups. Additionally, a self-immolative spacer, $L^1$, may be incorporated between the reactive functional group of the drug and the peptide, hydrazine or disulfide linker.

The drug-ligand conjugate is effective for the usual purposes for which the corresponding drugs are effective, but have superior efficacy because of the ability, inherent in the ligand, to transport the drug to the desired cell where it is of particular benefit.

Exemplary drugs include proteins, peptides, and small molecule drugs containing a functional group for linkage to the ligand. More specifically, these drugs include, for example, the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, differentiation inducers, and taxols.

Preferred drugs of the current invention include cytotoxic drugs useful in cancer therapy and other small molecules, proteins or polypeptides with desired biological activity, such as a toxin. The drug may be selected to be activated at a tumor cells by conjugation to a tumor-specific ligand. These tumor specific drug-ligand conjugates have tumor specificity arising from the specificity of the ligand. Examples of this are drug-ligand conjugates that are highly selective substrates for tumor specific enzymes, where these enzymes are present in the proximity of the tumor in sufficient amounts to generate cytotoxic levels of free drug in the vicinity of the tumor. One advantage of these tumor-specific drug-ligand complexes is that they are stable to adventitious proteases in the human serum. Another advantage of the drug-ligand complex is that they are less toxic than the corresponding free drug; additionally, the specificity of the complex may allow for lower overall concentrations to be used relative to the free drug since the increased specificity will result in a higher percentage of the complex to be present at the tumor site.

Cytotoxins

Cytotoxic drugs useful in the current invention include, for example, duocarmycins and CC-1065, and analogues thereof, including CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclopropa[c]benz[e]-indol-4-one)-based analogues of the duocarmycins and CC-1065, doxorubicin and doxorubicin conjugates such as morpholino-doxorubicin and cyanomorpholino-doxorubicin, dolastatins such as dolestatin-10, combretastatin, calicheamicin, maytansine, maytansine analogs, DM-1, auristatin E, auristatin EB (AEB), auristatin EFP (AEFP), monomethyl auristatin E (MMAE), 5-benzoylvaleric acid-AE ester (AEVB), tubulysins, disorazole, epothilones, Paclitaxel, docetaxel, SN-38, Topotecan, rhizoxin, echinomycin, colchicine, vinblastin, vindesine, estramustine, cemadotin, eleutherobin, methotrexate, methopterin, dichloromethotrexate, 5-fluorouracil, 6-mercaptopurine, cytosine arabinoside, melphalan, leurosine, leurosideine, actinomycin, daunorubicin and daunorubicin conjugates, mitomycin C, mitomycin A, caminomycin, aminopterin, tallysomycin, podophyllotoxin and podophyllotoxin derivatives such as etoposide or etoposide phosphate, vincristine, taxol, taxotere retinoic acid, butyric acid, $N^8$-acetyl spermidine, camptothecin, and their analogues. Other known drugs may be modified in order to provide a functional group for conjugation to the linker described herein. Such chemical modification is known in the art.

Preferred cytotoxins for use in the current invention include: duocarmycins and CC-1065, and CCBI-based and MCBI-based analogues thereof, morpholino-doxorubicin, cyanomorpholino-doxorubicin, dolastatin-10, combretastatin, calicheamicin, maytansine, DM-1, auristatin E, AEB, AEFP, MMAE, Tubulysin A, Disorazole, epothilone A and epothilone B.

Particularly preferred cytotoxins of the present invention are active, potent duocarmycin derivatives and CC-1065. The parent agents are exceptionally potent antitumor antibiotics that derive their biological effects through the reversible, stereoelectronically controlled sequence selective alkylation of DNA (Boger et al. *J. Org. Chem.* 55: 4499 (1990); Boger et al. *J. Am. Chem. Soc.* 112: 8961 (1990); Boger et al., *J. Am. Chem. Soc.* 113: 6645 (1991); Boger et al. *J. Am. Chem. Soc.* 115: 9872 (1993); Boger et al., *Bioorg. Med. Chem. Lett.* 2: 759 (1992)). Subsequent to the initial disclosure of the duocarmycins, extensive efforts have been devoted to elucidating the DNA alkylation selectivity of the duocarmycins and its structural origin.

A particularly preferred aspect of the current invention provides a cytotoxic compound having a structure according to Formula 7:

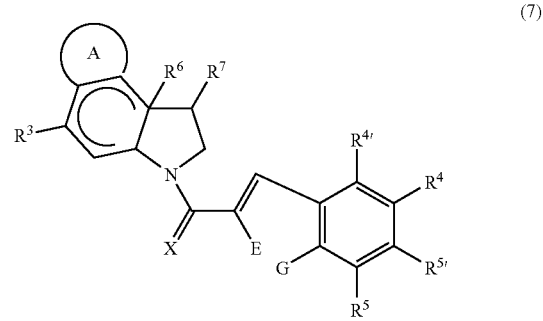

(7)

in which ring system A is a member selected from substituted or unsubstituted aryl substituted or unsubstituted heteroaryl and substituted or unsubstituted heterocycloalkyl groups. Exemplary ring systems include phenyl and pyrrole.

The symbols E and G are independently selected from H, substituted or unsubstituted alkyl, substituted or unsubstituted heteroalkyl, a heteroatom, a single bond or E and G are optionally joined to form a ring system selected from substituted or unsubstituted aryl, substituted or unsubstituted heteroaryl and substituted or unsubstituted heterocycloalkyl.

The symbol X represents a member selected from O, S and $NR^{23}$. $R^{23}$ is a member selected from H, substituted or unsubstituted alkyl, substituted or unsubstituted heteroalkyl, and acyl.

The symbol $R^3$ represents a member selected from (=O), $SR^{11}$, $NHR^{11}$ and $OR^{11}$, in which $R^{11}$ is H, substituted or unsubstituted alkyl, substituted or unsubstituted heteroalkyl, diphosphates, triphosphates, acyl, $C(O)R^{12}R^{13}$, $C(O)OR^{12}$, $C(O)NR^{12}R^{13}$, $P(O)(OR^{12})_2$, $C(O)CHR^{12}R^{13}$, $SR^{12}$ or $SiR^{12}R^{13}R^{14}$. The symbols $R^{12}$, $R^{13}$, and $R^{14}$ independently represent H, substituted or unsubstituted alkyl, substituted or unsubstituted heteroalkyl and substituted or unsubstituted aryl, wherein $R^{12}$ and $R^{13}$ together with the nitrogen or carbon atom to which they are attached are optionally joined to form a substituted or unsubstituted heterocycloalkyl ring system having from 4 to 6 members, optionally containing two or more heteroatoms. One or more of $R^{12}$, $R^{13}$, or $R^{14}$ can include a cleaveable group within its structure.

$R^4$, $R^{4'}$, $R^5$ and $R^{5'}$ are members independently selected from H, substituted or unsubstituted alkyl, substituted or unsubstituted aryl, substituted or unsubstituted heteroaryl, substituted or unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$, $OR^{15}$, $CR^{15}=NR^{16}$, and $O(CH_2)_nN(CH_3)_2$, wherein n is an integer from 1 to 20. $R^{15}$ and $R^{16}$ independently represent H, substituted or unsubstituted alkyl, substituted or unsubstituted heteroalkyl, substituted or unsubstituted aryl, substituted or unsubstituted heteroaryl, substituted or unsubstituted heterocycloalkyl and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms. One exemplarly structure is aniline.

$R^4$, $R^{4'}$, $R^5$, $R^{5'}$, $R^{11}$, $R^{12}$, $R^{13}$, $R^{15}$ and $R^{16}$ optionally contain one or more cleaveable groups within their structure. Exemplary cleaveable groups include, but are not limited to peptides, amino acids, hydrazines, and disulfides.

At least one of $R^{11}$, $R^{12}$, $R^{13}$, $R^{15}$ and $R^{16}$ is used to join the drug to a linker of the present invention, as described herein, for example to $L^1$, if present or to F, H, or J.

In a still further exemplary embodiment, at least one of $R^4$, $R^{4'}$, $R^5$, $R^{5'}$, $R^{11}$, $R^{12}$, $R^{13}$, $R^{15}$ and $R^{16}$ bears a reactive group appropriate for conjugating the compound. In a further exemplary embodiment, $R^4$, $R^{4'}$, $R^5$, $R^{5'}$, $R^{11}$, $R^{12}$, $R^{13}$, $R^{15}$ and $R^{16}$ are independently selected from H, substituted alkyl and substituted heteroalkyl and have a reactive functional group at the free terminus of the alkyl or heteroalkyl moiety. One or more of $R^4$, $R^{4'}$, $R^5$, $R^{5'}$, $R^{11}$, $R^{12}$, $R^{13}$, $R^{15}$ and $R^{16}$ may be conjugated to another species, e.g., targeting agent, detectable label, solid support, etc.

As will be apparent from the discussion herein, when at least one of $R^{15}$ and $R^{16}$ comprises a reactive functional group, that group can be a component of a bond between the drug and another molecule. In an exemplary embodiment in which at least one of $R^{15}$ and $R^{16}$ comprises a linkage between the drug and another species, at least one of $R^{15}$ and $R^{16}$ is a moiety that is cleaved by an enzyme.

In a further exemplary embodiment, at least one of $R^4$, $R^{4'}$, $R^5$ and $R^{5'}$ is:

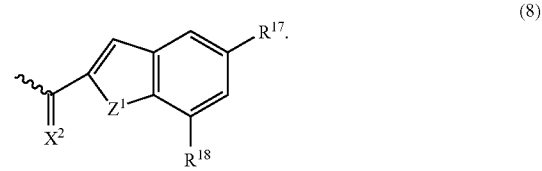

(8)

In Formula 8, the symbols $X^2$ and $Z^1$ represent members independently selected from O, S and $NR^{23}$. The groups $R^{17}$ and $R^{18}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, halogen, $NO_2$, $NR^{19}R^{20}$, $NC(O)R^{19}$, $OC(O)NR^{19}$, $OC(O)OR^{19}$, $C(O)R^{19}$, $SR^{19}$ or $OR^{19}$, with the proviso that at least one one of $R^{12}$, $R^{13}$, $R^{19}$, or $R^{20}$ comprises a linker of the present invention, as disclosed herein.

The symbols $R^{19}$ and $R^{20}$ independently represent substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted peptidyl, wherein $R^{19}$ and $R^{20}$ together with the nitrogen atom to which they are attached are optionally joined to form a substituted or unsubstituted heterocycloalkyl ring system having from 4 to 6 members, optionally containing two or more heteroatoms, with the proviso that when $Z^1$ is NH, both $R^{17}$ and $R^{18}$ are not H, and $R^{17}$ is not $NH_2$. Throughout the present specification, the symbols $R^{19}$ and $R^{20}$ also encompass the groups set forth for $R^4$ and $R^5$. Thus, for example, it is within the scope of the present invention to provide compounds having two or more of the fused phenyl-heterocyclic ring systems set forth immediately above linked in series, or a fused ring in combination with a linker. Moreover, in those embodiments in which a linker is present, the linker may be present as an $R^4$, $R^{4'}$, $R^5$, or $R^{5'}$ substituent or as an $R^{17}$ or $R^{18}$ substituent.

$R^6$ is a single bond which is either present or absent. When $R^6$ is present, $R^6$ and $R^7$ are joined to form a cyclopropyl ring. $R^7$ is $CH_2$—$X^1$ or $CH_2$—. When $R^7$ is $CH_2$— it is a component of the cyclopropane ring. The symbol $X^1$ represents a leaving group such as a halogen, for example Cl, Br or F. The combinations of $R^6$ and $R^7$ are interpreted in a manner that does not violate the principles of chemical valence.

The curved line within the six-membered ring indicates that the ring may have one or more degree of unsaturation, and it may be aromatic. Thus, ring structures such as those set forth below, and related structures, are within the scope of Formula (9):

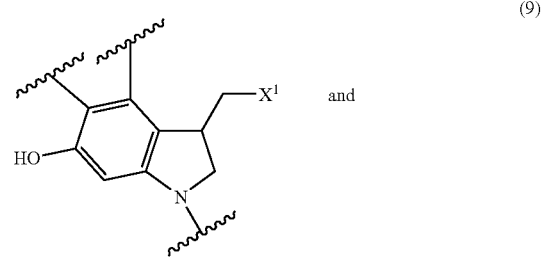

(9)

and

-continued

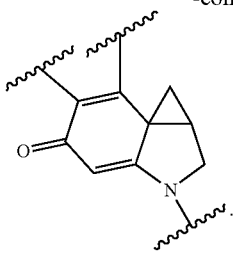

In an exemplary embodiment, ring system A is a substituted or unsubstituted phenyl ring. Ring system A is preferably substituted with one or more aryl group substituents as set forth in the definitions section herein. In one preferred embodiment, the phenyl ring is substituted with a CN or methoxy moiety.

In another exemplary embodiment, the invention provides a compound having a structure according to Formula 10:

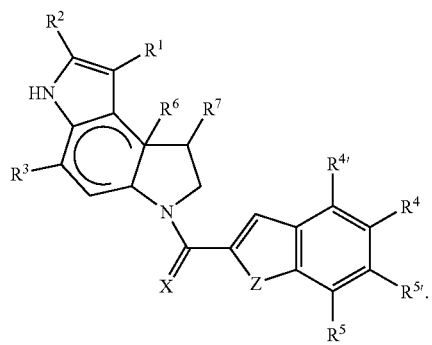

(10)

In this embodiment, the identities of the radicals $R^3$, $R^4$, $R^{4'}$, $R^5$, $R^{5'}$, $R_6$, $R^7$ and X are substantially as described above. The symbol Z is a member independently selected from O, S and $NR^{23}$. The symbol $R^{23}$ represents a member selected from H, substituted or unsubstituted alkyl, substituted or unsubstituted heteroalkyl, and acyl. Each $R^{23}$ is independently selected. The symbol $R^1$ represents H, substituted or unsubstituted lower alkyl, or $C(O)R^8$ or $CO_2R^8$. $R^8$ is a member selected from substituted alkyl, unsubstituted alkyl, $NR^9R^{10}$, $NR^9NHR^{10}$ and $OR^9$. $R^9$, and $R^{10}$ are independently selected from H, substituted or unsubstituted alkyl and substituted or unsubstituted heteroalkyl. The radical $R^2$ is H, or substituted or unsubstituted lower alkyl. It is generally preferred that when $R^2$ is substituted alkyl, it is other than a perfluoroalkyl, e.g., $CF_3$. In one embodiment, $R^2$ is a substituted alkyl wherein the substitution is not a halogen. In another embodiment, $R^2$ is an unsubstituted alkyl.

As discussed above, $X^1$ may be a leaving group. Useful leaving groups include, but are not limited to, halogens, azides, sulfonic esters (e.g., alkylsulfonyl, arylsulfonyl), oxonium ions, alkyl perchlorates, ammonioalkanesulfonate esters, alkylfluorosulfonates and fluorinated compounds (e.g., triflates, nonaflates, tresylates) and the like. Particular halogens useful as leaving groups are F, Cl and Br. The choice of these and other leaving groups appropriate for a particular set of reaction conditions is within the abilities of those of skill in the art (see, for example, March J, ADVANCED ORGANIC CHEMISTRY, 2nd Edition, John Wiley and Sons, 1992; Sandler S R, Karo W, ORGANIC FUNCTIONAL GROUP PREPARATIONS, 2nd Edition, Academic Press, Inc., 1983; and Wade L G, COMPENDIUM OF ORGANIC SYNTHETIC METHODS, John Wiley and Sons, 1980).

In an exemplary embodiment $R^1$ is an ester moiety, such as $CO_2CH_3$. In a further exemplary embodiment, $R^2$ is a lower alkyl group, which may be substituted or unsubstituted. A presently preferred lower alkyl group is $CH_3$. In a still further embodiment, $R^1$ is $CO_2CH_3$, and $R^2$ is $CH_3$.

In yet another exemplary embodiment, $R^4$, $R^{4'}$, $R^5$, and $R^{5'}$ are members independently selected from H, halogen, $NH_2$, OMe, $O(CH_2)_2N(Me)_2$ and $NO_2$.

In one embodiment, the drug is selected such that the leaving group $X^1$ is a member selected from the group consisting of halogen, alkylsulfonyl, arylsulfonyl, and azide. In another embodiment, Z is O. In certain embodiments, $R^1$ may be $CO_2CH_3$ or $R^2$ may be $CH_3$; additionally, $R^1$ may be $CO_2CH_3$, and $R^2$ may be $CH_3$. One of $R^4$, $R^{4'}$, $R^5$ or $R^{5'}$ may be $C(O)R^{15}$ and the other three of $R^4$, $R^{4'}$, $R^5$ and $R^{5'}$ are H. Additionally, at least one of $R^4$, $R^{4'}$, $R^5$ and $R^{5'}$ may be other than a member selected from H and $OCH_3$. In one embodiment, $R^4$, $R^{4'}$, $R^5$ and $R^{5'}$ are members independently selected from H, halogen, $NH_2$, $O(CH_2)_2N(Me)_2$ and $NO_2$.

In a preferred embodiment, one of $R^4$, $R^{4'}$, $R^5$ or $R^{5'}$ is $O(CH_2)_2N(Me)_2$ and the others of $R^4$, $R^{4'}$, $R^5$ and $R^{5'}$ are H. In another embodiment, $R^7$ is $CH_2$—$X^1$ where $X^1$ is F, Cl or Br and $R^6$ is absent.

In yet another exemplary embodiment, the invention provides compounds having a structure according to Formula 11 and 12:

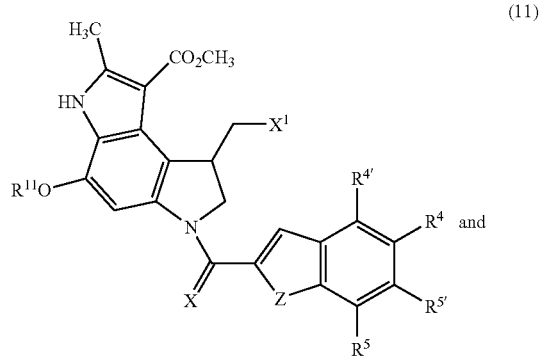

(11)

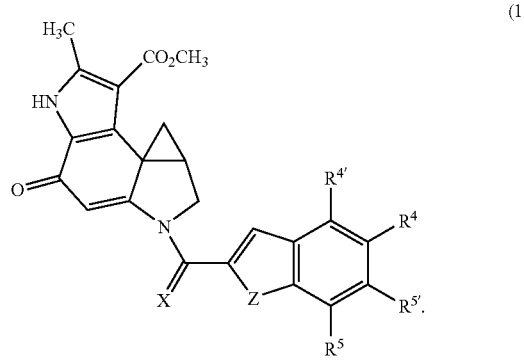

(12)

In one embodiment of the Formula above, X is preferably O; and Z is preferably O. In another embodiment, Z is $NR^{23}$ or O. Alternatively, one of $R^4$, $R^{4'}$, $R^5$ or $R^{5'}$ may be $O(CH_2)_2N(Me)_2$ while the other three of $R^4$, $R^{4'}$, $R^5$ or $R^{5'}$ are H. In one embodiment, $R^4$, $R^{4'}$, $R^5$ or $R^{5'}$ may be selected from the group consisting of $R^{29}$, $COOR^{29}$, $C(O)NR^{29}$, and $C(O)NNR^{29}$, wherein $R^{29}$ is selected from the group consisting of H, OH, substituted alkyl, unsubstituted alkyl, substituted cycloalkyl, unsubstituted cycloalkyl, substituted heteroalkyl, unsubstituted heteroalkyl, substituted cycloheteroalkyl, unsubstituted cycloheteroalkyl, substituted heteroaryl, and unsubstituted heteroaryl.

In another embodiment of the Formula above X is preferably O, Z is preferably O, $R_1$ is preferably $CO_2CH_3$, $R_7$ is preferably $CH_2$—Cl, $R_2$ is preferably $CH_3$, $R_3$ is preferably OH. Alternatively, one of $R^4$, $R^{4'}$, $R^5$ or $R^{5'}$ may be NHC(O) $(C_6H_4)NH_2$ while the other three of $R^4$, $R^{4'}$, $R^5$ or $R^{5'}$ are H.

In one embodiment, $R^{29}$ may be selected from the group consisting of:

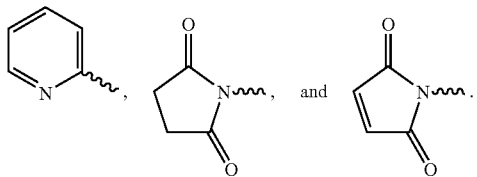

In yet another embodiment of the drug, one member selected from $R^4$ and $R^5$ is:

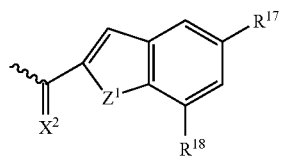

wherein $X^2$ and $Z^1$ are members independently selected from O, S and $NR^{23}$; $R^{17}$ and $R^{18}$ are members independently selected from the group consisting of H, substituted or unsubstituted alkyl, substituted or unsubstituted heteroalkyl, substituted or unsubstituted aryl, substituted or unsubstituted heteroaryl, substituted or unsubstituted heterocycloalkyl, halogen, $NO_2$, $NR^{19}R^{20}$, $NC(O)R^{19}$, $OC(O)NR^{19}$, $OC(O)OR^{19}$, $C(O)R^{19}$, $OR^{19}$, and $O(CH_2)_nN(CH_3)_2$. In this embodiment, n is an integer from 1 to 20; $R^{19}$ and $R^{20}$ are independently selected from substituted or unsubstituted alkyl, substituted or unsubstituted heteroalkyl, substituted or unsubstituted aryl, substituted or unsubstituted heteroaryl, and substituted or unsubstituted heterocycloalkyl, wherein $R^{19}$ and $R^{20}$ together with the nitrogen atom to which they are attached are optionally joined to form a substituted or unsubstituted heterocycloalkyl ring system having from 4 to 6 members, optionally containing two or more heteroatoms, wherein one of $R^{11}$, $R^{12}$, $R^{13}$, $R^{15}$, $R^{16}$, $R^{19}$, or $R^{20}$ links said drug to $L^1$, if present, or to F. In one preferred embodiment, $X^2$ is O and $Z^1$ is O or $NR^{23}$.

Another preferred structure of the duocarmycin analog of Formula 7 is a structure in which the ring system A is an unsubstituted or substituted phenyl ring. The preferred substituents on the drug molecule described hereinabove for the structure of Formula 7 when the ring system A is a pyrrole are also preferred substituents when the ring system A is an unsubstituted or substituted phenyl ring.

For example, in a preferred embodiment, the drug (D) comprises a structure:

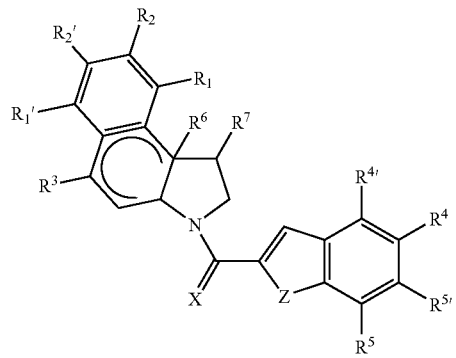

In this structure, $R^3$, $R^6$, $R^7$, X are as described above for Formula 7. Furthermore, Z is a member selected from O, S and $NR^{23}$, wherein $R^{23}$ is a member selected from H, substituted or unsubstituted alkyl, substituted or unsubstituted heteroalkyl, and acyl;

$R^1$ is H, substituted or unsubstituted lower alkyl, $C(O)R^8$, or $CO_2R^8$, wherein $R^8$ is a member selected from $NR^9R^{10}$ and $OR^9$, in which $R^9$ and $R^{10}$ are members independently selected from H, substituted or unsubstituted alkyl and substituted or unsubstituted heteroalkyl;

$R^{1'}$ is H, substituted or unsubstituted lower alkyl, or C(O) $R^8$, wherein $R^8$ is a member selected from $NR^9R^{10}$ and $OR^9$, in which $R^9$ and $R^{10}$ are members independently selected from H, substituted or unsubstituted alkyl and substituted or unsubstituted heteroalkyl;

$R^2$ is H, or substituted or unsubstituted lower alkyl or unsubstituted heteroalkyl or cyano or alkoxy; and $R^{2'}$ is H, or substituted or unsubstituted lower alkyl or unsubstituted heteroalkyl.

At least one of $R^{11}$, $R^{12}$, $R^{13}$, $R^{15}$ or $R^{16}$ links the drug to $L^1$, if present, or to F, H, or J.

In a preferred embodiment, one of $R^4$, $R^{4'}$, $R^5$ or $R^{5'}$ is $O(CH_2)_2N(Me)_2$ and the others of $R^4$, $R^{4'}$, $R^5$ and $R^{5'}$ are H. In another embodiment, $R^7$ is $CH_2$—$X^1$ where $X^1$ is F, Cl or Br and $R^6$ is absent.

In one embodiment, the invention provides a cytotoxic drug-ligand compound having a structure according to the following formula:

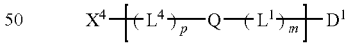

wherein the symbol $L^1$ represents a self-immolative spacer where m is an integer of 0, 1, 2, 3, 4, 5, or 6.

The symbol $X^4$ represents a member selected from the group consisting of protected reactive functional groups, unprotected reactive functional groups, detectable labels, and targeting agents.

The symbol $L^4$ represents a linker member, and p is 0 or 1. $L^4$ is a moiety that imparts increased solubility or decreased aggregation properties to the conjugates. Examples of $L^4$ moieties include substituted alkyl, unsubstituted alkyl, substituted aryl, unsubstituted aryl, substituted heteroalkyl, or unsubstituted heteroalkyl, any of which may be straight, branched, or cyclic, a positively or negatively charged amino acid polymer, such as polylysine or polyargenine, or other polymers such as polyethylene glycol.

The symbol Q represent any cleavable linker including, but not limited to, any of the peptidyl, hydrozone, and disulfide linkers described herein. Other suitable linkers include, but are not limited to, those described in U.S. Pat. No. 6,214,345; U.S. Patent Applications Publication Nos. 2003/0096743, 2003/0130189, and 2004/121940; PCT Patent Applications Publication Nos. WO 03/026577 and WO 04/043493; and European Patent Applications Publication Nos. EP1243276 and EP1370298, all of which are incorporated herein by reference. Cleavable linkers include those that can be selectively cleaved by a chemical or biological process and upon cleavage separate the drug, $D^1$, from $X^4$. Cleavage can occur anywhere along the length of the linker or at either terminus of the linker.

The symbol $D^1$ represents a drug having the following formula:

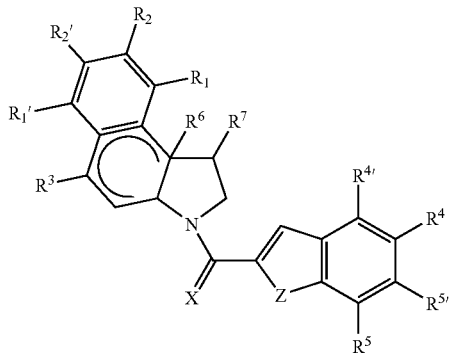

wherein X and Z are members independently selected from O, S and $NR^{23}$;

$R^{23}$ is a member selected from H, substituted or unsubstituted alkyl, substituted or unsubstituted heteroalkyl, and acyl;

$R^1$ is H, substituted or unsubstituted lower alkyl, $C(O)R^8$, or $CO_2R^8$, $R^{1'}$ is H, substituted or unsubstituted lower alkyl, or $C(O)R^8$, wherein $R^8$ is a member selected from $NR^9R^{10}$ and $OR^9$ and $R^9$ and $R^{10}$ are members independently selected from H, substituted or unsubstituted alkyl and substituted or unsubstituted heteroalkyl;

$R^2$ is H, or substituted or unsubstituted lower alkyl or unsubstituted heteroalkyl or cyano or alkoxy;

$R^{2'}$ is H, or substituted or unsubstituted lower alkyl or unsubstituted heteroalkyl, $R^3$ is a member selected from the group consisting of $SR^{11}$, $NHR^{11}$ and $OR^{11}$, wherein $R^{11}$ is a member selected from the group consisting of H, substituted alkyl, unsubstituted alkyl, substituted heteroalkyl, unsubstituted heteroalkyl, diphosphates, triphosphates, acyl, $C(O)R^{12}R^{13}$, $C(O)OR^{12}$, $C(O)NR^{12}R^{13}$, $P(O)(OR^{12})_2C(O)CHR^{12}R^{13}$, $SR^{12}$ and $SiR^{12}R^{13}R^{14}$, in which $R^{12}$, $R^{13}$, and $R^{14}$ are members independently selected from H, substituted or unsubstituted alkyl, substituted or unsubstituted heteroalkyl and substituted or unsubstituted aryl, wherein $R^{12}$ and $R^{13}$ together with the nitrogen or carbon atom to which they are attached are optionally joined to form a substituted or unsubstituted heterocycloalkyl ring system having from 4 to 6 members, optionally containing two or more heteroatoms;

wherein at least one of $R^{11}$, $R^{12}$, and $R^{13}$ links said drug to L', if present, or to Q, $R^6$ is a single bond which is either present or absent and when present $R^6$ and $R^7$ are joined to form a cyclopropyl ring; and $R^7$ is $CH_2-X^1$ or $CH_2-$ joined in said cyclopropyl ring with $R^6$, wherein $X^1$ is a leaving group, $R^4$, $R^{4'}$, $R^5$, and $R^{5'}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$, $OR^{15}$, $CR^{15}=NR^{16}$, and $O(CH_2)NR^{24}R^{25}$ wherein n is an integer from 1 to 20;

$R^{15}$ and $R^{16}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms;

and $R^{24}$ and $R^{25}$ are independently selected from unsubstituted alkyl, and wherein at least one of $R^4$, $R^{4'}$, $R^5$ and $R^{5'}$ is $O(CH_2)_n NR^{24}R^{25}$.

In some embodiments, n is 2. In some embodiments, $R^{24}$ and $R^{25}$ are methyl. In some embodiments, $R^4$ is $O(CH_2)_n NR^{24}R^{25}$ and $R^{4'}$, $R^5$ and $R^{5'}$ are H. In some embodiments, $R^4$ is $O(CH_2)_2 N(CH_3)_2$ and $R^{4'}$, $R^5$ and $R^{5'}$ are H. In some embodiment, Q is a linker selected from F, H, and J, as described above. In some embodiments, $R^1$, $R^{1'}$, $R^2$, and $R^{2'}$ are H.

A preferred formula for drug, $D^1$, is the following:

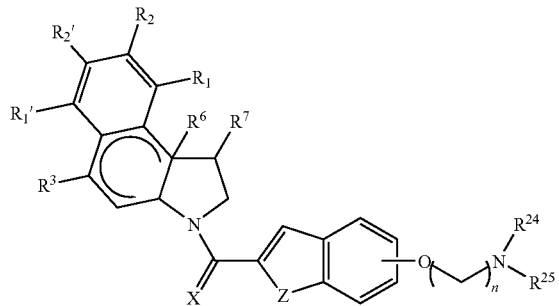

Another preferred embodiment of drug $D^1$ is the following:

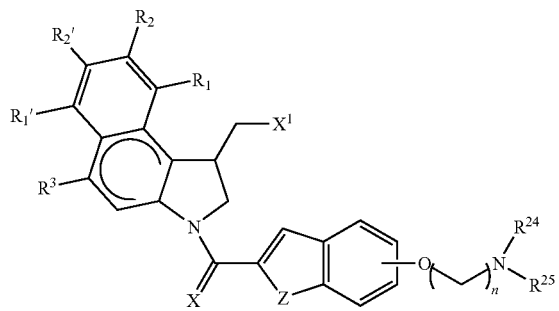

Yet additional preferred embodiments of drug $D^1$ are the following:

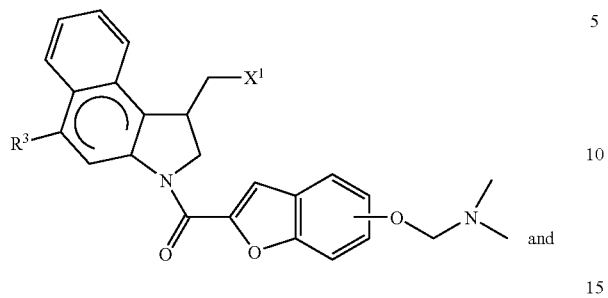

and

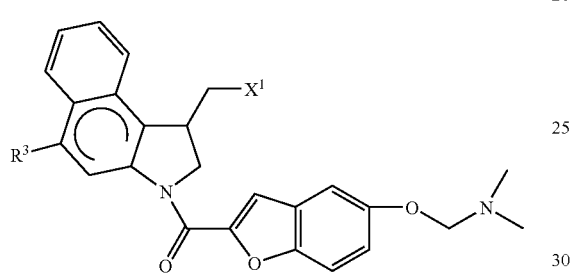

In another exemplary embodiment of the current invention, the cytotoxic drug may by a tubulysin analog or related compound, such as the compounds described by the structure according to Formula 13:

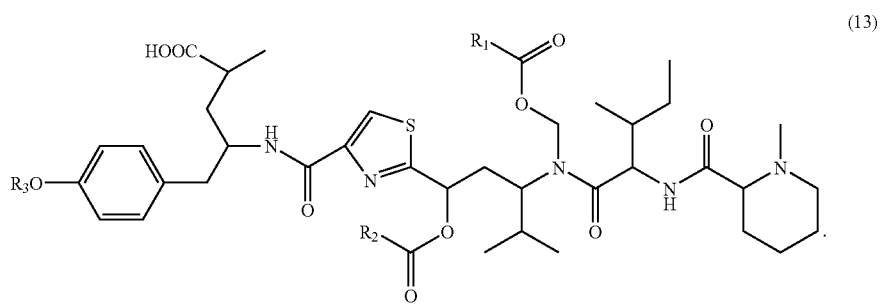

(13)

where $R_1$ and $R_2$ are H or a lower alkyl, or are more particularly isobutyl, ethyl, propyl, or t-butyl and $R_3$ is H or OH. Tubulysin and its use in treating cancer has been described in, for example, PCT Publications WO 2004/005327 and WO 2004/005326. The production of tubulysin compounds is described in DE10008089. Methods that may be used to link the tubulysin to various linkers of the current invention are provided in the examples. Preferred tubulysin analogs are Tubulysin A-F.

Preferred Duocarmycin and CBI Conjugates

The peptide, hydrazine or disulfide linkers of the invention can be used in conjugates containing duocarmycin or CBI analogs as cytotoxic agents. Preferred conjugates of the invention are described in further detail below. Unless otherwise indicated, substituents are defined as set forth above in the sections regarding cytotoxins, peptide linkers, hydrazine linkers and disulfide linkers.

A. Peptide Linker Conjugates

In a preferred embodiment, the invention provides a peptide linker conjugate having the structure:

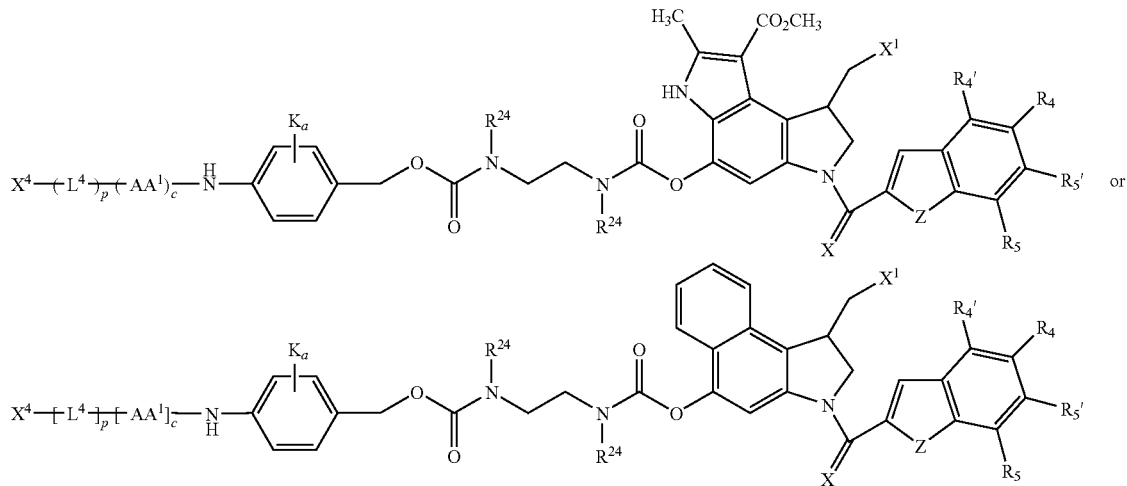

wherein $X^1$ is a halogen;

X is a member selected from O, S and $NR^{23}$;

$R^{23}$ is a member selected from H, substituted or unsubstituted alkyl, substituted or unsubstituted heteroalkyl, and acyl; and $R^4$, $R^{4'}$, $R^5$ and $R^{5'}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $OR^{15}$, and $O(CH_2)_nN(CH_3)_2$ wherein n is an integer from 1 to 20; and $R^{15}$ and $R^{16}$ are independently selected from H, substituted or unsubstituted alkyl, substituted or unsubstituted heteroalkyl, substituted or unsubstituted aryl, substituted or unsubstituted heteroaryl, and substituted or unsubstituted, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms.

Non-limiting examples of such conjugates include the following structures:

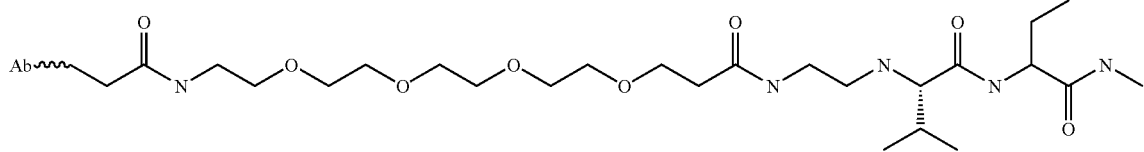

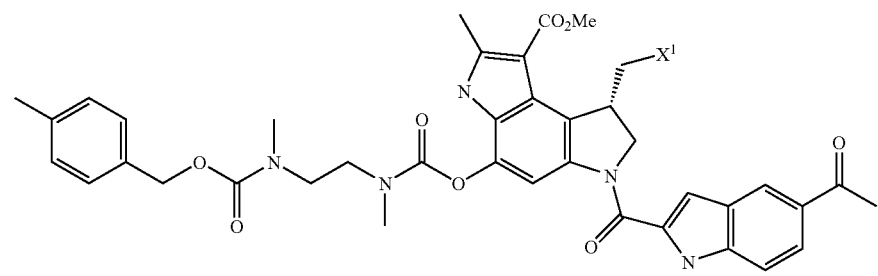

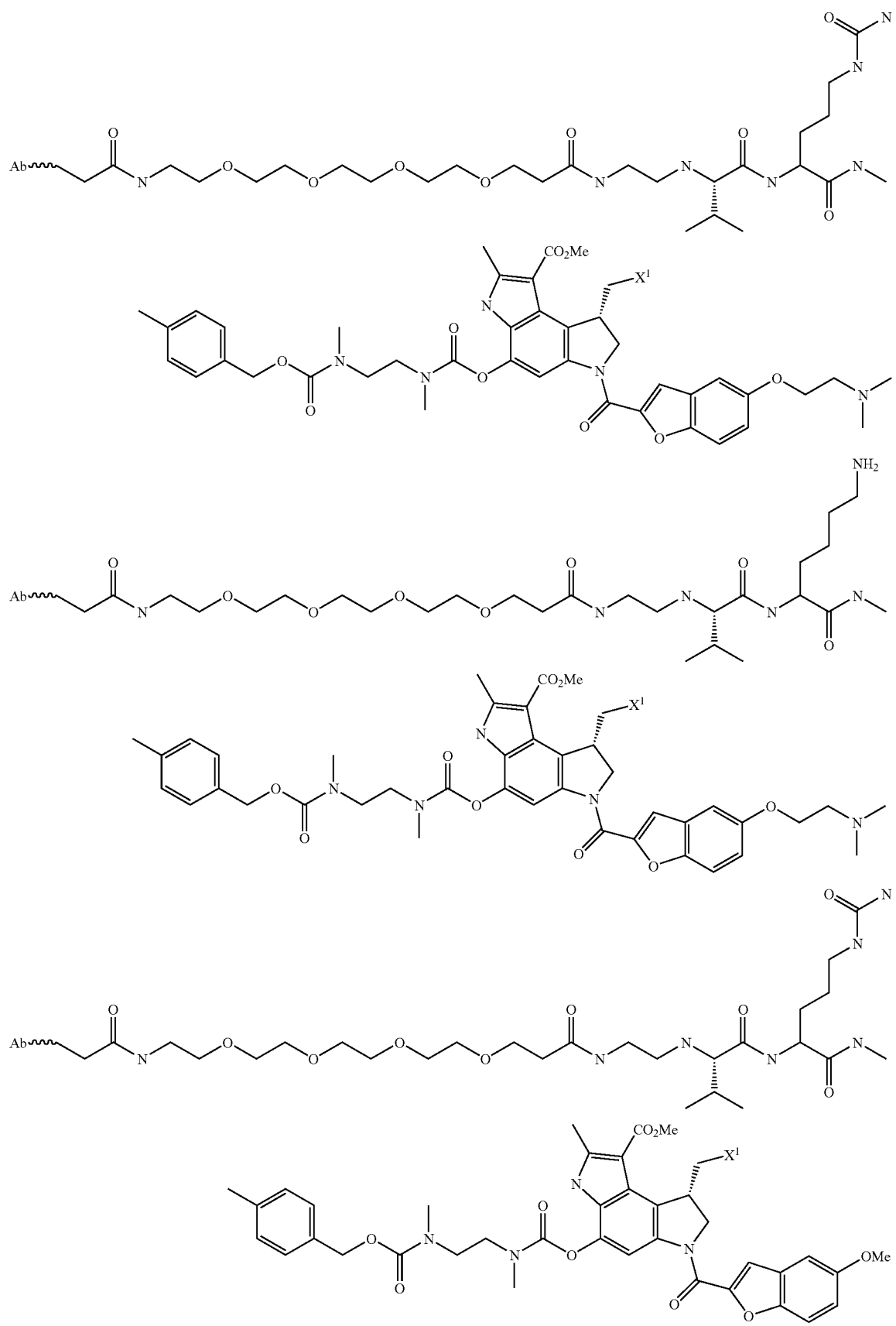

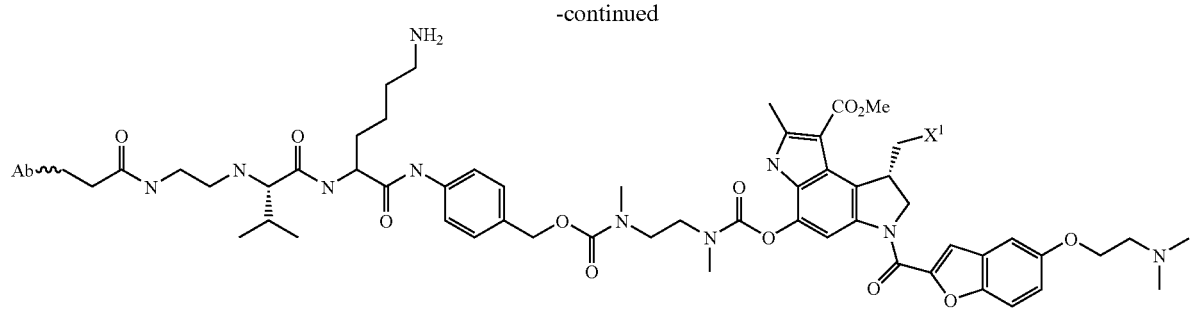
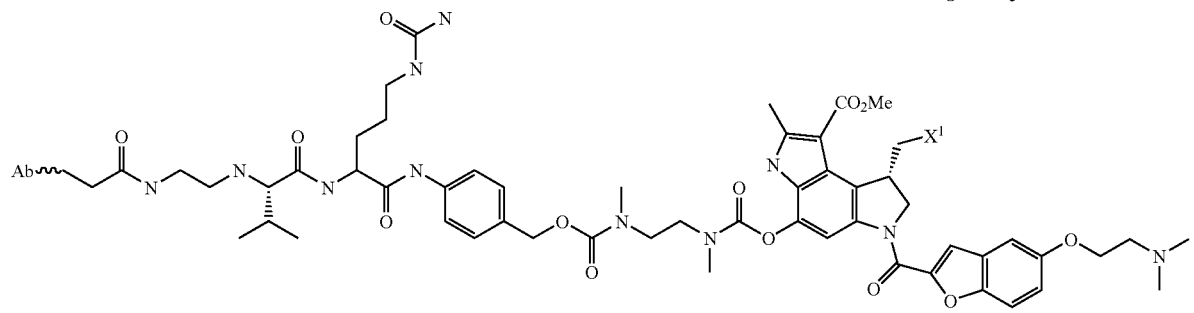
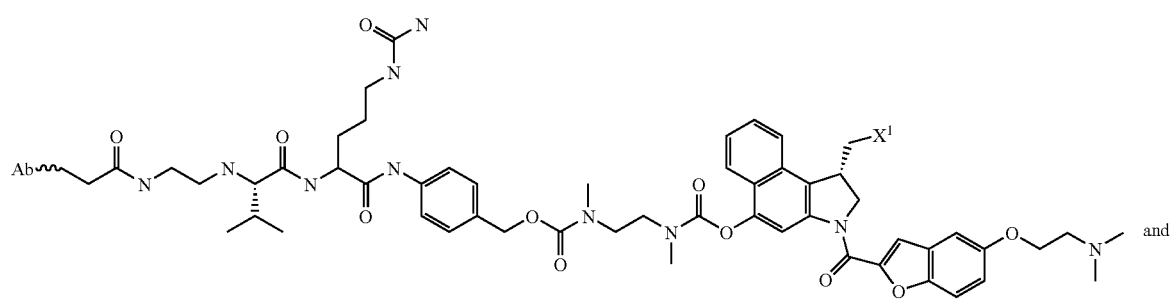
and
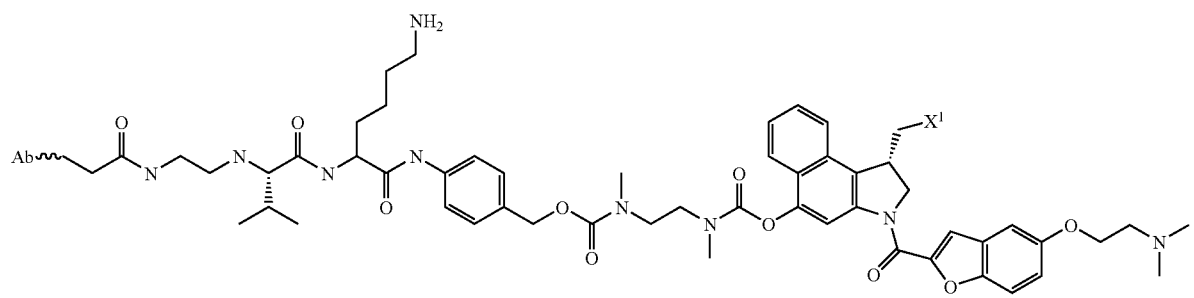
wherein $X^1$ is Cl or Br;
and wherein Ab is an antibody, or fragment thereof.
In another preferred embodiment, the invention provides a conjugate having the structure:
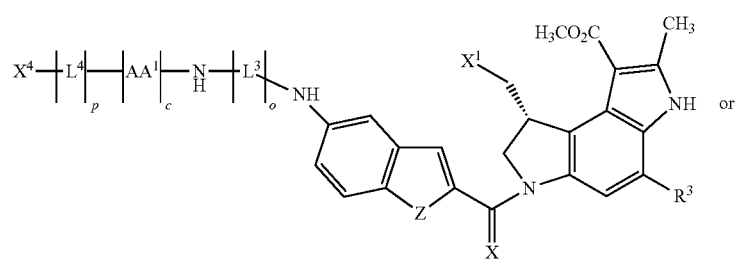

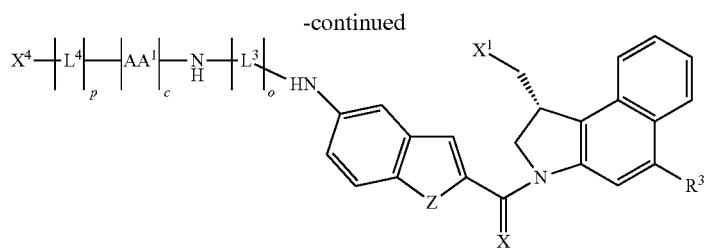

wherein $X^1$ is a leaving group;

Z and X are members independently selected from O, S and $NR^{23}$, wherein $R^{23}$ is a member selected from H, substituted or unsubstituted alkyl, substituted or unsubstituted heteroalkyl, and acyl; and $R^3$ is selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $OR^{15}$, and $O(CH_2)_nN(CH_3)_2$ wherein n is an integer from 1 to 20;

$R^{15}$ and $R^{16}$ are independently selected from H, substituted or unsubstituted alkyl, substituted or unsubstituted heteroalkyl, substituted or unsubstituted aryl, substituted or unsubstituted heteroaryl, and substituted or unsubstituted, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms.

Non-limiting examples of such conjugates include the following structures:

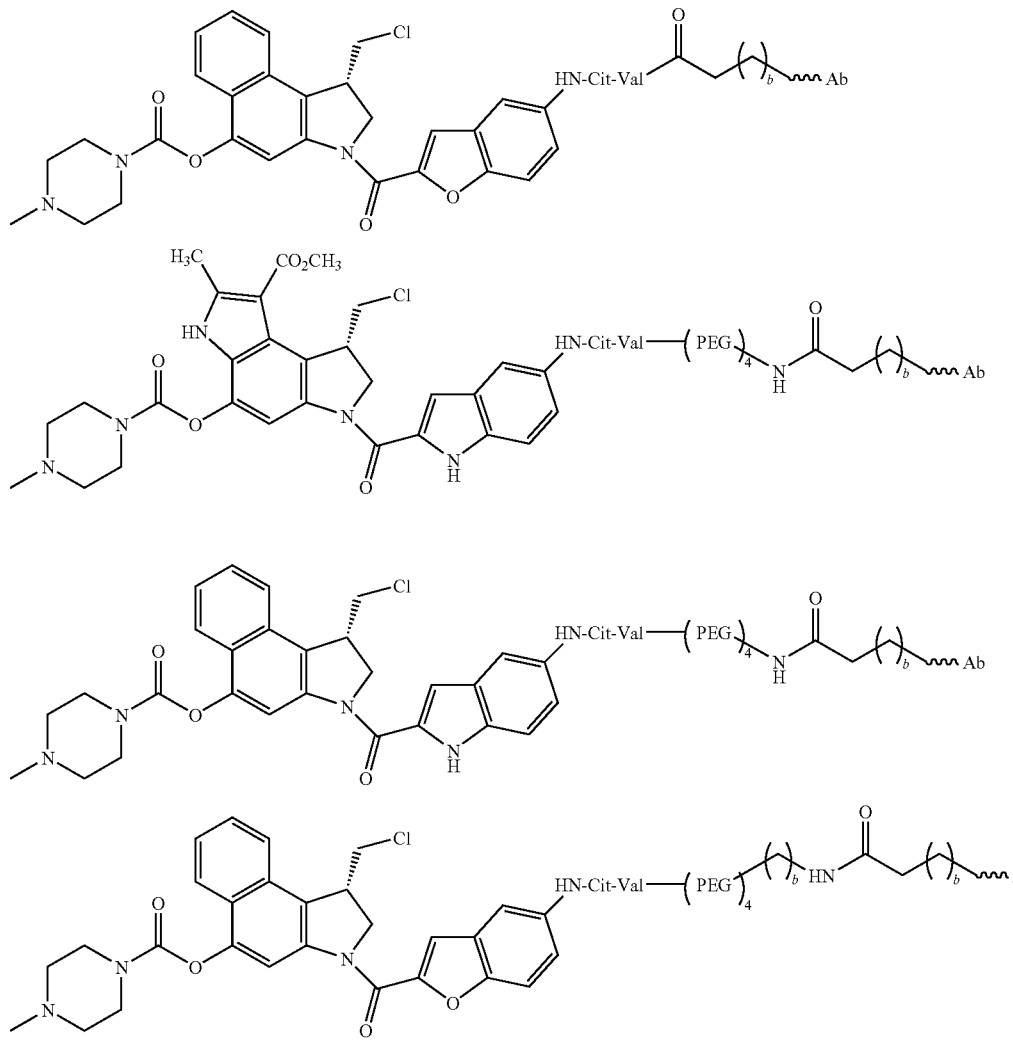

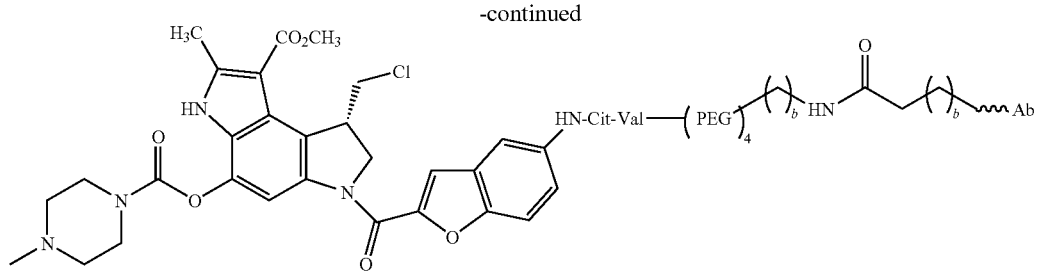
wherein each b is independently an integer from 0 to 20, and Ab is an antibody, or fragment thereof.
In yet other preferred embodiments, the invention provides a peptide linker conjugate selected from the following structures:
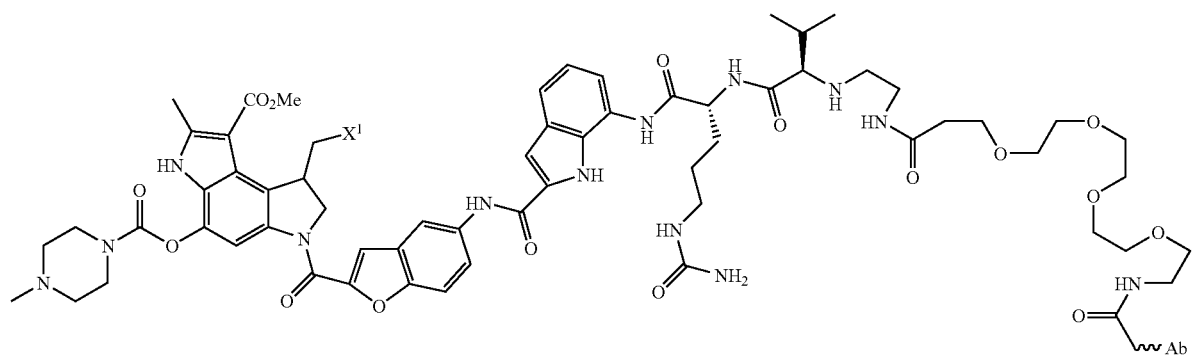
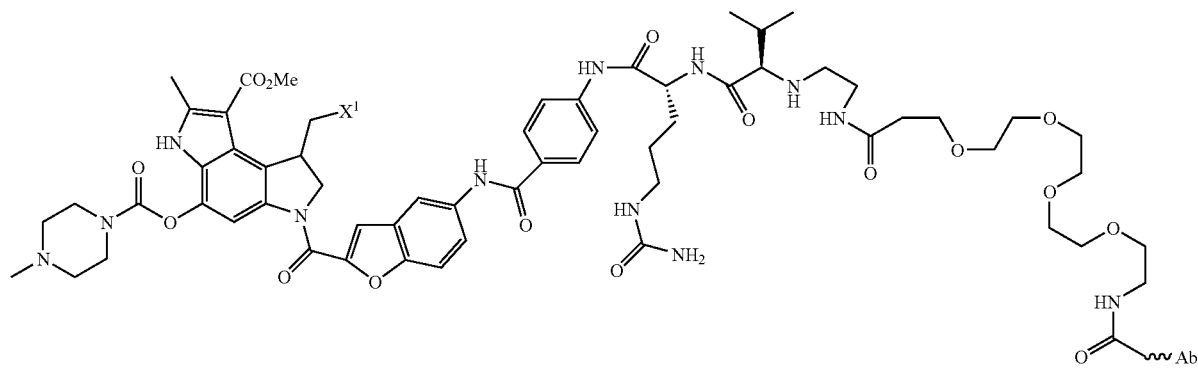
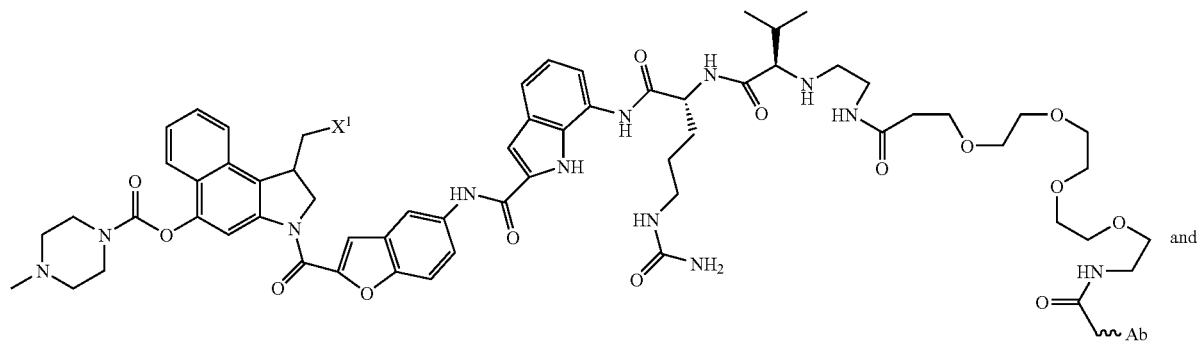

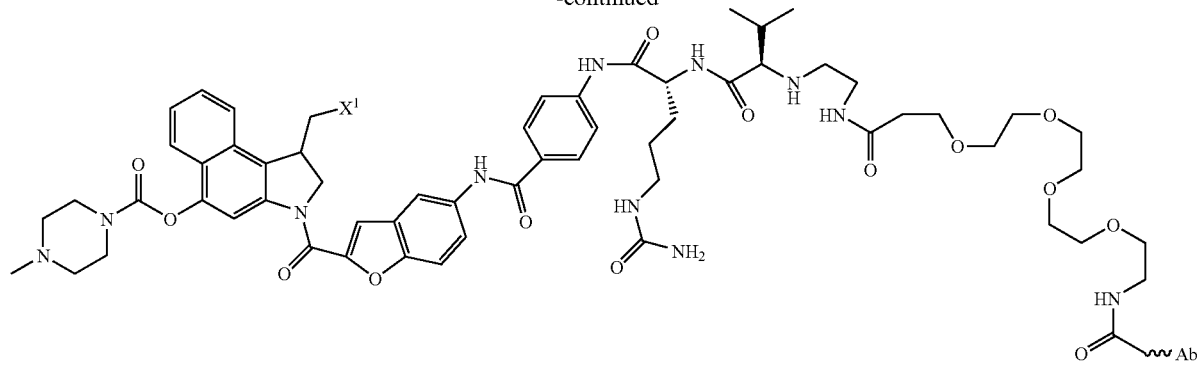
wherein $X^1$ is Cl or Br, and Ab is an antibody, or fragment thereof.
In still other embodiments, the invention provides a peptide linker conjugate selected from the following structures:
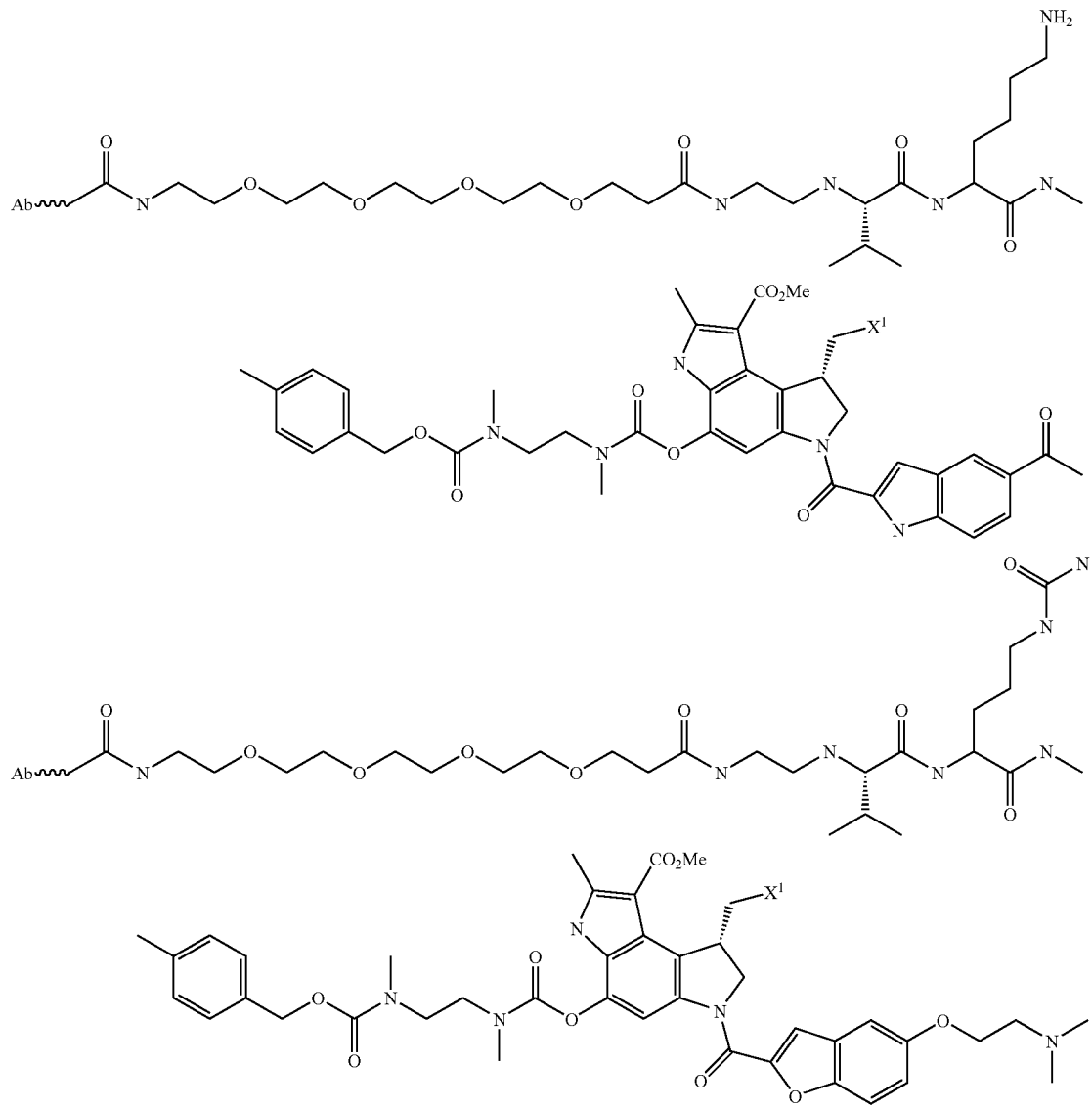

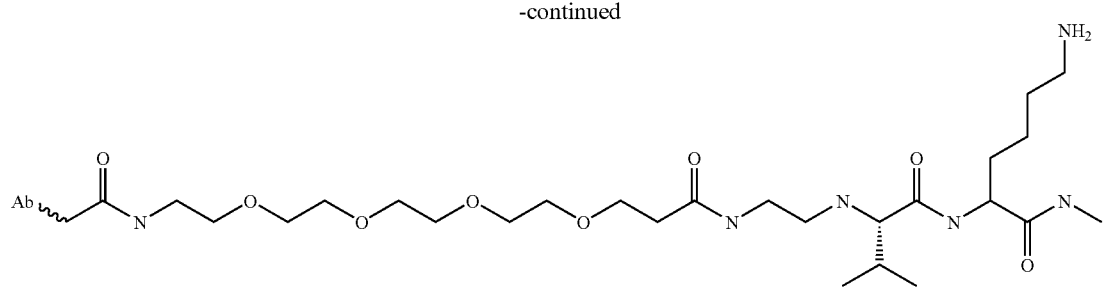
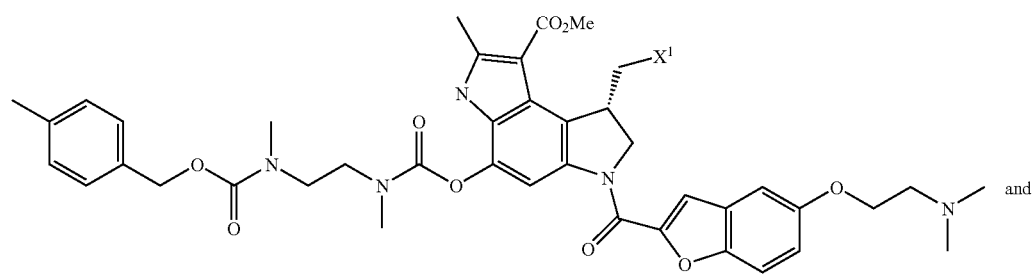
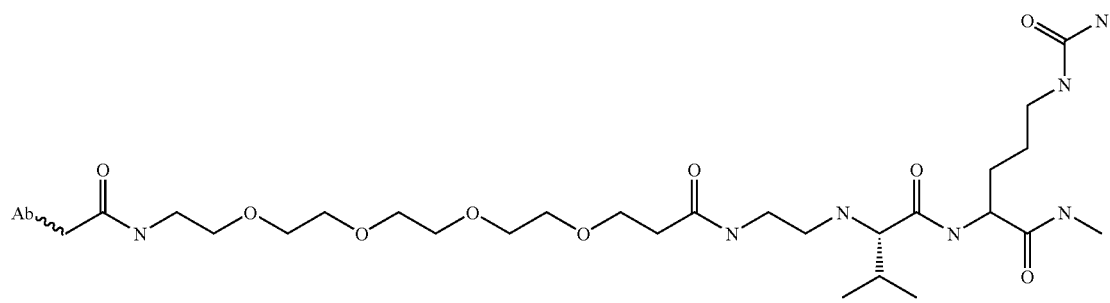
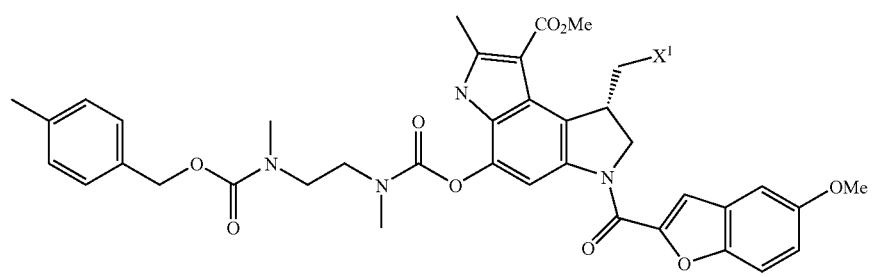
wherein $X^1$ is Cl or Br, and Ab is an antibody, or fragment thereof.
In still other embodiments, the invention provides a peptide linker conjugate having the following structure:
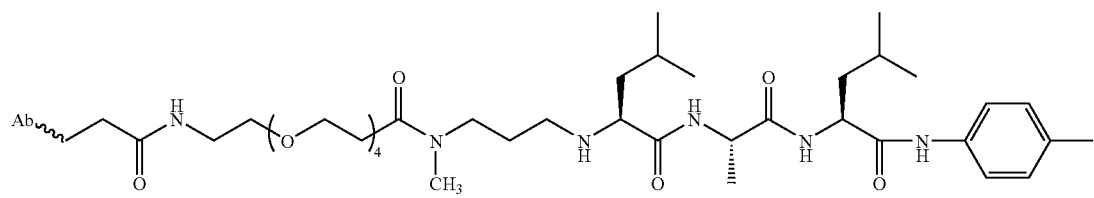

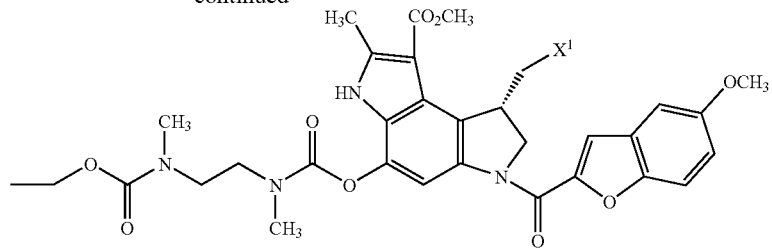
wherein $X^1$ is Cl or Br, and Ab is an antibody or fragment thereof.
B. Hydrazine Linker Conjugates
In a preferred embodiment, the invention provides a hydrazine linker conjugate having the structure:
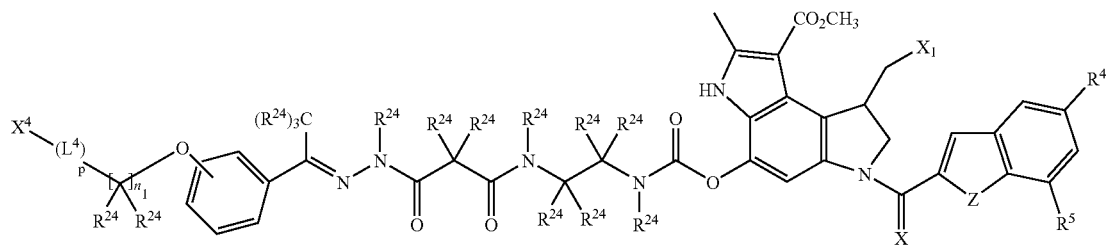
In another preferred embodiment, the invention provides a hydrazine linker conjugate having the structure:
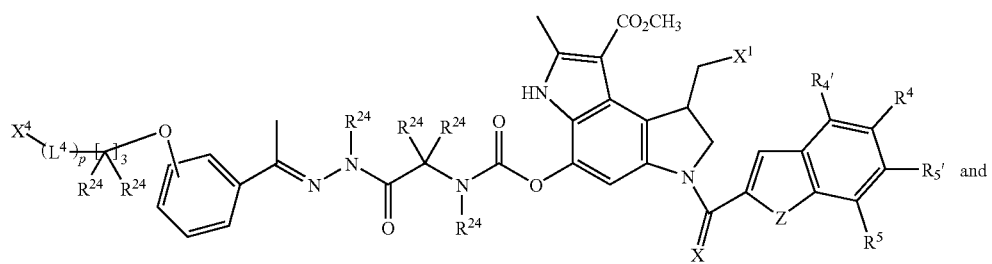
and
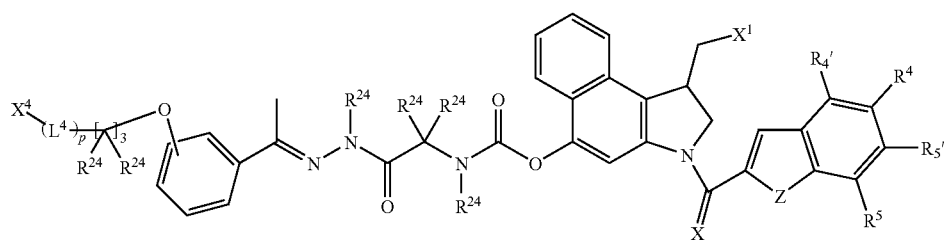

In yet other preferred embodiments, the invention provides a hydrazine linker conjugate having structure selected from:
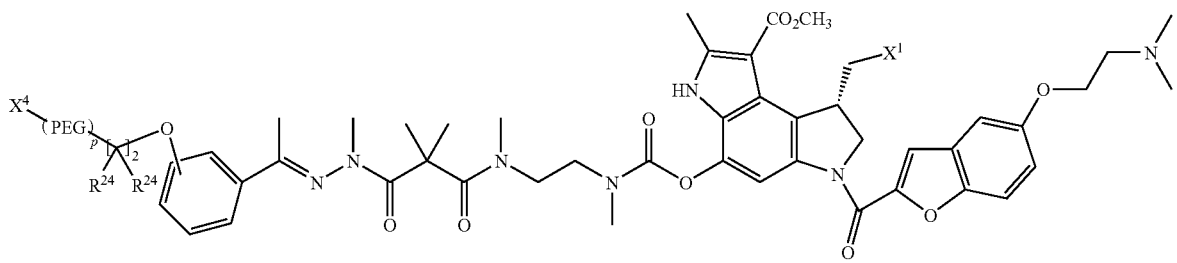
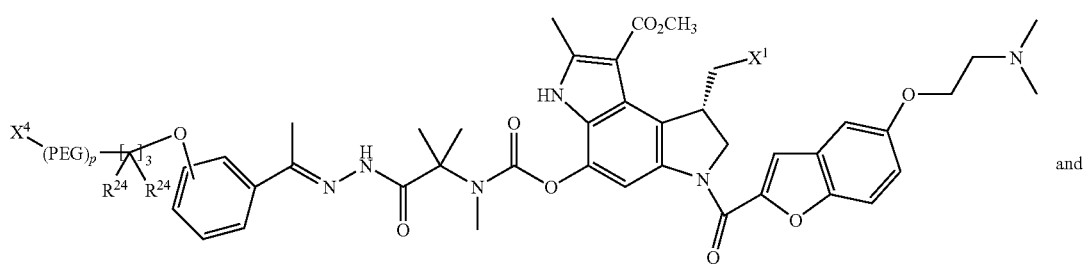
and
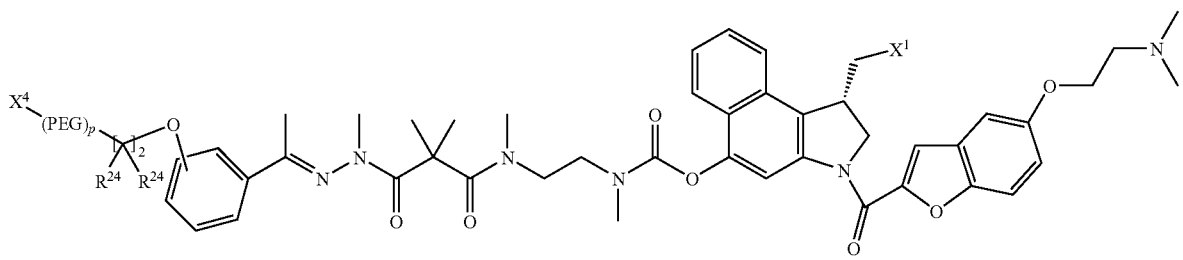
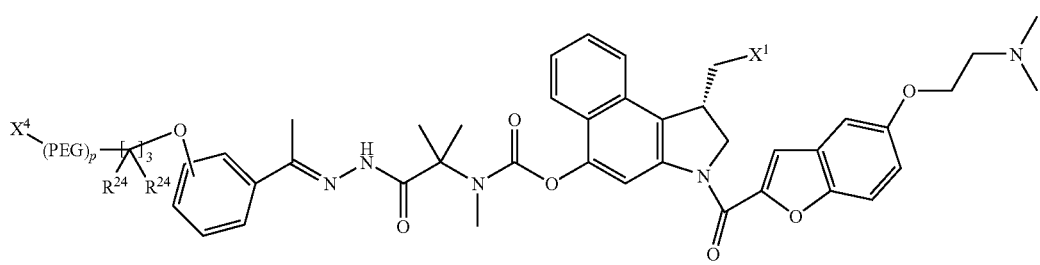
wherein PEG is a polyethylene glycol moiety and $X^1$ is Cl or Br.
In still other preferred embodiments, the invention provides a hydrazine linker conjugate selected from the following structures:

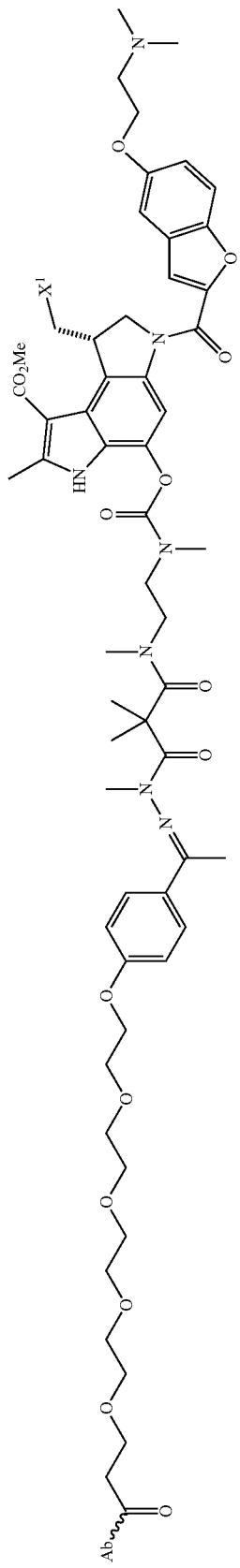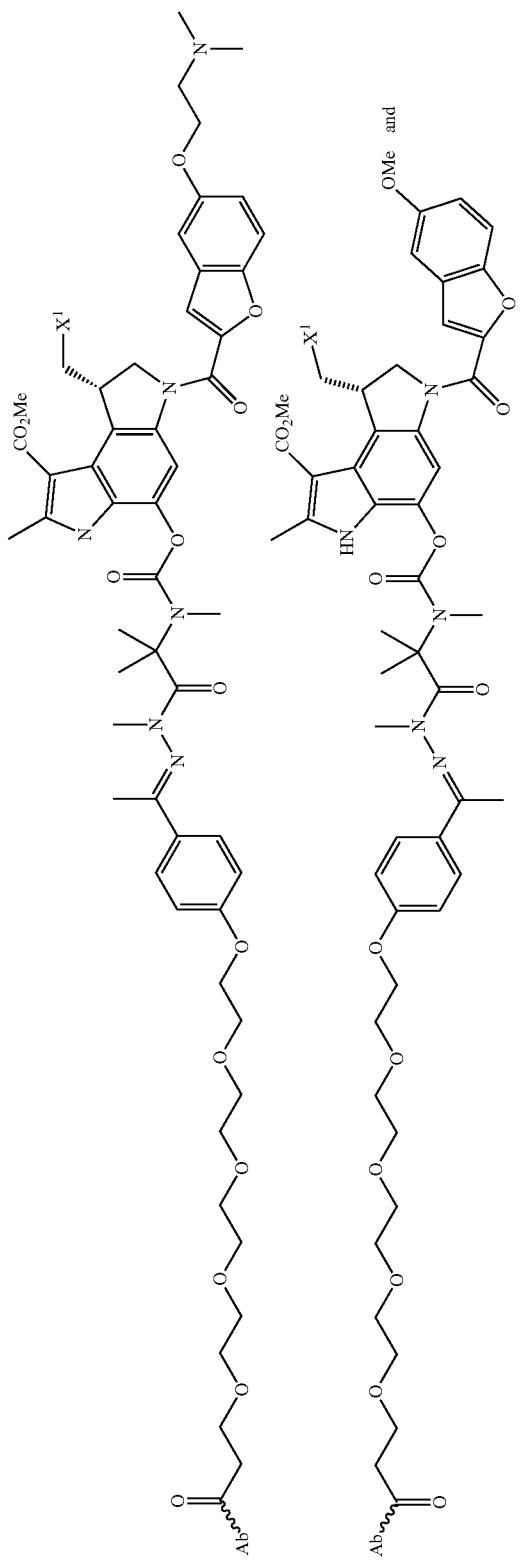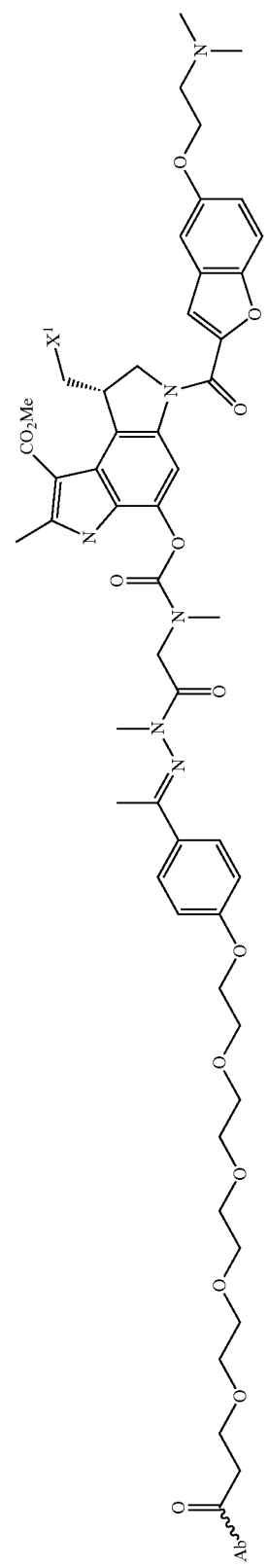

wherein $X^1$ is Cl or Br, and Ab is an antibody, or fragment thereof.
In yet another preferred embodiment, there is a hydrazine linker conjugate selected from the following structures:
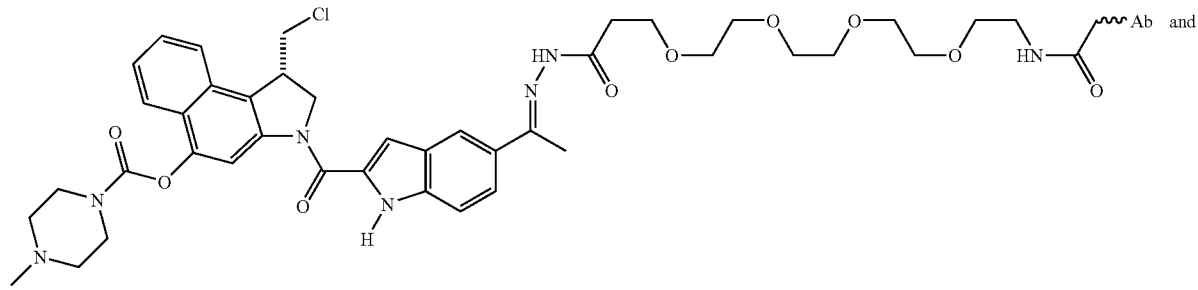
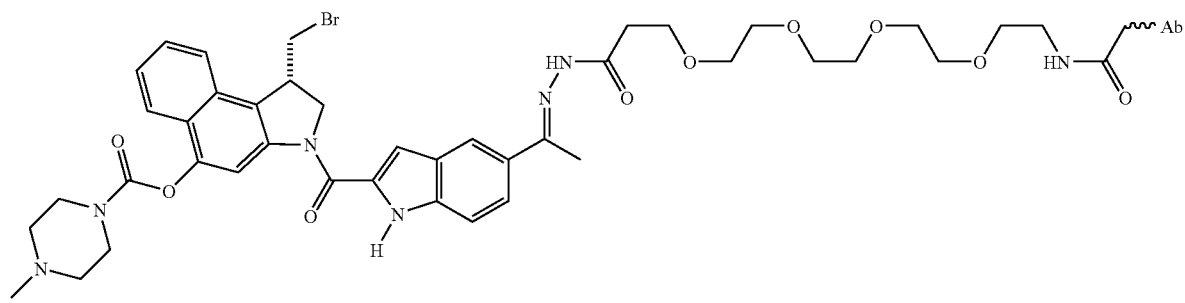
C. Disulfide Linker Conjugates
In a preferred embodiment, the invention provides a disulfide linker conjugate having the structure:
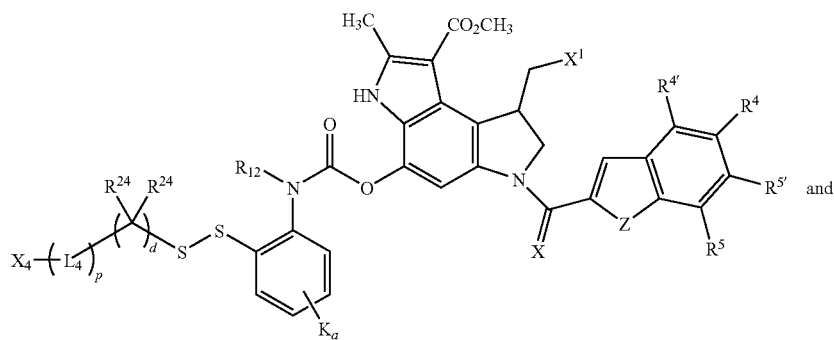
and
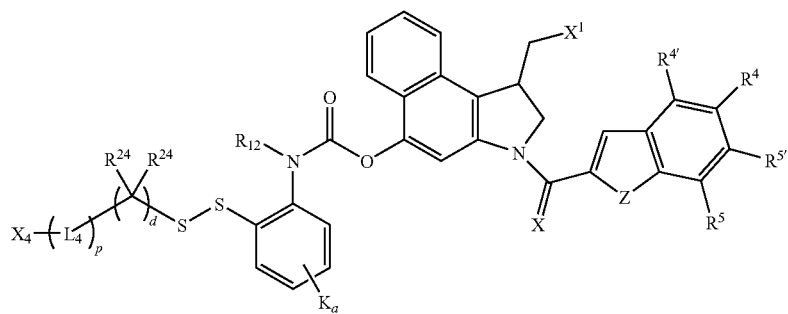

Non-limiting examples of such structures include the following:
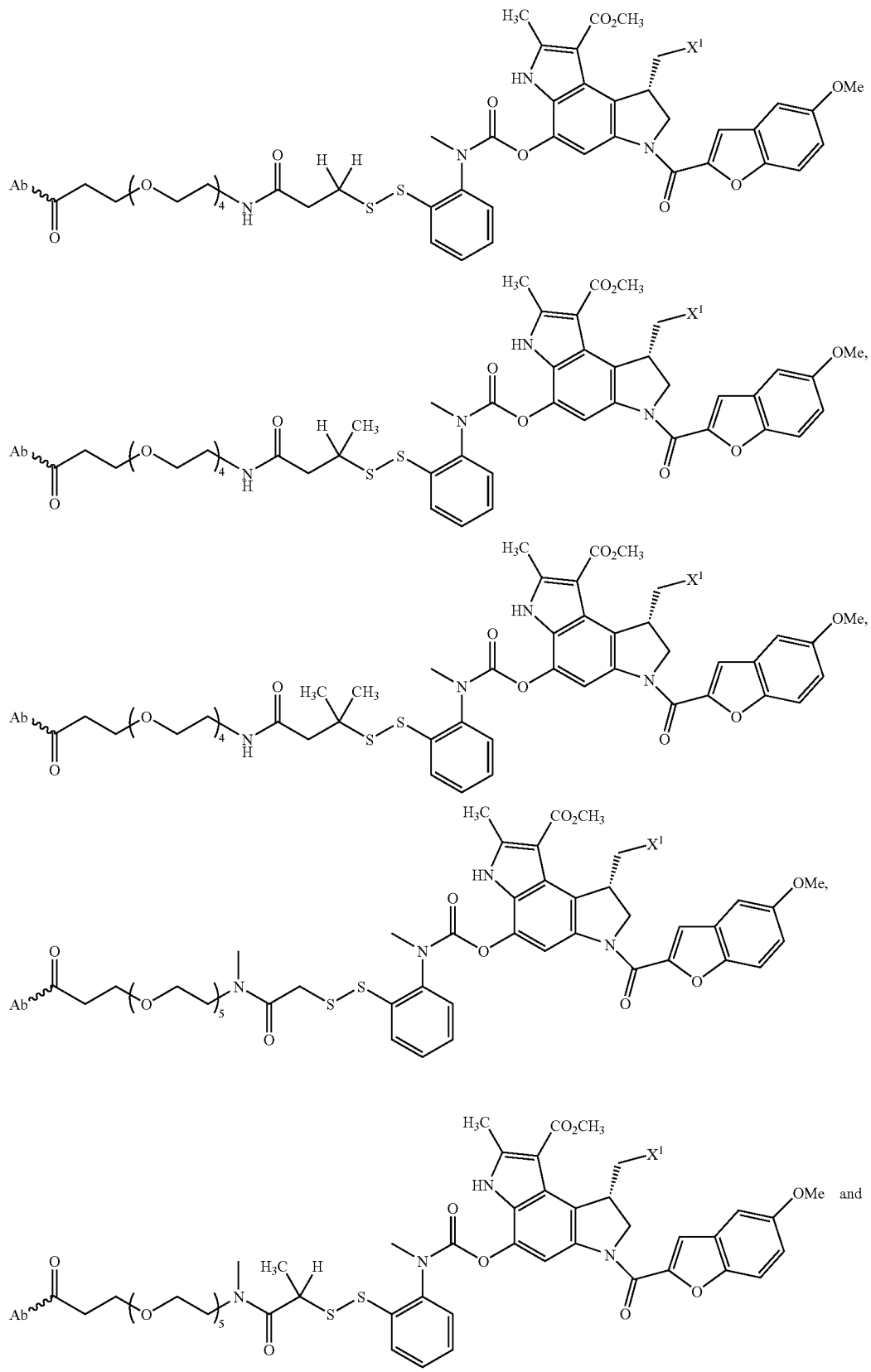

-continued

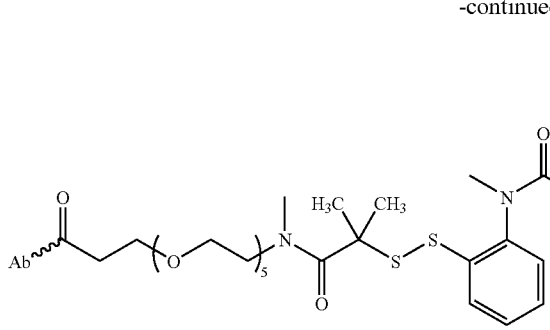 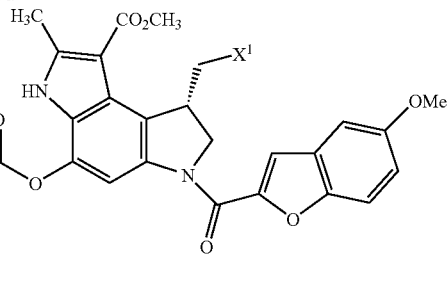

wherein $X^1$ is Cl or Br, and Ab is an antibody, or fragment thereof.

Ligands

The ligands of the current invention are depicted as "$X^4$". In this invention, $X^4$ represents a member selected from the group consisting of protected reactive functional groups, unprotected reactive functional groups, detectable labels, and targeting agents. Preferred ligands are targeting agents, such as antibodies and fragments thereof.

In a preferred embodiment, the group $X^4$ can be described as a member selected from $R^{29}$, $COOR^{29}$, $C(O)NR^{29}$, and $C(O)NNR^{29}$ wherein $R^{29}$ is a member selected from substituted or unsubstituted alkyl, substituted or unsubstituted heteroalkyl and substituted or unsubstituted heteroaryl. In yet another exemplary embodiment, $R^{29}$ is a member selected from H; OH; $NHNH_2$;

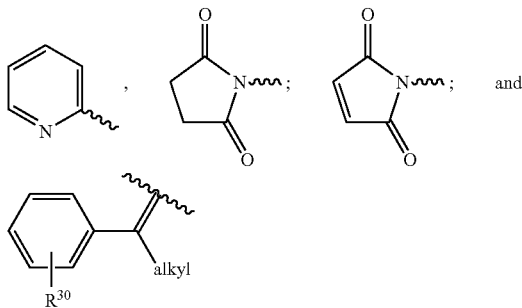

wherein $R^{30}$ represents substituted or unsubstituted alkyl terminated with a reactive functional group, substituted or unsubstituted heteroaryl terminated with a functional group. The above structures act as reactive protective groups that can be reacted with, for example, a side chain of an amino acid of a targeting agent, such as an antibody, to thereby link the targeting agent to the linker-drug moiety.

Targeting Agents

The linker arms and cytotoxins of the invention can be linked to targeting agents that selectively deliver a payload to a cell, organ or region of the body. Exemplary targeting agents such as antibodies (e.g., chimeric, humanized and human), ligands for receptors, lectins, saccharides, antibodies, and the like are recognized in the art and are useful without limitation in practicing the present invention. Other targeting agents include a class of compounds that do not include specific molecular recognition motifs include macromolecules such as poly(ethylene glycol), polysaccharide, polyamino acids and the like, which add molecular mass to the cytotoxin. The additional molecular mass affects the pharmacokinetics of the cytotoxin, e.g., serum half-life.

In an exemplary embodiment, the invention provides a cytotoxin, linker or cytotoxin-linker conjugate with a targeting agent that is a biomolecule, e.g., an antibody, receptor, peptide, lectin, saccharide, nucleic acid or a combination thereof. Routes to exemplary conjugates of the invention are set forth in the Schemes above.

Biomolecules useful in practicing the present invention can be derived from any source. The biomolecules can be isolated from natural sources or can be produced by synthetic methods. Proteins can be natural proteins or mutated proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal, but most preferably are monoclonal. Peptides and nucleic acids can be isolated from natural sources or can be wholly or partially synthetic in origin.

In a preferred embodiment, the targeting agent is an antibody, or antibody fragment, that is selected based on its specificity for an antigen expressed on a target cell, or at a target site, of interest. A wide variety of tumor-specific or other disease-specific antigens have been identified and antibodies to those antigens have been used or proposed for use in the treatment of such tumors or other diseases. The antibodies that are known in the art can be used in the conjugates of the invention, in particular for the treatment of the disease with which the target antigen is associated. Non-limiting examples of target antigens (and their associated diseases) to which an antibody-linker-drug conjugate of the invention can be targeted include: Her2 (breast cancer), CD20 (lymphomas), EGFR (solid tumors), CD22 (lymphomas, including non-Hodgkin's lymphoma), CD52 (chronic lymphocytic leukemia), CD33 (acute myelogenous leukemia), CD4 (lymphomas, autoimmune diseases, including rheumatoid arthritis), CD30 (lymphomas, including non-Hodgkin's lymphoma), Muc18 (melanoma), integrins (solid tumors), PSMA (prostate cancer, benign prostatic hyperplasia), CEA (colorectal cancer), CD11a (psoriasis), CD80 (psoriasis), CD23 (asthma), CD40L (immune thromobcytopenic purpura), CTLA4 (T cell lymphomas) and BLys (autoimmune diseases, including systemic lupus erythematosus).

In those embodiments wherein the recognition moiety is a protein or antibody, the protein can be tethered to a surface or a self assembled monolayer (SAM) component or connected through a spacer arm by any reactive peptide residue available on the surface of the protein. In preferred embodiments, the reactive groups are amines or carboxylates. In particularly preferred embodiments, the reactive groups are the ε-amine groups of lysine residues. Furthermore, these molecules can be adsorbed onto the surface of the substrate or SAM by non-specific interactions (e.g., chemisorption, physisorption).

Recognition moieties which are antibodies can be used to recognize analytes which are proteins, peptides, nucleic acids, saccharides or small molecules such as drugs, herbicides, pesticides, industrial chemicals and agents of war. Methods of raising antibodies for specific molecules are well-known to those of skill in the art. See, U.S. Pat. No. 5,147,786, issued to Feng et al. on Sep. 15, 1992; U.S. Pat. No. 5,334, 528, issued to Stanker et al. on Aug. 2, 1994; U.S. Pat. No. 5,686,237, issued to Al-Bayati, M. A. S. on Nov. 11, 1997; and U.S. Pat. No. 5,573,922, issued to Hoess et al. on Nov. 12, 1996. Methods for attaching antibodies to surfaces are also art-known. See, Delamarche et al. *Langmuir* 12:1944-1946 (1996).

Targeting agents can be attached to the linkers of the invention by any available reactive group. For example, peptides can be attached through an amine, carboxyl, sulfhydryl, or hydroxyl group. Such a group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al. *Nucleic Acids Res.* 24:3031-3039 (1996).

When the peptide or nucleic acid is a fully or partially synthetic molecule, a reactive group or masked reactive group can be incorporated during the process of the synthesis. Many derivatized monomers appropriate for reactive group incorporation in both peptides and nucleic acids are know to those of skill in the art. See, for example, THE PEPTIDES: ANALYSIS, SYNTHESIS, BIOLOGY, Vol. 2: "Special Methods in Peptide Synthesis," Gross, E. and Melenhofer, J., Eds., Academic Press, New York (1980). Many useful monomers are commercially available (Bachem, Sigma, etc.). This masked group can then be unmasked following the synthesis, at which time it becomes available for reaction with a component of a compound of the invention.

Exemplary nucleic acid targeting agents include aptamers, antisense compounds, and nucleic acids that form triple helices. Typically, a hydroxyl group of a sugar residue, an amino group from a base residue, or a phosphate oxygen of the nucleotide is utilized as the needed chemical functionality to couple the nucleotide-based targeting agent to the cytotoxin. However, one of skill in the art will readily appreciate that other "non-natural" reactive functionalities can be appended to a nucleic acid by conventional techniques. For example, the hydroxyl group of the sugar residue can be converted to a mercapto or amino group using techniques well known in the art.

Aptamers (or nucleic acid antibody) are single- or double-stranded DNA or single-stranded RNA molecules that bind specific molecular targets. Generally, aptamers function by inhibiting the actions of the molecular target, e.g., proteins, by binding to the pool of the target circulating in the blood. Aptamers possess chemical functionality and thus, can covalently bond to cytotoxins, as described herein.

Although a wide variety of molecular targets are capable of forming non-covalent but specific associations with aptamers, including small molecules drugs, metabolites, cofactors, toxins, saccharide-based drugs, nucleotide-based drugs, glycoproteins, and the like, generally the molecular target will comprise a protein or peptide, including serum proteins, kinins, eicosanoids, cell surface molecules, and the like.

Examples of aptamers include Gilead's antithrombin inhibitor GS 522 and its derivatives (Gilead Science, Foster City, Calif.). See also, Macaya et al. *Proc. Natl. Acad. Sci. USA* 90:3745-9 (1993); Bock et al. *Nature (London)* 355:564-566 (1992) and Wang et al. Biochem. 32:1899-904 (1993).

Aptamers specific for a given biomolecule can be identified using techniques known in the art. See, e.g., Toole et al. (1992) PCT Publication No. WO 92/14843; Tuerk and Gold (1991) PCT Publication No. WO 91/19813; Weintraub and Hutchinson (1992) PCT Publication No. 92/05285; and Ellington and Szostak, *Nature* 346:818 (1990). Briefly, these techniques typically involve the complexation of the molecular target with a random mixture of oligonucleotides. The aptamer-molecular target complex is separated from the uncomplexed oligonucleotides. The aptamer is recovered from the separated complex and amplified. This cycle is repeated to identify those aptamer sequences with the highest affinity for the molecular target.

For diseases that result from the inappropriate expression of genes, specific prevention or reduction of the expression of such genes represents an ideal therapy. In principle, production of a particular gene product may be inhibited, reduced or shut off by hybridization of a single-stranded deoxynucleotide or ribodeoxynucleotide complementary to an accessible sequence in the mRNA, or a sequence within the transcript that is essential for pre-mRNA processing, or to a sequence within the gene itself. This paradigm for genetic control is often referred to as antisense or antigene inhibition. Additional efficacy is imparted by the conjugation to the nucleic acid of an alkylating agent, such as those of the present invention.

Antisense compounds are nucleic acids designed to bind and disable or prevent the production of the mRNA responsible for generating a particular protein. Antisense compounds include antisense RNA or DNA, single or double stranded, oligonucleotides, or their analogs, which can hybridize specifically to individual mRNA species and prevent transcription and/or RNA processing of the mRNA species and/or translation of the encoded polypeptide and thereby effect a reduction in the amount of the respective encoded polypeptide. Ching et al. *Proc. Natl. Acad. Sci. U.S.A.* 86:10006-10010 (1989); Broder et al. *Ann. Int. Med.* 113:604-618 (1990); Loreau et al. *FEBS Letters* 274:53-56 (1990); Holcenberg et al. WO91/11535; WO91/09865; WO91/04753; WO90/13641; WO 91/13080, WO 91/06629, and EP 386563). Due to their exquisite target sensitivity and selectivity, antisense oligonucleotides are useful for delivering therapeutic agents, such as the cytotoxins of the invention to a desired molecular target.

Others have reported that nucleic acids can bind to duplex DNA via triple helix formation and inhibit transcription and/or DNA synthesis. Triple helix compounds (also referred to as triple strand drugs) are oligonucleotides that bind to sequences of double-stranded DNA and are intended to inhibit selectively the transcription of disease-causing genes, such as viral genes, e.g., HIV and herpes simplex virus, and oncogenes, i.e., they stop protein production at the cell nucleus. These drugs bind directly to the double stranded DNA in the cell's genome to form a triple helix and prevent the cell from making a target protein. See, e.g., PCT publications Nos. WO 92/10590, WO 92/09705, WO91/06626, and U.S. Pat. No. 5,176,996. Thus, the cytotoxins of the present invention are also conjugated to nucleic acid sequences that form triple helices.

The site specificity of nucleic acids (e.g., antisense compounds and triple helix drugs) is not significantly affected by modification of the phosphodiester linkage or by chemical modification of the oligonucleotide terminus. Consequently, these nucleic acids can be chemically modified; enhancing the overall binding stability, increasing the stability with respect to chemical degradation, increasing the rate at which the oligonucleotides are transported into cells, and conferring chemical reactivity to the molecules. The general approach to constructing various nucleic acids useful in antisense therapy has been reviewed by van der Krol et al., *Biotechniques* 6:958-976 (1988) and Stein et al. *Cancer Res.* 48:2659-2668 (1988). Therefore, in an exemplary embodiment, the cytotoxins of the invention are conjugated to a nucleic acid by modification of the phosphodiester linkage.

Moreover, aptamers, antisense compounds and triple helix drugs bearing cytotoxins of the invention can also can include nucleotide substitutions, additions, deletions, or transpositions, so long as specific hybridization to or association with the relevant target sequence is retained as a functional property of the oligonucleotide. For example, some embodiments will employ phosphorothioate analogs which are more resistant to degradation by nucleases than their naturally occurring phosphate diester counterparts and are thus expected to have a higher persistence in vivo and greater potency (see, e.g., Campbell et al., *J. Biochem. Biophys. Methods* 20:259-267 (1990)). Phosphoramidate derivatives of oligonucleotides also are known to bind to complementary polynucleotides and have the additional capability of accommodating covalently attached ligand species and will be amenable to the methods of the present invention. See, for example, Froehler et al., *Nucleic Acids Res.* 16(11):4831 (1988).

In some embodiments the aptamers, antisense compounds and triple helix drugs will comprise O-methylribonucleotides (EP Publication No. 360609). Chimeric oligonucleotides may also be used (Dagle et al., *Nucleic Acids Res.* 18: 4751 (1990)). For some applications, antisense oligonucleotides and triple helix may comprise polyamide nucleic acids (Nielsen et al., Science 254: 1497 (1991) and PCT publication No. WO 90/15065) or other cationic derivatives (Letsinger et al., *J. Am. Chem. Soc.* 110: 4470-4471 (1988)). Other applications may utilize oligonucleotides wherein one or more of the phosphodiester linkages has been substituted with an isosteric group, such as a 2-4 atom long internucleoside linkage as described in PCT publication Nos. WO 92/05186 and 91/06556, or a formacetal group (Matteucci et al., *J. Am. Chem. Soc.* 113: 7767-7768 (1991)) or an amide group (Nielsen et al., *Science* 254: 1497-1500 (1991)).

In addition, nucleotide analogs, for example wherein the sugar or base is chemically modified, can be employed in the present invention. "Analogous" forms of purines and pyrimidines are those generally known in the art, many of which are used as chemotherapeutic agents. An exemplary but not exhaustive list includes 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyluracil, 5-methoxyaminomethyl-2-thiouracil, β-D-mannosylqueosine, 5' methoxycarbonylmethyluracil, 5-methoxyuracil, 2-methylthio-$N^6$-isopentenyladenine, uracil-5-oxyacetic acid methylester, uracil-5-oxyacetic acid (v), wybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid (v), pseudouracil, queosine, 2-thiocytosine, and 2,6-diaminopurine. In addition, the conventional bases by halogenated bases. Furthermore, the 2'-furanose position on the base can have a non-charged bulky group substitution. Examples of non-charged bulky groups include branched alkyls, sugars and branched sugars.

Terminal modification also provides a useful procedure to conjugate the cytotoxins to the nucleic acid, modify cell type specificity, pharmacokinetics, nuclear permeability, and absolute cell uptake rate for oligonucleotide pharmaceutical agents. For example, an array of substitutions at the 5' and 3' ends to include reactive groups are known, which allow covalent attachment of the cytotoxins. See, e.g., OLIGODEOXYNUCLEOTIDES: ANTISENSE INHIBITORS OF GENE EXPRESSION, (1989) Cohen, Ed., CRC Press; PROSPECTS FOR ANTISENSE NUCLEIC ACID THERAPEUTICS FOR CANCER AND AIDS, (1991), Wickstrom, Ed., Wiley-Liss; GENE REGULATION: BIOLOGY OF ANTISENSE RNA AND DNA, (1992) Erickson and Izant, Eds., Raven Press; and ANTISENSE RNA AND DNA, (1992), Murray, Ed., Wiley-Liss. For general methods relating to antisense compounds, see, ANTISENSE RNA AND DNA, (1988), D. A. Melton, Ed., Cold Spring Harbor Laboratory, Cold Spring Harbor, N.Y.).

Detectable Labels

The particular label or detectable group used in conjunction with the compounds and methods of the invention is generally not a critical aspect of the invention, as long as it does not significantly interfere with the activity or utility of the compound of the invention. The detectable group can be any material having a detectable physical or chemical property. Such detectable labels have been well developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., 3H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to a compound of the invention according to methods well known in the art. As indicated above, a wide variety of labels may be used, with the choice of label depending on sensitivity required, ease of conjugation with the compound, stability requirements, available instrumentation, and disposal provisions.

When the compound of the invention is conjugated to a detectable label, the label is preferably a member selected from the group consisting of radioactive isotopes, fluorescent agents, fluorescent agent precursors, chromophores, enzymes and combinations thereof. Methods for conjugating various groups to antibodies are well known in the art. For example, a detectable label that is frequently conjugated to an antibody is an enzyme, such as horseradish peroxidase, alkaline phosphatase, β-galactosidase, and glucose oxidase.

Non-radioactive labels are often attached by indirect means. Generally, a ligand molecule (e.g., biotin) is covalently bound to a component of the conjugate. The ligand then binds to another molecules (e.g., streptavidin) molecule, which is either inherently detectable or covalently bound to a signal system, such as a detectable enzyme, a fluorescent compound, or a chemiluminescent compound.

Components of the conjugates of the invention can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Fluorescent labels are presently preferred as they have the advantage of requiring few precautions in handling, and being amenable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Many fluorescent labels are commercially available from the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

In addition to small molecule fluorophores, naturally occurring fluorescent proteins and engineered analogues of such proteins are useful in the present invention. Such proteins include, for example, green fluorescent proteins of cnidarians (Ward et al., *Photochem. Photobiol.* 35:803-808 (1982); Levine et al., *Comp. Biochem. Physiol.*, 72B:77-85 (1982)), yellow fluorescent protein from *Vibrio fischeri* strain (Baldwin et al., *Biochemistry* 29:5509-15 (1990)), Peridininchlorophyll from the dinoflagellate *Symbiodinium* sp. (Morris et al., *Plant Molecular Biology* 24:673:77 (1994)), phycobiliproteins from marine cyanobacteria, such as *Synechococcus*, e.g., phycoerythrin and phycocyanin (Wilbanks et al., *J. Biol. Chem.* 268:1226-35 (1993)), and the like.

Generally, prior to forming the linkage between the cytotoxin and the targeting (or other) agent, and optionally, the spacer group, at least one of the chemical functionalities will be activated. One skilled in the art will appreciate that a variety of chemical functionalities, including hydroxy, amino, and carboxy groups, can be activated using a variety of standard methods and conditions. For example, a hydroxyl group of the cytotoxin or targeting agent can be activated through treatment with phosgene to form the corresponding chloroformate, or p-nitrophenylchloroformate to form the corresponding carbonate.

In an exemplary embodiment, the invention makes use of a targeting agent that includes a carboxyl functionality. Carboxyl groups may be activated by, for example, conversion to the corresponding acyl halide or active ester. This reaction may be performed under a variety of conditions as illustrated in March, supra pp. 388-89. In an exemplary embodiment, the acyl halide is prepared through the reaction of the carboxyl-containing group with oxalyl chloride. The activated agent is reacted with a cytotoxin or cytotoxin-linker arm combination to form a conjugate of the invention. Those of skill in the art will appreciate that the use of carboxyl-containing targeting agents is merely illustrative, and that agents having many other functional groups can be conjugated to the linkers of the invention.

Reactive Functional Groups

For clarity of illustration the succeeding discussion focuses on the conjugation of a cytotoxin of the invention to a targeting agent. The focus exemplifies one embodiment of the invention from which, others are readily inferred by one of skill in the art. No limitation of the invention is implied, by focusing the discussion on a single embodiment.

Exemplary compounds of the invention bear a reactive functional group, which is generally located on a substituted or unsubstituted alkyl or heteroalkyl chain, allowing their facile attachment to another species. A convenient location for the reactive group is the terminal position of the chain.

Reactive groups and classes of reactions useful in practicing the present invention are generally those that are well known in the art of bioconjugate chemistry. The reactive functional group may be protected or unprotected, and the protected nature of the group may be changed by methods known in the art of organic synthesis. Currently favored classes of reactions available with reactive cytotoxin analogues are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Exemplary reaction types include the reaction of carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters. Hydroxyl groups can be converted to esters, ethers, aldehydes, etc. Haloalkyl groups are converted to new species by reaction with, for example, an amine, a carboxylate anion, thiol anion, carbanion, or an alkoxide ion. Dienophile (e.g., maleimide) groups participate in Diels-Alder. Aldehyde or ketone groups can be converted to imines, hydrazones, semicarbazones or oximes, or via such mechanisms as Grignard addition or alkyllithium addition. Sulfonyl halides react readily with amines, for example, to form sulfonamides. Amine or sulfhydryl groups are, for example, acylated, alkylated or oxidized. Alkenes, can be converted to an array of new species using cycloadditions, acylation, Michael addition, etc. Epoxides react readily with amines and hydroxyl compounds.

One skilled in the art will readily appreciate that many of these linkages may be produced in a variety of ways and using a variety of conditions. For the preparation of esters, see, e.g., March supra at 1157; for thioesters, see, March, supra at 362-363, 491, 720-722, 829, 941, and 1172; for carbonates, see, March, supra at 346-347; for carbamates, see, March, supra at 1156-57; for amides, see, March supra at 1152; for ureas and thioureas, see, March supra at 1174; for acetals and ketals, see, Greene et al. supra 178-210 and March supra at 1146; for acyloxyalkyl derivatives, see, PRODRUGS: TOPICAL AND OCULAR DRUG DELIVERY, K. B. Sloan, ed., Marcel Dekker, Inc., New York, 1992; for enol esters, see, March supra at 1160; for N-sulfonylimidates, see, Bundgaard et al., *J. Med. Chem.*, 31:2066 (1988); for anhydrides, see, March supra at 355-56, 636-37, 990-91, and 1154; for N-acylamides, see, March supra at 379; for N-Mannich bases, see, March supra at 800-$O_2$, and 828; for hydroxymethyl ketone esters, see, Petracek et al. *Annals NY Acad. Sci.*, 507:353-54 (1987); for disulfides, see, March supra at 1160; and for phosphonate esters and phosphonamidates.

The reactive functional groups can be unprotected and chosen such that they do not participate in, or interfere with, the reactions. Alternatively, a reactive functional group can be protected from participating in the reaction by the presence of a protecting group. Those of skill in the art will understand how to protect a particular functional group from interfering with a chosen set of reaction conditions. For examples of useful protecting groups, See Greene et al., PROTECTIVE GROUPS IN ORGANIC SYNTHESIS, John Wiley & Sons, New York, 1991.

Typically, the targeting agent is linked covalently to a cytotoxin using standard chemical techniques through their respective chemical functionalities. Optionally, the linker or agent is coupled to the agent through one or more spacer groups. The spacer groups can be equivalent or different when used in combination.

Generally, prior to forming the linkage between the cytotoxin and the reactive functional group, and optionally, the spacer group, at least one of the chemical functionalities will be activated. One skilled in the art will appreciate that a variety of chemical functionalities, including hydroxy, amino, and carboxy groups, can be activated using a variety of standard methods and conditions. In an exemplary embodiment, the invention comprises a carboxyl functionality as a reactive functional group. Carboxyl groups may be activated as described hereinabove.

Pharmaceutical Formulations and Administration

In another preferred embodiment, the present invention provides a pharmaceutical formulation comprising a compound of the invention and a pharmaceutically acceptable carrier.

The compounds described herein including pharmaceutically acceptable carriers such as addition salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections. Preferably, the conjugates of the invention comprising an antibody or antibody fragment as the targeting moiety are administered parenterally, more preferably intravenously.

As used herein, the terms "administering" or "administration" are intended to encompass all means for directly and indirectly delivering a compound to its intended site of action.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to patients suffering from a disease state caused by an organism that relies on an autoinducer, the compounds of the invention can be administered in cocktails containing agents used to treat the pain, infection and other symptoms and side effects commonly associated with the disease. Such agents include, e.g., analgesics, antibiotics, etc.

When administered to a patient undergoing cancer treatment, the compounds may be administered in cocktails containing anti-cancer agents and/or supplementary potentiating agents. The compounds may also be administered in cocktails containing agents that treat the side-effects of radiation therapy, such as anti-emetics, radiation protectants, etc.

Supplementary potentiating agents that can be co-administered with the compounds of the invention include, e.g., tricyclic anti-depressant drugs (e.g., imipramine, desipramine, amitriptyline, clomipramine, trimipramine, doxepin, nortriptyline, protriptyline, amoxapine and maprotiline); non-tricyclic and anti-depressant drugs (e.g., sertraline, trazodone and citalopram); $Ca^{+2}$ antagonists (e.g., verapamil, nifedipine, nitrendipine and caroverine); amphotericin; triparanol analogues (e.g., tamoxifen); antiarrhythmic drugs (e.g., quinidine); antihypertensive drugs (e.g., reserpine); thiol depleters (e.g., buthionine and sulfoximine); and calcium leucovorin.

The active compound(s) of the invention are administered per se or in the form of a pharmaceutical composition wherein the active compound(s) is in admixture with one or more pharmaceutically acceptable carriers, excipients or diluents. Pharmaceutical compositions for use in accordance with the present invention are typically formulated in a conventional manner using one or more physiologically acceptable carriers comprising excipients and auxiliaries, which facilitate processing of the active compounds into preparations which, can be used pharmaceutically. Proper formulation is dependent upon the route of administration chosen.

For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired. to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Injection is a preferred method of administration for the compositions of the current invention. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions. For injection, the agents of the invention may be formulated in aqueous solutions, preferably in physiologically compatible buffers such as Hanks's solution, Ringer's solution, or physiological saline buffer.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

A preferred pharmaceutical composition is a composition formulated for injection such as intravenous injection and includes about 0.01% to about 100% by weight of the drug-ligand conjugate, based upon 100% weight of total pharmaceutical composition. The drug-ligand conjugate may be an antibody-cytotoxin conjugate where the antibody has been selected to target a particular cancer.

Libraries

Also within the scope of the present invention are libraries of the cytotoxin, cytotoxin-linker and agent-linker conjugates of the cytotoxins and linkers of the invention. Exemplary libraries include at least 10 compounds, more preferably at least 100 compound, even more preferably at least 1000 compounds and still more preferably at least 100,000 compounds. The libraries in a form that is readily queried for a particular property, e.g., cytotoxicity, cleavage of a linker by an enzyme, or other cleavage reagent. Exemplary forms include chip formats, microarrays, and the like.

Parallel, or combinatorial, synthesis has as its primary objective the generation of a library of diverse molecules which all share a common feature, referred to throughout this description as a scaffold. By substituting different moieties at each of the variable parts of the scaffold molecule, the amount of space explorable in a library grows. Theories and modern medicinal chemistry advocate the concept of occupied space as a key factor in determining the efficacy of a given compound against a given biological target. By creating a diverse library of molecules, which explores a large percentage of the targeted space, the odds of developing a highly efficacious lead compound increase dramatically.

Parallel synthesis is generally conducted on a solid phase support, such as a polymeric resin. The scaffold, or other suitable intermediate is cleavably tethered to the resin by a chemical linker. Reactions are carried out to modify the scaffold while tethered to the particle. Variations in reagents and/or reaction conditions produce the structural diversity, which is the hallmark of each library.

Parallel synthesis of "small" molecules (non-oligomers with a molecular weight of 200-1000) was rarely attempted prior to 1990. See, for example, Camps. et al., *Annaks de Quimica,* 70: 848 (1990). Recently, Ellmann disclosed the solid phase-supported parallel (also referred to as "combinatorial") synthesis of eleven benzodiazepine analogs along with some prostaglandins and beta-turn mimetics. These disclosures are exemplified in U.S. Pat. No. 5,288,514. Another relevant disclosure of parallel synthesis of small molecules may be found in U.S. Pat. No. 5,324,483. This patent discloses the parallel synthesis of between 4 and 40 compounds in each of sixteen different scaffolds. Chen et al. have also applied organic synthetic strategies to develop non-peptide libraries synthesized using multi-step processes on a polymer support. (Chen et al., *J. Am. Chem. Soc.,* 116: 2661-2662 (1994)).

Once a library of unique compounds is prepared, the preparation of a library of immunoconjugates, or antibodies can be prepared using the library of autoinducers as a starting point and using the methods described herein.

Kits

In another aspect, the present invention provides kits containing one or more of the compounds or compositions of the invention and directions for using the compound or composition. In an exemplary embodiment, the invention provides a kit for conjugating a linker arm of the invention to another molecule. The kit includes the linker, and directions for attaching the linker to a particular functional group. The kit may also include one or more of a cytotoxic drug, a targeting agent, a detectable label, pharmaceutical salts or buffers. The kit may also include a container and optionally one or more vial, test tube, flask, bottle, or syringe. Other formats for kits will be apparent to those of skill in the art and are within the scope of the present invention.

Purification

In another exemplary embodiment, the present invention provides a method for isolating a molecular target for a ligand-cytotoxin of the invention, which binds to the ligand $X^4$. The method preferably comprises, contacting a cellular preparation that includes the target with an immobilized compound, thereby forming a complex between the receptor and the immobilized compound.

The cytotoxin of the invention can be immobilized on an affinity support by any art-recognized means. Alternatively, the cytotoxin can be immobilized using one or more of the linkers of the invention.

In yet another exemplary embodiment, the invention provides an affinity purification matrix that includes a linker of the invention.

The method of the invention for isolating a target will typically utilize one or more affinity chromatography techniques. Affinity chromatography enables the efficient isolation of species such as biological molecules or biopolymers by utilizing their recognition sites for certain supported chemical structures with a high degree of selectivity. The literature is replete with articles, monographs, and books on the subject of affinity chromatography, including such topics as affinity chromatography supports, crosslinking members, ligands and their preparation and use. A sampling of those references includes: Ostrove, *Methods Enzymol.* 182: 357-71 (1990); Ferment, *Bioeng.* 70: 199-209 (1990). Huang et al., *J. Chromatogr.* 492: 431-69 (1989); "Purification of enzymes by heparin-Sepharose affinity chromatography," *J. Chromatogr.,* 184: 335-45 (1980); Farooqi, *Enzyme Eng.,* 4: 441-2 (1978); Nishikawa, *Chem. Technol.,* 5(9): 564-71 (1975); Guilford et al., in, PRACT. HIGH PERFORM. LIQ. CHROMATOGR., Simpson (ed.), 193-206 (1976); Nishikawa, *Proc. Int. Workshop Technol. Protein Sep. Improv. Blood Plasma Fractionation,* Sandberg (ed.), 422-35; (1977) "Affinity chromatography of enzymes," *Affinity Chromatogr., Proc. Int. Symp.* 25-38, (1977) (Pub. 1978); and AFFINITY CHROMATOGRAPHY: A PRACTICAL APPROACH, Dean et al. (ed.), IRL Press Limited, Oxford, England (1985). Those of skill in the art have ample guidance in developing particular affinity chromatographic methods utilizing the materials of the invention.

In the present method, affinity chromatographic media of varying chemical structures can be used as supports. For example, agarose gels and cross-linked agarose gels are useful as support materials, because their hydrophilicity makes them relatively free of nonspecific binding. Other useful supports include, for example, controlled-pore glass (CPG) beads, cellulose particles, polyacrylamide gel beads and Sephadex™ gel beads made from dextran and epichlorohydrin.

Drug-Ligand Conjugate Methods of Use

In addition to the compositions and constructs described above, the present invention also provides a number of methods that can be practiced utilizing the compounds and conjugates of the invention. Methods for using the drug-ligand conjugate of the current invention include: killing or inhibiting the growth or replication of a tumor cell or cancer cell, treating cancer, treating a pre-cancerous condition, killing or inhibiting the growth or replication of a cell that expresses an auto-immune antibody, treating an autoimmune disease, treating an infectious disease, preventing the multiplication of a tumor cell or cancer cell, preventing cancer, preventing the multiplication of a cell that expresses an auto-immune antibody, preventing an autoimmune disease, and preventing an infectious disease. These methods of use comprise administering to an animal such as a mammal or a human in need thereof an effective amount of a drug-ligand conjugate. Preferred ligands for many of the methods of use described herein include antibodies and antibody fragments which target the particular tumor cell, cancer cell, or other target area.

The drug-ligand complex of the current invention is useful for treating cancer, autoimmune disease and infectious disease in an animal. Compositions and methods for treating tumors by providing a subject the composition in a pharmaceutically acceptable manner, with a pharmaceutically effective amount of a composition of the present invention are provided.

The current invention is particularly useful for the treatment of cancer and for the inhibition of the multiplication of a tumor cell or cancer cell in an animal. Cancer, or a precancerous condition, includes, but is not limited to, a tumor, metastasis, or any disease or disorder characterized by uncontrolled cell growth, can be treated or prevented by administration the drug-ligand complex of the current invention. The complex delivers the drug a tumor cell or cancer cell. In one embodiment, the ligand specifically binds to or associates with a cancer-cell or a tumor-cell-associated antigen. Because of its close proximity to the ligand, the drug can be taken up inside a tumor cell or cancer cell through, for example, receptor-mediated endocytosis. The antigen can be attached to a tumor cell or cancer cell or can be an extracellular matrix protein associated with the tumor cell or cancer cell. Once inside the cell, the linker is hydrolytically cleaved by a tumor-cell or cancer-cell-associated proteases, thereby releasing the drug. The released drug is then free to diffuse and induce cytotoxic activities. In an alternative embodiment, the drug is cleaved from the drug-ligand complex outside the tumor cell or cancer cell, and the drug subsequently penetrates the cell.

The ligand may bind to, for example, a tumor cell or cancer cell, a tumor cell or cancer cell antigen which is on the surface of the tumor cell or cancer cell, or a tumor cell or cancer cell antigen which is an extracellular matrix protein associated with the tumor cell or cancer cell. The ligand can be designed specifically for a particular tumor cell or cancer cell type.

Therefore, the type of tumors or cancers that can be effectively treated can be altered by the choice of ligand.

Representative examples of precancerous conditions that may be targeted by the drug-ligand conjugate, include, but are not limited to: metaplasia, hyperplasia, dysplasia, colorectal polyps, actinic ketatosis, actinic cheilitis, human papillomaviruses, leukoplakia, lychen planus and Bowen's disease.

Representative examples of cancers or tumors that may be targeted by the drug-ligand conjugate include, but are not limited to: lung cancer, colon cancer, prostate cancer, lymphoma, melanoma, breast cancer, ovarian cancer, testicular cancer, CNS cancer, renal cancer, kidney cancer, pancreatic cancer, stomach cancer, oral cancer, nasal cancer, cervical cancer and leukemias. It will be readily apparent to the ordinarily skilled artisan that the particular targeting ligand used in the conjugate can be chosen such that it targets the drug to the tumor tissue to be treated with the drug (i.e., a targeting agent specific for a tumor-specific antigen is chosen). Examples of such targeting ligands are well known in the art, non-limiting examples of which include anti-Her2 for treatment of breast cancer, anti-CD20 for treatment of lymphoma, anti-PSMA for treatment of prostate cancer and anti-CD30 for treatment of lymphomas, including non-Hodgkin's lymphoma.

In an embodiment, the present invention provides a method of killing a cell. The method includes administering to the cell an amount of a compound of the invention sufficient to kill said cell. In an exemplary embodiment, the compound is administered to a subject bearing the cell. In a further exemplary embodiment, the administration serves to retard or stop the growth of a tumor that includes the cell (e.g., the cell can be a tumor cell). For the administration to retard the growth, the rate of growth of the cell should be at least 10% less than the rate of growth before administration. Preferably, the rate of growth will be retarded at least 20%, 30%, 40%, 50%, 60%, 70%, 80%, 90%, or completely stopped.

Effective Dosages

Pharmaceutical compositions suitable for use with the present invention include compositions wherein the active ingredient is contained in a therapeutically effective amount, i.e., in an amount effective to achieve its intended purpose. The actual amount effective for a particular application will depend, inter alfa, on the condition being treated. Determination of an effective amount is well within the capabilities of those skilled in the art, especially in light of the detailed disclosure herein.

For any compound described herein, the therapeutically effective amount can be initially determined from cell culture assays. Target plasma concentrations will be those concentrations of active compound(s) that are capable of inhibition cell growth or division. In preferred embodiments, the cellular activity is at least 25% inhibited. Target plasma concentrations of active compound(s) that are capable of inducing at least about 50%, 75%, or even 90% or higher inhibition of cellular activity are presently preferred. The percentage of inhibition of cellular activity in the patient can be monitored to assess the appropriateness of the plasma drug concentration achieved, and the dosage can be adjusted upwards or downwards to achieve the desired percentage of inhibition.

As is well known in the art, therapeutically effective amounts for use in humans can also be determined from animal models. For example, a dose for humans can be formulated to achieve a circulating concentration that has been found to be effective in animals. The dosage in humans can be adjusted by monitoring cellular inhibition and adjusting the dosage upwards or downwards, as described above.

A therapeutically effective dose can also be determined from human data for compounds which are known to exhibit similar pharmacological activities. The applied dose can be adjusted based on the relative bioavailability and potency of the administered compound as compared with the known compound.

Adjusting the dose to achieve maximal efficacy in humans based on the methods described above and other methods as are well-known in the art is well within the capabilities of the ordinarily skilled artisan.

In the case of local administration, the systemic circulating concentration of administered compound will not be of particular importance. In such instances, the compound is administered so as to achieve a concentration at the local area effective to achieve the intended result.

For use in the prophylaxis and/or treatment of diseases related to abnormal cellular proliferation, a circulating concentration of administered compound of about 0.001 µM to 20 µM is preferred, with about 0.01 µM to 5 µM being preferred.

Patient doses for oral administration of the compounds described herein, typically range from about 1 mg/day to about 10,000 mg/day, more typically from about 10 mg/day to about 1,000 mg/day, and most typically from about 50 mg/day to about 500 mg/day. Stated in terms of patient body weight, typical dosages range from about 0.01 to about 150 mg/kg/day, more typically from about 0.1 to about 15 mg/kg/day, and most typically from about 1 to about 10 mg/kg/day for example 5 mg/kg/day or 3 mg/kg/day For other modes of administration, dosage amount and interval can be adjusted individually to provide plasma levels of the administered compound effective for the particular clinical indication being treated. For example, in one embodiment, a compound according to the invention can be administered in relatively high concentrations multiple times per day. Alternatively, it may be more desirable to administer a compound of the invention at minimal effective concentrations and to use a less frequent administration regimen. This will provide a therapeutic regimen that is commensurate with the severity of the individual's disease.

Utilizing the teachings provided herein, an effective therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds, compositions and methods of the present invention are further illustrated by the examples that follow. These examples are offered to illustrate, but not to limit the claimed invention.

EXAMPLES

Material and Methods

In the examples below, unless otherwise stated, temperatures are given in degrees Celsius (° C.); operations were carried out at room or ambient temperature (typically a range of from about 18-25° C.; evaporation of solvent was carried out using a rotary evaporator under reduced pressure (typically, 4.5-30 mmHg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), LC-MS (liquid chromatography-mass spectrometry) and h (hours).

$^1$H-NMR spectra were measured on a Varian Mercury 300 MHz spectrometer and were consistent with the assigned structures. Chemical shifts were reported in parts per million (ppm) downfield from tetramethylsilane. Electrospray mass spectra were recorded on a Perkin Elmer Sciex API 365 mass spectrometer. Elemental analyses were performed by Robertson Microlit Laboratories, Madison, N.J. Silica gel for flash chromatography was E. Merck grade (230-400 mesh). Reverse-Phase analytical HPLC was performed on either a HP 1100 or a Varian ProStar 210 instrument with a Phenomenex Luna 5 μm C-18(2) 150 mm×4.6 mm column or a Varian Microsorb-MV 0.1 μm C-18 150 mm×4.6 mm column. A flow rate of 1 mL/min was with either a gradient of 0% to 50% buffer B over 15 minutes or 10% to 100% buffer B over 10 minutes with detection by UV at 254 nm. Buffer A, 20 mM ammonium formate+20% acetonitrile or 0.1% trifluoroacetic acid in acetonitrile; buffer B, 20 mM ammonium formate+ 80% acetonitrile or 0.1% aqueous trifluoroacetic acid. Reverse phase preparative HPLC were performed on a Varian ProStar 215 instrument with a Waters Delta Pak 15 μm C-18 300 mm×7.8 mm column.

Example 1

Synthesis of Peptide Linker Conjugates 1.1a Synthesis Methodology

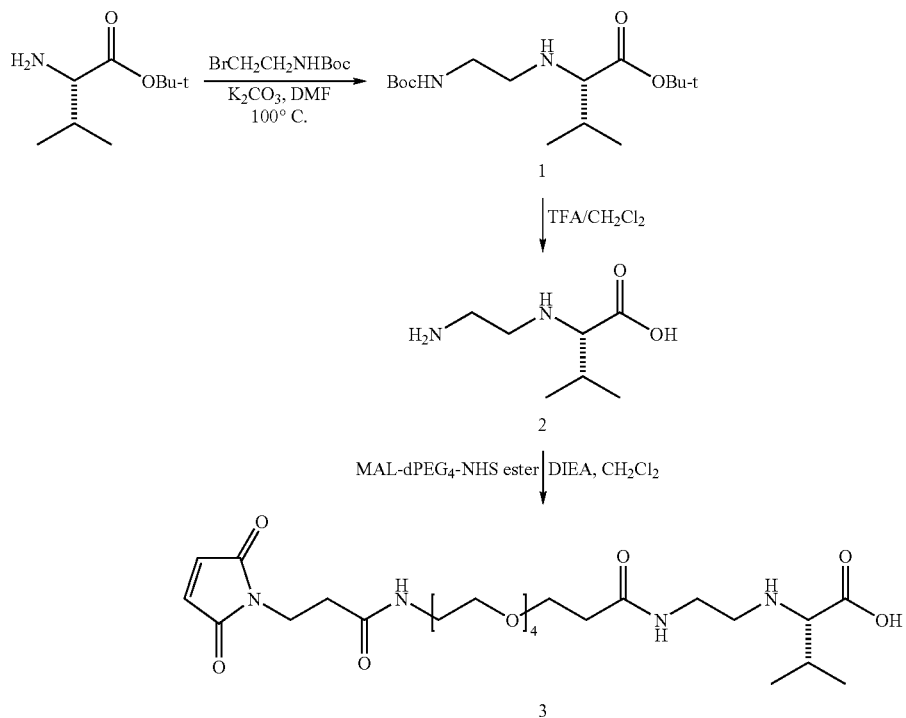

Scheme 1

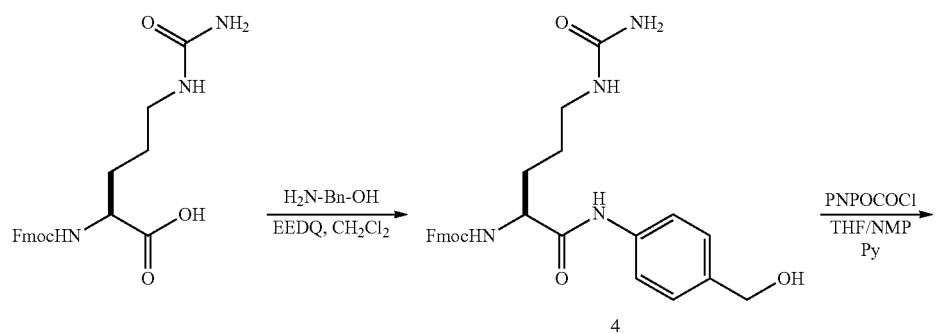

Scheme 2

-continued
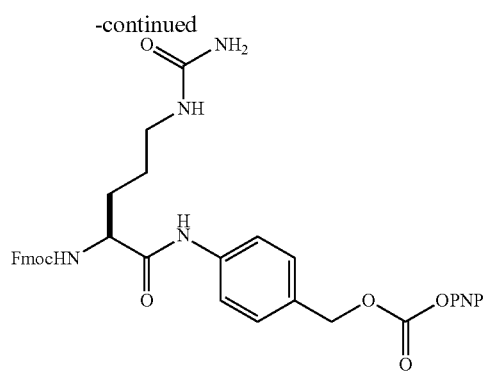
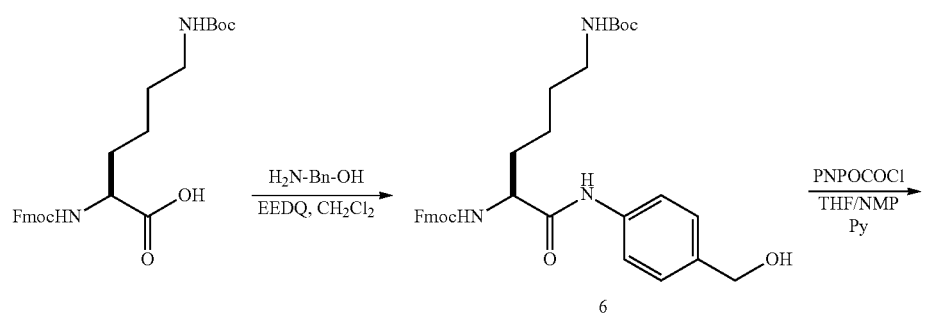
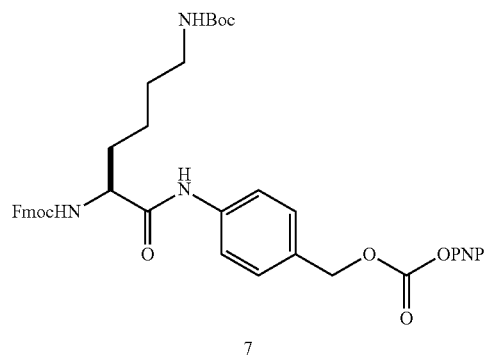
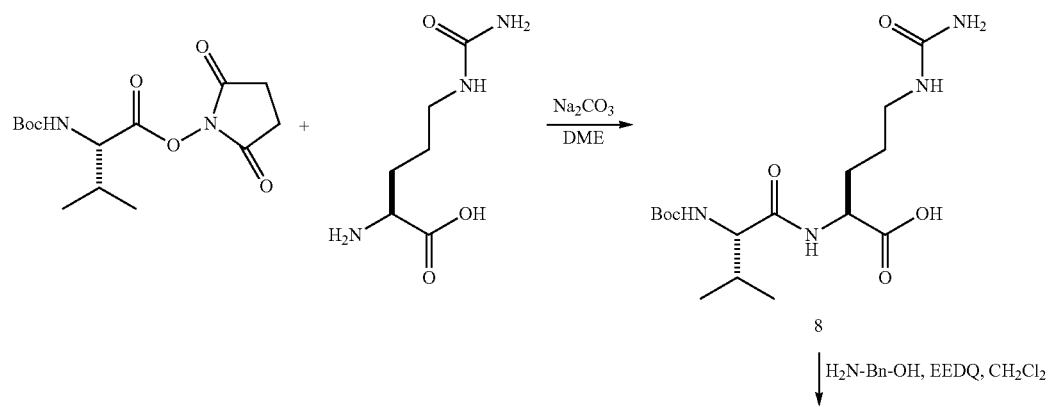

103 104
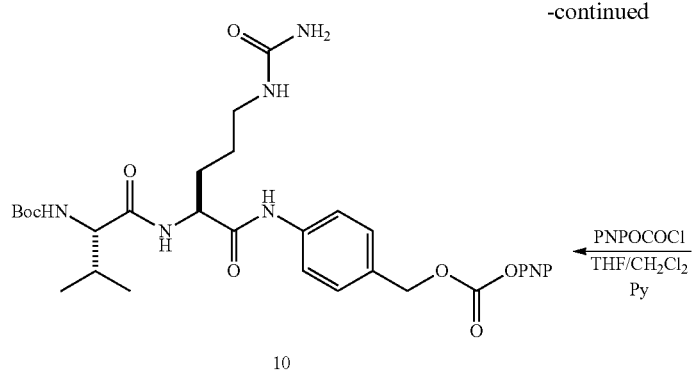 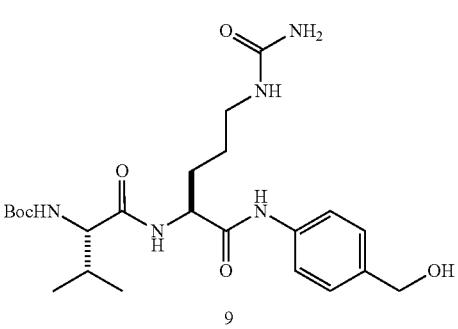
Scheme 3
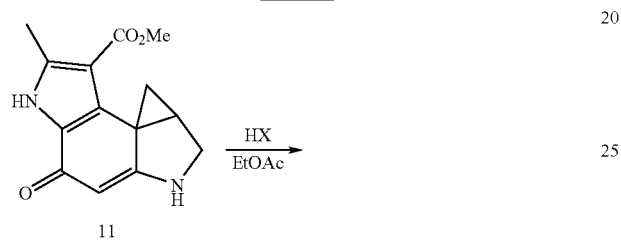
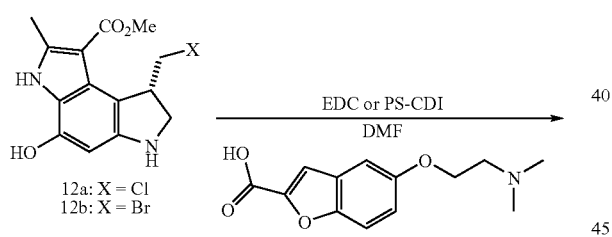
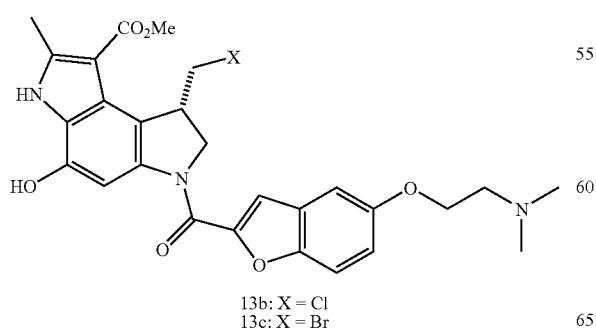

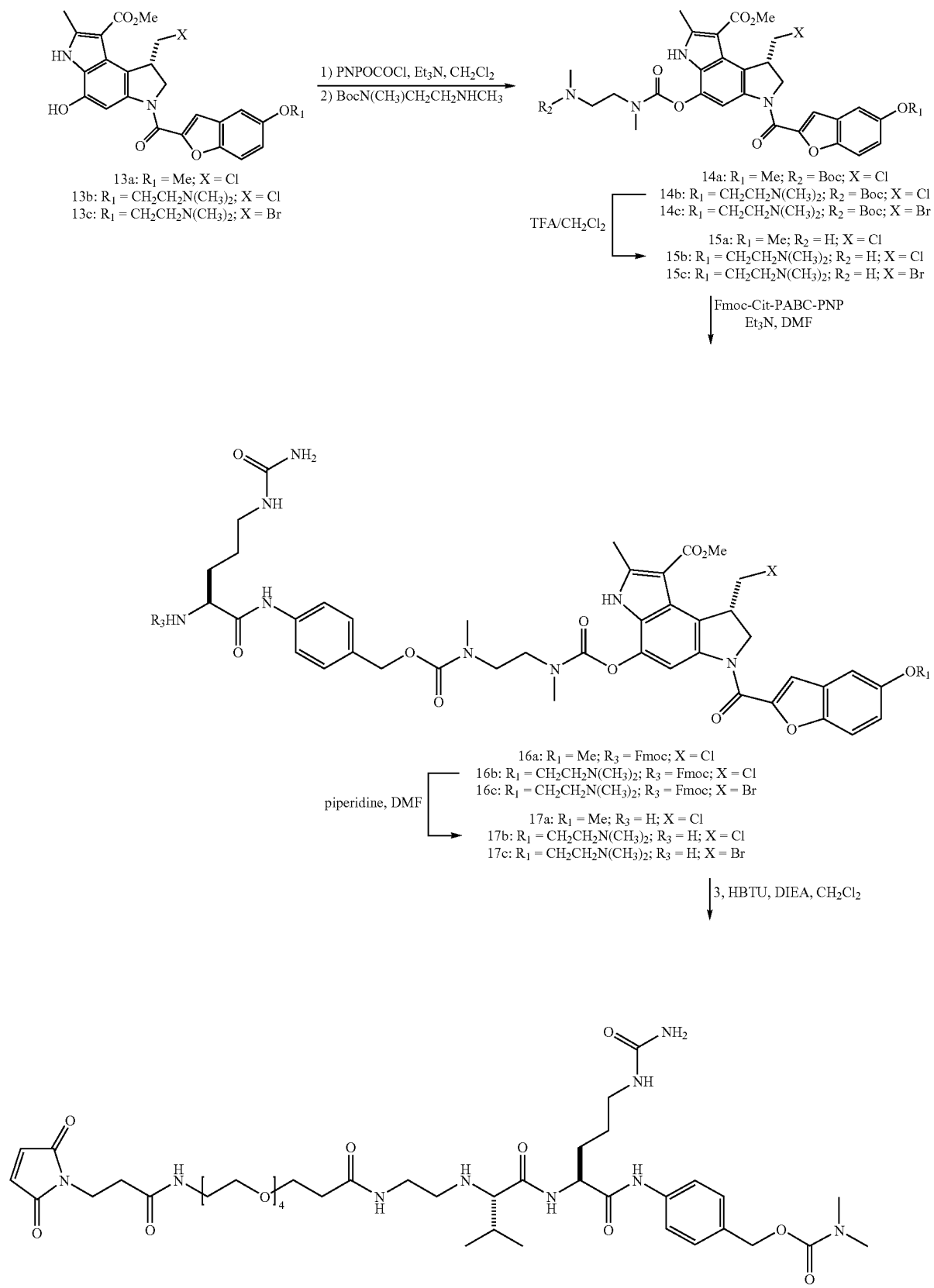
Scheme 4

-continued
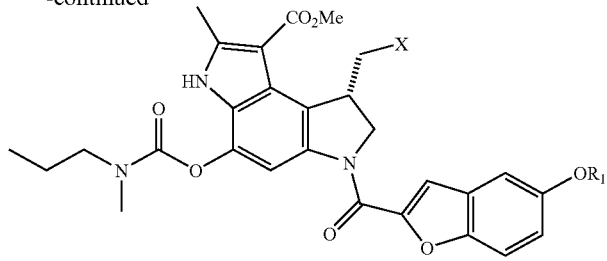
18a: $R_1$ = Me; X = Cl
18b: $R_1$ = $CH_2CH_2N(CH_3)_2$; X = Cl
18c: $R_1$ = $CH_2CH_2N(CH_3)_2$; X = Br
Scheme 5
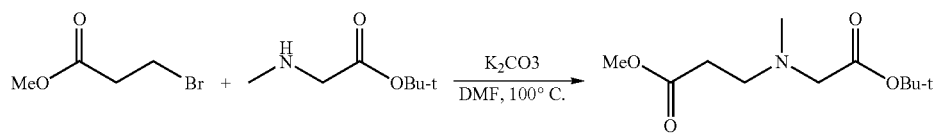
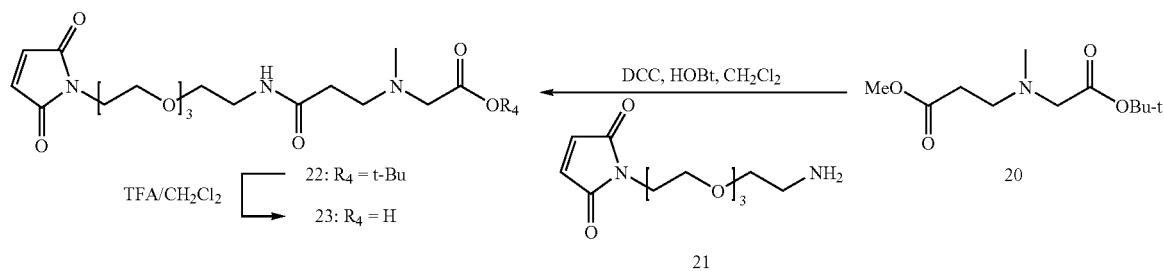
14a
14b + 10 → Et₃N / DMF
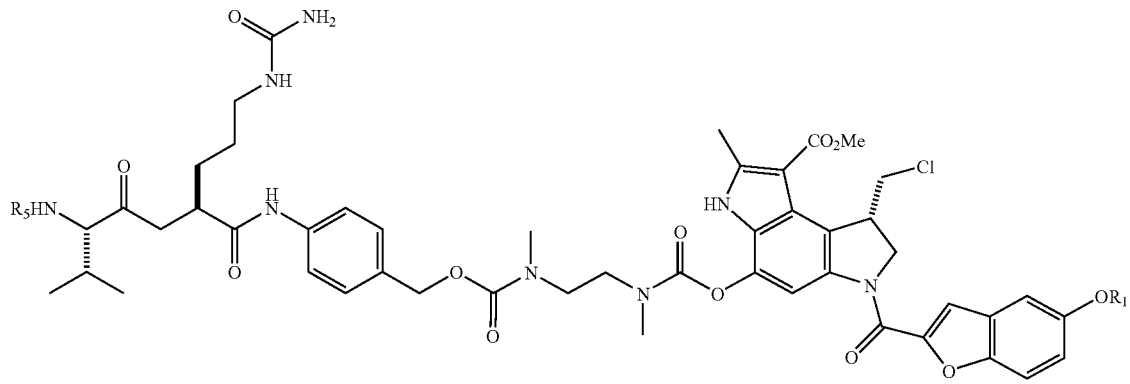
24a: $R_1$ = Me; $R_5$ = Boc
24b: $R_1$ = $CH_2CH_2N(CH_3)_2$; $R_5$ = Boc
1) TFA/$CH_2Cl_2$
2) $Na_2CO_3$ →
25a: $R_1$ = Me; $R_5$ = H
25b: $R_1$ = $CH_2CH_2N(CH_3)_2$; $R_5$ = H
↓ 23, DCC, HOBt, Et₃N, $CH_2Cl_2$ -continued
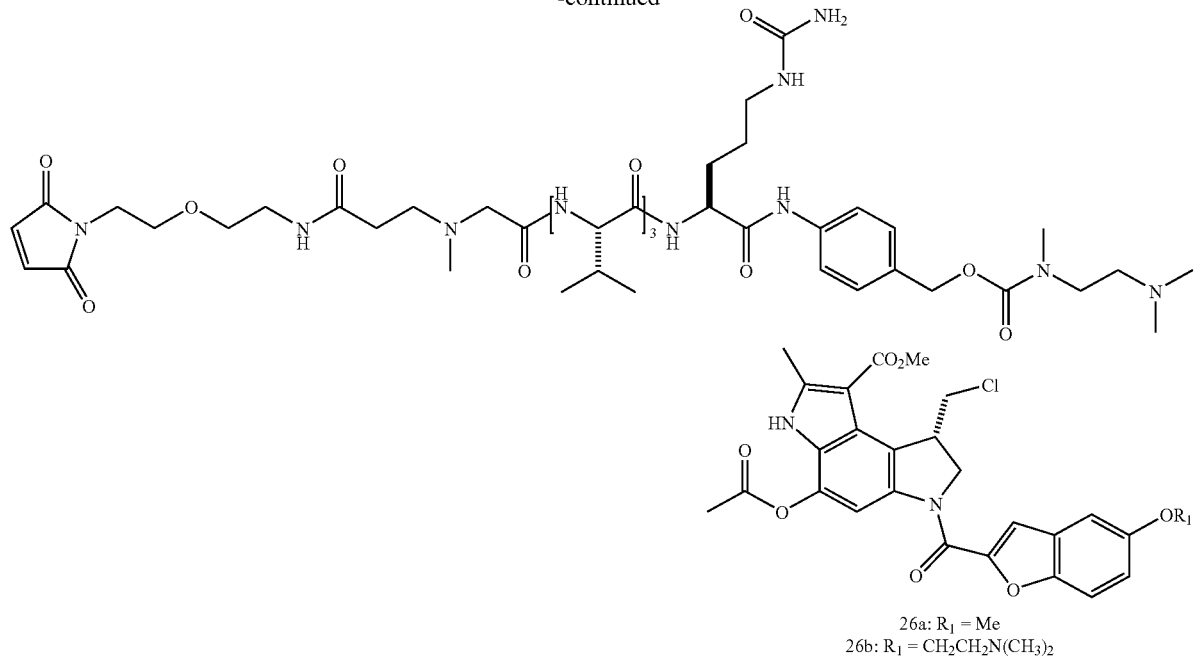
26a: R₁ = Me
26b: R₁ = CH₂CH₂N(CH₃)₂
Scheme 6
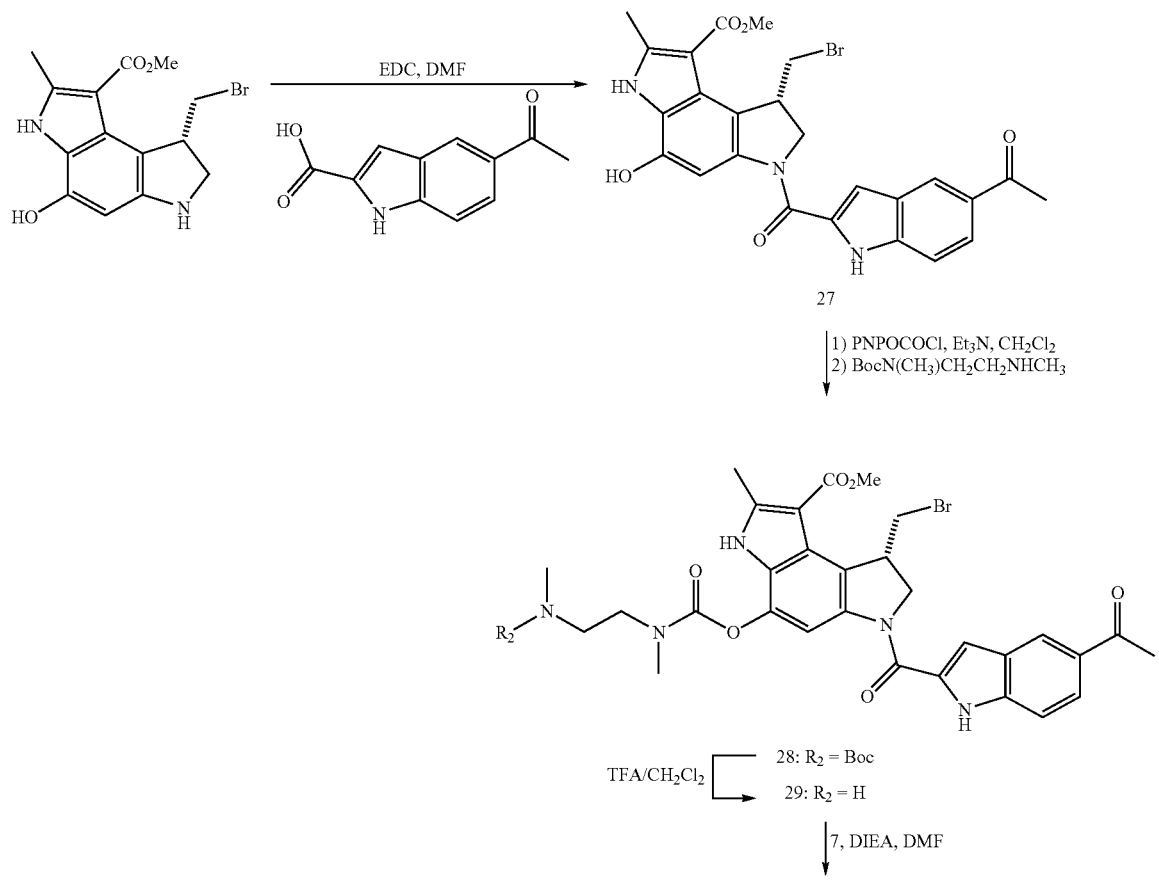

-continued

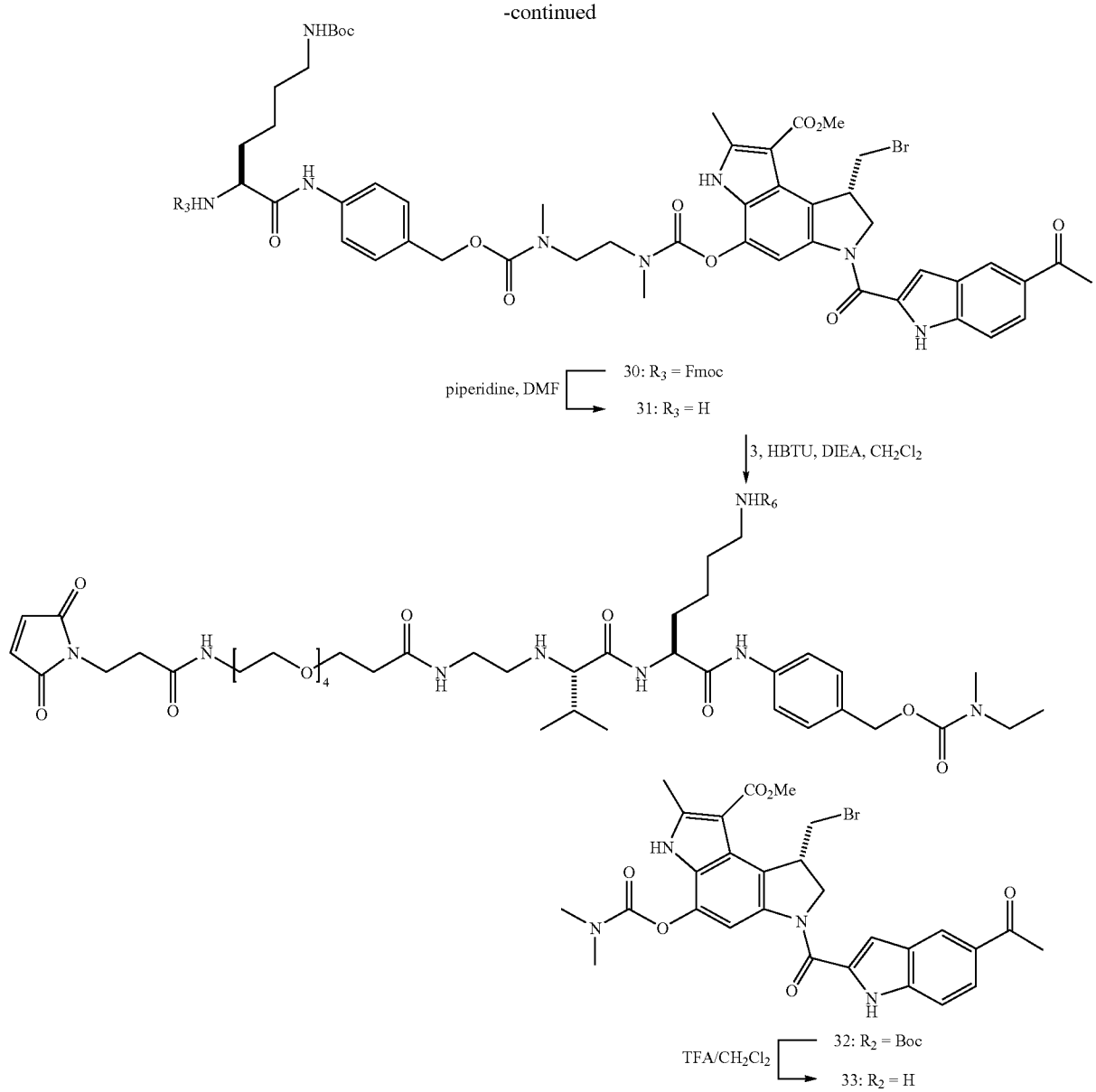

1.1b Synthesis of Compound 1: N-[2'-(N'-tert-butoxycarbonyl-animo)-ethyl]-valine tert-butyl ester.

To a solution of 2-(N-tert-butoxycarbonyl-amino)-ethyl bromide (1 g, 4.5 mmole) and valine tert-butyl ester (0.936 g, 4.5 mmole) in DMF (10 mL) was added potassium carbonate (1.85 g, 13.5 mmole). The mixture thus obtained was stirred at 100° C. overnight. The reaction mixture was concentrated and the residue was purified by flash chromatography on silica gel with ethyl acetate/hexanes (3/7) as eluent to give the title compound as an oil (0.16 g, 12%). $^1$H NMR (CDCl$_3$) δ 0.94 (ft, 6H), 1.44 (s, 9H), 1.473 and 1.475 (2s, 9H), 1.88 (m, 1H), 2.51 (m, 1H), 2.78 (m, 2H), 3.11 (m, 1H), 3.22 (m, 1H), 3.39 and 4.13 (2bt, 1H), 5.00 (bs, 1H) ppm; LC-MS (ESI) 205 (M+H$^+$-112), 261 (M+H$^+$-Bu), 317 (M+H$^+$).

1.1c Synthesis of Compound 2: N-(2-Aminoethyl)-valine.

The compound 1 (137 mg, 0.43 mmole) was dissolved in a solution of TFA/dichloromethane (2 mL, 1/1) at room temperature. The mixture thus obtained was stirred at room temperature for 30 min. The reaction mixture was concentrated to dryness to give the title compound as an oil (0.18 g, 95%) $^1$H NMR (CD$_3$OD) δ 1.07 and 1.16 (2d, 6H), 2.35 (m, 1H), 3.2 (m, 1H), 3.38 (m, 4H) ppm; LC-MS (ESI) 217 (M+H$^+$).

1.1d Synthesis of Compound 3.

To a solution of maleamide-dPEG$_4$-NHS ester (61 mg, 0.16 mmole) in dichloromethane (2 mL) was added dropwise compound 2 (80.7 mg, 0.16 mmole) and diisopropylethylamine (55.5 µL, 0.32 mmole) in dichloromethane (1 mL). The mixture thus obtained was stirred overnight. The solvent were removed on the rotovap, and the residue was purified by flash chromatography on silica gel with dichloromethane, followed by 5% methanol in dichloromethane and finally 100% methanol as eluent to give the title compound as colorless oil (87 mg, 97%). $^1$H NMR (CDCl$_3$) δ 1.08 (dd, 6H), 2.25 (m, 1H), 2.49 (t, 2H), 2.52 (t, 2H), 3.10-3.79 (m, 25H), 6.82 (s, 2H) ppm; LC-MS (ESI) 559 (M+H$^+$)

1.1e Synthesis of Compound 4: Fmoc-Cit-PABOH.

To a solution of Fmoc-Cit-OH (1.0 g, 2.52 mmole) and 4-aminobenzylalcohol (341 mg, 2.77 mmole) in dichloromethane (10 mL) and methanol (5 mL) was added 2-ethoxy-1-ethoxycarbonyl-1,2-dihydroquinoline[EEDQ] (1.24 g, 5.04 mmole) in one portion. The mixture was stirred in the dark for 16 hours. The solvents were removed on the rotovap, and the white solid was triturated with ether (100 mL). The resulting suspension was sonicated for 5 min and then left to stand for 30 min. The white solid was collected by filtration, washed with ether and dried in vacuo (1.23 g, 97%). $^1$H-NMR (DMSO) δ 1.32 to 1.52 (m, 2H), 1.52 to 1.74 (dm, 2H), 2.86 to 3.06 (dm, 2H), 4.1 (M, 1H), 4.42 (d, 2H), 5.07 (t, 1H), 5.40 (bs, 2H), 5.97 (t, 1H), 7.19 to 7.95 (m, 12H), 8.10 (d, 1H), 9.97 (s, 1H) ppm; LC-MS (ESI) 503.1 (M+H$^+$).

1.1f Synthesis of Compound 5: Fmoc-Cit-PABC-PNP.

To a solution of Compound 4 (309 mg, 0.62 mmole) and p-nitrophenylchloroformate (372 mg, 1.85 mmole) in Tetrahydrofuran (30 mL) and 1-methyl-2-pyrrolidine (1 mL) was added pyridine (100 μL, 1.23 mmole) in one portion. The mixture thus obtained was stirred at room temperature for 30 minutes. The solvents were removed on the rotovap, and the residue was purified by flash chromatography on silica gel with dichloromethane, followed by 3% methanol in dichloromethane and finally 10% methanol in dichloromethane as eluent to give the title compound as a white solid (97.9 mg, 70%). LC-MS (ESI) 668 (M+H$^+$).

1.1g Synthesis of Compound 6: Fmoc-Lys(Boc)-PABOH.

Compound 6 was prepared as described above for Compound 4 in 98% yield. $^1$H NMR (DMSO) δ 1.40 (s, 9H), 1.38 (m, 2H), 1.50 to 1.74 (dm, 2H), 3.04 (t, 2H), 3.30 (q, 3H), 4.19 to 4.31 (m, 2H), 4.41 (d, 2H), 4.55 (s, 2H), 7.28 to 7.68 (m, 12H), 8.00 (d, 1H) ppm; LC-MS (ESI) 574 (M+H$^+$).

1.1h Synthesis of Compound 7: Fmoc-Lys(Boc)-PABC-PNP.

Compound 7 was prepared as described above for Compound 5 in 70% yield. $^1$H NMR (CD$_3$Cl) δ 1.44 (s, 9H), 1.49-1.60 (m, 6H), 1.73 (m, 1H), 2.00 (m, 1H), 3.11 (m, 1H), 3.20 (bs, 1H), 4.23 (m, 2H), 4.46 (bs, 2H), 4.67 (bs, 1H), 5.56 (bs, 1H), 7.28 (m, 2H), 7.36-7.41 (m, 6H), 7.59 (m, 4H), 7.76 (d, 2H), 8.26 (dd, 2H), 8.45 (bs, 1H) ppm; LC-MS (ESI) 639 (M+H$^+$-Boc), 684 (M+H$^+$-Bu), 739 (M+H$^+$), 778 (M+K$^+$).

1.1i Synthesis of Compound 8: Boc-Val-Cit-OH.

To a solution of Citrulline (2.54 g, 14.50 mmole) and Sodium Bicarbonate (1.28 g) in water (40 mL) was added Boc-Val-OSu (4.34 g, 13.81 mmole) dissolved in dimethoxyethane (DME). To aid the solubility of the mixture tetrahydrofuran (10 mL) was added. The mixture thus obtained was let stir overnight at room temperature. Aqueous citric acid (15%, 75 mL) was added and the mixture was extracted with 10% 2-propanol/ethyl acetate (2×100 mL). The organic layer was washed with brine (2×150 mL) and the solvents were removed on the rotovap. The resulting white solid was dried in vacuo for 5 hours and then treated with ether (100 mL). After brief sonication and trituration, the white solid product was collected by filtration (1.39 g, 27%). $^1$H NMR (CD$_3$OD) δ 0.91 (dd, 3H), 0.98 (dd, 3H), 1.44 (s, 9H), 1.70 (m, 2H), 1.87 (m, 2H), 2.02 (m, 2H), 3.11 (t, 2H), 3.89 (t, 1H), 4.39 (q, 1H), 8.22 (d, 1H) ppm; LC-MS (ESI) 375 (M+H$^+$).

1.1j Synthesis of Compound 9: Boc-Val-Cit-PABOH.

Compound 9 was prepared as described above for Compound 4 in 71% yield. $^1$H NMR (CD$_3$OD) δ 0.93 and 0.97 (2d, 6H), 1.44 (s, 9H), 1.58 (m, 2H), 1.75 (m, 1H), 1.90 (m, 1H), 2.05 (m, 1H), 3.10 (m, 1H), 3.19 (m, 1H), 3.91 (d, 1H), 4.52 (m, 1H), 5.25 (s, 2H), 7.40 (d, 2H), 7.45 (dd, 2H), 7.64 (d, 4H), 8.29 (dd, 2H) ppm; LC-MS (ESI) 480 (M+H$^+$).

1.1k Synthesis of Compound 10: Boc-Val-Cit-PABC-PNP.

A solution of Boc-Val-Cit-PABOH (178 mg, 0.370 mmole) in THF (8 mL) in CH$_2$Cl$_2$ (4 mL) was stirred at room temperature with PNP chloroformate (160 mg, 0.80 mmole) and pyridine (65 μL, 0.80 mmole) for 3 h. Ethyl acetate (100 mL) and 10% aqueous citric acid (50 mL) were added to the reaction mixture and organic layer was washed with brine, dried and concentrated and the residue was purified by flash chromatography on silica gel with 5% methanol in as eluent to give the title compound as a white solid (165 mg, 70%). $^1$H NMR (CD$_3$OD) δ 0.93 (dd, 3H), 0.97 (dd, 3H), 1.44 (s, 9H), 1.58 (m, 2H), 1.75 (m, 1H), 1.89 (m, 1H), 2.05 (m, 1H), 3.10 (m, 1H), 3.20 (m, 1H), 3.90 (d, 1H), 4.51 (m, 1H), 4.55 (s, 2H), 7.29 (d, 2H), 7.55 (d, 2H) ppm; LC-MS (ESI) 545 (M+H$^+$-Boc), 645 (M+H$^+$), 667 (M+Na$^+$), 683 (M+K$^+$).

1.1l Synthesis of Compound 12a.

To a suspension of Compound 11 (20 mg, 0.078 mmole) in ethyl acetate (5 mL) was bubbled HCl gas for 20 min (by the time, the suspension became to a clean solution). The reaction mixture was stirred for additional 5 min then the mixture was concentrated to dryness to give the title compound as yellow solid (26 mg, 100%) which was used in next step without further purification. LC-MS (ESI) 260 (M+H$^+$—CO, 295 (M+H$^+$).

1.1m Synthesis of Compound 12b.

To a suspension of Compound 11 (20 mg, 0.078 mmole) in ethyl acetate (5 mL) was bubbled HBr gas for 20 min (by the time, the suspension became to a clean solution). The reaction mixture was stirred for additional 5 min then the mixture was concentrated to dryness to give the title compound as yellow solid (33 mg, 100%) which was used in next step without further purification. LC-MS (ESI) 260 (M+H$^+$-Br), 339 (M+H$^+$), 341 (M+H$^+$+2).

1.1n Synthesis of Compound 13b.

To a solution of Compound 12a (26 mg, 0.078 mmole) in DMF (2 mL) were added 5-(2-dimethylamino-ethoxy)-benzofuran-2-carboxylic acid (44 mg, 0.155 mmole) and EDC (30 mg, 0.155 mmole). The mixture thus obtained was stirred at room temperature for 2 h. The mixture was concentrated and the residue was dissolved in H$_2$O/CH$_3$CN/TFA (4/1.5/0.5, 6 mL) and it was placed in freezer for 3 h. A yellow solid was collected by filtration (35 mg, 85%). $^1$H NMR (CD$_3$OD) δ 2.67 (s, 3H), 3.01 (s, 6H), 3.34 (m, 2H), 3.63 (ft, 1H), 3.89 (s, 3H), 3.91 (m, 1H), 4.41 (m, 3H), 4.54 (m, 1H), 4.65 (m, 1H), 7.20 (dd, 1H), 7.36 (d, 1H), 7.54 (s, 1H), 7.59 (d, 1H), 7.73 (bs, 1H), 11.75 (s, 1H) ppm; LC-MS (ESI) 490 (M+H$^+$-Cl), 526 (M+H$^+$)

1.1o Synthesis of Compound 13c.

To a solution of Compound 12b (19 mg, 0.0387) in DMF (2 mL) were added 5-(2-dimethylamino-ethoxy)-benzofuran-2-carboxylic acid HBr salt (25 mg, 0.0775 mmole) and PS-carbodiimide (82 mg, mmole/g: 0.94, 0.0775 mmole). The reaction mixture was stirred at room temperature for 24 h. After filtration, the filtrate was concentrated and the residue was dissolved in H$_2$O/CH$_3$CN/TFA (2/0.75/0.25, 3 mL) and it was placed in freezer for 3 h. The yellow solid was collected by filtration and dried to give the title compound (18 mg, 82%). LC-MS (ESI) 490 (M+H$^+$-Br), 570 (M+H$^+$), 572 (M+H$^+$+2)

1.1p Synthesis of Compound 14a.

To a suspension of Compound 13a (48 mg, 0.10 mmole) in dichloromethane (4 mL) were added p-nitrophenyl chloroformate (80 mg, 0.40 mmole) and triethylamine (56 μL, 0.40 m mole) at ±78° C. The mixture was warmed up to room temperature slowly and the stirring was continued for additional 30 mM. To the reaction mixture was added compound N-Boc-N,N'-dimethylethylenediamine (166 mg, 0.80 mmole) and stirred overnight. The mixture was concentrated and the residue was purified by flash chromatography on silica gel with 1.25% methanol in dichloromethane as eluent to give the title compound as a white solid (71 mg, 100%) $^1$H NMR δ1.45-1.47 (m, 9H), 2.69 (s, 3H), 2.97 (s, 3H), 3.14-3.34 (m, 4H), 3.81-3.92 (m, 8H), 4.38-4.47 (m, 3H), 4.70 (d, 1H), 7.05 (dd, 1H), 7.11 (d, 1H), 7.45 (s, 1H), 7.48 (d, 1H), 7.99 (s, 1H), 10.43 (s, 1H) ppm. LC-MS (ESI) 710 (M–H$^+$)

1.1q Synthesis of Compound 14b.

To a suspension of Compound 13b (48 mg, 0.075 mmole) in dichloromethane (2 mL) were added 4-nitrophenyl chloroformate (80 mg, 0.4 m mole) and triethylamine (40 mg, 0.4 m mole, 56 µL) at 0° C. The mixture was warmed up to room temperature and stirring was continued additional 6 h. The solvent was evaporated and the residue was washed with ether to give the intermediate. The intermediate was dissolved in dichloromethane (2 mL) and to the reaction solution were added N-Boc-N,N'-dimethylethylenediamine (44 mg, 0.2 m mole) and triethylamine (20 mg, 0.2 mmole, 28 µL). The mixture thus obtained was stirred at room temperature overnight. The mixture was concentrated and the residue was purified by HPLC on C-18 column with ammonium formate (20 mM, pH 7.0) and acetonitrile as eluent to give the title compound as white solid (31 mg, 54%). LC-MS (ESI) 755 (M+H$^+$)

1.1r Synthesis of Compound 14c.

To a suspension of Compound 13c (24 mg, 0.04 mmole) in CH$_2$Cl$_2$ (2 mL) were added p-nitrophenyl chloroformate (64 mg, 0.32 mmole) and triethylamine (22 µL, 0.16 mmole) at 0° C. The reaction mixture thus obtained was stirred at room temperature for 18 h. To the reaction mixture was added N-Boc-N,N'-dimethylethylenediamine (94 mg, 0.50 mmole) and the stirring was continued for additional 50 min. The reaction mixture was concentrated and the residue was purified by flash chromatography on silica gel with 5% methanol in dichloromethane as eluent to give the title compound as white solid (28 mg, 83%). LC-MS (ESI) 490, 570, 684 (M+H$^+$-Boc), 784 (M+H$^+$), 805 (M+Na$^+$), 722 (M+K$^+$)

1.1s Synthesis of Compound 15a.

Compound 14a (70 mg, 0.10 m mole) was dissolved in trifluoroacetic acid (5 mL) and the mixture was stirred at room temperature for 30 min and concentrated to dryness and the product (72 mg, 100%) was used in next step without further purification. HPLC showed it to be >95% pure. $^1$H NMR δ 2.64 (s, 3H), 2.93 (s, 3H), 3.19 (s, 3H), 3.30 (t, 1H), 3.79 (s, 3H), 3.85 (s, 3H), 3.81-3.85 (m, 1H), 4.27-4.49 (m, 3H), 4.59 (d, 1H), 4.68 (d, 1H), 6.97 (dd, 1H), 7.03 (d, 1H), 7.38 (s, 1H), 7.41 (d, 1H), 8.00 (br s, 1H), 10.61 (br s, 1H) ppm. LC-MS (ESI) 612 (M+H$^+$), 634 (M+Na$^+$)

1.1t Synthesis of Compound 15b.

Compound 15b was prepared as described above for Compound 15a in 100% yield. $^1$H NMR (CD$_3$OD) δ 2.69 (s, 3H), 2.76 (s, 3H), 2.83 (bs, 1H), 3.01 (s, 6H), 3.08 (bs, 1H), 3.24 (bs, 2H), 3.42 (m, 2H), 3.63 (bs, 3H), 3.74 (bs, 1H), 3.91 (s, 3H), 3.92 (m, 1H), 4.40 (bs, 2H), 4.57 (bs, 2H), 4.71 (bs, 1H), 7.22 (bd, 1H), 7.36 (s, 1H), 7.56 (s, 1H), 7.59 (d, 1H), 8.04 (bs, 1H) ppm; LC-MS (ESI) 490, 526, 640 (M+H$^+$), 678 (M+K$^+$).

1.1u Synthesis of Compound 15c.

Compound 15c was prepared as described above for Compound 15a in 100% yield. LC-MS (ESI) 490, 570, 684 (M+H$^+$), 722 (M+K$^+$)

1.1v Synthesis of Compound 16a.

To a solution of Compound 5 (12.5 mg, 0.019 mmole) and Compound 15a (10 mg, 0.014) in dimethylformamide (200 µL) was added triethylamine (6 µL, 0.044 mmole). The mixture thus obtained was stirred at room temperature overnight. Ether (5 mL) was added to the mixture and a white solid precipitated out of solution. The solid was filtered and purified by flash chromatography on silica gel with dichloromethane, followed by 1% methanol in dichloromethane, 2% methanol in dichloromethane, 3% methanol in dichloromethane and finally 4% methanol in dichloromethane as eluent to give the title compound as a white solid (8.7 mg, 56%). LC-MS (ESI) 470, 1112 (M+H$^+$), 1134 (M+Na$^+$), 1150 (M+K$^+$)

1.1w Synthesis of Compound 16b.

To a solution of Compound 15b (5 mg, 0.0056 mmole) in DMF (0.35 mL) were added Compound 5 (3.8 mg, 0.0056 mmole) and DIEA (2 µL, 0.011 mmole). The mixture thus obtained was stirred at room temperature for 5 h. The mixture was concentrated and the residue was purified by flash chromatography on silica gel with 10% methanol in dichloromethane as eluent to give the title compound as a solid (3 mg, 45%). LC-MS (ESI) 490, 526, 1169 (M+H$^+$), 1208 (M+K$^+$)

1.1x Synthesis of Compound 16c.

Compound 16c was prepared as described above for Compound 16b in 50% yield. LC-MS (ESI) 490, 570, 1212 (M+H$^+$), 1250 (M+K$^+$)

1.1y Synthesis of Compound 17a.

To a solution of Compound 16a (8.7 mg, 0.008 mmole) in dimethylformamide (500 µL) was added piperidine (100 µL) in one portion. The mixture thus obtained was stirred for 20 minutes at room temperature. The solvent were removed on the rotovap, and placed on the high vacuum for 1.5 h. The residue was take up in the minimal amount of dichloromethane (100 µL) and hexane (3 mL) was add to the solution, a white solid crashed out of solution which was filtered off and dried (6.7 mg, 96.7%). MS (ES) 470, 890.1 (M+H$^+$), 912 (M+Na$^+$), 928 (M+K$^+$).

1.1z Synthesis of Compound 17b.

Compound 17b was prepared as described above for Compound 17a in 95% yield. LC-MS (ESI) 947 (M+H$^+$)

1.1aa Synthesis of Compound 17c.

Compound 17c was prepared as described above for Compound 17a in 95% yield. LC-MS (ESI) 1015 (M+H$^+$)

1.1bb Synthesis of Compound 18a.

To a solution of Compound 17a (4.2 mg, 0.005 mmole) and Compound 3 (2.64 mg, 0.005 mmole) in dichloromethane (1 mL) was added in one portion PyBOP (3.7 mg, 0.007 mmole) followed by diisopropylethylamine (1 µL). The mixture thus obtained was stirred overnight at room temperature. The solvents were removed on the rotovap. The residue was purified by Prep HPLC to yield a beige solid (2.6 mg, 38.7%). MS (ES) 470, 1431 (M+H$^+$), 1453 (M+Na$^+$), 1469 (M+K$^+$)

1.1cc Synthesis of Compound 18b.

To a solution of Compound 17b (2.2 mg, 0.0025 mmole) and Compound 3 in 5% methanol in dichloromethane (400 µL) were added HBTU (9 mg, 0.0046 mmole) and DIEA (1.4 µL, 0.0046 mmole). The mixture thus obtained was stirred at room temperature overnight. The solvent was evaporated and the residue was purified on semi-preparative HPLC with 10 mM ammonium formate and acetonitrile as eluent to give the title compound as an oil (1.1 mg, 30%). LC-MS (ESI) 490, 526, 1488 (M+H$^+$), 1527 (M+K$^+$)

1.1 dd Synthesis of Compound 18c.

To a solution of Compound 17c (6.5 mg, 0.0065 mmole) and the Compound 3 (5.5 mg, 0.0097 mmole) in 5% methanol in dichloromethane (0.5 mL) were added HBTU (3.7 mg, 0.0097 mmole) and DIEA (3.4 µL, 0.0194 m mole). The mixture thus obtained was stirred at room temperature overnight. The solvent was evaporated and the residue was purified by flash chromatography on silica gel with 30% methanol in dichloromethane as eluent to give the title compound as an oil (4 mg, 30%). LC-MS (ESI) 1532 (M+H$^+$), 1554 (M+Na$^+$), 1570 (M+K$^+$).

1.2 Synthesis Methodology for Duocarmycin-Containing Peptide Linker without Self-Immolative Spacer
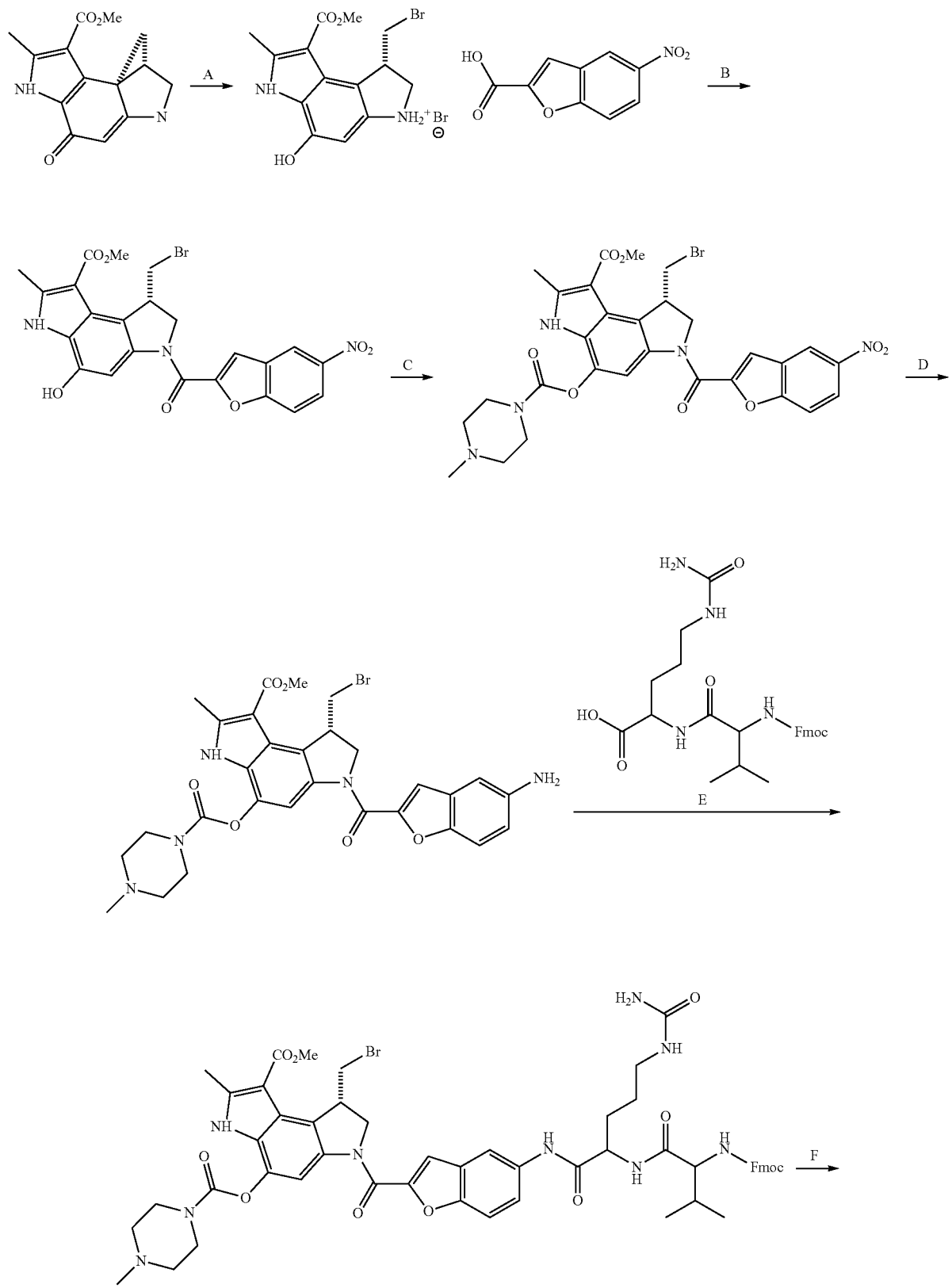

-continued

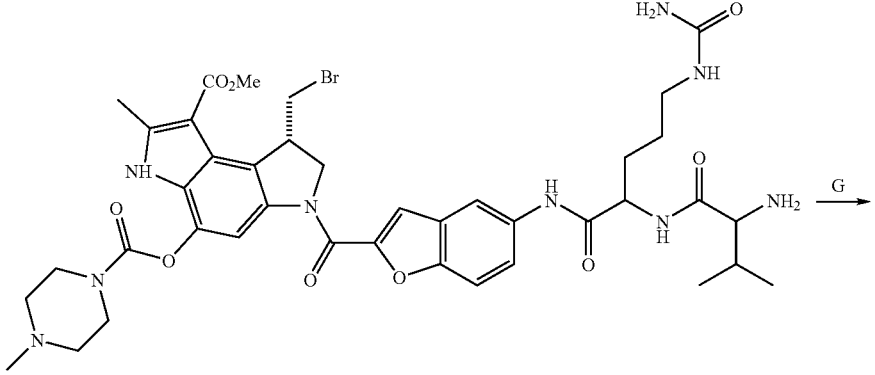

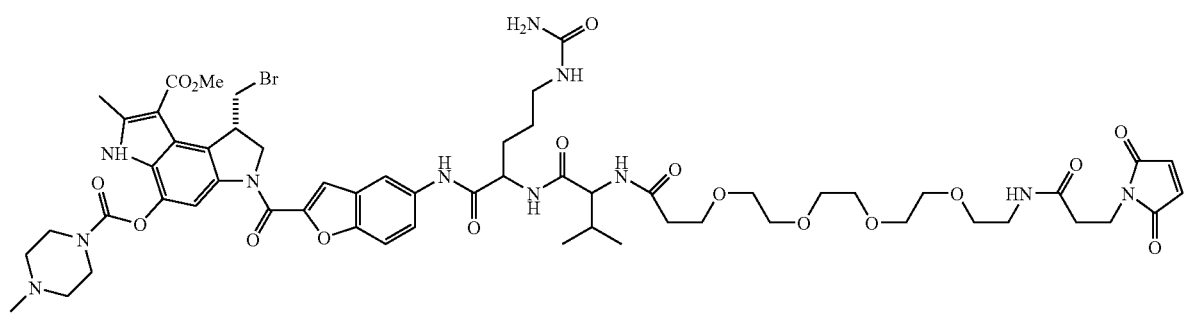

1.2a Reaction A:

To a suspension of Alkylating core 7 mg in 2 mL of Ethyl Acetate was passed a slow stream of dry HBr gas until a clear solution is formed which took approximately 15 minutes. The reaction mixture was concentrated and dried overnight under high vacuum.

1.2b Reaction B:

To a suspension of the bromo methyl seco compound prepared in step A in DMF was added EDC (10 mg, 0.054 mMoles) and 5-Nitro benzofuran carboxylic acid (12 mg, 0.054 mMoles) and allowed to stir for 6 hours. To this reaction mixture was then added ethyl acetate and brine. The combined organic layers were concentrated after three extractions with ethyl acetate. And filtered over silica gel using MeOH/DCM with increasing amounts of MeOH The product was confirmed by Mass Spec, M+1=530

1.2c Reaction C:

The 4'-OH was protected using methyl piperazine carbonyl chloride (11 mg, 0.054 mMoles) in 2 mL DCM, 200 µL Allyl alcohol and pyridine (21 µL) for 2 hours. The product was purified by silica gel column chromatography and Identified by Mass Spec, MS+1=654

1.2d Reaction D:

Reduction of Nitro group was done by hydrogenolysis over Pd/C in DCM/MeOH (2:1) under 40 PSI for 45 minutes. The product was filtered and the filtrate concentrated and dried under high vacuum. The product was confirmed by mass spec analysis MS+1=and carried out to the next step without further purification.

1.2e Reaction E:

To a solution of above compound (18 mg, 0.024 mMoles) in MeOH/DCM (2:1, 3 mL) was added Fmoc-Val-Citruline (29 mg, 0.06 mMoles) the resultant mixture was stirred for 10 minutes until all the acid dissolved. 15 mg, 0.06 moles of EEDQ was added and the reaction mixture was stirred in the dark overnight. The reaction mixture was then concentrated, rinsed with diethyl ether and the residue was purified by reverse phase Prep HPLC to give the product which was identified by Mass Spec M+1=1103.

1.2f Reaction F:

Deprotection of Fmoc protecting group was done using 5% piperidine in 1 mL DMF for 10 minutes. Concentration of the reaction mixture was followed by rinsing the solid residue with diethyl ether. Product was confirmed by Mass Spec, MS+1=880 and M+K=919

1.2g Reaction G:

To a solution of the free amine in DMF (1.5 mL) prepared in step F was added Mal-(PEG)$_4$-NHS-ester (20 mg) and the reaction mixture stirred for 1 hr. Concentration followed by purification reverse phase Prep HPLC gave 2.8 mg of (11% overall yield, beginning from Alkylating core) which was confirmed by mass spec MS+1=2178, M+Na=1300 and M+K=1316

1.3 Synthesis of Peptide Linker Conjugated with Tubulysine A
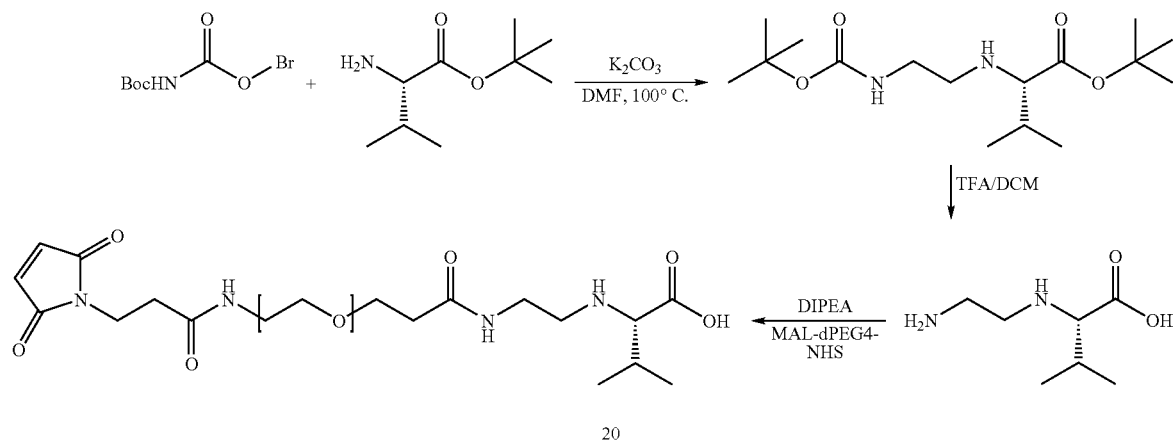
The ligand can be linked to PEG and peptide linker by the synthesis shown.
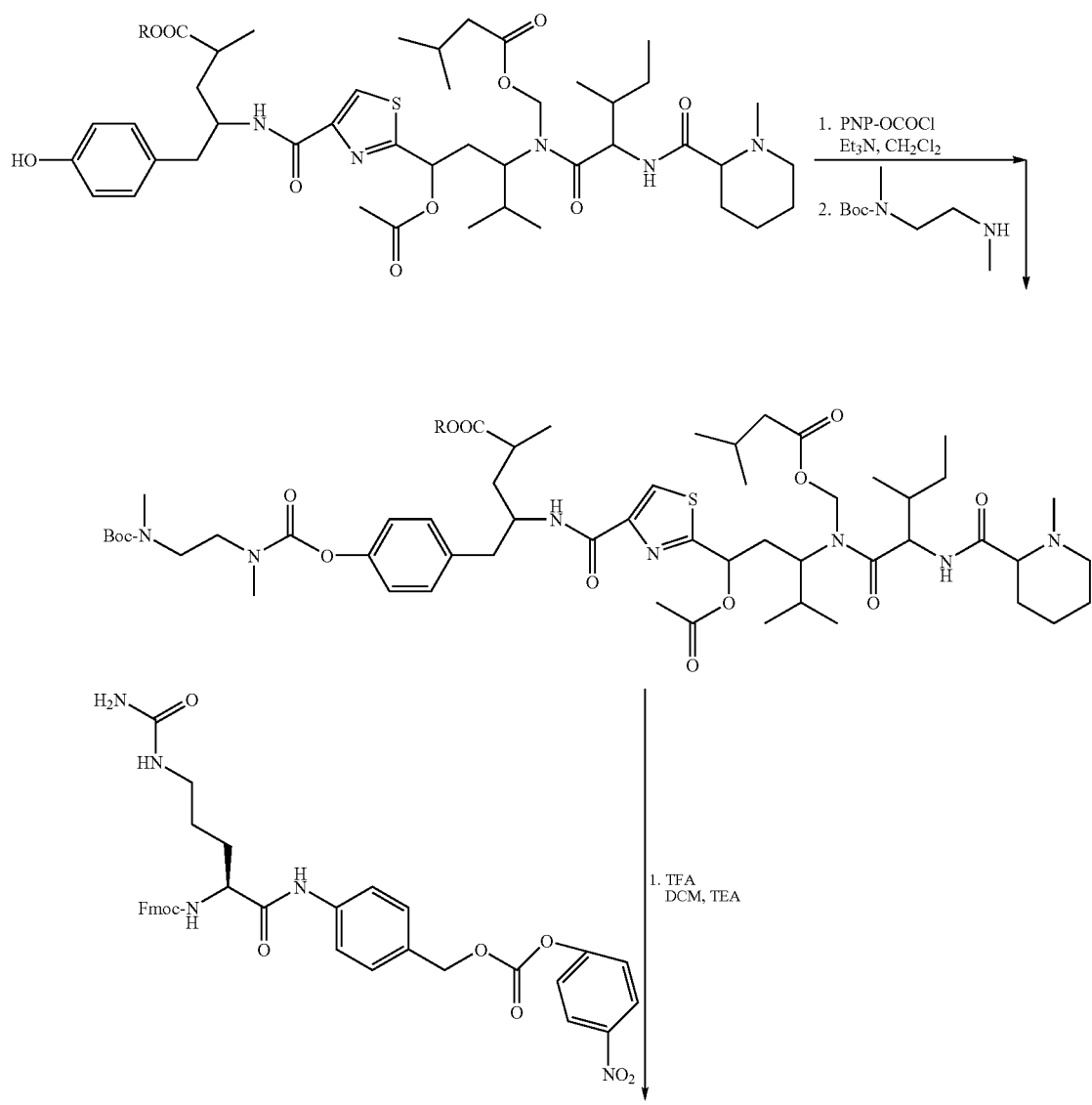

-continued
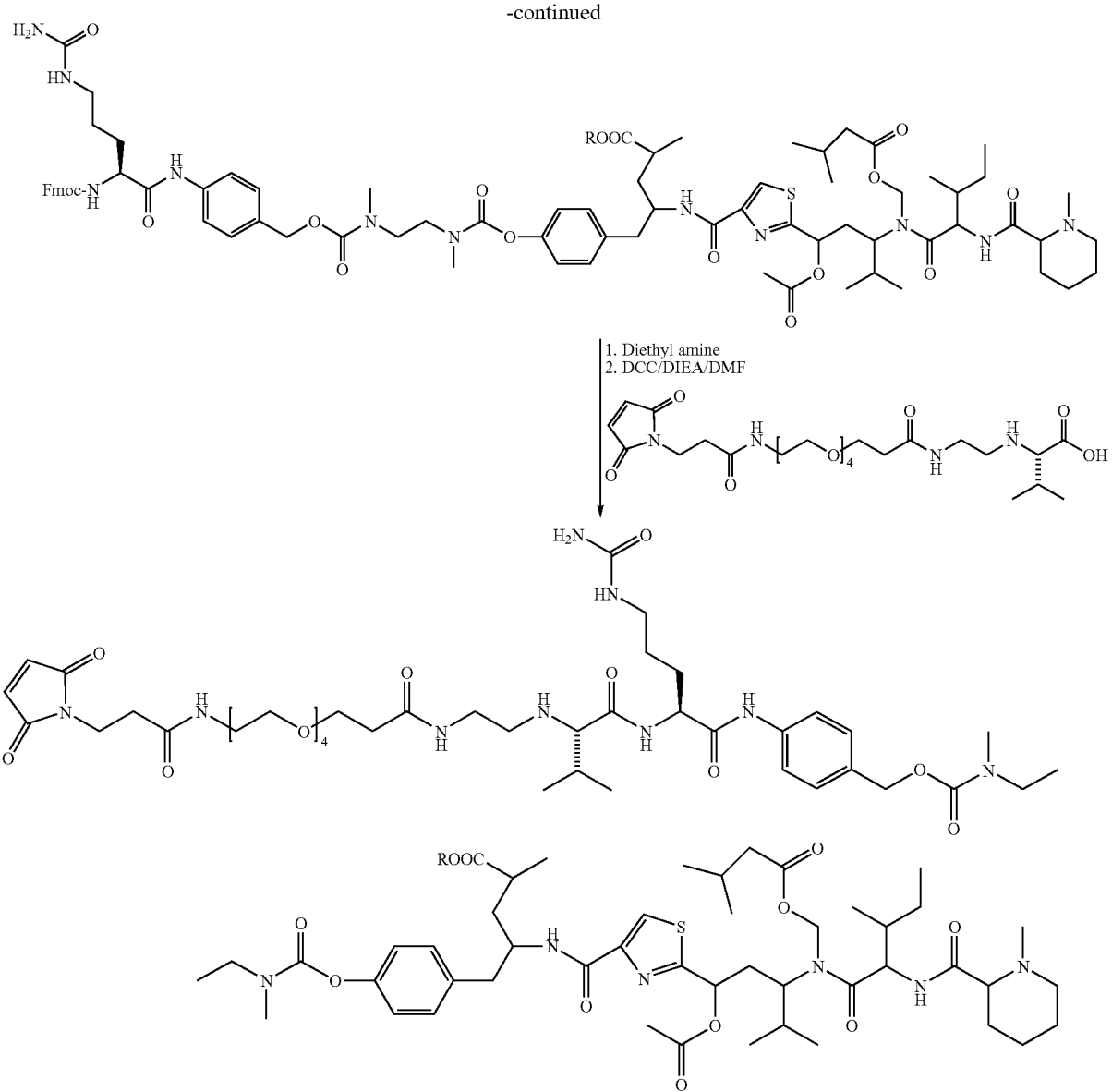
The synthesis of intermediates and ligand-drug conjugate having a peptide linker where the drug is Tubulysine A is shown hereinabove. This basic method may be used with other drugs.
1.4a Synthesis of Peptide-Linker Conjugate 111

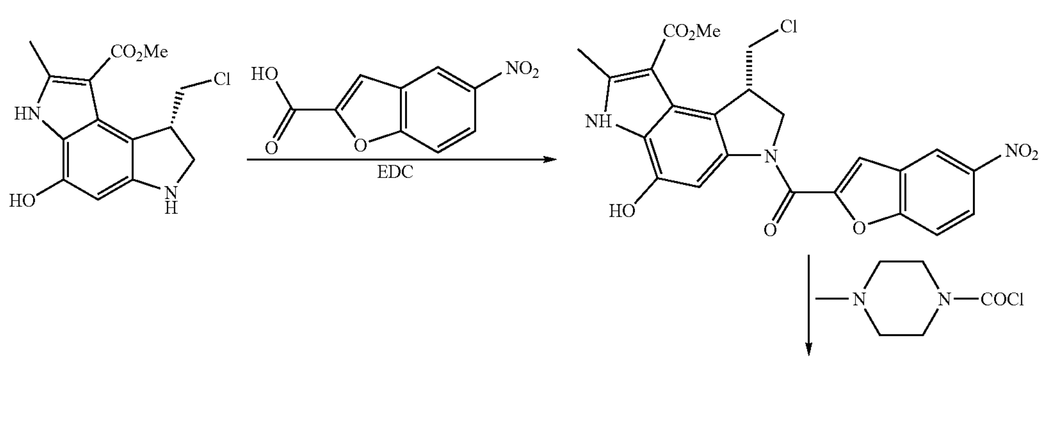

125 126
-continued
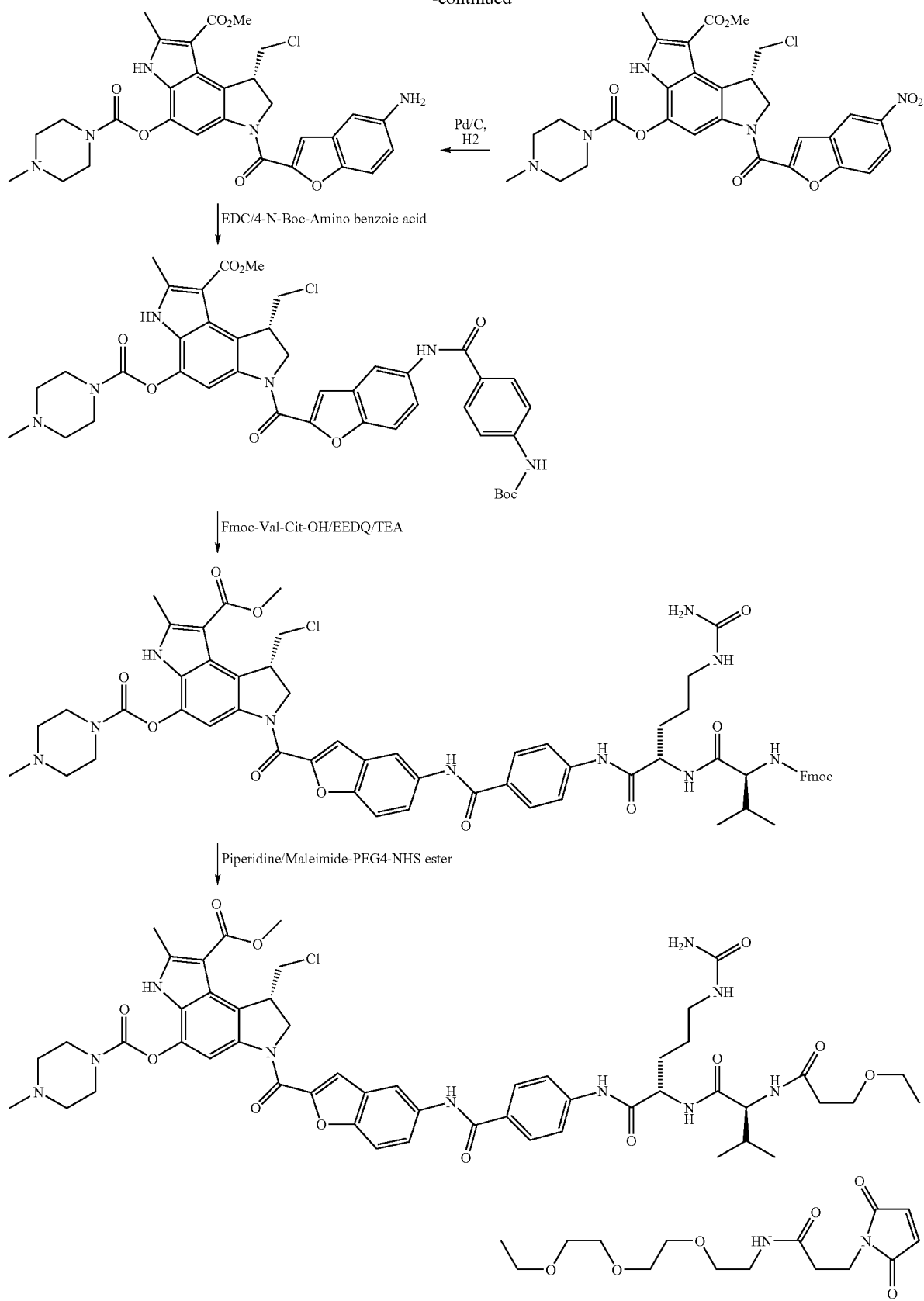

1.4b Synthesis of Peptide-Linker Conjugate 112
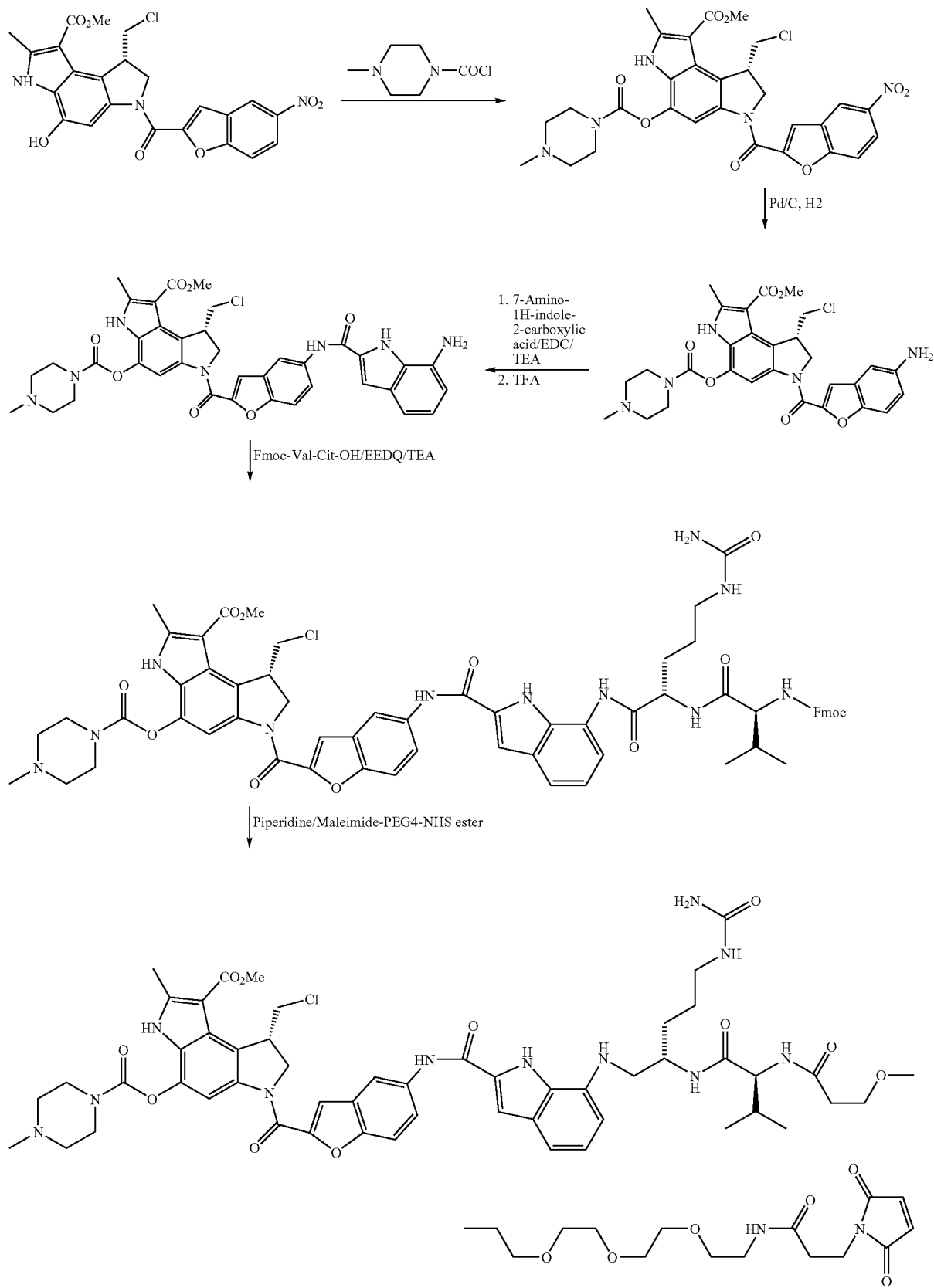

1.4c Synthesis of Peptide-Linker Conjugate 113
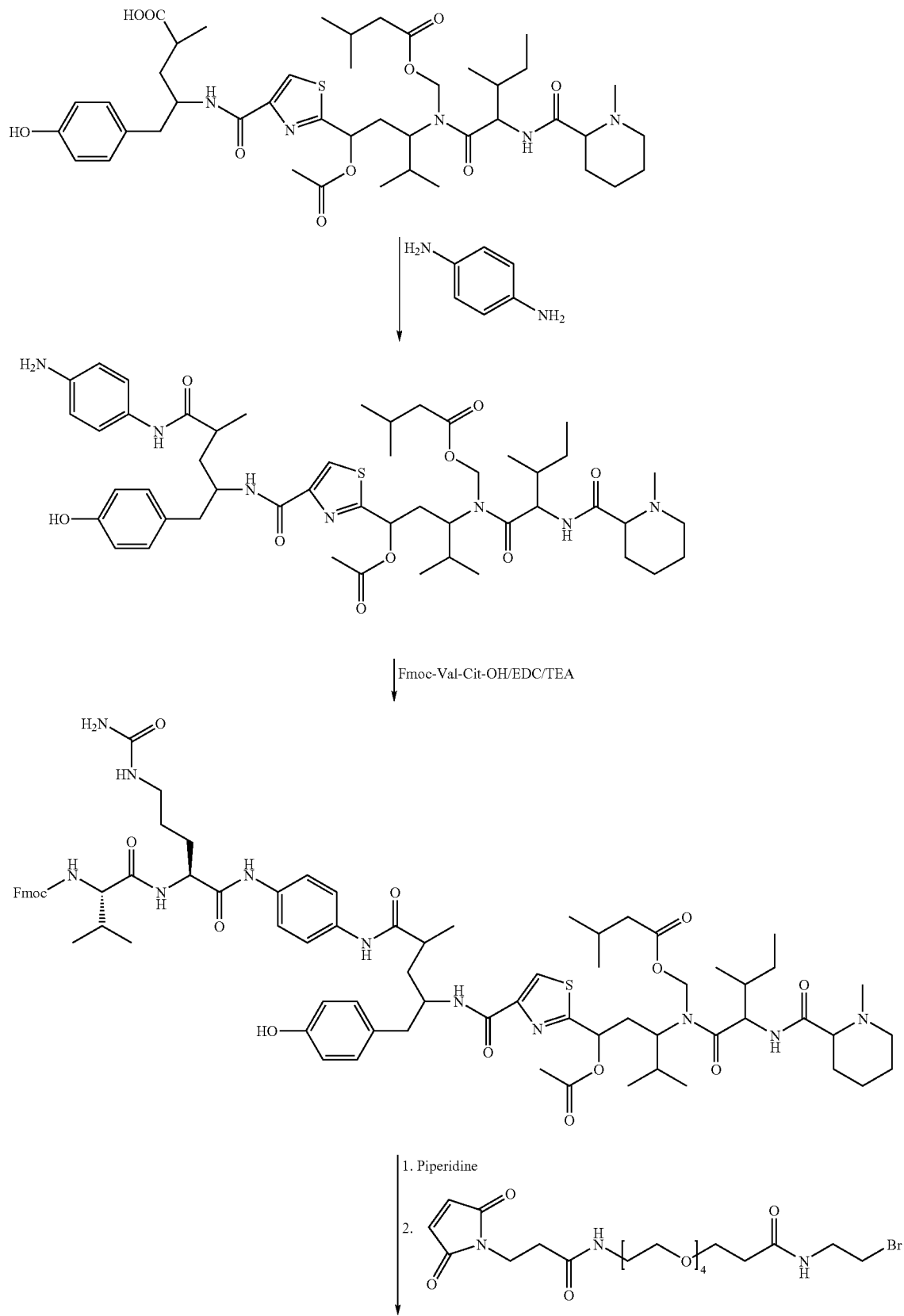

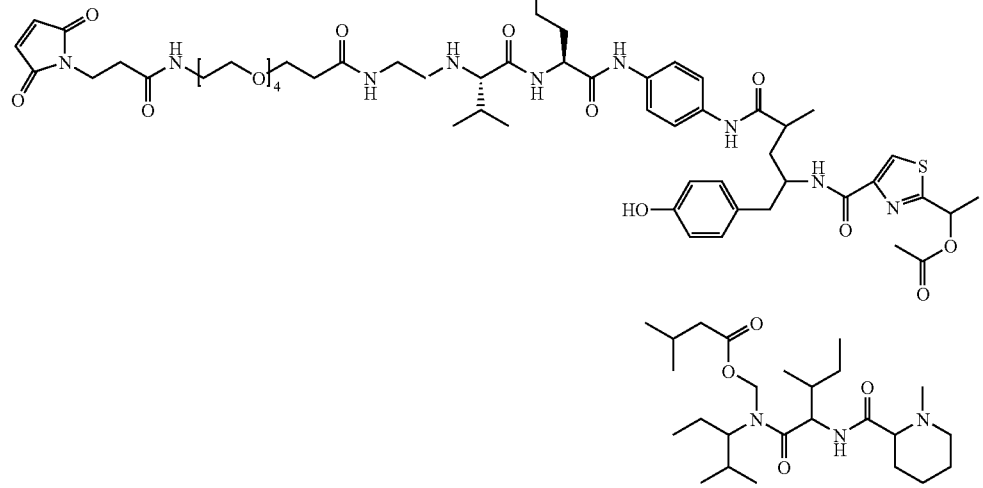
113
Example 2
Synthesis of 6-Membered Hydrazine Linker Conjugates
2.1 Synthesis of a 6-Membered Gem-Dimethyl Hydrazine Linker Conjugated to a Duocarmycin Derivative Cytotoxin
2.1a Synthesis Scheme for Compound 109
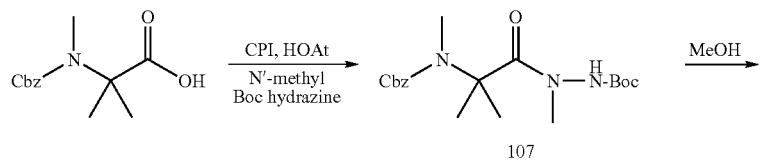
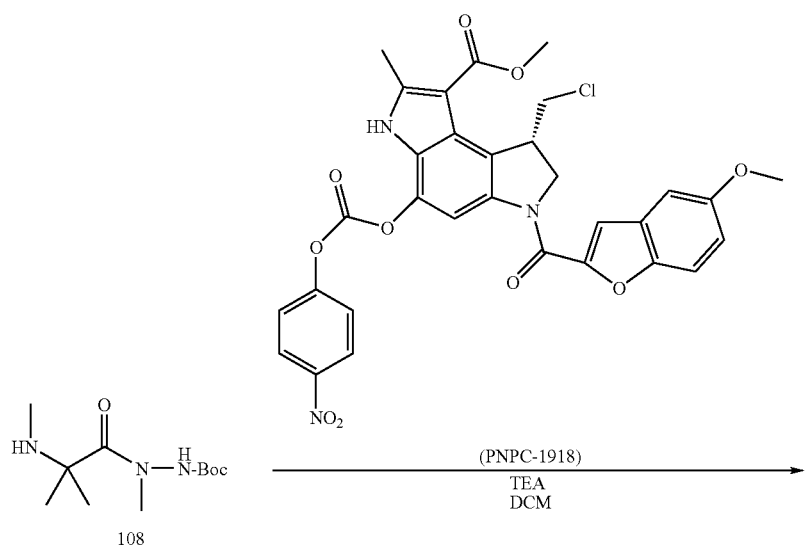

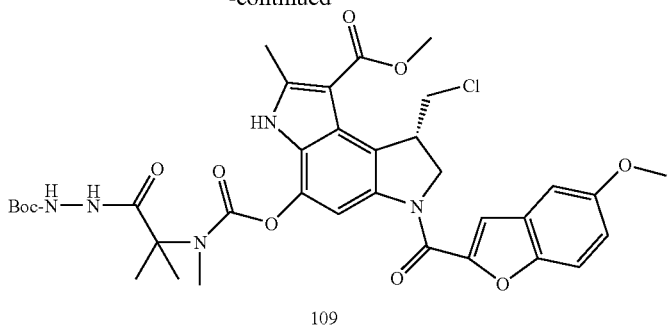

109

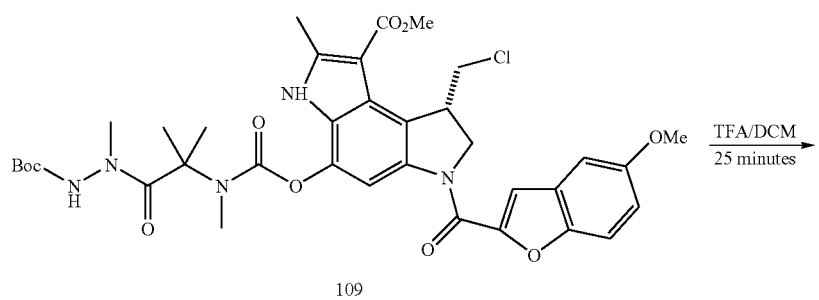

109 TFA/DCM 25 minutes

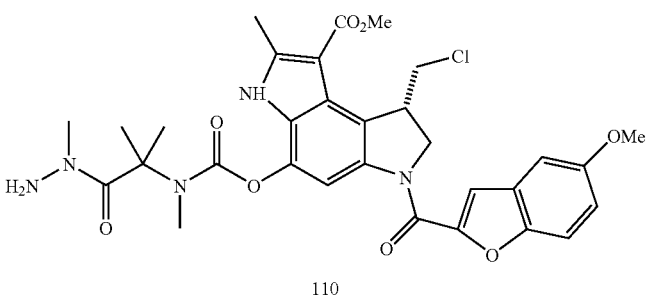

110

2.1b Synthesis of Compound 110

To a suspension of Cbz-dimethyl alanine (1 g, 3.98 mMoles) in 30 mL of DCM at ice-bath temperature was added HOAT (catalytic, 0.25 equivalents), DIPEA (2.8 mL, 16 mmoles) followed by 2-chloro-1,3-dimethylimidazolidinium hexafluorophosphate (CIP) (1.2 g, 4.4 mmoles). To this reaction mixture was then added Boc-NN(Me) (643 moles, 4.4 mmoles). The reaction mixture was allowed to stir overnight at room temperature. To the reaction mixture is added 10% citric acid solution (100 mL) and extracted with DCM. The organic phase was washed with water and then with a saturated solution of sodiumbicarbonate followed by water again. The organic phase was then concentrated and purified by silica gel column with increasing polarity of ethyl acetate in hexanes to give 860 mg, 57% yield 107 which identified by mass spec M+1=380 and M+NH$_4^+$=397.

The Cbz protecting group was removed by catalytic hydrogenation using Pd/C in MeOH to give compound 108 which was confirmed by MS.

To a solution of PNPC-1918 (10 mg, 0.1 mmoles) in 2 mL DCM was added drop wise a solution of Compound 108 (60 mg, 0.25 mmoles) in 8 mL of DCM and the reaction mixture was allowed to stir for 2 days till all the starting material had disappeared. The reaction mixture was filtered through a short silica gel pad and then concentrated and purified by reverse phase Prep HPLC to give 4.2 mg of Compound 109. This was identified by Mass Spec M+1=740. Boc Deprotection of Compound 109 was done with pure TFA for 20 minutes to give Compound 110. The product was identified by Mass Spec, M+1=640.

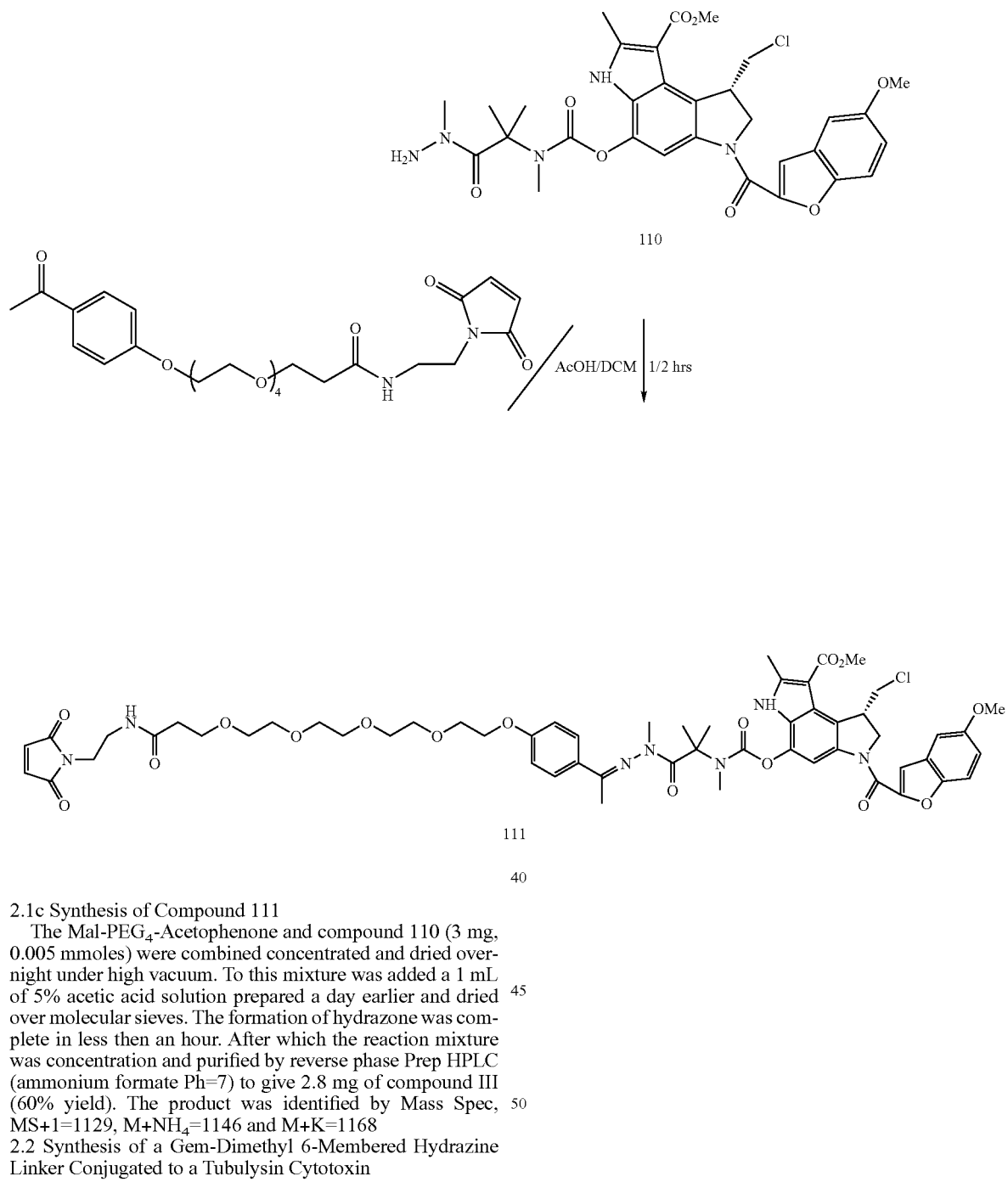

2.1c Synthesis of Compound 111

The Mal-PEG$_4$-Acetophenone and compound 110 (3 mg, 0.005 mmoles) were combined concentrated and dried overnight under high vacuum. To this mixture was added a 1 mL of 5% acetic acid solution prepared a day earlier and dried over molecular sieves. The formation of hydrazone was complete in less then an hour. After which the reaction mixture was concentration and purified by reverse phase Prep HPLC (ammonium formate Ph=7) to give 2.8 mg of compound III (60% yield). The product was identified by Mass Spec, MS+1=1129, M+NH$_4$=1146 and M+K=1168

2.2 Synthesis of a Gem-Dimethyl 6-Membered Hydrazine Linker Conjugated to a Tubulysin Cytotoxin

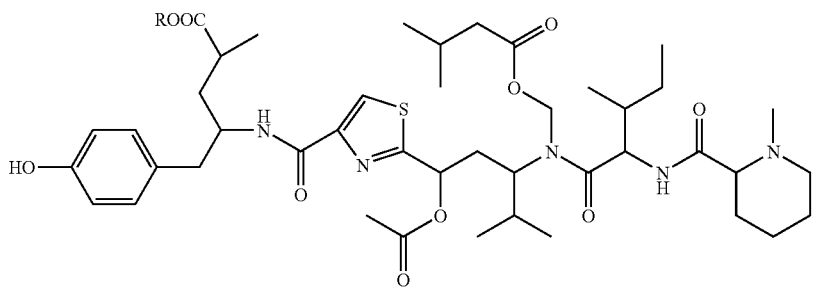

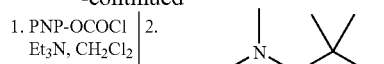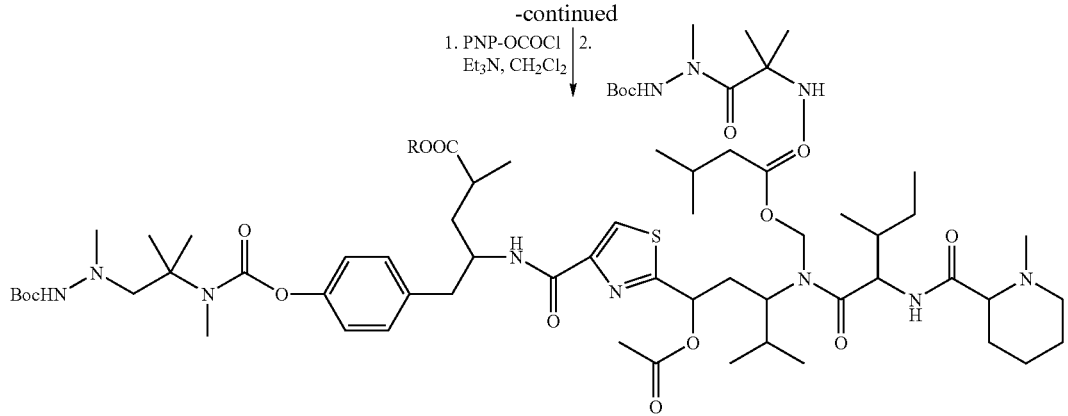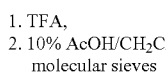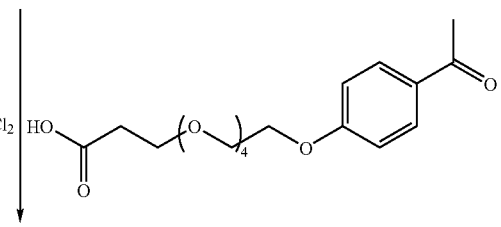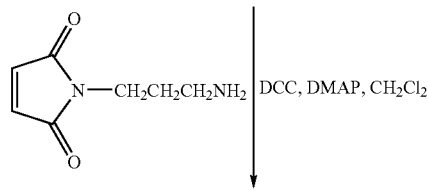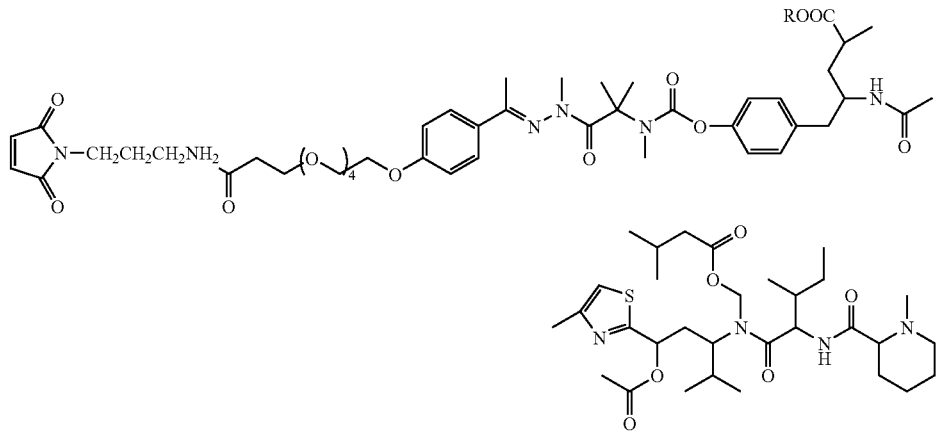
Similar methodology as shown in Example 2.1 can be applied for the synthesis of a geminal dimethyl 6-membered hydrazine linker complexed with a drug such as tubulysin A is shown.

2.3 Synthesis of a Hydrazine Linker Conjugated to a Duocarmycin Analog

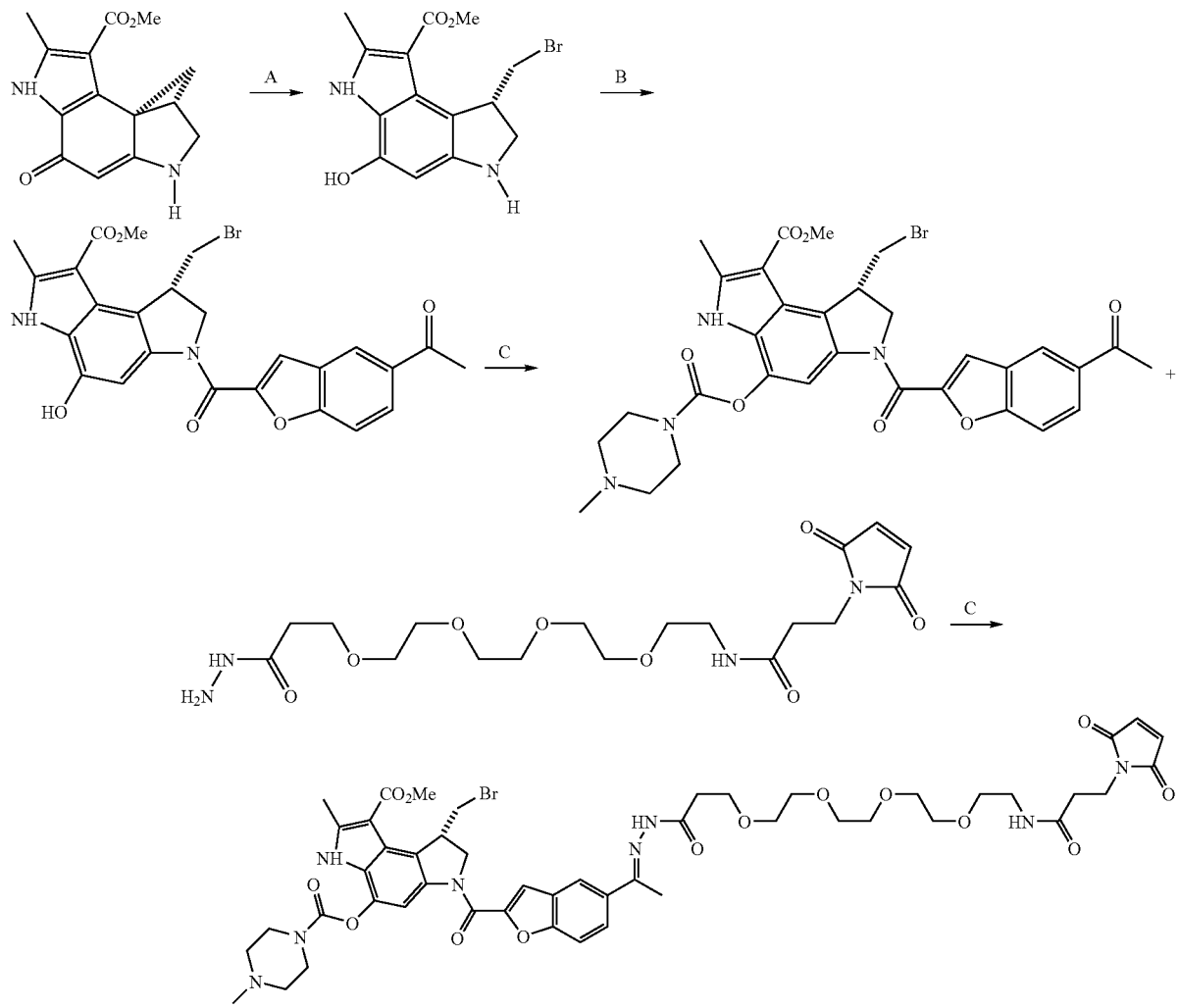

To a solution of the bromo methyl seco compound (0.074 mMoles) in 3 mL DMF was added the 5-actyl indole-2-carboxylate (30 mg, 0.15 mMoles) and EDC (28 mg, 0.15 mMoles) and the resulting mixture was stirred overnight. The reaction mixture was concentrated and purified by silica gel chromatography using 5% MeOH in DCM Tt give 29 mg (74% yield) of product which was confirmed by mass spec M+1=523.

To a solution of the compound synthesized in step C in 5 mL DCM and 300 μL allyl alcohol was added methyl piperazine carbonyl chloride (22 mg, 0.11 mMoles) and pyridine 44 μL. The reaction mixture was stirred at room temperature for 5 hours. Concentration followed by purification by silica gel chromatography using 5% MeOH/DCM as eluant gave 48 mg of the desired product (73% yield). The product was confirmed by Mass Spec. M+1=650.

A solution of the above compound (8.2 mg, 0.012 mmoles) and Mal-PEG$_4$-hydrazine in 5% acetic acid in anhydrous DCM was stirred at room temperature for 20 minutes followed by evaporation of Solvents and Reverse phase Prep HPLC using acetonitrile and ammonium formate buffered aqueous phase gave 2.5 mg of the desired final product which was confirmed by mass Spec, M+1=1063

2.4a Rate of Cyclization of a Dimethyl 6-Membered Hydrazine Linker

A duocarmycin analog conjugated to a dimethyl 6-membered hydrazine linker was incubated in buffer at pH 7.4 for 24 hours and the generation of cyclized product resulting from cyclization of the hydrazine linker, thereby releasing free duocarmycin analog, was assessed over time.

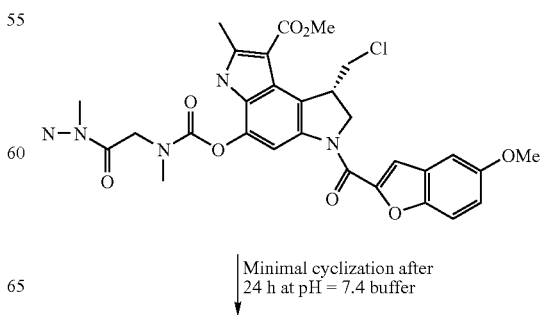

Minimal cyclization after 24 h at pH = 7.4 buffer

141

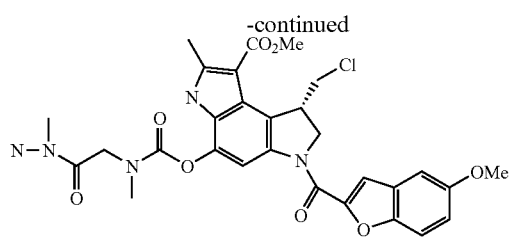

Minimal amounts of cyclized product were detected over 24 hours at pH=7.4, indicating this form of 6-membered hydrazine linker exhibits a relatively slow rate of cyclization.

2.4b Rate of Cyclization of a Gem-Dimethyl 6-Membered Hydrazine Linker

A duocarmycin analog conjugated to a gem-dimethyl 6-membered hydrazine linker was incubated in buffer at pH 7.4 and the generation of cyclized product resulting from cyclization of the hydrazine linker, thereby releasing free duocarmycin analog, was assessed over time.

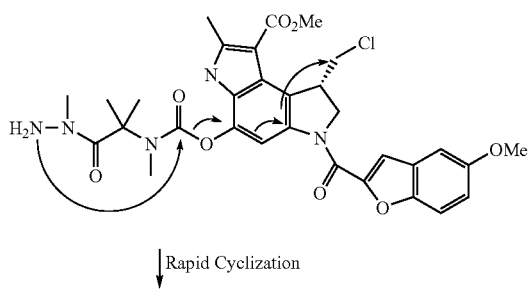

142

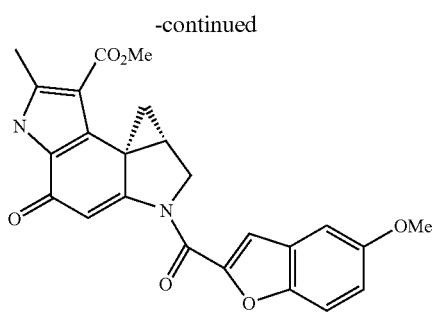

With the 6-membered gem-dimethyl linker, the cyclization reaction was quite rapid, proceeding to completion within a few minutes. Thus, the rate of cyclization for the gem-dimethyl 6-membered hydrazine linker proceeded at a much faster rate than that of the 6-membered linker that did not contain the gem-dimethyl moiety.

Example 3

Synthesis of 5-Membered Hydrazine Linker Conjugates 3.1 Synthesis Methodology for Compound 4

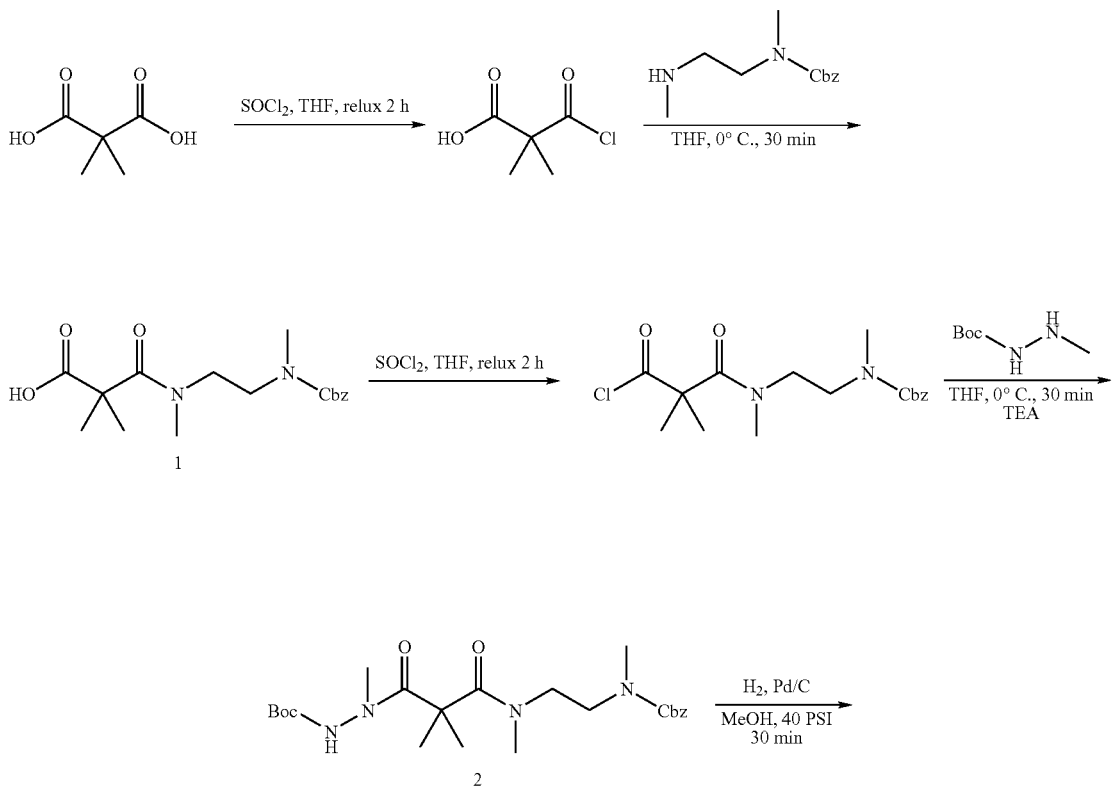

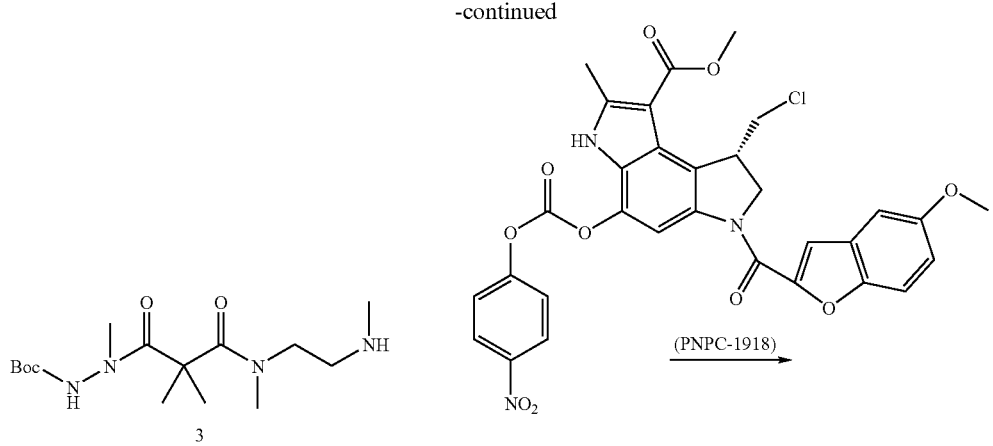

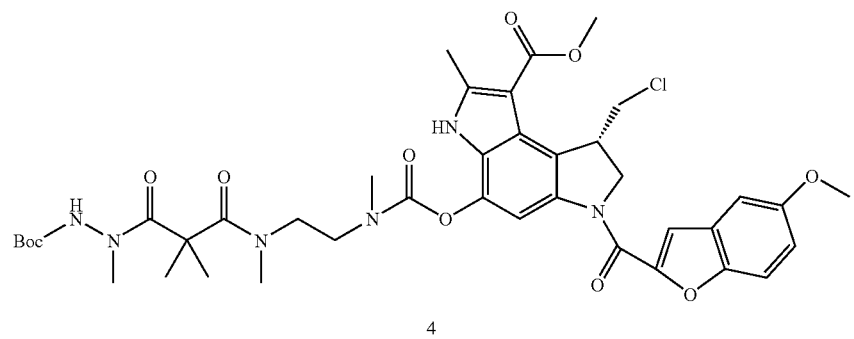

Cbz-DMDA-2,2-Dimethylmalonic Acid (1)

To a solution of 2,2-Dimethyl-malonic acid (2.0 gm, 0.0151 moles), Thionyl chloride (1.35 ml, 0.0182 moles) in THF (15 ml) in a 25 mL flask equipped with a stir bar, temperature probe, and reflux condenser was added a drop of DMF and the reaction mixture was heated to reflux for 2 hrs then cooled to room temperature. This reaction mixture was transferred to drop wise to a solution of Cbz-DMDA (4 gm, 0.0182 moles) and triethylamine (4 ml, 0.0287 moles) in THF (5 ml) at 0 C and was stirred for 30 min at this temperature. The solvent was removed in vacuo and the residue dissolved in 1N HCl (50 ml) and extracted with DCM (2×25 ml). The combined organic layers were extracted with 1N NaOH (2×25 ml) and the combined aqueous layer were acidified (pH<1) with conc. HCl and extracted with EtOAc (2×25 ml), dried over MgSO$_4$, filtered and concentrated in vacuo to an off-white sticky solid, 3.44 gm, 68% yield. Compound 1 was confirmed by mass spec: m/z 337.0 [M+1]$^+$ HPLC retention time: 3.77 min (mass spec)

Cbz-DMDA-2,2-Dimethylmalonic-Boc-N'-methylhydrazine (2)

To a solution of Compound 1 (3.0 gm, 0.0089 moles), Thionyl chloride (0.78 ml, 0.0107 moles) in THF (25 ml) in a 50 ml 3N RBF equipped with a stir bar, temperature probe, and reflux condenser was added a drop of DMF and the reaction mixture was refluxed for 2 hrs then cooled to room temperature. This reaction mixture was then added dropwise to a solution of Boc-N-methyl hydrazine (1.33 gm, 0.091 moles) and triethylamine (3 ml, 0.0215 moles) in THF (25 ml) at 0 C and stirred for 30 min. The solvent was removed in vacuo and the residue dissolved in EtOAc (50 ml), dried over MgSO$_4$, filtered and concentrated in vacuo to a brown oil. The oil was dissolved in EtOAc and purified by column chromatography (100% EtOAc) resulting in 3.45 gm, 83% yield of a clear oil. Compound 2 was confirmed by mass spec: m/z 465.2 [M+1] HPLC retention time: 3.97 min (mass spec)

DMDA-2,2-Dimethylmalonic-Boc N'-methylhydrazine (3)

To a solution of Compound 2 (0.5 gm, 0.0011 moles) in MeOH (30 ml) was added 10% Pd/C (15 mg) and the reaction placed on a Parr hydrogenator for 30 minutes. The catalyst was filtered off and filtrate concentrated in vacuo to a clear oil to yield Compound 3 (0.38 gm). Product was confirmed by NMR ('H, CDCl$_3$): δ 1.45 (s, 15H) 2.45 (s, 3H) 2.85 (s, 6H), 3.16 (s, 3H) 4.64 (m, 1H) 10.6 (bs, 1H); NMR (13C, CDCl$_3$) δ 24.1, 28.57, 35.15, 35.58, 36.66, 47.01, 48.51, 81.11, 155.17, 173.56, 176.24

Synthesis of Compound 4

To a 15 ml RBF equipped with a stir bar, was combined Compound 3 (50 mg, 0.1513 mmoles), PNPC-1918 (20 mg, 0.0315 mmoles) and DCM (5 ml). The solution was stirred for 30 minutes, then triethylamine (25 uL, 0.1794 mmoles) was added and the bright yellow solution was stirred for 1 hr. The solution was concentrated in vacuo to a yellow oil and purified by column chromatography (100% DCM to 1:1 EtOAc/DCM) to yield Compound 4 as an off-white solid, 22 mg, (84%). Product was confirmed by mass spec: m/z 825.7 [M+1]$^+$ HPLC retention time: 7.65 min (mass spec)

3.2 Synthesis of an Antibody-Drug Conjugate having a 5-Membered Hydrazine Linker

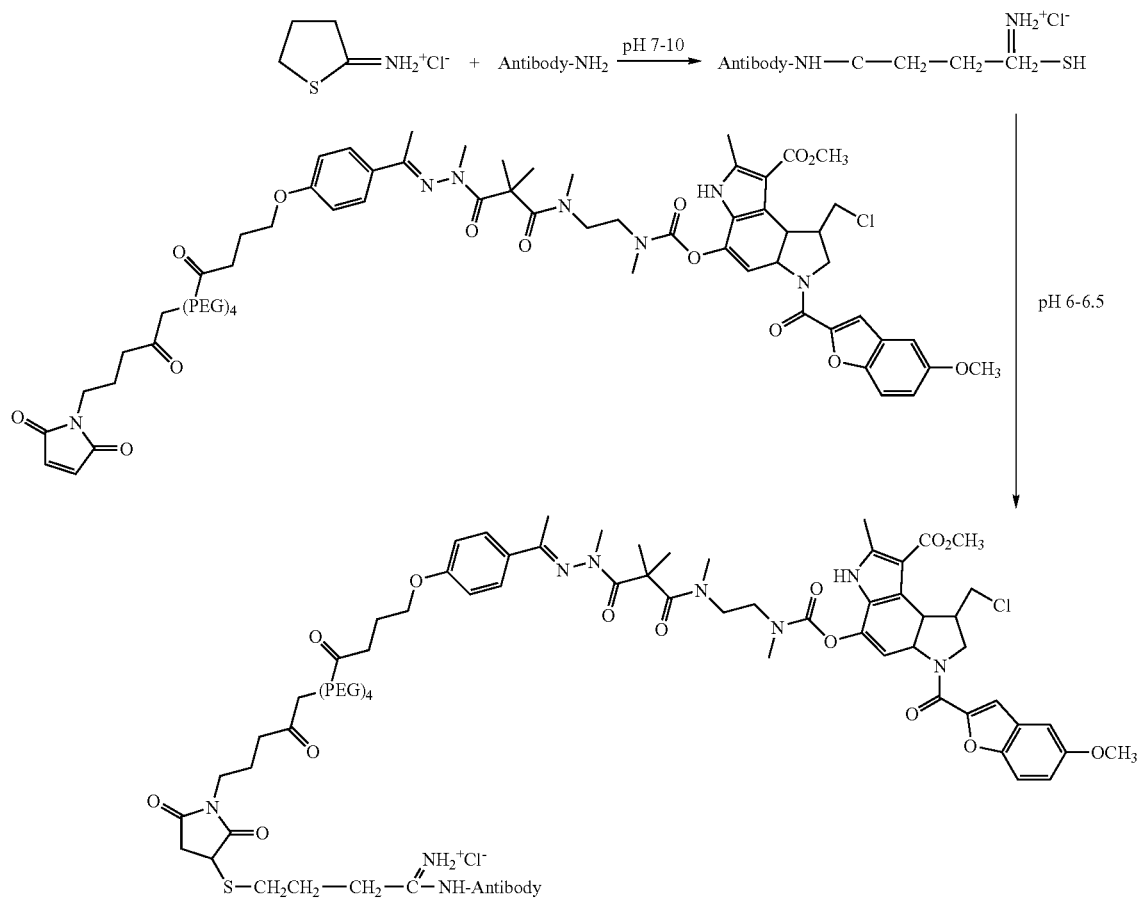

This scheme demonstrates the conjugation of an antibody to a linker-drug complex. These methodologies are well known in the pharmaceutical art. Examples of other reactive sites includes maleimides, haloacetamides with thiols on a ligand, thiols that react with disulfides on a ligand, hydrazides that react with aldehydes and ketones on a ligand, and hydroxysuccinimides, isocynates, isothiocyanates, and anhydride that react with amino group on a ligand.

Example 4

Synthesis of Disulfide Membered Linker Conjugates

Scheme 1

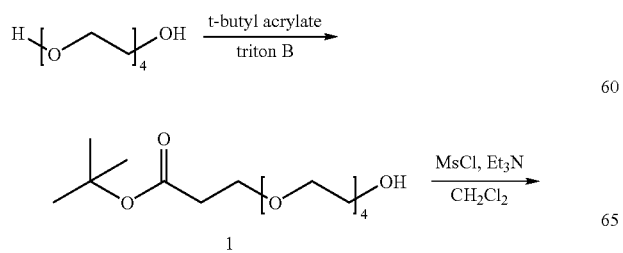

-continued

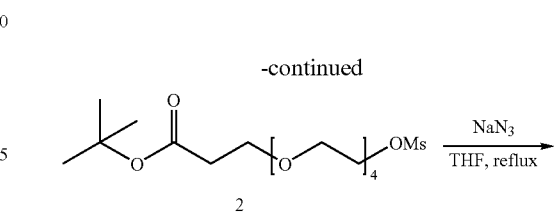

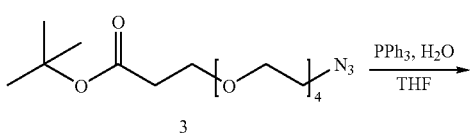

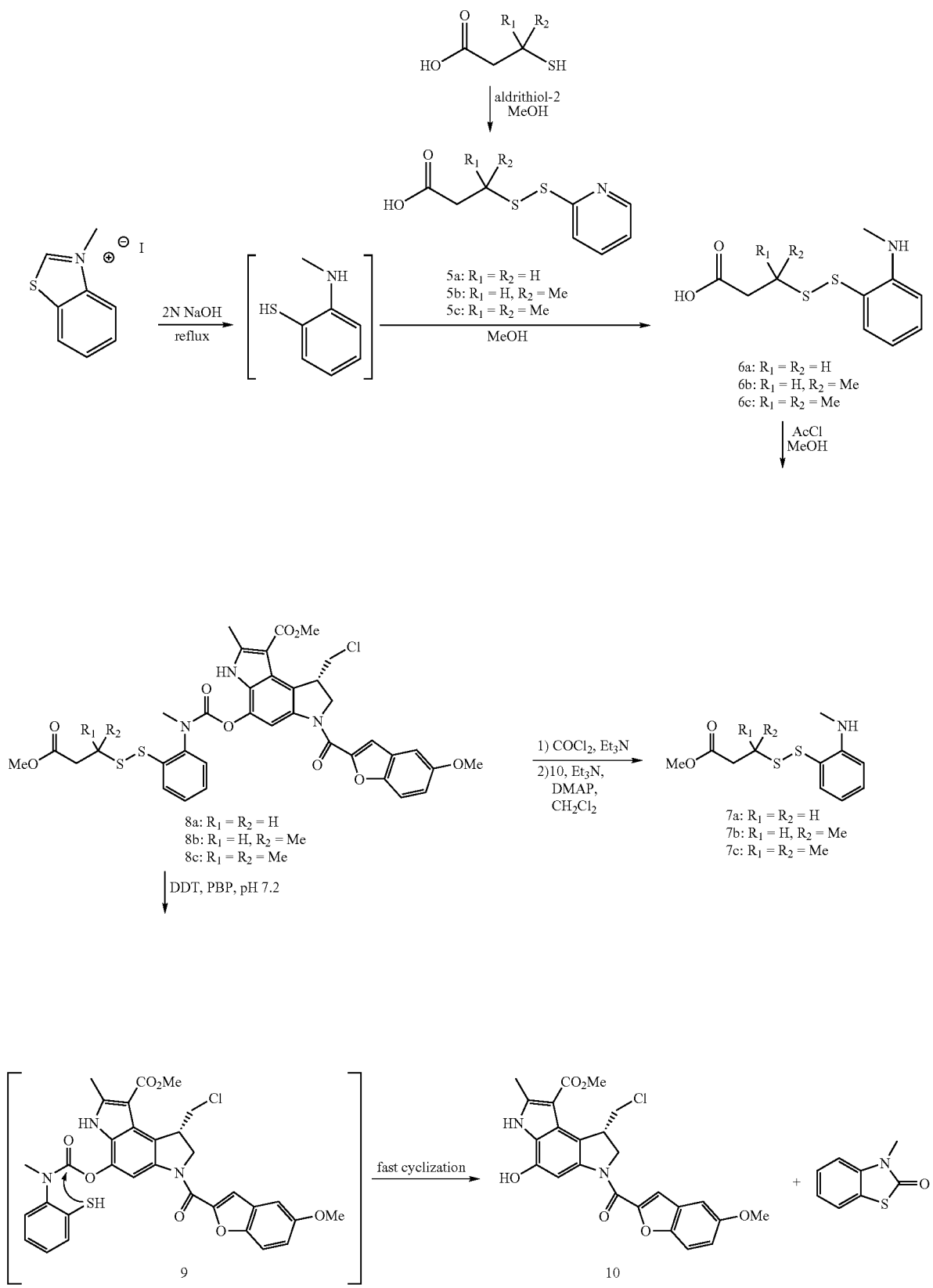

Scheme 3
6a: R₁ = R₂ = H
6b: R₁ = H, R₂ = Me
6c: R₁ = R₂ = Me
$\xrightarrow{\text{4, CH}_2\text{Cl}}_{\text{DCC, HOBt}}$
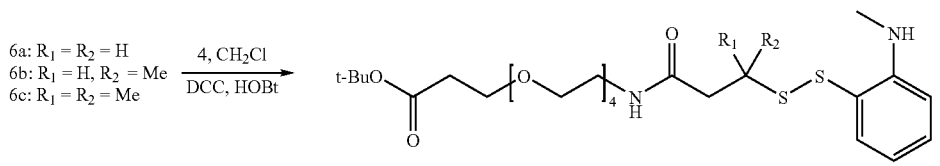
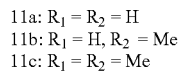
11a: R₁ = R₂ = H
11b: R₁ = H, R₂ = Me
11c: R₁ = R₂ = Me
1) COCl₂, Et₃N, CH₂Cl₂
2) 10, Et₃N, DMAP, CH₂Cl₂
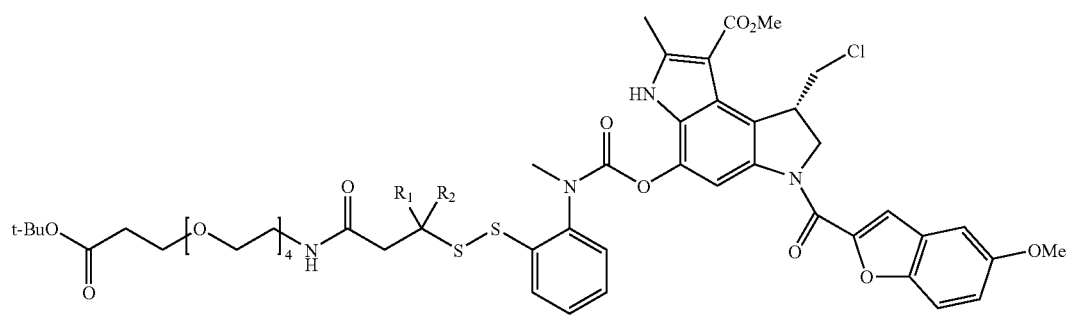
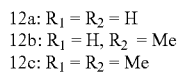
12a: R₁ = R₂ = H
12b: R₁ = H, R₂ = Me
12c: R₁ = R₂ = Me
TFA/CH₂Cl₂
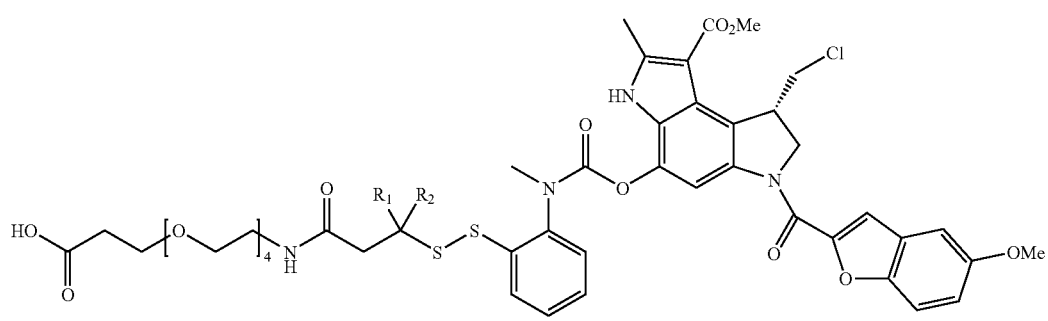
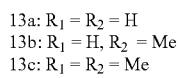
13a: R₁ = R₂ = H
13b: R₁ = H, R₂ = Me
13c: R₁ = R₂ = Me
N-hydroxysuccinimide, CH₂Cl₂
PS-carbodiimide, PS-DMAP -continued

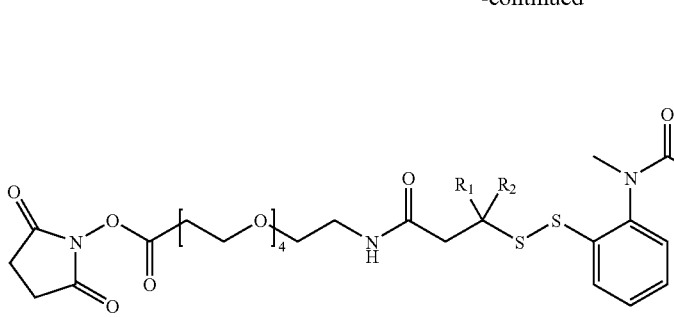
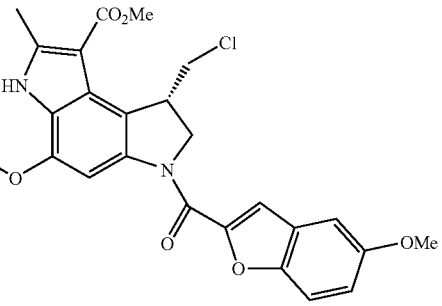

14a: R₁ = R₂ = H
14b: R₁ = H, R₂ = Me
14c: R₁ = R₂ = Me 4.1a Synthesis of Compound 1.

To a flask containing PEG₄ (3.88 g, 20 mmole) was added triton B (40% solution in methanol, 1.08 mL, 0.25 mmole) and tert-butyl acrylate (3.62 mL, 24 mmole) followed after 15 min. The mixture was stirred at room temperature overnight. The mixture was concentrated in vacuo and the residue was purified by flash chromatography on silica gel with 1% methanol in dichloromethane as eluent to give the title compound as an colorless oil (2.35 g, 36%). $^1$H NMR δ 1.45 (s, 9H), 2.5 (t, 2H), 3.65 (m, 18H).

4.1b Synthesis of Compound 2.

To a solution of Compound 1 (1.17 g, 3.6 mmole) in dichloromethane (10 mL) were added triethylamine (532 μL, 4 mmole) and methanesulfonyl chloride (309 μL, 4 mmole). The mixture thus obtained was stirred at room temperature overnight. The solvent was evaporated and the residue was purified by flash chromatography on silica gel with 1% methanol in dichloromethane as eluent to give the title compound as an yellow oil (1.3 g, 89%). $^1$H NMR δ 1.43 (s, 9H), 2.48 (t, 2H), 3.07 (s, 3H), 3.62-3.70 (m, 14H), 3.76 (m, 2H), 4.37 (m, 2H).

4.1c Synthesis of Compound 3.

To a solution of Compound 2 (1.3 g, 3.25 mmole) in ethanol (10 mL) was added sodium azide (423 mg, 6.5 mmole). The mixture thus obtained was refluxed overnight. The solvent was evaporated and the residue was purified by flash chromatography on silica gel with 1% methanol in dichloromethane as eluent to give the title compound as an yellow oil (1.01 g, 90%). $^1$H NMR δ 1.45 (s, 9H), 2.50 (t, 2H), 3.40 (t, 2H), 3.62-3.73 (m, 16H).

4.1d Synthesis of Compound 4.

To a solution of Compound 3 (470 mg, 1.35 mmol) in ether (5 mL) containing H₂O (25 μL) was added triphenylphosphine (391 mg, 1.48 mmole). The mixture thus obtained was stirred at room temperature overnight. The solvent was evaporated and the residue was purified by flash chromatography on silica gel with 1% methanol in dichloromethane as eluent to give the title compound as an yellow oil (325 mg, 75%). $^1$H NMR δ 1.45 (s, 9H), 2.24 (bs, 2H), 2.51 (t, 2H), 2.91 (t, 2H), 3.56 (m, 2H), 3.63-3.66 (m, 12H). 3.72 (m, 2H).

4.1e Synthesis of Compound 5.

To a solution of 3-mercaptopropionic acid (1.22 g, 11.5 mmole) in methanol (10 mL) was added aldrithiol-2 (3.78 g, 17.25 mmole). The mixture thus obtained was stirred at room temperature for 3 hours. The solvent was evaporated and the residue was purified by flash chromatography on silica gel with 30% ethyl acetate in hexanes as eluent to give the title compound as an oil (2.44 g, 98%). $^1$H NMR δ 2.8 (t, 2H), 3.05 (t, 2H), 7.14 (m, 1H), 7.67 (m, 2H), 8.48 (m, 1H).

Compound 5b: $^1$H NMR δ 1.43 (d, 3H), 2.61 (m, 1H), 2.76 (m, 1H), 3.40 (m, 1H), 7.17 (m, 1H), 7.66 (m, 2H), 8.45 (m, 1H).

4.1f Synthesis of Compound 6.

3-Methyl benzothiazolium iodide (1 g, 3.6 mmole) was dissolved in 2 N sodium hydroxide aqueous solution (10 mL) and the mixture was stirred for 6 hours at 100° C. then acidified with 6 N hydrochloric acid aqueous solution to pH 4 and extracted with diethyl ether. The organic layer was dried over Na₂SO₄, rotary evaporated in vacuo and the residue was dissolved in methanol (10 mL) and compound 5a (776 mg, 3.6 m mole) was added. The mixture was stirred at room temperature for 1 hour. The mixture was concentrated to dryness and the residue was purified by flash chromatography on silica gel with 1% methanol in dichloromethane as eluent to give the title compound as a yellow oil (482 mg, 55%). $^1$H NMR δ 2.85 (m, 2H), 2.95 (m, 5H), 6.64 (m, 2H), 7.3 (m, 1H), 7.4 (dd, 1H); MS (ES) 244 (M+H⁺), 487 (2M+H⁺).

Compound 6b: $^1$H NMR δ 1.35 (d, 3H), 2.48 (m, 1H), 2.92 (s, 3H), 3.02 (m, 1H), 3.34 (m, 1H), 6.62 (m, 2H), 7.28 (m, 1H), 7.44 (m, 1H); MS (ES) 258 (M+H⁺).

Compound 6c: $^1$H NMR δ 1.45 (s, 6H), 2.70 (s, 2H), 2.93 (s, 3H), 6.62 (m, 2H), 7.24 (m, 1H), 7.51 (m, 1H); MS (ES) 272 (M+H⁺), 294 (M+Na⁺), 310 (M+K⁺).

4.1g Synthesis of Compound 7.

To a solution of Compound 6a (28 mg, 0.115 mmole) in anhydrous methanol (1 mL) was added acetyl chloride (13 μL, 0.173 mmole). The mixture thus obtained was stirred at room temperature overnight. The solvent was evaporated and the residue was purified by flash chromatography on silica gel with 10% ethyl acetate in hexanes as eluent to give the title compound as an oil (24 mg, 83%). $^1$H NMR δ 2.08 (m, 2H), 2.93 (s, 3H), 2.95 (m, 2H), 3.70 (s, 3H), 6.63 (m, 2H), 7.28 (m, 2H), 7.40 (m, 2H); MS (ES) 258 (M+H⁺), 280 (M+Na⁺), 296 (M+K⁺).

Compound 7b: $^1$H NMR δ 1.32 (d, 3H), 2.45 (m, 1H), 2.92 (s, 3H), 2.93 (m, 1H), 3.35 (m, 1H), 3.67 (s, 3H), 6.62 (m, 2H), 7.26 (m, 1H), 7.44 (m, 1H); MS (ES) 272 (M+H⁺).

Compound 7c: $^1$H NMR δ 1.42 (s, 6H), 2.66 (s, 2H), 2.93 (s, 3H), 3.62 (s, 3H), 6.62 (m, 2H), 7.24 (m, 1H), 7.51 (m, 1H); MS (ES) 286 (M+H⁺), 308 (M+Na⁺), 324 (M+K⁺).

4.1h Synthesis of Compound 8.

To a solution of Compound 7a (24 mg, 0.093 mmole) in dichloromethane (1 mL) were added triphosgene (28 mg, 0.093 mmole) and triethylamine (37 μL, 0.28 mmole) at 0° C. The mixture was stirred for 1 hour. The mixture was concentrated to dryness and the residue was used in next step without further purification.

The crude material was dissolved in dichloromethane (1 mL) and the Compound 8a (35 mg, 0.074 mmole), and DMAP (23 mg, 0.190 mmole) were added. The mixture thus obtained was stirred at room temperature for overnight. The solvent was evaporated and the residue was purified by flash chromatography on silica gel with 1% methanol in dichloromethane as eluent to give the title compound as an yellow oil (53 mg, 76%). $^1$H NMR δ 2.70 (s, 3H), 2.74 (m, 2H), 3.06 (m, 2H), 3.34 (m, 1H), 3.35 and 3.36 (2s, 3H), 3.63 and 3.64 (2s, 3H), 3.86 (m, 1H), 3.88 (s, 3H), 3.93 and 3.94 (2s, 3H), 4.48 (m, 1H), 4.55 (m, 1H), 4.79 (m, 1H), 7.05 (m, 1H), 7.11 (m, 1H), 7.26-7.52 (m, 5H), 7.85 (d, 1H), 8.1 (bs, 1H), 8.98 and 9.08 (2s, 1H); MS (ES) 753 (M+H$^+$).

Compound 8b: $^1$H NMR δ 1.38 (m, 3H), 2.52 (m, 1H), 2.69 (m, 3H), 2.79 (m, 1H), 3.33 (m, 1H), 3.37 (2s, 3H), 3.64 (m, 3H), 3.88 (s, 3H), 3.84-3.90 (m, 1H), 3.93 (2s, 3H), 4.48 (m, 1H), 4.57 (m, 1H), 4.78 (m, 1H), 7.06 (m, 1H), 7.12 (m, 1H), 7.26-7.43 (m, 3H), 7.50 (m, 2H), 7.86 (m, 1H), 8.1 (bs, 1H), 8.99, 9.08, 9.13 and 9.22 (4s, 1H); MS (ES) 767 (M+H$^+$).

Compound 8c: $^1$H NMR δ 1.44 (m, 6H), 2.63 (d, 2H), 2.70 (s, 3H), 3.35 (m, 1H), 3.38 and 3.39 (2s, 3H), 3.63 and 3.64 (2s, 3H), 3.87 (m, 1H), 3.88 (s, 3H), 3.93 and 3.94 (2s, 3H), 4.48 (m, 1H), 4.55 (m, 1H), 4.79 (m, 1H), 7.05 (m, 1H), 7.12 (m, 1H), 7.31-7.39 (m, 3H), 7.49 (m, 2H), 7.89 (d, 1H), 8.1 (bs, 1H), 9.12 and 9.23 (2s, 1H); MS (ES) 781 (M+H$^+$).

4.1i Synthesis of Compounds 9 and 10.

To a solution of Compound 8a (0.1 mg) in PBS buffer solution (pH 7.2)/methanol (300 μL, 2/1) was added a 20 mM solution of DTT (100 μL, 15 equiv.) and monitored the progress of the reaction by HPLC. The reaction underwent too fast to detect, after few seconds the reaction was completed already to give product Compound 10 quantitatively. The reaction intermediate Compound 9 was not detected.

4.1j Synthesis of Compound 11.

To a solution of Compound 6a (66 mg, 0.2 m mole) in dichloromethane (1 mL) were added DCC (47 mg, 0.22 m mole), HOBt (31 mg, 0.22 mmole) and the compound 4 (50 mg, 0.2 m mole). The mixture thus obtained was stirred at room temperature overnight. The solvent was evaporated and the residue was purified by flash chromatography on silica gel with 1% methanol in dichloromethane as eluent to give the title compound as an yellow oil (70 mg, 62%). $^1$H NMR δ 1.44 (s, 9H), 2.51 (t, 1H), 2.63 (t, 2H), 2.93 (d, 3H), 3.01 (t, 2H), 3.45 (m, 2H), 3.55 (m, 2H), 3.64 (m, 12H), 3.71 (t, 2H), 5.01 (bs, 1H), 6.38 (bt, 1H), 6.62 (m, 2H), 7.27 (m, 1H), 7.43 (dd, 1H). MS (ES) 491 (M-56+H$^+$), 513 (M-56+Na$^+$), 547 (M+H$^+$), 569 (M+Na$^+$)

Compound 11b: $^1$H NMR δ 1.34 (d, 3H), 1.45 (s, 9H), 2.30 (m, 1H), 2.5 (t, 2H), 2.69 (m, 1H), 2.93 (d, 3H), 3.37-3.55 (m, 5H), 3.63 (m, 12H), 3.71 (t, 2H), 4.99 (bs, 1H), 6.13 (bt, 1H), 6.62 (m, 2H), 7.25 (m, 1H), 7.48 (dd, 1H). MS (ES) 505 (M-56+H$^+$), 527 (M-56+Na$^+$), 543 (M-56+K$^+$), 561 (M+H$^+$), 583 (M+Na$^+$).

Compound 11c: 1.43 (s, 3H), 1.45 (s, 9H), 2.46 (s, 2H), 2.5 (t, 2H), 2.92 and 2.94 (2s, 3H), 3.33 (m, 2H), 3.47 (t, 2H), 3.63 (m, 12H), 3.70 (t, 2H), 6.06 (bt, 1H), 6.63 (m, 2H), 7.25 (m, 1H), 7.54 (d, 1H); MS (ES) 519 (M-56+H$^+$), 541 (M-56+Na$^+$), 575 (M+H$^+$), 597 (M+Na$^+$).

4.1k Synthesis of Compound 12:

To a suspension of Compound 11a (20 mg, 0.037 mmole) in dichloromethane (1 mL) were added triethylamine (15 μL, 0.11 mmole) and a solution of 2 N phosgene in toluene (55 μL, 0.11 m mole) at 0° C. The mixture was stirred at room temperature for 1 hour. The mixture was concentrated and the residue was dissolved in dichloromethane (1 mL) and the compound 10 (14 mg, 0.030 mmole) and DMAP (9 mg, 0.076 m mole) were added. The mixture thus obtained was stirred at room temperature overnight. The solvent was evaporated and the residue was purified by flash chromatography on silica gel with 1% methanol in dichloromethane as eluent to give the title compound as an yellow oil (23 mg, 74%). $^1$H NMR δ 1.44 (s, 9H), 2.49 (t, 2H), 2.67 (m, 2H), 2.65 and 2.67 (2s, 3H), 3.07 (m, 2H), 3.33 (s, 3H), 3.40 (m, 3H), 3.51 (m, 2H), 3.60 (m, 12H), 3.69 (m, 2H), 3.87 (s, 3H), 3.92 (s, 3H), 3.93 (m, 1H), 4.52 (m, 2H), 4.78 (m, 1H), 6.65, 6.74 and 6.97 (3bt, 1H), 7.06 (d, 1H), 7.12 (s, 1H), 7.29-7.42 (m, 3H), 7.50 (m, 2H), 7.87 (d, 1H), 8.10 and 8.15 (2bs, 1H), 9.79 and 9.58 (2s, 1H); MS (ES) 986 (M+H$^+$−56), 1042 (M+H$^+$).

Compound 12b: $^1$H NMR δ 1.32 (m, 3H), 1.44 (s, 9H), 2.39 (m, 1H), 2.48 (m, 2H), 2.60 (m, 1H), 2.67 and 2.69 (2s, 3H), 3.32 and 3.35 (2s, 3H), 3.38-3.72 (m, 20H), 3.88 (s, 3H), 3.93 (s, 3H), 3.94 (m, 1H), 4.52 (m, 2H), 4.77 (m, 1H), 6.53, 6.67 and 6.72 (3bt, 1H), 7.06 (d, 1H), 7.12 (s, 1H), 7.29-7.39 (m, 3H), 7.49 (m, 2H), 7.88 (d, 1H), 8.12 and 8.25 (2bs, 1H), 9.13, 9.36, 10.08 and 10.21 (4s, 1H); MS (ES) 1000 (M+H$^+$−56), 1056 (M+H$^+$), 1078 (M+Na$^+$), 1084 (M+K$^+$).

Compound 12c: $^1$H NMR δ 1.30-1.42 (m, 3H), 1.44 (s, 9H), 2.45-2.52 (m, 4H), 2.69 and 2.72 (2s, 3H), 3.34 and 3.35 (2s, 3H), 3.39-3.72 (m, 19H), 3.88 (s, 3H), 3.925 and 3.93 (2s, 3H), 3.94 (m, 1H), 4.53 (m, 2H), 4.80 (m, 1H), 6.63 (m, 1H), 7.06 (dd, 1H), 7.13 (d, 1H), 7.25-7.39 (m, 3H), 7.50 (m, 2H), 7.89 (d, 1H), 8.10 and 8.27 (2bs, 1H), 9.99 and 10.191 (2s, 1H); MS (ES) 1014 (M+H$^+$−56), 1070 (M+H$^+$), 1108 (M+K$^+$).

4.1l Synthesis of Compound 13.

Compound 12a (23 mg, 0.022 mmole) was dissolved in the solution of trifluoroacetic acid and dichloromethane (1 mL, 1/1) and the mixture was stirred at room temperature for 30 min and concentrated to give the product (21 mg, 100%) $^1$H NMR δ 2.60 (t, 2H), 2.67 and 2.68 (2s, 3H), 2.75 (m, 2H), 3.07 (m, 2H), 3.34 (s, 3H), 3.38-3.64 (m, 21H), 3.76 (t, 2H), 3.88 (s, 3H), 3.92 (s, 3H), 3.93 (m, 1H), 4.53 (m, 2H), 4.78 (m, 1H), 7.06 (d, 1H), 7.13 (s, 1H), 7.31-7.43 (m, 3H), 7.49 (m, 2H), 7.87 (d, 1H), 8.10 and 8.15 (2bs, 1H), 9.44 and 9.65 (2s, 1H); MS (ES) 986 (M+H$^+$), 1008 (M+Na$^4$), 1024 (M+K$^+$).

Compound 13b: $^1$H NMR δ 1.34 (m, 3H), 2.56 (m, 1H), 2.62 (m, 2H), 2.68 (m, 3H), 2.8 (m, 1H), 3.35-3.36 (2s, 3H), 3.40-3.70 (m, 18H), 3.77 (t, 2H), 3.88 (s, 3H), 3.93 and 3.95 (2s, 3H), 3.94 (m, 1H), 4.54 (m, 2H), 4.79 (m, 1H), 7.07 (d, 2H), 7.13 (s, 1H), 7.30-7.42 (m, 3H), 7.49 (m, 2H), 7.88 (d, 1H), 8.11 and 8.25 (2bs, 1H), 9.22, 9.37, 9.80 and 9.92 (4s, 1H); MS (ES) 1000 (M+H$^+$), 1022 (M+Na$^+$), 1038 (M+K$^+$).

Compound 13c: $^1$H NMR δ 1.30-1.45 (m, 6H), 2.54 (m, 2H), 2.61 (m, 2H), 2.68 and 2.69 (2s, 3H), 3.35-3.36 (2s, 3H), 3.40-3.70 (m, 17H), 3.77 (t, 2H), 3.88 (s, 3H), 3.92 and 3.93 (2s, 3H), 3.94 (m, 1H), 4.50 (m, 2H), 4.80 (m, 1H), 7.08 (m, 2H), 7.12 (d, 1H), 7.29-7.39 (m, 3H), 7.49 (m, 2H), 7.89 (m, 1H), 8.10 and 8.25 (2bs, 1H), 9.88 and 10.04 (2s, 1H); MS (ES) 1014 (M+H$^+$), 1036 (M+Na$^+$), 1054 (M+K$^+$).

4.1m Synthesis of Compound 14a.

To a solution of Compound 13a (5.4 mg, 0.0054 mmole) in dichloromethane (1 mL) were added PS-carbodiimide (11.5 mg, 0.94 mmole/g, 0.0108 mmole), and PS-DMAP (7.2 mal 1.49 m mole/g, 0.0108 m mole). The mixture thus obtained was stirred at room temperature overnight, filtrated and concentrated to give the product. MS (ES) 1082 (M+H$^+$).

4.2 Synthesis of Disulfide Linker Conjugated with Tubulysin A
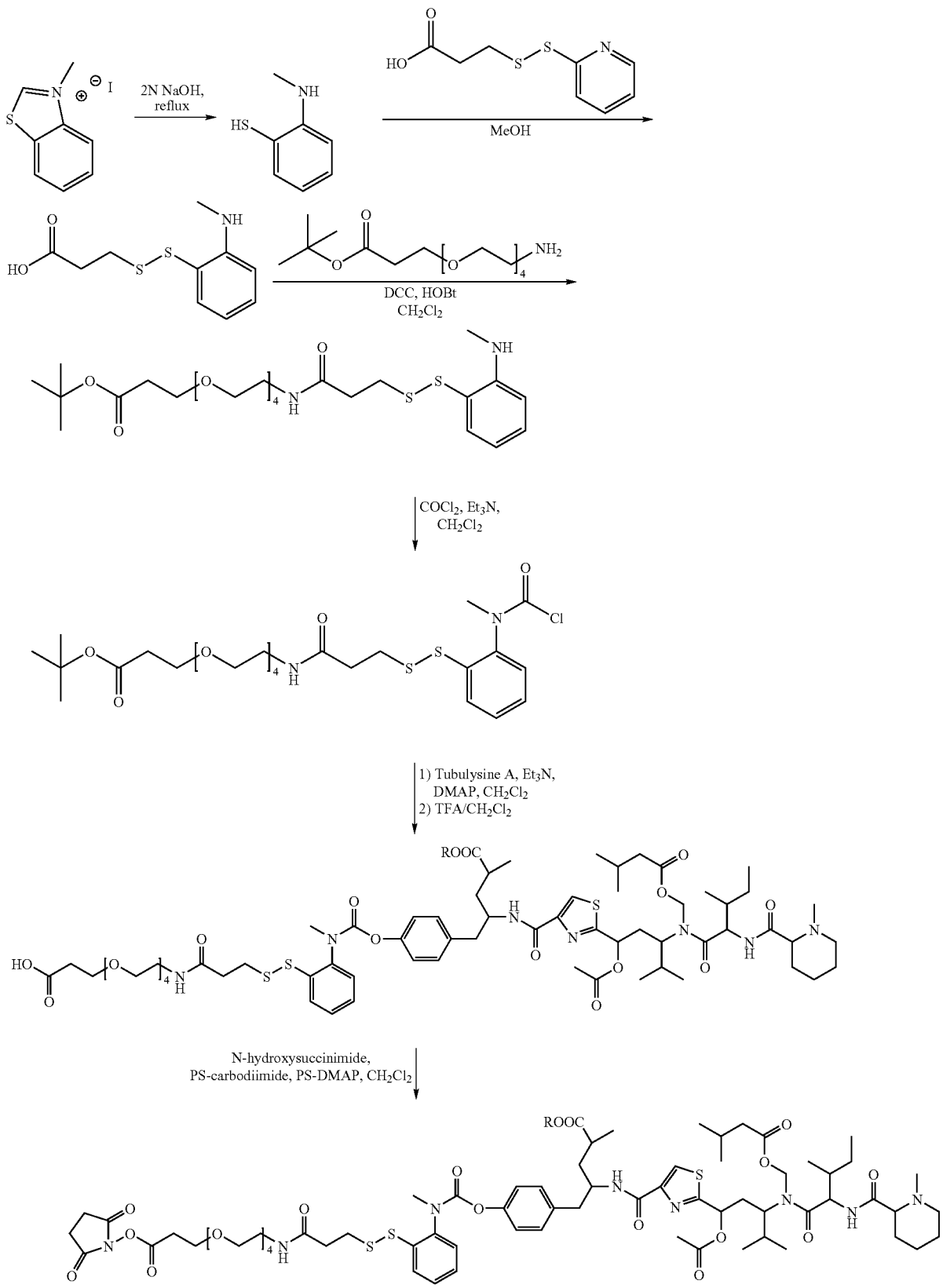

The drug Tubulysin A can be conjugated to the disulfide linker of the current invention using the mechanism shown hereinabove. Other drugs and other linkers of the current invention can be synthesized using similar reaction schemes.

4.3 Rate of Cyclization of a Disulfide Linker

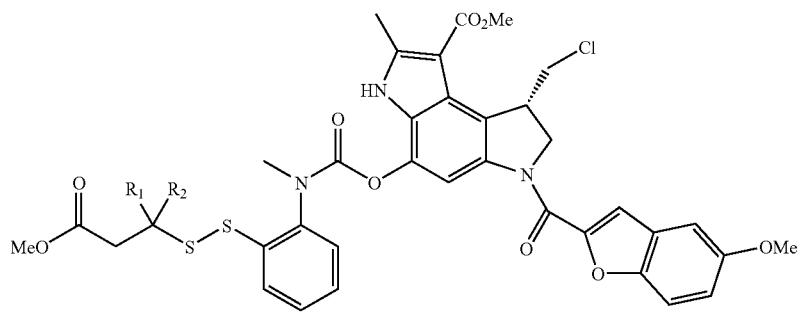

8a: $R_1 = R_2 = H$
8b: $R_1 = H, R_2 = Me$
8c: $R_1 = R_2 = Me$

↓ DDT, PBP, pH 7.2

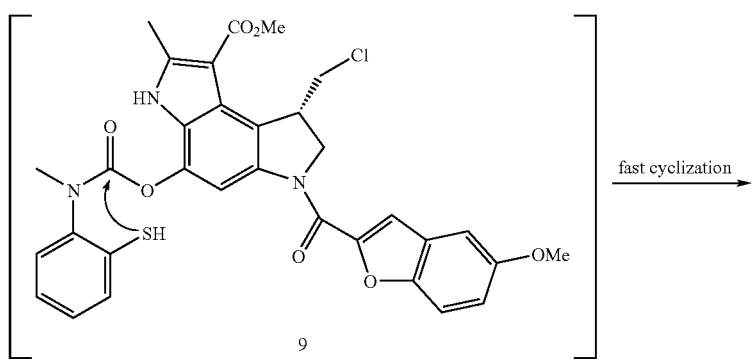

9 fast cyclization →

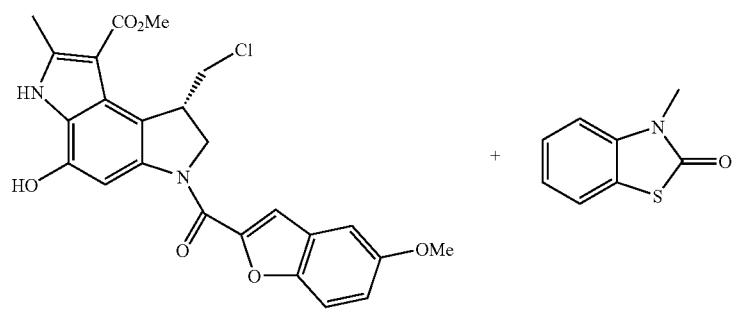

10

To a solution of Compound 8a (0.1 mg) in PBS buffer solution (pH 7.2)/methanol (300 μL, 2/1) was added a 20 mM solution of DTT (100 μL, 15 equiv.) and the progress of the reaction was monitored by HPLC. The reaction underwent rapid cyclization, with the reaction being completed within a few seconds to give product 10 quantitatively. The reaction intermediate 9 was not detected.

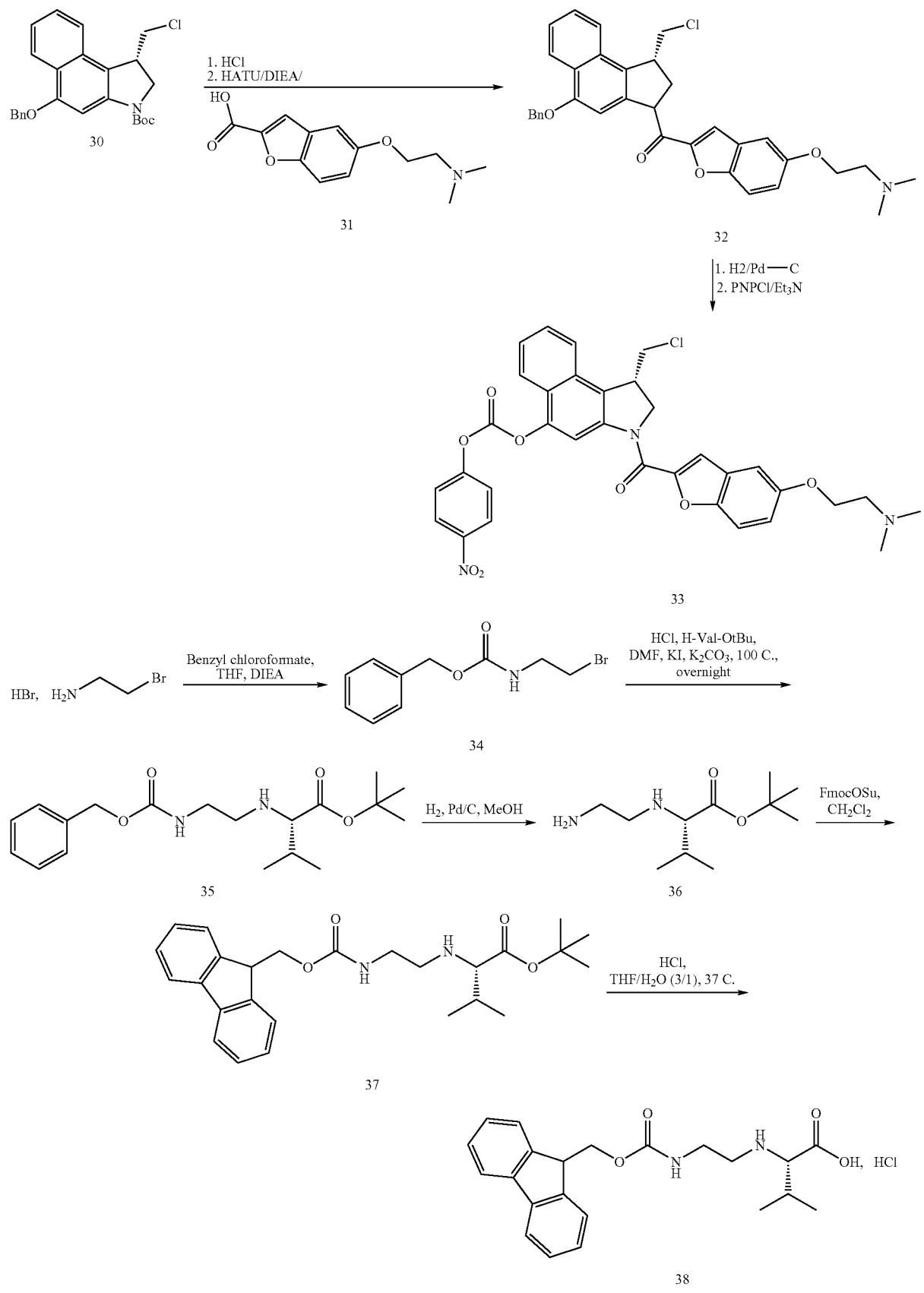

-continued
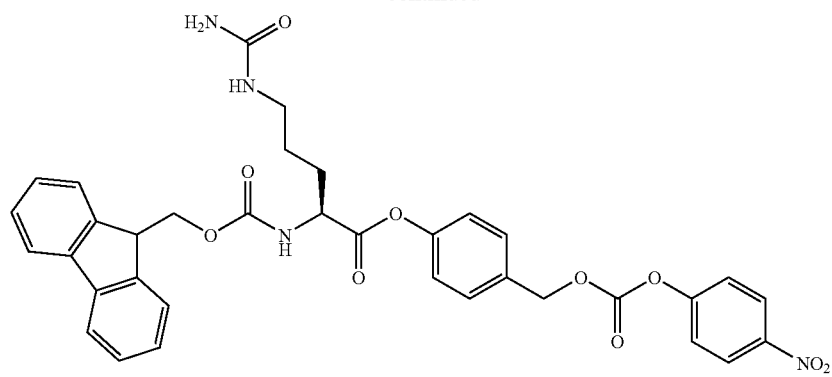
5
BocN(CH₃)CH₂CH₂NHCH₃,
CH₂Cl₂
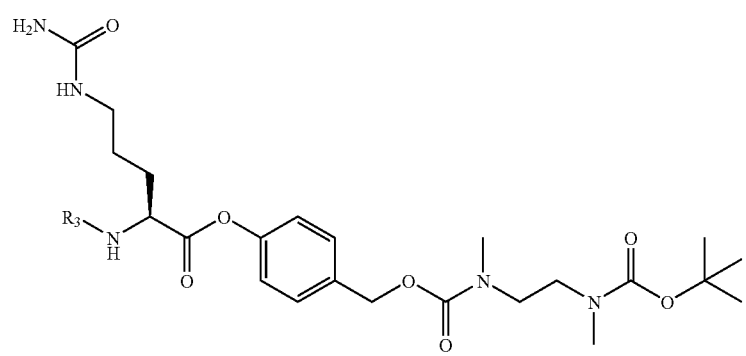
piperidine, DMF ⎡ 39: R₃ = Fmoc
            ⎣→ 40: R₃ = H
EDC, HOBt, DMF, 38
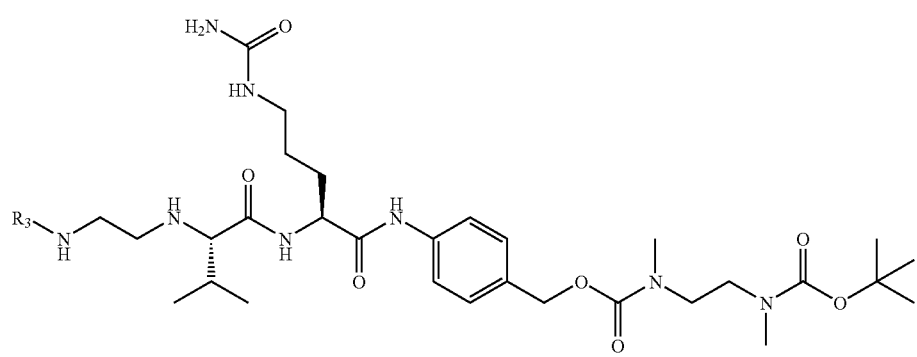
piperidine, DMF ⎡ 41: R₃ = Fmoc
            ⎣→ 42: R₃ = H
GMBS,
DIEA, CH₂Cl₂

-continued

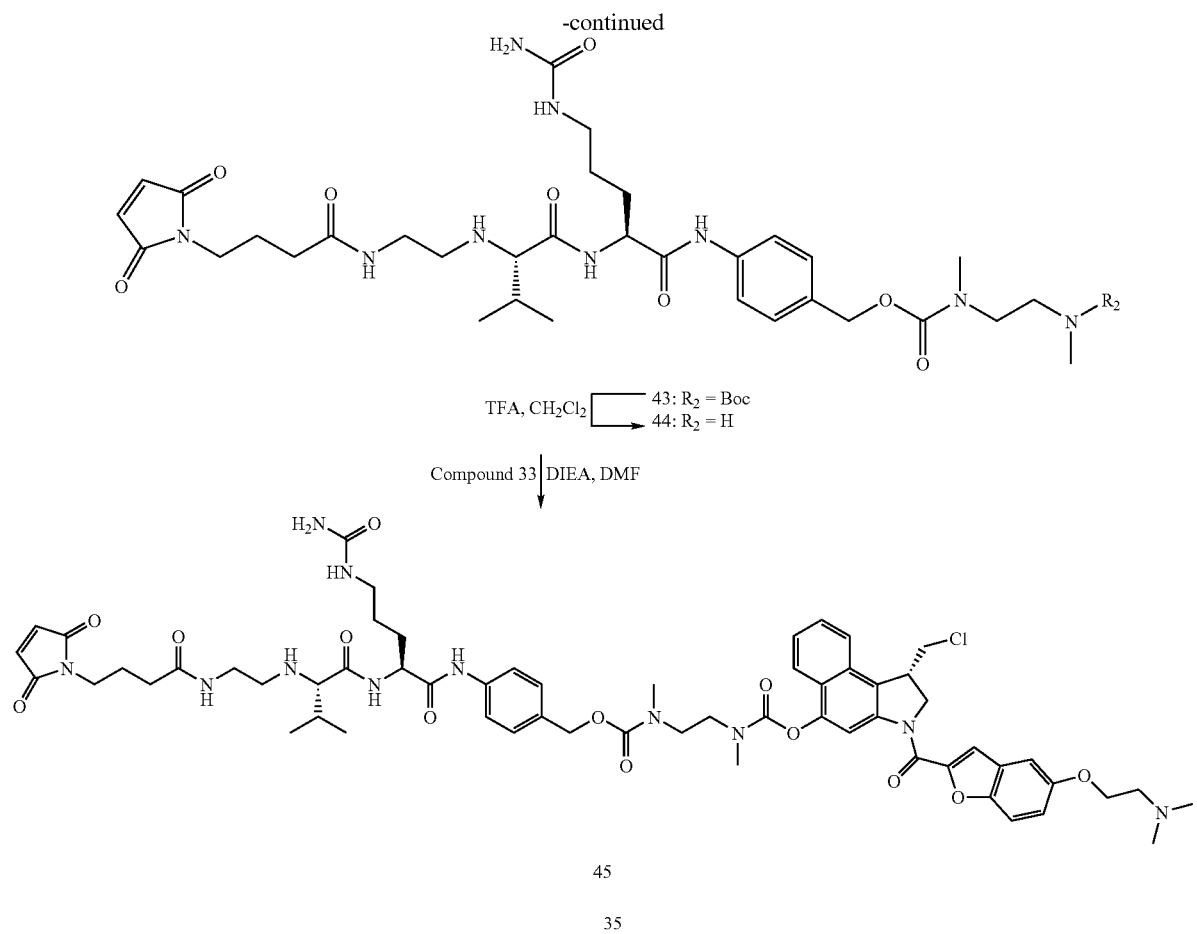

Example 5

Synthesis of Compound 32.

To a solution of Compound 30 (120 mg, 0.28 mmole) in ethyl acetate (10 mL) was bubbled HCl gas for 5 min. The reaction mixture was stirred at RT for another 30 min and then the mixture was concentrated. Ether was added to the reaction mixture and the white precipitate was collected on a filter funnel. Solid was dried overnight under vacuum to give 100 mg of the desired product which was confirmed by LC-MS (ESI) 324 (M+H$^+$) and used in next step without further purification. To a solution of this compound (100 mg, 0.24 mmole) in DMF (5 mL) were added compound 31 (65 mg, 0.26 mmole), HATU (100 mg, 0.26 mmole) and TEA (91 uL, 0.52 mmole). The mixture thus obtained was stirred at room temperature for 3 hrs. The solvent was evaporated and the residue was purified on semi-preparative HPLC with 0.1% TFA in water and acetonitrile as eluent to give compound 32 as an oil (110 mg, 80%). The desired product was confirmed by LC-MS (ESI) 555 (M+H$^+$).

Synthesis of Compound 33.

A solution of Compound 32 (110 mg, 0.2 mmole) and palladium on charcoal (20 mg) in DCM (10 mL) and methanol (5 mL) was stirred under hydrogen atmospheric pressure at room temperature for 12 hrs. The palladium was filtrated and the reaction mixture was concentrated and the residue was purified on semi-preparative HPLC with 0.1% TFA in water and acetonitrile as eluent to give the desired compound as an oil (80 mg, 78%) LC-MS (ESI) 465 (M+H$^+$). To a solution of the residue (80 mg, 0.17 mmole) in dichloromethane (10 mL) and THF (5 mL) was added PNPCl (4-nitrophenyl chloroformate) (137 mg, 0.68 mmole) and triethyl amine (144 uL, 1.02 mmol) at 0° C. The mixture thus obtained was stirred for 30 min at 0° C. and then at room temperature for 12 hrs. The reaction mixture was concentrated under vacuum, and the residue was precipitated using ethyl ether (100 mL) to give compound 33 as a yellow solid (90 mg, 82%) which was dried under vacuum and confirmed by LC-MS (ESI) 631 (M+H$^+$).

Synthesis of Compound 34:

To a solution of 2-bromoethylamine bromide (5 g, 24.4 mmole) in DMF (50 mL) was added diisopropylethylamine (8.5 mL, 48.8 mmole) and benzyl chloroformate (3.48 mL, 24.4 mmole). The mixture thus obtained was stirred at room temperature for 2 hours. The reaction mixture was concentrated and the residue was purified by flash chromatography on silica gel with ethyl acetate/hexanes (3/7) as eluent to give the desired compound 34 as an oil (4 g, 64%). $^1$H NMR (CDCl$_3$)±3.54 (bs, 2H), 3.61 (bs, 2H), 5.12 (s, 2H), 7.36 (m, 5H).

Synthesis of Compound 35:

To a solution of Compound 34 (3.34 g, 12.99 mmole) and valine tert-butyl ester (3.27 g, 15.59 mmole) in DMF (50 mL) was added potassium carbonate (5.39 g, 38.97 mmole) and potassium iodide (2.59 g, 15.59 mmole). The mixture thus obtained was stirred at 100° C. overnight. The reaction mixture was concentrated and the residue was purified by flash chromatography on silica gel with ethyl acetate/hexanes (2/8) as eluent to give the desired compound 35 as an oil (3.12 g, 69%). $^1$H NMR (CDCl$_3$) δ 0.92 (m, 6H), 1.46 (s, 9H), 1.86 (m, 1H), 2.53 (m, 1H), 2.80 (m, 2H), 3.18 (m, 1H), 3.31 (m, 1H), 5.10 (s, 2H), 5.25 (bs, 1H), 7.36 (m, 5H); LC-MS (ESI) 296 (M+H-tbutyl$^+$), 352 (M+H$^+$).

Synthesis of Compound 36.

A solution of Compound 35 (3.4 g, 9.72 mmole) and palladium on charcoal (200 mg) in methanol (30 mL) was placed under hydrogen atmospheric pressure at room temperature. The mixture thus obtained was stirred at room temperature for 2 hours. The palladium was filtrated and the reaction mixture was concentrated to dryness to give the desired compound 36 as an oil (2.1 g, 98%)

Synthesis of Compound 37.

To a solution of Compound 36 (2.1 g, 9.72 mmole) in dichloromethane (30 mL) was added FmocOSu (9-fluorenyl-methoxycarbonyl-N-hydroxysuccinimide ester) (3.28 g, 9.72 mmole) at 0° C. The mixture thus obtained was stirred for 2 hours at 0° C. The solvent were removed on the rotovap, and the residue was purified by flash chromatography on silica gel with dichloromethane, followed by 0.5% methanol in dichloromethane and finally 1% methanol in dichloromethane as eluent to give the desired compound 37 as colorless oil (2.55 g, 60%). $^1$H-NMR (CDCl$_3$) δ 0.95 (ft, 6H), 1.48 (s, 9H), 1.90 (m, 1H), 2.55 (m, 1H), 2.82 (m, 2H), 3.18 (m, 1H), 3.32 (m, 1H), 4.24 (m, 1H), 4.37 (m, 2H), 5.40 (bs, 1H), 7.30 (m, 2H), 7.39 (m, 2H), 7.60 (d, 2H), 7.75 (d, 2H) ppm; LC-MS (ESI) 383 (M+H-tbutyl$^+$), 440 (M+H$^+$), 462 (M+Na$^+$), 478 (M+K$^+$).

Synthesis of Compound 38.

To a solution of Compound 37 (177 mg, 0.4 mmole) in tetrahydrofuran-water (3/1, 8 mL) was bubbled HCl gas for 5 min. The reaction mixture was stirred at 37° C. overnight then the mixture was concentrated to dryness to give the desired compound 38 as solid (168 mg, 98%) which was confirmed by LC-MS (ESI) 383 (M+H$^+$), 405 (M+Na$^+$) and used in next step without further purification. LC-MS (ESI) 383 (M+H$^+$), 405 (M+Na$^+$).

Synthesis of Compound 39.

To a solution of Compound 5 (525 mg, 0.79 mmole) in DMF (5 mL) was added N-Boc-N,N'-dimethylethylenediamine (177 mg, 0.94 mmole). The mixture thus obtained was stirred at room temperature for 30 min. The solvent was removed and the residue was purified by flash chromatography on silica gel with dichloromethane, followed by 2% methanol in dichloromethane and finally 5% methanol in dichloromethane as eluent to give the desired compound 39 as colorless oil (364 mg, 65%). $^1$H-NMR (CD$_3$OD) δ 1.39 (s, 9H), 1.56 (m, 2H), 1.70 (m, 1H), 1.82 (m, 1H), 2.70 and 2.82 (2s, 3H), 2.90 (s, 3H), 3.09 (m, 1H), 3.17 (m, 1H), 3.30 to 3.37 (m, 4H), 4.16 (t, 1H), 4.27 (m, 1H), 4.33 (d, 2H), 5.02 (bs, 2H), 7.24 to 7.36 (m, 6H), 7.51 to 7.65 (m, 4H), 7.74 (d, 2H) ppm; LC-MS (ESI) 618 (M+H-Boc$^+$), 662 (M+H-tbutyl$^+$), 718 (M+H$^+$), 740 (M+Na$^+$), 1435 (2M+H$^+$).

Synthesis of Compound 40.

Compound 40 was prepared as described above for Compound 17a in 98% yield. LC-MS (ESI) 396 (M+H-Boc$^+$), 496 (M+H$^+$), 517 (M+Na$^+$), 533 (M+K$^+$), 992 (2M+H$^+$).

Synthesis of Compound 41.

To a solution of Compound 40 (138 mg, 0.28 mmole) in DMF (4 mL) were added the Compound 38 (110 mg, 0.28 mmole), HOBt (36 mg, 0.28 mmole) and EDC (1-(3-dimethylaminopropyl)-3-ethylcarbodiimide hydrochloride (50 mg, 0.28 mmole). The mixture thus obtained was stirred at room temperature overnight. The solvent was evaporated and the residue was purified on semi-preparative HPLC with 0.1% TFA in water and acetonitrile as eluent to give the desired compound 41 as an oil (178 mg, 70%). $^1$H-NMR (CD$_3$OD) δ 1.04 and 1.11 (2d, 6H), 1.40 (s, 9H), 1.58 (m, 2H), 1.77 (m, 1H), 1.88 (m, 1H), 2.24 (m, 1H), 2.72 and 2.84 (2s, 3H), 2.92 (s, 3H), 3.10 to 3.18 (m, 4H), 3.35 to 3.46 (m, 6H), 3.82 (d, 1H), 4.22 (t, 1H), 4.41 (m, 2H), 4.59 (m, 1H), 5.04 (bs, 2H), 7.28 to 7.40 (m, 6H), 7.55 (m, 2H), 7.63 (m, 2H), 7.78 (d, 2H) ppm; LC-MS (ESI) 760 (M+H-Boc$^+$), 804 (M+H-tbutyl$^+$), 860 (M+H$^+$), 882 (M+Na$^+$), 899 (M+K$^+$).

Synthesis of Compound 42.

Compound 42 was prepared as described above for Compound 17a in 98% yield. LC-MS (ESI) 538 (M+H-Boc$^+$), 582 (M+H-tbutyl$^+$), 638 (M+H$^+$), 660 (M+Na$^+$).

Synthesis of Compound 43.

To a solution of Compound 42 (23 mg, 0.036 mmole) in dichloromethane (1 mL) were added GMBS (N-(maleimidobutyryloxy)succinimide ester) (14 mg, 0.05 mmole) and diisopropylethylamine (8.4 µL, 0.05 mmole) at 0° C. The mixture was warmed up to room temperature slowly and the stirring was continued for additional 30 min. The solvent was evaporated and the residue was purified on semi-preparative HPLC with 0.1% TFA in water and acetonitrile as eluent to give the desired compound 43 as an oil (26 mg, 79%). $^1$H-NMR (CD$_3$OD) δ 1.06 and 1.12 (2d, 6H), 1.41 (s, 9H), 1.59 (m, 2H), 1.78 (m, 1H), 1.86 to 1.93 (m, 3H), 2.24 (m, 3H), 2.74 and 2.84 (2s, 3H), 2.93 (bs, 3H), 3.13 to 3.22 (m, 4H), 3.40 to 3.60 (m, 8H), 3.82 (d, 1H), 4.60 (m, 1H), 5.05 (bs, 2H), 6.80 (s, 2H), 7.32 (m, 2H), 7.57 (d, 2H), 8.78 (d, 1H) ppm; LC-MS (ESI) 703 (M+H-Boc$^+$), 747 (M+H-tbutyl$^+$), 803 (M+H$^+$), 825 (M+Na$^+$), 841 (M+K$^+$).

Synthesis of Compound 44.

Compound 44 was prepared as described above for Compound 15a in 98% yield. LC-MS (ESI) 703 (M+H$^+$), 725 (M+Na$^+$).

Synthesis of Compound 45.

To a solution of Compound 44 (15 mg, 0.016 mmole) and Compound 33 (10 mg, 0.016 mmole) in DMF (0.8 mL) was added diisopropylethylamine (5.5 µL, 0.032 mmole) at room temperature. The mixture thus obtained was stirred at room temperature overnight. The solvent was evaporated and the residue was purified on semi-preparative HPLC with 0.1% TFA in water and acetonitrile as eluent to give the desired compound 45 as an oil (10 mg, 45%). $^1$H-NMR (CD$_3$OD) δ 1.02 to 1.13 (m, 6H), 1.55 (m, 2H), 1.74 (m, 1H), 1.84 to 1.92 (m, 3H), 2.20 to 2.27 (m, 3H), 2.95 to 3.14 (m, 16H), 3.47 to 3.84 (m, 12H), 3.98 (m, 1H), 4.2 to 4.34 (m, 3H), 4.57 (m, 1H), 4.69 (m, 2H), 5.07 to 5.17 (m, 2H), 6.78 (s, 2H), 7.16 to 7.23 (m, 3H), 7.30 (m, 1H), 7.38 to 7.47 (m, 3H), 7.52 to 7.58 (m, 3H), 7.81 to 7.92 (m, 2H), 8.25 (bs, 1H) ppm; LC-MS (ESI) 1194 (M+H$^+$), 1215 (M+Na$^+$), 1233 (M+K$^+$).

Example 6

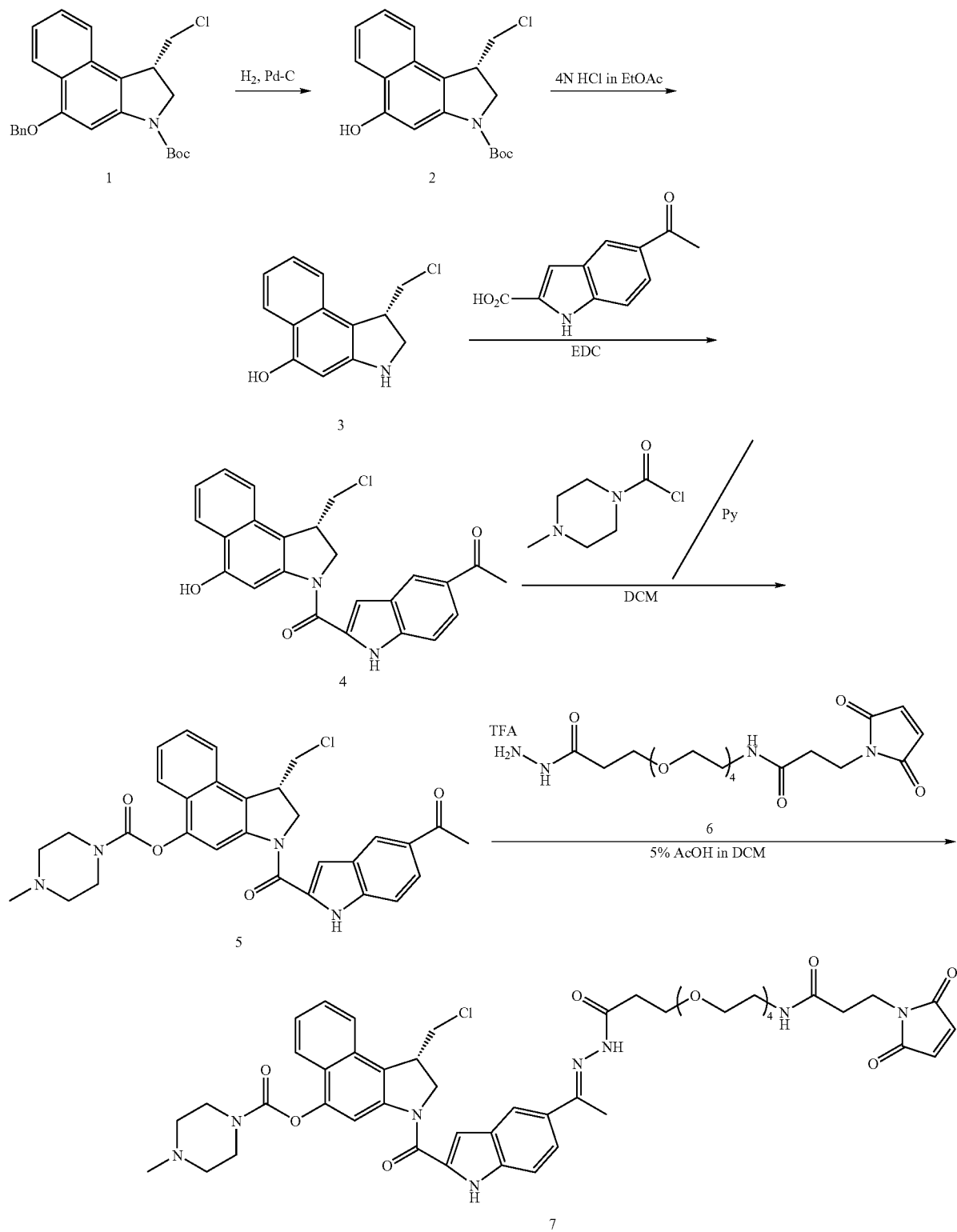

40 s. The resulting mixture was placed under an atmosphere of hydrogen and stirred at 25° C. for 7 h. The reaction mixture was filtered through Celite (CH₂Cl₂ wash). The solvent was removed in vacuo. Chromatography on silica gel eluted with EtOAc/Hex (2/8) afforded 2 (77 mg, 98%). ¹NMR DMSO- Synthesis of Compound (2).

A solution of 1 (100 mg, 0.24 mmol) and 10% Pd—C (35 mg) in MeOH/CH₂Cl₂ (1/2, 10 ml) was degassed in vacuo for d$_6$) δ 10.36 (s, 1H), 8.04 (d, 1H, J=8.2 Hz), 7.72 (d, 1H, J=8.2 Hz), 7.61 (br s, 1H), 7.45 (t, 1H, J=8.4 Hz), 7.261 (t, 1H, J=8.4 Hz), 4.06 (m, 4H), 3.73 (m, 1H), 1.52 (s, 9H).

Synthesis of Compound (4).

A solution of 2 (35 mg, 0.1 mmol) in 4 M HCl-EtOAc (5 ml) was stirred at 25° C. under Ar for 30 min. The solvent was removed in vacuo. To the residue was added 5-acetylindone-2-carboxylic acid (24.4 mg, 0.12 mmol). A solution of EDC (22.9 mg, 0.12 mmol) in DMF (3 ml) was added and the reaction mixture was stirred at 25° C. for 5 h. The solvent was removed. The crude product was chromatographed on silica gel eluted with 10% MeOH in CH$_2$Cl$_2$ to give 4 (40.7 mg, 93%). $^1$HNMR DMSO-d$_6$) δ12.13 (s, 1H), 10.47 (s, 1H), 8.45 (s, 1H), 8.10 (d, 1H, J=8.4 Hz), 7.96 (br s, 1H), 7.85 (d, 2H, J=8.4 Hz), 7.54 (d, 1H, J=8.4 Hz), 7.51 (t, 1H, J=8.2 Hz), 7.36 (t, 1H, J=7.6), 7.35 (s, 1H), 4.81 (t, 1H, 11.2 Hz), 4.54 (dd, 1H, 8.8 Hz), 4.23 (m, 1H), 4.01 (dd, 1H, J=10.2 Hz), 3.86 (dd, 1H, J=10.7 Hz), 2.61 (s, 3H).

Synthesis of Compound (5).

4-Methyl-1-piperazinecarbonyl chloride hydrochloride (19.9 mg, 0.1 mmol) was added to a solution of 4 (20 mg, 0.05 mmol) and anhydrous pyridine (25 μml, 0.3 mmol) in 3% allyl alcohol in dry methylene chloride (4 ml) and the mixture was stirred for 16 h. Purification of the crude product on silica gel yielded 5 (23.6 mg, 91%). $^1$NMR DMSO-d$_6$) δ 12.03 (s, 1H), 8.41 (s, 1H), 8.21 (s, 1H), 8.01 (d, 1H, J=8.4 Hz), 7.88 (d, 1H, J=8.4 Hz), 7.82 (dd, 1H, J=8.4 Hz), 7.58 (t, 1H, J=8.1 Hz), 7.51 (d, 1H, J=8.4 Hz), 7.46 (t, 1H, J=7.6 Hz), 7.37 (s, 1H), 4.86 (t, 1H, J=10.8 Hz), 4.57 (dd, 1H, J=10.8 Hz), 4.38 (m, 1H), 4.06 (dd, 1H, J=10.8 Hz), 3.86 (dd, 1H, J=11 Hz), 3.41 (br, 4H), 3.29 (br, 4H), 2.82 (s, 3H), 2.57 (s, 3H).

Synthesis of Compound (7).

A solution of 5 (13 mg, 24 umol) and linker 6 (16.9 mg, 31 umol) in 5% acetic acid in dry methylene chloride (1 ml) was stirred for 30 min at 25° C. The solvent was completely removed in vacuo and purified by HPLC (SymmetryPrep C$_{18}$, 7 μm, 19×150 mm column) to give 7 (18.5 mg, 81%). MS: calcd for C$_{48}$H$_{57}$ClN$_8$O$_{11}$ (M+H) m/z 958.38. found 958.10.

Example 7

Proliferation Assays

The biological activity of the cytotoxic compounds of the invention can be assayed using the well established $^3$H-thymidine proliferation assay. This is a convenient method for quantitating cellular proliferation, as it evaluates DNA synthesis by measuring the incorporation of exogenous radiolabeled $^3$H-thymidine. This assay is highly reproducible and can accommodate large numbers of compounds.

To carry out the assay, promyelocytic leukemia cells, HL-60, are cultured in RPMI media containing 10% heat inactivated fetal calf serum (FCS). On the day of the study, the cells are collected, washed and resuspended at a concentration of 0.5×10$^6$ cells/ml in RPMI containing 10% FCS. 100 μl of cell suspension is added to 96 well plates. Serial dilutions (3-fold increments) of doxorubicin (as a positive control) or test compounds are made and 100 μl of compounds are added per well. Finally 10 μl of a 100 μCi/ml$^3$H-thymidine is added per well and the plates are incubated for 24 hours. The plates are harvested using a 96 well Harvester (Packard Instruments) and counted on a Packard Top Count counter. Four parameter logistic curves are fitted to the $^3$H-thymidine incorporation as a function of drug molarity using Prism software to determine IC$_{50}$ values.

The compounds of the invention generally have an IC$_{50}$ value in the above assay of from about 1 pM to about 100 nM, preferably from about 10 pM to about 10 nM.

Example 8

Conjugation of Drug-Linker Molecules to Antibodies

This example describes reaction conditions and methodologies for conjugating a drug-linker molecule of the invention (optionally including other groups, such as spacers, reactive functional groups and the like) to an antibody as a targeting agent, X$^4$. The conditions and methodologies are intended to be exemplary only and non-limiting. Other approaches for conjugating drug-linker molecules to antibodies are known in the art.

The conjugation method described herein is based on introduction of free thiol groups to the antibody through reaction of lysines of the antibody with 2-iminothiolane, followed by reaction of the drug-linker molecule with an active maleimide group. Initially the antibody to be conjugated was buffer exchanged into 0.1M phosphate buffer pH 8.0 containing 50 mM NaCl, 2 mM DTPA, pH 8.0 and concentrated to 5-10 mg/ml. Thiolation was achieved through addition of 2-iminothiolane to the antibody. The amount of 2-iminothiolane to be added was determined in preliminary experiments and varies from antibody to antibody. In the preliminary experiments, a titration of increasing amounts of 2-iminothiolane was added to the antibody, and following incubation with the antibody for one hour at room temperature, the antibody was desalted into 50 mM HEPES buffer pH 6.0 using a Sephadex G-25 column and the number of thiol groups introduced determined rapidly by reaction with dithiodipyridine (DTDP). Reaction of thiol groups with DTDP results in liberation of thiopyridine which is monitored at 324 nm. Samples at a protein concentration of 0.5-1.0 mg/ml were used. The absorbance at 280 nm was used to accurately determine the concentration of protein in the samples, and then an aliquot of each sample (0.9 ml) was incubated with 0.1 ml DTDP (5 mM stock solution in ethanol) for 10 minutes at room temperature. Blank samples of buffer alone plus DTDP were also incubated alongside. After 10 minutes, absorbance at 324 nm was measured and the number of thiols present quantitated using an extinction coefficient for thiopyridine of 19800M$^{-1}$.

Typically a thiolation level of three thiol groups per antibody is desired. For example, with one particular antibody this was achieved through adding a 15 fold molar excess of 2-iminothiolane followed by incubation at room temperature for 1 hour. Antibody to be conjugated was therefore incubated with 2-iminothiolane at the desired molar ratio and then desalted into conjugation buffer (50 mM HEPES buffer pH 6.0 containing 5 mM Glycine, 3% Glycerol and 2 mM DTPA). The thiolated material was maintained on ice whilst the number of thiols introduced was quantitated as described above.

After verification of the number of thiols introduced, the drug-linker molecule containing an active maleimide group was added at a 3-fold molar excess per thiol. The conjugation reaction was carried out in conjugation buffer also containing a final concentration of 5% ethylene glycol dimethyl ether (or a suitable alternative solvent). Commonly, the drug-linker stock solution was dissolved in 90% ethylene glycol dimethyl ether, 10% dimethyl sulfoxide. For addition to antibody, the stock solution can be added directly to the thiolated antibody, which has enough ethylene glycol dimethyl ether added to bring the final concentration to 5%, or pre-diluted in conjugation buffer containing a final concentration of 10% ethylene glycol dimethyl ether, followed by addition to an equal volume of thiolated antibody.

The conjugation reaction was incubated at room temperature for 2 hours with mixing. Following incubation the reaction mix was centrifuged at 14000 RPM for 15 minutes and the pH was adjusted to 7.2 if purification was not immediate. Purification of conjugate was achieved through chromatography using a number of methods. Conjugate can be purified using size-exclusion chromatography on a Sephacryl S200 column pre-equilibrated with 50 mM HEPES buffer pH 7.2 containing 5 mM glycine, 50 mM NaCl and 3% glycerol. Chromatography was carried out at a linear flow rate of 28 cm/h. Fractions containing conjugate were collected, pooled and concentrated. Alternatively purification can be achieved through ion-exchange chromatography. Conditions vary from antibody to antibody and need to be optimized in each case. For example, antibody-drug conjugate reaction mix was applied to an SP-Sepharose column pre-equilibrated in 50 mM HEPES, 5 mM Glycine, 3% glycerol, pH 6.0. The antibody conjugate was eluted using a gradient of 0-1 M NaCl in equilibration buffer. Fractions containing the conjugate were pooled, the pH was adjusted to 7.2 and the sample concentrated as required.

Each of the patent applications, patents, publications, and other published documents mentioned or referred to in this specification is herein incorporated by reference in its entirety, to the same extent as if each individual patent application, patent, publication, and other published document was specifically and individually indicated to be incorporated by reference.

While the present invention has been described with reference to the specific embodiments thereof, it should be understood by those skilled in the art that various changes may be made and equivalents may be substituted without departing from the true spirit and scope of the invention and the appended claims. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A compound of the formula

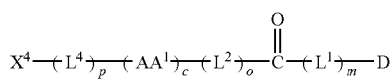

wherein D is a drug moiety comprising a structure:

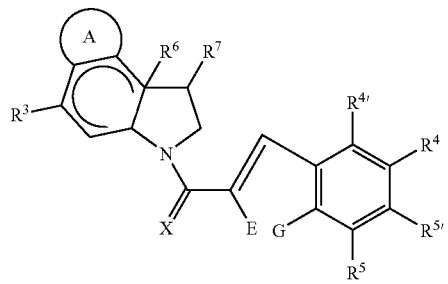

wherein the ring system A is a member selected from substituted and unsubstituted aryl, substituted and unsubstituted heteroaryl, and substituted and unsubstituted heterocycloalkyl groups;

E and G are members independently selected from H, substituted and unsubstituted alkyl, substituted and unsubstituted heteroalkyl, a heteroatom, a single bond, or E and G are joined to form a ring system selected from substituted and unsubstituted aryl, substituted and unsubstituted heteroaryl, and substituted and unsubstituted heterocycloalkyl;

X is a member selected from O, S and $NR^{23}$;

$R^{23}$ is a member selected from H, substituted and unsubstituted alkyl, substituted and unsubstituted heteroalkyl, and acyl;

$R^3$ is a member selected from the group consisting of (=O), $SR^{11}$, $NHR^{11}$ and $OR^{11}$, wherein $R^{11}$ is a member selected from the group consisting of H, substituted alkyl, unsubstituted alkyl, substituted heteroalkyl, unsubstituted heteroalkyl, diphosphates, triphosphates, acyl, $C(O)R^{12}R^{13}$, $C(O)OR^{12}$, $C(O)NR^{12}R^{13}$, $P(O)(OR^{12})_2$, $C(O)CHR^{12}R^{13}$, $SR^{12}$ and $SiR^{12}R^{12}R^{14}$, in which $R^{12}$, $R^{13}$, and $R^{14}$ are members independently selected from H, substituted and unsubstituted alkyl, substituted and unsubstituted heteroalkyl and substituted and unsubstituted aryl, wherein $R^{12}$ and $R^{13}$ together with the nitrogen or carbon atom to which they are attached are optionally joined to form a substituted or unsubstituted heterocycloalkyl ring system having from 4 to 6 members, optionally containing two or more heteroatoms;

$R^4$, $R^{4'}$, $R^5$ and $R^{5'}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$, $OR^{15}$, $CR^{15}=NR^{16}$, and $O(CH_2)_n N(CH_3)_2$ wherein n is an integer from 1 to 20;

$R^{15}$ and $R^{16}$ are independently selected from H, substituted and unsubstituted alkyl, substituted and unsubstituted heteroalkyl, substituted and unsubstituted aryl, substituted and unsubstituted heteroaryl, substituted and unsubstituted heterocycloalkyl, and substituted and unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms;

$R^6$ is a single bond which is either present or absent and when present $R^6$ and $R^7$ are joined to form a cyclopropyl ring; and $R^7$ is $CH_2$—$X^1$ or —$CH_2$— joined in said cyclopropyl ring with $R^6$, wherein $X^1$ is a leaving group, wherein at least one of $R^{11}$, $R^{12}$, $R^{13}$, $R^{15}$ or $R^{16}$, links said drug moiety D to $L^1$, if present, or to —C(O)—;

each $AA^1$ is independently selected from the group consisting of natural amino acids and unnatural α-amino acids;

c is an integer from 1 to 20;

$L^2$ is a substituted alkyl, unsubstituted alkyl, substituted heteroalkyl, unsubstituted heteroalkyl, unsubstituted heterocycloalkyl, substituted heterocycloalkyl, substituted and unsubstituted aryl, and substituted and unsubstituted heteroaryl;

$L^1$ is a self-immolative linker;

m is an integer 0, 1, 2, 3, 4, 5, or 6;

o is 0 or 1;

$L^4$ is selected from substituted alkyl, unsubstituted alkyl, substituted aryl, unsubstituted aryl, substituted heteroalkyl, and unsubstituted heteroalkyl, any of which may be straight, branched, or cyclic; positively and negatively charged amino acid polymers; a polymer; and combinations thereof, wherein $L^4$ does not comprise a carboxylic acyl group directly attached to the N-terminus of $(AA^1)_c$;

p is 1; and $X^4$ is a member selected from the group consisting of protected reactive functional groups, unprotected reactive functional groups, detectable labels, and targeting agents.

2. The compound of claim 1, wherein o is 1 and -$(AA^1)_c$-$(L^2)$—C(O)— has the structure:

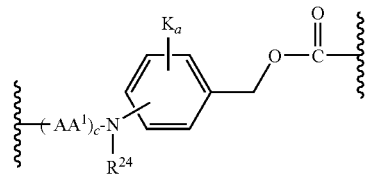

wherein $R^{24}$ is selected from the group consisting of H, substituted alkyl, unsubstituted alkyl, substituted heteroalkyl, and unsubstituted heteroalkyl;

each K is a member independently selected from the group consisting of substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, halogen, $NO_2$, $NR^{21}R^{22}$, $NR^{21}COR^{22}$, $OCONR^{21}R^{22}$, $OCOR^{21}$, and $OR^{21}$;

wherein $R^{21}$ and $R^{22}$ are independently selected from the group consisting of H, substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl; and a is an integer of 0, 1, 2, 3, or 4.

3. The compound of claim 2, wherein m is not 0 and -$(AA^1)_c$-$(L^2)$—C(O)-$(L^1)_m$- comprises the structure:

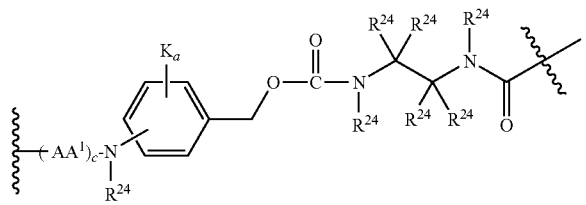

wherein each $R^{24}$ is a member independently selected from the group consisting of H, substituted alkyl, unsubstituted alkyl, substituted heteroalkyl, and unsubstituted heteroalkyl.

4. The compound of claim 2, having the structure:

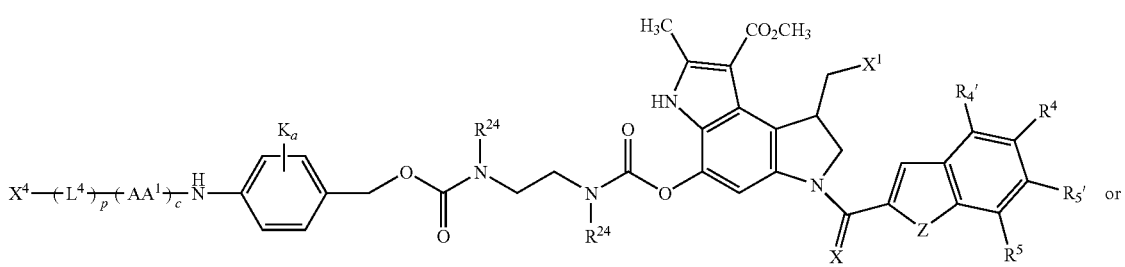

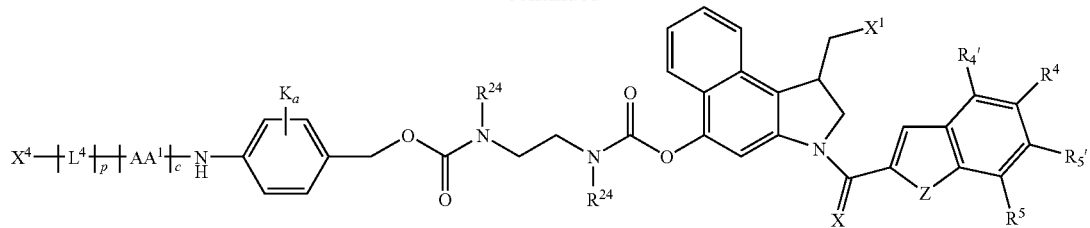
wherein Z is a member selected from O, S and $NR^{23}$,
    wherein $R^{23}$ is a member selected from H, substituted and unsubstituted alkyl, substituted and unsubstituted heteroalkyl, and acyl; and
wherein $X^1$ is a halogen.
5. The compound of claim 1, which is selected from the group consisting of:
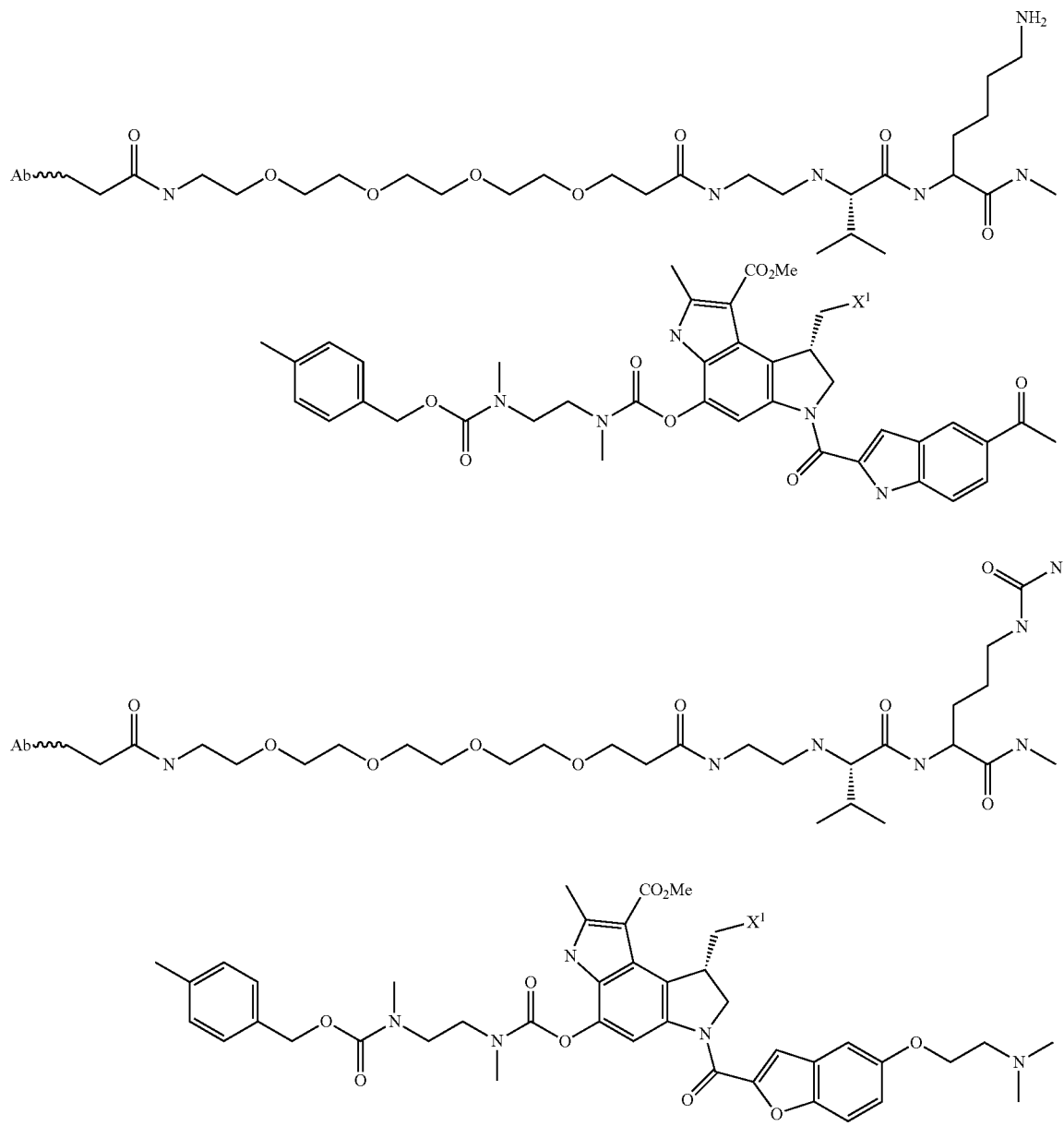

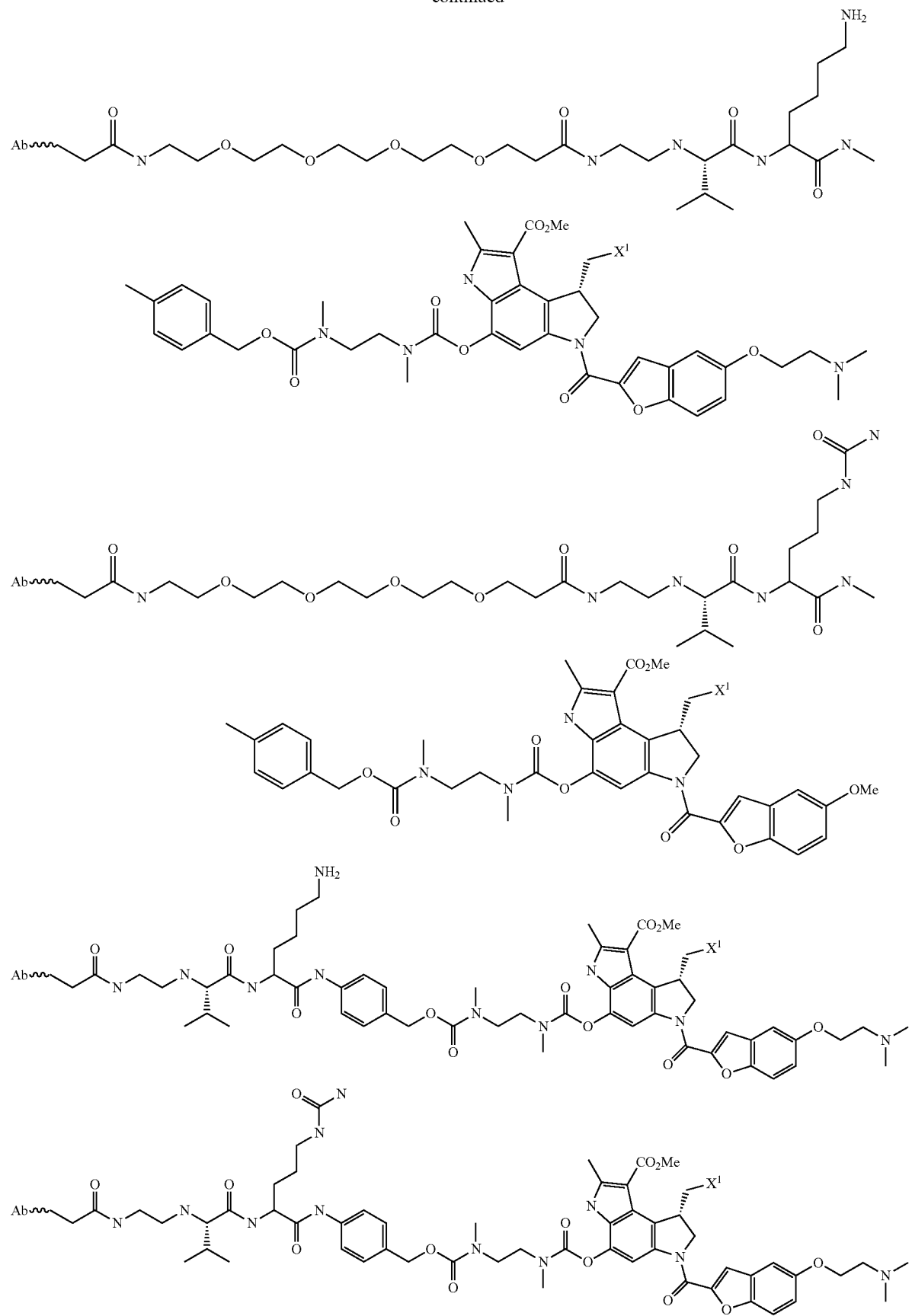

-continued

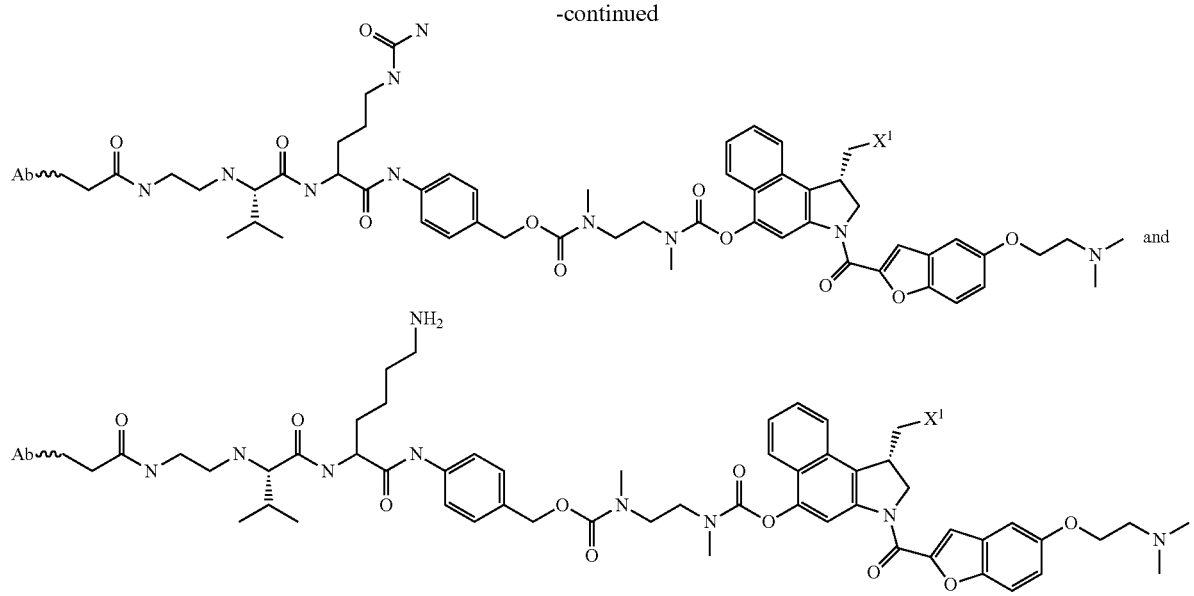

wherein $X^1$ is Cl or Br, and Ab is an antibody, or fragment thereof.

6. The compound of claim 1, wherein $L^4$ comprises a polyethylene glycol moiety.

7. The compound of claim 6, wherein the polyethylene glycol moiety contains 2-6 repeat units.

8. The compound of claim 1, wherein $(AA^1)_c$ is a peptide sequence cleavable by a protease expressed in tumor tissue.

9. The compound of claim 1, wherein $(AA^1)_c$ is a peptide sequence selected from the group consisting of Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), β-Ala-Leu-Ala-Leu (SEQ ID NO: 2) and Gly-Phe-Leu-Gly (SEQ ID NO: 3).

10. The compound of claim 1, wherein $(AA^1)_c$ is Val-Cit or Val-Lys.

11. The compound of claim 1, wherein D has the structure:

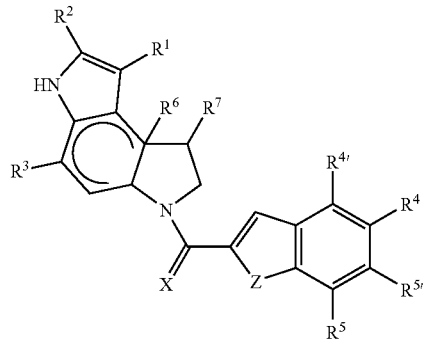

wherein Z is a member selected from O, S and $NR^{23}$
wherein $R^{23}$ is a member selected from H, substituted and unsubstituted alkyl, substituted and unsubstituted heteroalkyl, and acyl;

$R^1$ is H, substituted or unsubstituted lower alkyl, $C(O)R^8$, or $CO_2R^8$, wherein $R^8$ is a member selected from group consisting of substituted alkyl, unsubstituted alkyl, $NR^9R^{10}$, $NR^9NHR^{10}$, and $OR^9$ in which $R^9$ and $R^{10}$ are members independently selected from H, substituted and unsubstituted alkyl, and substituted and unsubstituted heteroalkyl; and $R^2$ is H, substituted alkyl or unsubstituted lower alkyl.

12. The compound of claim 1, wherein D has the structure:

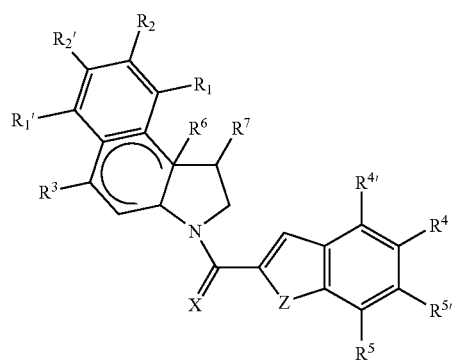

wherein Z is a member selected from O, S and $NR^{23}$
wherein $R^{23}$ is a member selected from H, substituted or unsubstituted alkyl, substituted or unsubstituted heteroalkyl, and acyl;

$R^1$ is H, substituted or unsubstituted lower alkyl, $C(O)R^8$, or $CO_2R^8$, wherein $R^8$ is a member selected from $NR^9R^{10}$ and $OR^9$, in which $R^9$ and $R^{10}$ are members independently selected from H, substituted or unsubstituted alkyl and substituted or unsubstituted heteroalkyl;

$R^{1'}$ is H, substituted or unsubstituted lower alkyl, or $C(O)R^8$, wherein $R^8$ is a member selected from $NR^9R^{10}$ and $OR^9$, in which $R^9$ and $R^{10}$ are members independently selected from H, substituted or unsubstituted alkyl and substituted or unsubstituted heteroalkyl;

$R^2$ is H, or substituted or unsubstituted lower alkyl or unsubstituted heteroalkyl or cyano or alkoxy; and $R^{2'}$ is H, or substituted or unsubstituted lower alkyl or unsubstituted heteroalkyl.

13. A pharmaceutical formulation comprising a compound according to claim 1 and a pharmaceutically acceptable carrier.

* * * * *